United States Patent
Papadopoulos et al.

(10) Patent No.: US 8,343,737 B2
(45) Date of Patent: *Jan. 1, 2013

(54) CELL CULTURE COMPOSITIONS CAPABLE OF PRODUCING A VEGF-BINDING FUSION POLYPEPTIDE

(75) Inventors: Nicholas J. Papadopoulos, Lagrangeville, NY (US); Samuel Davis, New York, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/106,910

(22) Filed: May 13, 2011

(65) Prior Publication Data

US 2012/0064621 A1    Mar. 15, 2012

Related U.S. Application Data

(60) Continuation of application No. 12/334,927, filed on Dec. 15, 2008, now Pat. No. 7,964,377, which is a continuation of application No. 12/102,648, filed on Apr. 14, 2008, now Pat. No. 7,524,499, which is a division of application No. 11/016,097, filed on Dec. 17, 2004, now Pat. No. 7,374,757, which is a division of application No. 10/009,852, filed as application No. PCT/US00/14142 on May 23, 2000, now Pat. No. 7,070,959.

(60) Provisional application No. 60/138,133, filed on Jun. 8, 1999.

(51) Int. Cl.
| | |
|---|---|
| C12N 5/10 | (2006.01) |
| C12N 5/16 | (2006.01) |
| C12N 15/62 | (2006.01) |
| C12N 15/63 | (2006.01) |
| C07H 21/04 | (2006.01) |

(52) U.S. Cl. .................. 435/69.7; 435/252.3; 435/320.1; 435/325; 435/358; 536/23.4

(58) Field of Classification Search ........................ None
See application file for complete search history.

(56) References Cited

U.S. PATENT DOCUMENTS

| | | | |
|---|---|---|---|
| 5,712,380 A | 1/1998 | Kendall et al. | |
| 6,011,003 A | 1/2000 | Charnock-Jones et al. | |
| 6,100,071 A | 8/2000 | Davis-Smyth et al. | |
| 6,833,349 B2 | 12/2004 | Xia et al. | |
| 6,897,294 B2 | 5/2005 | Davis-Smyth et al. | |
| 7,070,959 B1 | 7/2006 | Papadopoulos et al. | |
| 7,087,411 B2 | 8/2006 | Daly et al. | |
| 7,279,159 B2 | 10/2007 | Daly et al. | |
| 7,303,746 B2 | 12/2007 | Wiegand et al. | |
| 7,303,747 B2 | 12/2007 | Wiegand et al. | |
| 7,306,799 B2 | 12/2007 | Wiegand et al. | |
| 7,374,757 B2 | 5/2008 | Papadopoulos et al. | |
| 7,374,758 B2 | 5/2008 | Papadopoulos et al. | |
| 7,396,664 B2 | 7/2008 | Daly et al. | |
| 7,399,612 B2 | 7/2008 | Daly et al. | |
| 7,521,049 B2 | 4/2009 | Wiegand et al. | |
| 7,524,499 B2 | 4/2009 | Papadopoulos et al. | |
| 7,635,474 B2 | 12/2009 | Daly et al. | |
| 7,704,500 B2 | 4/2010 | Papadopoulos et al. | |
| 2004/0265309 A1 | 12/2004 | Kendall et al. | |
| 2005/0175610 A1 | 8/2005 | Wiegand et al. | |
| 2005/0260203 A1 | 11/2005 | Wiegand et al. | |
| 2005/0281822 A1 | 12/2005 | Cedarbaum et al. | |
| 2005/0281831 A1 | 12/2005 | Davis-Smyth et al. | |
| 2006/0210566 A1 | 9/2006 | Holash et al. | |
| 2007/0037748 A1 | 2/2007 | Stahl et al. | |
| 2009/0081217 A1 | 3/2009 | Papadopoulos et al. | |
| 2009/0155899 A1 | 6/2009 | Papadopoulos et al. | |
| 2009/0234103 A1 | 9/2009 | Davis-Smyth et al. | |
| 2010/0087632 A1 | 4/2010 | Daly et al. | |
| 2010/0221782 A1 | 9/2010 | Papadopoulos et al. | |

FOREIGN PATENT DOCUMENTS

| | | |
|---|---|---|
| WO | WO 94/21679 | 9/1994 |
| WO | WO 97/44453 | 11/1997 |
| WO | WO 98/13071 | 4/1998 |
| WO | WO 99/03996 | 1/1999 |
| WO | WO 00/75319 | 12/2000 |

OTHER PUBLICATIONS

Terman at al. (1991), Identification of a new endothelial cell growth factor receptor tyrosine kinase, Oncogene 6:1677-1683.
Hileman et al. (1998), Glycosaminoglycan-protein interactions: definitions of consensus sites in glycosaminoglycan binding proteins, BioEssays 20:156-167.
Devries et al. (1992), The fms-like tyrosine kinase, a receptor for vascular endothelial growth factor, Science 225:989-991.
Sharifi et al. (1998), Improving monoclonal antibody pharmacokinetics via chemical modification, Quart. J. Nucl. Med. 42:242-249.
Jensen-Pippo et al. (1996), Enteral bioavailability of human granulocyte colony stimulating factor conjugated with poly(ethylene glycol), Pharm. Res. 13(1)102-107.
Tanaka et al. (1997), Characterization of the extracellular domain in vascular endothelial growth factor receptor-1 (Flt-1 tyrosine kinase). Jpn. J. Cancer Res. 88:867-876.
Yang et al. (1995), The use of polyethylene glycol-modified interleukin-2 (PEG-IL-2) in the treatment of patients with metastatic renal cell carcinoma . . . Cancer 76:687-694.
Davis-Smyth et al. (1996), The second immunoglobulin-like domain of the VEGF tyrosine kinase receptor Flt-1 determines ligand binding and may initiate . . . EMBO J. 15:4919-4927.

(Continued)

*Primary Examiner* — Christine J Saoud
*Assistant Examiner* — Jon M Lockard
(74) *Attorney, Agent, or Firm* — Frank R. Cottingham

(57) ABSTRACT

The present invention provides cell culture compositions capable of producing fusion polypeptides that bind vascular endothelial growth factor (VEGF). The cell culture compositions of the invention comprise cells which contain an expression vector comprising a nucleic acid molecule encoding a fusion polypeptide that binds VEGF. The fusion polypeptides may comprise a VEGF receptor component having an immunoglobulin-like (Ig) domain 2 of a first VEGF receptor, an Ig domain 3 of a second VEGF receptor, and a multimerizing component.

12 Claims, 55 Drawing Sheets

OTHER PUBLICATIONS

Terman et al. (1992), Identification of the KDR tyrosine kinase as a receptor for vascular endothelial cell growth factor, Biochem Biophys Res Commun 187:1579-1586.

Tsutsumi et al. (1997), PEGylation of interleukin-6 effectively increases its thrombopoietic potency, Thrombosis and Haemostasis 77(1):168-173.

Dunca and Spreafico (1994), Polymer conjugates, Drug Delivery Systems 27(4):290-306.

Kendall et al. (1993), Inhibition of vascular endothelial cell growth factor activity by an endogenously encoded soluble receptor, Proc. Natl. Acad. Sci. USA 90:10705-10709.

Kendall et al. (1996), Identification of a natural soluble form of the vascular endothelial growth factor receptor, FLT-1, and its . . . Biochem Biophys Res Commun 226:324-328.

Autiero et al. (2003), Role of PIGF in the intra~ and intermolecular cross talk between the VEGF receptors Flt1 and Flk1, Nature Medicine 9:936-943.

Mahdadevan et al. (1995), Structural role of extracellular domain 1 of alpha-platelet-derived growth factor (PDGF) receptor for PDGF-AA and . . . J Biol. Chem. 270:27595-27600.

Yu et al, (1995), Differential requirement of a motif within the carboxyl-terminal domain of alpha-platelet-derived growth factor . . . J. Biol. Chem. 270:7033-7036.

Tanaka et al. (1995). Characterization of the ligand binding domain of FLT-1, . . . The 8th Annual Meeting of Japanese Molecular Biology, Nov. 21, 1995, Abstract 2P-227.

Keyt et al. (1996), Identification of vascular endothelial growth factor determinants for binding KDR and FLT-1 receptors; generation of . . . J. Biol. Chem. 271:5638-5646.

Heidaran et al. (1990), Chimeric alpha- and beta-platelet derived growth factor (PDGF) receptors define three immunoglobulin-like domains . . . J. Biol. Chem. 265:18741-18744.

Park et al. (1994), Placenta growth factor; potentiation of vascular endothelial growth factor bioactivity, in vitro and in vivo, and high . . . J. Biol. Chem. 269:25646-25654.

Shibuya et al. (1990), Nucleotide sequence and expression of a novel human receptor-type tyrosine kinase gene (flt) closely related to the fms family, Oncogene 5:519-524.

Heidaran et al. (1995), Beta-PDGFR-IgG chimera demonstrates that human beta-PDGFR Ig-like domains 1 to 3 are sufficient for high affinity PDGF BB . . . FASEB Journal 9:140-145.

Yu et al. (1994), Structural coincidence of alpha-PDGFR pitopes binding to platelet-derived growth factor-AA and a potent neutralizing . . . J. Biol. Chem. 269:10668-10674.

Herley et al. (1999), Characterization of the VEGF binding site on the Flt-1 receptor, Biochem Biophys Res Commun 262:731-738.

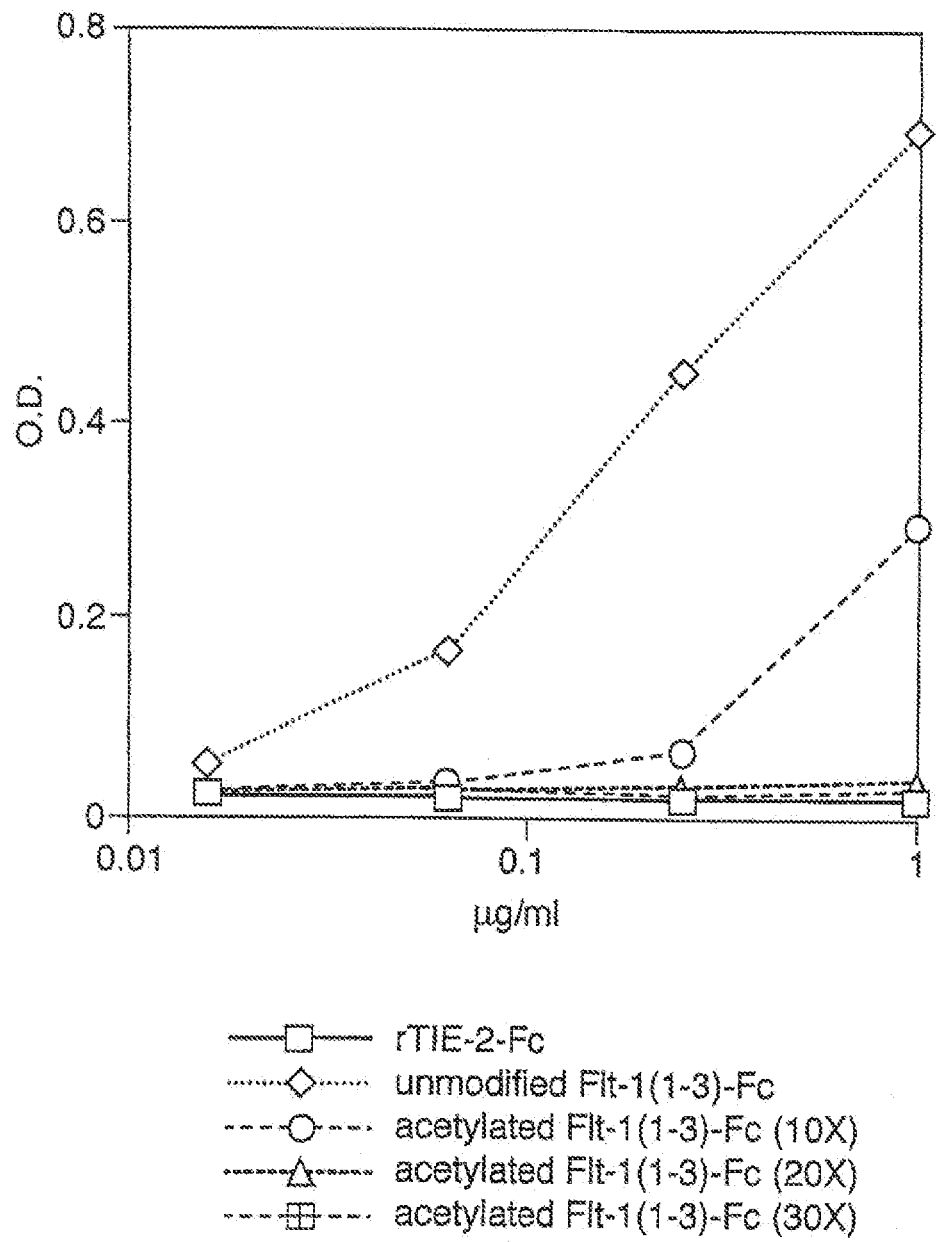

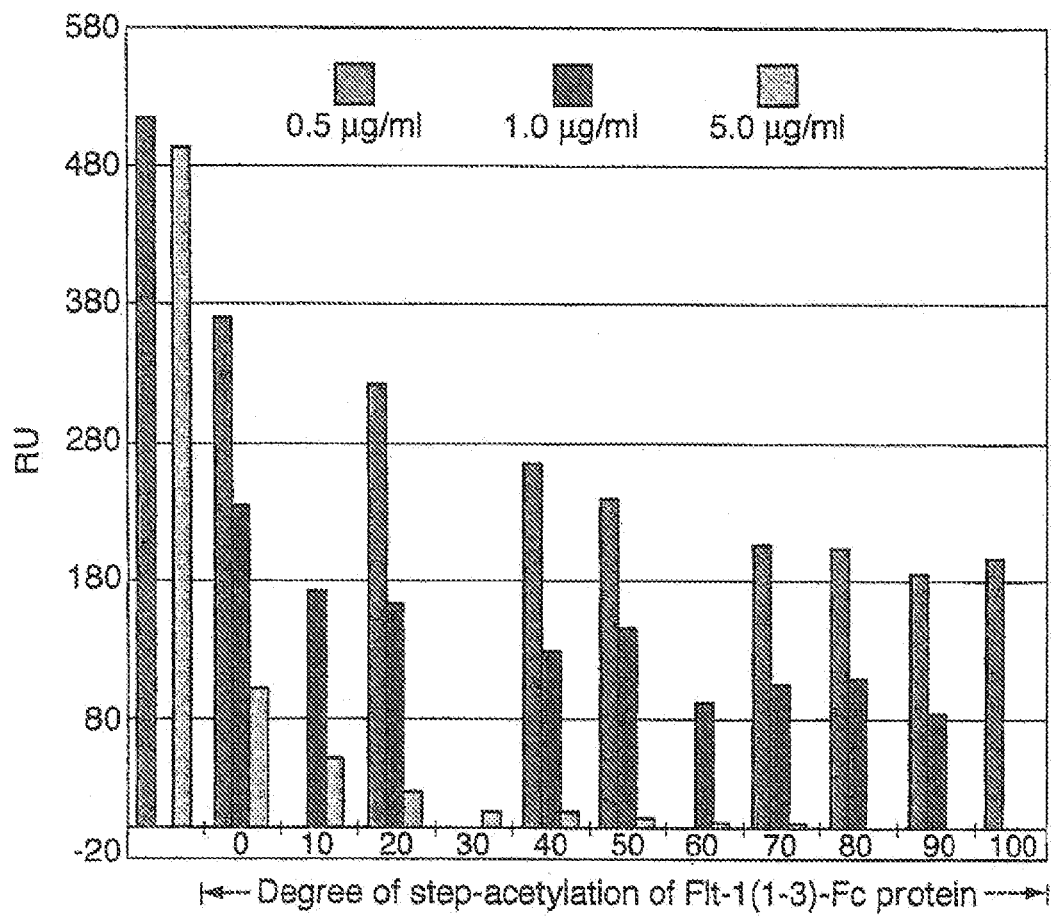

Fig.10A.

```
          10         20         30         40         50         60
           *          *          *          *          *          *
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu>

70         80         90        100        110        120
           *          *          *          *          *          *
ACA GGA TCT AGT TCA GGT TCA AAA TTA AAA GAT CCT GAA CTG AGT TTA AAA GGC ACC CAG
TGT CCT AGA TCA AGT CCA AGT TTT AAT TTT CTA GGA CTT GAC TCA AAT TTT CCG TGG GTC
Thr Gly Ser Ser Ser Gly Ser Lys Leu Lys Asp Pro Glu Leu Ser Leu Lys Gly Thr Gln>

130        140        150        160        170        180
           *          *          *          *          *          *
CAC ATC ATG CAA GCA GGC CAG ACA CTG CAT CTC CAA TGC AGG GGG GAA GCA GCC CAT AAA
GTG TAG TAC GTT CGT CCG GTC TGT GAC GTA GAG GTT ACG TCC CCC CTT CGT CGG GTA TTT
His Ile Met Gln Ala Gly Gln Thr Leu His Leu Gln Cys Arg Gly Glu Ala Ala His Lys>

190        200        210        220        230        240
           *          *          *          *          *          *
TGG TCT TTG CCT GAA ATG GTG AGT AAG GAA AGC GAA AGG CTG AGC ATA ACT AAA TCT GCC
ACC AGA AAC GGA CTT TAC CAC TCA TTC CTT TCG CTT TCC GAC TCG TAT TGA TTT AGA CGG
Trp Ser Leu Pro Glu Met Val Ser Lys Glu Ser Glu Arg Leu Ser Ile Thr Lys Ser Ala>

250        260        270        280        290        300
           *          *          *          *          *          *
TGT GGA AGA AAT GGC AAA CAA TTC TGC AGT ACT TTA ACC TTG AAC ACA GCT CAA GCA AAC
ACA CCT TCT TTA CCG TTT GTT AAG ACG TCA TGA AAT TGG AAC TTG TGT CGA GTT CGT TTG
Cys Gly Arg Asn Gly Lys Gln Phe Cys Ser Thr Leu Thr Leu Asn Thr Ala Gln Ala Asn>

310        320        330        340        350        360
           *          *          *          *          *          *
CAC ACT GGC TTC TAC AGC TGC AAA TAT CTA GCT GTA CCT ACT TCA AAG AAG AAG GAA ACA
GTG TGA CCG AAG ATG TCG ACG TTT ATA GAT CGA CAT GGA TGA AGT TTC TTC TTC CTT TGT
His Thr Gly Phe Tyr Ser Cys Lys Tyr Leu Ala Val Pro Thr Ser Lys Lys Lys Glu Thr>

370        380        390        400        410        420
           *          *          *          *          *          *
GAA TCT GCA ATC TAT ATA TTT ATT AGT GAT ACA GGT AGA CCT TTC GTA GAG ATG TAC AGT
CTT AGA CGT TAG ATA TAT AAA TAA TCA CTA TGT CCA TCT GGA AAG CAT CTC TAC ATG TCA
Glu Ser Ala Ile Tyr Ile Phe Ile Ser Asp Thr Gly Arg Pro Phe Val Glu Met Tyr Ser>

430        440        450        460        470        480
           *          *          *          *          *          *
GAA ATC CCC GAA ATT ATA CAC ATG ACT GAA GGA AGG GAG CTC GTC ATT CCC TGC CGG GTT
CTT TAG GGG CTT TAA TAT GTG TAC TGA CTT CCT TCC CTC GAG CAG TAA GGG ACG GCC CAA
Glu Ile Pro Glu Ile Ile His Met Thr Glu Gly Arg Glu Leu Val Ile Pro Cys Arg Val>

490        500        510        520        530        540
           *          *          *          *          *          *
ACG TCA CCT AAC ATC ACT GTT ACT TTA AAA AAG TTT CCA CTT GAC ACT TTG ATC CCT GAT
TGC AGT GGA TTG TAG TGA CAA TGA AAT TTT TTC AAA GGT GAA CTG TGA AAC TAG GGA CTA
Thr Ser Pro Asn Ile Thr Val Thr Leu Lys Lys Phe Pro Leu Asp Thr Leu Ile Pro Asp>
```

Fig.10B.

```
         550         560         570         580         590         600
          *           *           *           *           *           *
GGA AAA CGC ATA ATC TGG GAC AGT AGA AAG GGC TTC ATC ATA TCA AAT GCA ACG TAC AAA
CCT TTT GCG TAT TAG ACC CTG TCA TCT TTC CCG AAG TAG TAT AGT TTA CGT TGC ATG TTT
Gly Lys Arg Ile Ile Trp Asp Ser Arg Lys Gly Phe Ile Ile Ser Asn Ala Thr Tyr Lys>

610         620         630         640         650         660
          *           *           *           *           *           *
GAA ATA GGG CTT CTG ACC TGT GAA GCA ACA GTC AAT GGG CAT TTG TAT AAG ACA AAC TAT
CTT TAT CCC GAA GAC TGG ACA CTT CGT TGT CAG TTA CCC GTA AAC ATA TTC TGT TTG ATA
Glu Ile Gly Leu Leu Thr Cys Glu Ala Thr Val Asn Gly His Leu Tyr Lys Thr Asn Tyr>

670         680         690         700         710         720
          *           *           *           *           *           *
CTC ACA CAT CGA CAA ACC AAT ACA ATC ATA GAT GTC CAA ATA AGC ACA CCA CGC CCA GTC
GAG TGT GTA GCT GTT TGG TTA TGT TAG TAT CTA CAG GTT TAT TCG TGT GGT GCG GGT CAG
Leu Thr His Arg Gln Thr Asn Thr Ile Ile Asp Val Gln Ile Ser Thr Pro Arg Pro Val>

730         740         750         760         770         780
          *           *           *           *           *           *
AAA TTA CTT AGA GGC CAT ACT CTT GTC CTC AAT TGT ACT GCT ACC ACT CCC TTG AAC ACG
TTT AAT GAA TCT CCG GTA TGA GAA CAG GAG TTA ACA TGA CGA TGG TGA GGG AAC TTG TGC
Lys Leu Leu Arg Gly His Thr Leu Val Leu Asn Cys Thr Ala Thr Thr Pro Leu Asn Thr>

790         800         810         820         830         840
          *           *           *           *           *           *
AGA GTT CAA ATG ACC TGG AGT TAC CCT GAT GAA AAA AAT AAG AGA GCT TCC GTA AGG CGA
TCT CAA GTT TAC TGG ACC TCA ATG GGA CTA CTT TTT TTA TTC TCT CGA AGG CAT TCC GCT
Arg Val Gln Met Thr Trp Ser Tyr Pro Asp Glu Lys Asn Lys Arg Ala Ser Val Arg Arg>

850         860         870         880         890         900
          *           *           *           *           *           *
CGA ATT GAC CAA AGC AAT TCC CAT GCC AAC ATA TTC TAC AGT GTT CTT ACT ATT GAC AAA
GCT TAA CTG GTT TCG TTA AGG GTA CGG TTG TAT AAG ATG TCA CAA GAA TGA TAA CTG TTT
Arg Ile Asp Gln Ser Asn Ser His Ala Asn Ile Phe Tyr Ser Val Leu Thr Ile Asp Lys>

910         920         930         940         950         960
          *           *           *           *           *           *
ATG CAG AAC AAA GAC AAA GGA CTT TAT ACT TGT CGT GTA AGG AGT GGA CCA TCA TTC AAA
TAC GTC TTG TTT CTG TTT CCT GAA ATA TGA ACA GCA CAT TCC TCA CCT GGT AGT AAG TTT
Met Gln Asn Lys Asp Lys Gly Leu Tyr Thr Cys Arg Val Arg Ser Gly Pro Ser Phe Lys>

970         980         990        1000        1010        1020
          *           *           *           *           *           *
TCT GTT AAC ACC TCA GTG CAT ATA TAT GAT AAA GCA GGC CCG GGC GAG CCC AAA TCT TGT
AGA CAA TTG TGG AGT CAC GTA TAT ATA CTA TTT CGT CCG GCC CGC CTC GGG TTT AGA ACA
Ser Val Asn Thr Ser Val His Ile Tyr Asp Lys Ala Gly Pro Gly Glu Pro Lys Ser Cys>

1030        1040        1050        1060        1070        1080
          *           *           *           *           *           *
GAC AAA ACT CAC ACA TGC CCA CCG TGC CCA GCA CCT GAA CTC CTG GGG GGA CCG TCA GTC
CTG TTT TGA GTG TGT ACG GGT GGC ACG GGT CGT GGA CTT GAG GAC CCC CCT GGC AGT CAG
Asp Lys Thr His Thr Cys Pro Pro Cys Pro Ala Pro Glu Leu Leu Gly Gly Pro Ser Val>
```

Fig. 10C.

```
         1090        1100        1110        1120        1130        1140
           *           *           *           *           *           *
TTC CTC TTC CCC CCA AAA CCC AAG GAC ACC CTC ATG ATC TCC CGG ACC CCT GAG GTC ACA
AAG GAG AAG GGG GGT TTT GGG TTC CTG TGG GAG TAC TAG AGG GCC TGG GGA CTC CAG TGT
Phe Leu Phe Pro Pro Lys Pro Lys Asp Thr Leu Met Ile Ser Arg Thr Pro Glu Val Thr>

1150        1160        1170        1180        1190        1200
           *           *           *           *           *           *
TGC GTG GTG GTG GAC GTG AGC CAC GAA GAC CCT GAG GTC AAG TTC AAC TGG TAC GTG GAC
ACG CAC CAC CAC CTG CAC TCG GTG CTT CTG GGA CTC CAG TTC AAG TTG ACC ATG CAC CTG
Cys Val Val Val Asp Val Ser His Glu Asp Pro Glu Val Lys Phe Asn Trp Tyr Val Asp>

1210        1220        1230        1240        1250        1260
           *           *           *           *           *           *
GGC GTG GAG GTG CAT AAT GCC AAG ACA AAG CCG CGG GAG GAG CAG TAC AAC AGC ACG TAC
CCG CAC CTC CAC GTA TTA CGG TTC TGT TTC GGC GCC CTC CTC GTC ATG TTG TCG TGC ATG
Gly Val Glu Val His Asn Ala Lys Thr Lys Pro Arg Glu Glu Gln Tyr Asn Ser Thr Tyr>

1270        1280        1290        1300        1310        1320
           *           *           *           *           *           *
CGT GTG GTC AGC GTC CTC ACC GTC CTG CAC CAG GAC TGG CTG AAT GGC AAG GAG TAC AAG
GCA CAC CAG TCG CAG GAG TGG CAG GAC GTG GTC CTG ACC GAC TTA CCG TTC CTC ATG TTC
Arg Val Val Ser Val Leu Thr Val Leu His Gln Asp Trp Leu Asn Gly Lys Glu Tyr Lys>

1330        1340        1350        1360        1370        1380
           *           *           *           *           *           *
TGC AAG GTC TCC AAC AAA GCC CTC CCA GCC CCC ATC GAG AAA ACC ATC TCC AAA GCC AAA
ACG TTC CAG AGG TTG TTT CGG GAG GGT CGG GGG TAG CTC TTT TGG TAG AGG TTT CGG TTT
Cys Lys Val Ser Asn Lys Ala Leu Pro Ala Pro Ile Glu Lys Thr Ile Ser Lys Ala Lys>

1390        1400        1410        1420        1430        1440
           *           *           *           *           *           *
GGG CAG CCC CGA GAA CCA CAG GTG TAC ACC CTG CCC CCA TCC CGG GAT GAG CTG ACC AAG
CCC GTC GGG GCT CTT GGT GTC CAC ATG TGG GAC GGG GGT AGG GCC CTA CTC GAC TGG TTC
Gly Gln Pro Arg Glu Pro Gln Val Tyr Thr Leu Pro Pro Ser Arg Asp Glu Leu Thr Lys>

1450        1460        1470        1480        1490        1500
           *           *           *           *           *           *
AAC CAG GTC AGC CTG ACC TGC CTG GTC AAA GGC TTC TAT CCC AGC GAC ATC GCC GTG GAG
TTG GTC CAG TCG GAC TGG ACG GAC CAG TTT CCG AAG ATA GGG TCG CTG TAG CGG CAC CTC
Asn Gln Val Ser Leu Thr Cys Leu Val Lys Gly Phe Tyr Pro Ser Asp Ile Ala Val Glu>

1510        1520        1530        1540        1550        1560
           *           *           *           *           *           *
TGG GAG AGC AAT GGG CAG CCG GAG AAC AAC TAC AAG ACC ACG CCT CCC GTG CTG GAC TCC
ACC CTC TCG TTA CCC GTC GGC CTC TTG TTG ATG TTC TGG TGC GGA GGG CAC GAC CTG AGG
Trp Glu Ser Asn Gly Gln Pro Glu Asn Asn Tyr Lys Thr Thr Pro Pro Val Leu Asp Ser>

1570        1580        1590        1600        1610        1620
           *           *           *           *           *           *
GAC GGC TCC TTC TTC CTC TAC AGC AAG CTC ACC GTG GAC AAG AGC AGG TGG CAG CAG GGG
CTG CCG AGG AAG AAG GAG ATG TCG TTC GAG TGG CAC CTG TTC TCG TCC ACC GTC GTC CCC
Asp Gly Ser Phe Phe Leu Tyr Ser Lys Leu Thr Val Asp Lys Ser Arg Trp Gln Gln Gly>
```

Fig.10D.

```
        1630          1640          1650          1660          1670          1680
    *       *       *       *       *       *       *       *       *       *       *       *
AAC GTC TTC TCA TGC TCC GTG ATG CAT GAG GCT CTG CAC AAC CAC TAC ACG CAG AAG AGC
TTG CAG AAG AGT ACG AGG CAC TAC GTA CTC CGA GAC GTG TTG GTG ATG TGC GTC TTC TCG
Asn Val Phe Ser Cys Ser Val Met His Glu Ala Leu His Asn His Tyr Thr Gln Lys Ser>

1690          1700
    *       *       *       *
CTC TCC CTG TCT CCG GGT AAA TGA
GAG AGG GAC AGA GGC CCA TTT ACT
Leu Ser Leu Ser Pro Gly Lys ***>
```

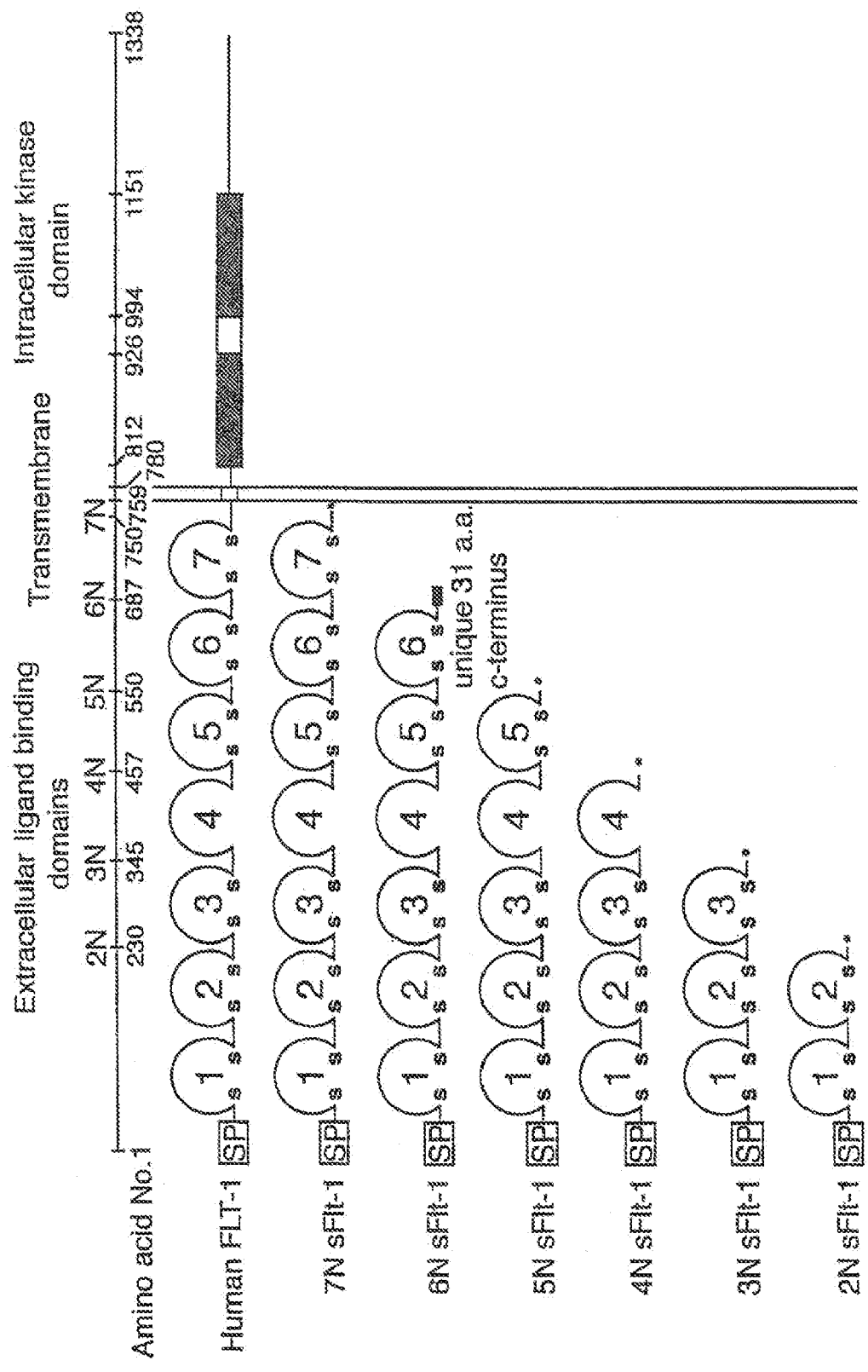

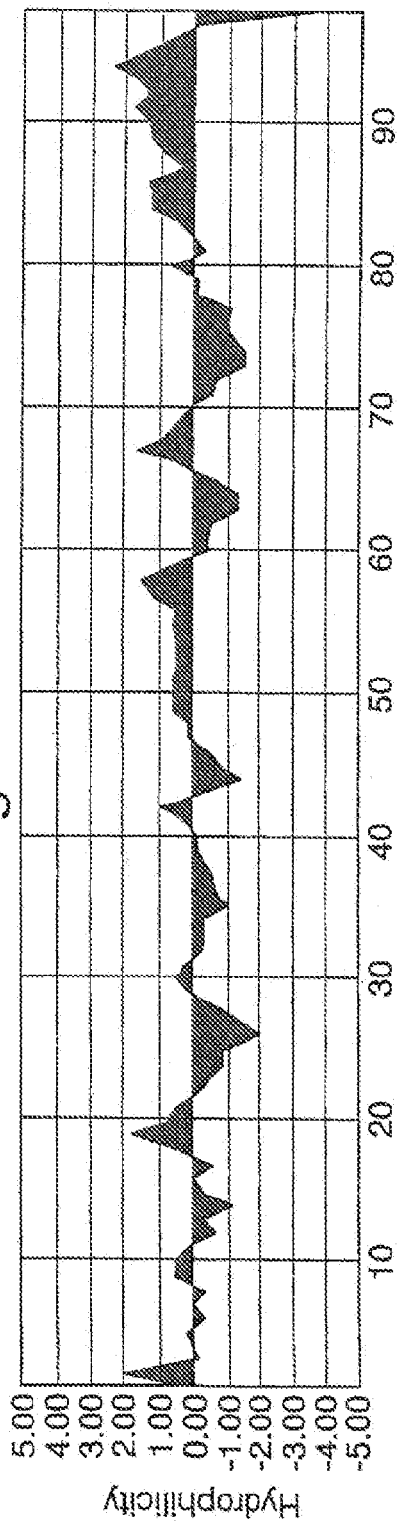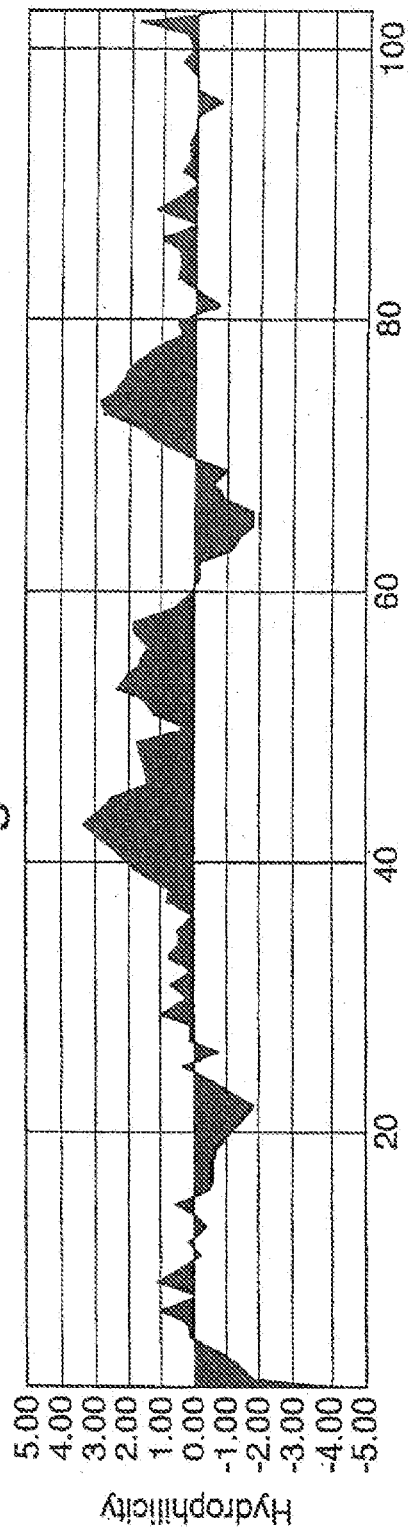

Fig.13A.

```
         10         20         30         40         50         60
          *          *          *          *          *          *
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu>

70         80         90        100        110        120
          *          *          *          *          *          *
ACA GGA TCT AGT TCA GGT TCA AAA TTA AAA GAT CCT GAA CTG AGT TTA AAA GGC ACC CAG
TGT CCT AGA TCA AGT CCA AGT TTT AAT TTT CTA GGA CTT GAC TCA AAT TTT CCG TGG GTC
Thr Gly Ser Ser Ser Gly Ser Lys Leu Lys Asp Pro Glu Leu Ser Leu Lys Gly Thr Gln>

130        140        150        160        170        180
          *          *          *          *          *          *
CAC ATC ATG CAA GCA GGC CAG ACA CTG CAT CTC CAA TGC AGG GGG GAA GCA GCC CAT AAA
GTG TAG TAC GTT CGT CCG GTC TGT GAC GTA GAG GTT ACG TCC CCC CTT CGT CGG GTA TTT
His Ile Met Gln Ala Gly Gln Thr Leu His Leu Gln Cys Arg Gly Glu Ala Ala His Lys>

190        200        210        220        230        240
          *          *          *          *          *          *
TGG TCT TTG CCT GAA ATG GTG AGT AAG GAA AGC GAA AGG CTG AGC ATA ACT AAA TCT GCC
ACC AGA AAC GGA CTT TAC CAC TCA TTC CTT TCG CTT TCC GAC TCG TAT TGA TTT AGA CGG
Trp Ser Leu Pro Glu Met Val Ser Lys Glu Ser Glu Arg Leu Ser Ile Thr Lys Ser Ala>

250        260        270        280        290        300
          *          *          *          *          *          *
TGT GGA AGA AAT GGC AAA CAA TTC TGC AGT ACT TTA ACC TTG AAC ACA GCT CAA GCA AAC
ACA CCT TCT TTA CCG TTT GTT AAG ACG TCA TGA AAT TGG AAC TTG TGT CGA GTT CGT TTG
Cys Gly Arg Asn Gly Lys Gln Phe Cys Ser Thr Leu Thr Leu Asn Thr Ala Gln Ala Asn>

310        320        330        340        350        360
          *          *          *          *          *          *
CAC ACT GGC TTC TAC AGC TGC AAA TAT CTA GCT GTA CCT ACT TCA AAG AAG AAG GAA ACA
GTG TGA CCG AAG ATG TCG ACG TTT ATA GAT CGA CAT GGA TGA AGT TTC TTC TTC CTT TGT
His Thr Gly Phe Tyr Ser Cys Lys Tyr Leu Ala Val Pro Thr Ser Lys Lys Lys Glu Thr>

370        380        390        400        410        420
          *          *          *          *          *          *
GAA TCT GCA ATC TAT ATA TTT ATT AGT GAT ACA GGT AGA CCT TTC GTA GAG ATG TAC AGT
CTT AGA CGT TAG ATA TAT AAA TAA TCA CTA TGT CCA TCT GGA AAG CAT CTC TAC ATG TCA
Glu Ser Ala Ile Tyr Ile Phe Ile Ser Asp Thr Gly Arg Pro Phe Val Glu Met Tyr Ser>

430        440        450        460        470        480
          *          *          *          *          *          *
GAA ATC CCC GAA ATT ATA CAC ATG ACT GAA GGA AGG GAG CTC GTC ATT CCC TGC CGG GTT
CTT TAG GGG CTT TAA TAT GTG TAC TGA CTT CCT TCC CTC GAG CAG TAA GGG ACG GCC CAA
Glu Ile Pro Glu Ile Ile His Met Thr Glu Gly Arg Glu Leu Val Ile Pro Cys Arg Val>

490        500        510        520        530        540
          *          *          *          *          *          *
ACG TCA CCT AAC ATC ACT GTT ACT TTA AAA AAG TTT CCA CTT GAC ACT TTG ATC CCT GAT
TGC AGT GGA TTG TAG TGA CAA TGA AAT TTT TCA AAG GTG AAC TGT GAA ACT AGG GAC CTA
Thr Ser Pro Asn Ile Thr Val Thr Leu Lys Lys Phe Pro Leu Asp Thr Leu Ile Pro Asp>
```

Fig.13B.

```
          550         560         570         580         590         600
           *           *           *           *           *           *
GGA AAA CGC ATA ATC TGG GAC AGT AGA AAG GGC TTC ATC ATA TCA AAT GCA ACG TAC AAA
CCT TTT GCG TAT TAG ACC CTG TCA TCT TTC CCG AAG TAG TAT AGT TTA CGT TGC ATG TTT
Gly Lys Arg Ile Ile Trp Asp Ser Arg Lys Gly Phe Ile Ile Ser Asn Ala Thr Tyr Lys>

610         620         630         640         650         660
           *           *           *           *           *           *
GAA ATA GGG CTT CTG ACC TGT GAA GCA ACA GTC AAT GGG CAT TTG TAT AAG ACA AAC TAT
CTT TAT CCC GAA GAC TGG ACA CTT CGT TGT CAG TTA CCC GTA AAC ATA TTC TGT TTG ATA
Glu Ile Gly Leu Leu Thr Cys Glu Ala Thr Val Asn Gly His Leu Tyr Lys Thr Asn Tyr>

670         680         690         700         710         720
           *           *           *           *           *           *
CTC ACA CAT CGA CAA ACC AAT ACA ATC ATA GAT GTC CAA ATA AGC ACA CCA CGC CCA GTC
GAG TGT GTA GCT GTT TGG TTA TGT TAG TAT CTA CAG GTT TAT TCG TGT GGT GCG GGT CAG
Leu Thr His Arg Gln Thr Asn Thr Ile Ile Asp Val Gln Ile Ser Thr Pro Arg Pro Val>

730         740         750         760         770         780
           *           *           *           *           *           *
AAA TTA CTT AGA GGC CAT ACT CTT GTC CTC AAT TGT ACT GCT ACC ACT CCC TTG AAC ACG
TTT AAT GAA TCT CCG GTA TGA GAA CAG GAG TTA ACA TGA CGA TGG TGA GGG AAC TTG TGC
Lys Leu Leu Arg Gly His Thr Leu Val Leu Asn Cys Thr Ala Thr Thr Pro Leu Asn Thr>

790         800         810         820         830         840
           *           *           *           *           *           *
AGA GTT CAA ATG ACC TGG AGT TAC CCT GAT GAA ATT GAC CAA AGC AAT TCC CAT GCC AAC
TCT CAA GTT TAC TGG ACC TCA ATG GGA CTA CTT TAA CTG GTT TCG TTA AGG GTA CGG TTG
Arg Val Gln Met Thr Trp Ser Tyr Pro Asp Glu Ile Asp Gln Ser Asn Ser His Ala Asn>

850         860         870         880         890         900
           *           *           *           *           *           *
ATA TTC TAC AGT GTT CTT ACT ATT GAC AAA ATG CAG AAC AAA GAC AAA GGA CTT TAT ACT
TAT AAG ATG TCA CAA GAA TGA TAA CTG TTT TAC GTC TTG TTT CTG TTT CCT GAA ATA TGA
Ile Phe Tyr Ser Val Leu Thr Ile Asp Lys Met Gln Asn Lys Asp Lys Gly Leu Tyr Thr>

910         920         930         940         950         960
           *           *           *           *           *           *
TGT CGT GTA AGG AGT GGA CCA TCA TTC AAA TCT GTT AAC ACC TCA GTG CAT ATA TAT GAT
ACA GCA CAT TCC TCA CCT GGT AGT AAG TTT AGA CAA TTG TGG AGT CAC GTA TAT ATA CTA
Cys Arg Val Arg Ser Gly Pro Ser Phe Lys Ser Val Asn Thr Ser Val His Ile Tyr Asp>

970         980         990        1000        1010        1020
           *           *           *           *           *           *
AAA GCA GGC CCG GGC GAG CCC AAA TCT TGT GAC AAA ACT CAC ACA TGC CCA CCG TGC CCA
TTT CGT CCG GGC CCG CTC GGG TTT AGA ACA CTG TTT TGA GTG TGT ACG GGT GGC ACG GGT
Lys Ala Gly Pro Gly Glu Pro Lys Ser Cys Asp Lys Thr His Thr Cys Pro Pro Cys Pro>

1030        1040        1050        1060        1070        1080
           *           *           *           *           *           *
GCA CCT GAA CTC CTG GGG GGA CCG TCA GTC TTC CTC TTC CCC CCA AAA CCC AAG GAC ACC
CGT GGA CTT GAG GAC CCC CCT GGC AGT CAG AAG GAG AAG GGG GGT TTT GGG TTC CTG TGG
Ala Pro Glu Leu Leu Gly Gly Pro Ser Val Phe Leu Phe Pro Pro Lys Pro Lys Asp Thr>
```

Fig.13C.

```
          1090          1100           1110          1120           1130          1140
            *             *              *             *              *             *
       CTC ATG ATC TCC CGG ACC CCT GAG GTC ACA TGC GTG GTG GTG GAC GTG AGC CAC GAA GAC
       GAG TAC TAG AGG GCC TGG GGA CTC CAG TGT ACG CAC CAC CAC CTG CAC TCG GTG CTT CTG
       Leu Met Ile Ser Arg Thr Pro Glu Val Thr Cys Val Val Val Asp Val Ser His Glu Asp>

1150          1160           1170          1180           1190          1200
            *             *              *             *              *             *
       CCT GAG GTC AAG TTC AAC TGG TAC GTG GAC GGC GTG GAG GTG CAT AAT GCC AAG ACA AAG
       GGA CTC CAG TTC AAG TTG ACC ATG CAC CTG CCG CAC CTC CAC GTA TTA CGG TTC TGT TTC
       Pro Glu Val Lys Phe Asn Trp Tyr Val Asp Gly Val Glu Val His Asn Ala Lys Thr Lys>

1210          1220           1230          1240           1250          1260
            *             *              *             *              *             *
       CCG CGG GAG GAG CAG TAC AAC AGC ACG TAC CGT GTG GTC AGC GTC CTC ACC GTC CTG CAC
       GGC GCC CTC CTC GTC ATG TTG TCG TGC ATG GCA CAC CAG TCG CAG GAG TGG CAG GAC GTG
       Pro Arg Glu Glu Gln Tyr Asn Ser Thr Tyr Arg Val Val Ser Val Leu Thr Val Leu His>

1270          1280           1290          1300           1310          1320
            *             *              *             *              *             *
       CAG GAC TGG CTG AAT GGC AAG GAG TAC AAG TGC AAG GTC TCC AAC AAA GCC CTC CCA GCC
       GTC CTG ACC GAC TTA CCG TTC CTC ATG TTC ACG TTC CAG AGG TTG TTT CGG GAG GGT CGG
       Gln Asp Trp Leu Asn Gly Lys Glu Tyr Lys Cys Lys Val Ser Asn Lys Ala Leu Pro Ala>

1330          1340           1350          1360           1370          1380
            *             *              *             *              *             *
       CCC ATC GAG AAA ACC ATC TCC AAA GCC AAA GGG CAG CCC CGA GAA CCA CAG GTG TAC ACC
       GGG TAG CTC TTT TGG TAG AGG TTT CGG TTT CCC GTC GGG GCT CTT GGT GTC CAC ATG TGG
       Pro Ile Glu Lys Thr Ile Ser Lys Ala Lys Gly Gln Pro Arg Glu Pro Gln Val Tyr Thr>

1390          1400           1410          1420           1430          1440
            *             *              *             *              *             *
       CTG CCC CCA TCC CGG GAT GAG CTG ACC AAG AAC CAG GTC AGC CTG ACC TGC CTG GTC AAA
       GAC GGG GGT AGG GCC CTA CTC GAC TGG TTC TTG GTC CAG TCG GAC TGG ACG GAC CAG TTT
       Leu Pro Pro Ser Arg Asp Glu Leu Thr Lys Asn Gln Val Ser Leu Thr Cys Leu Val Lys>

1450          1460           1470          1480           1490          1500
            *             *              *             *              *             *
       GGC TTC TAT CCC AGC GAC ATC GCC GTG GAG TGG GAG AGC AAT GGG CAG CCG GAG AAC AAC
       CCG AAG ATA GGG TCG CTG TAG CGG CAC CTC ACC CTC TCG TTA CCC GTC GGC CTC TTG TTG
       Gly Phe Tyr Pro Ser Asp Ile Ala Val Glu Trp Glu Ser Asn Gly Gln Pro Glu Asn Asn>

1510          1520           1530          1540           1550          1560
            *             *              *             *              *             *
       TAC AAG ACC ACG CCT CCC GTG CTG GAC TCC GAC GGC TCC TTC TTC CTC TAC AGC AAG CTC
       ATG TTC TGG TGC GGA GGG CAC GAC CTG AGG CTG CCG AGG AAG AAG GAG ATG TCG TTC GAG
       Tyr Lys Thr Thr Pro Pro Val Leu Asp Ser Asp Gly Ser Phe Phe Leu Tyr Ser Lys Leu>

1570          1580           1590          1600           1610          1620
            *             *              *             *              *             *
       ACC GTG GAC AAG AGC AGG TGG CAG CAG GGG AAC GTC TTC TCA TGC TCC GTG ATG CAT GAG
       TGG CAC CTG TTC TCG TCC ACC GTC GTC CCC TTG CAG AAG AGT ACG AGG CAC TAC GTA CTC
       Thr Val Asp Lys Ser Arg Trp Gln Gln Gly Asn Val Phe Ser Cys Ser Val Met His Glu>
```

Fig.13D.

```
         1630            1640            1650            1660            1670
    *       *       *       *       *       *       *       *       *       *
GCT CTG CAC AAC CAC TAC ACG CAG AAG AGC CTC TCC CTG TCT CCG GGT AAA TGA
CGA GAC GTG TTG GTG ATG TGC GTC TTC TCG GAG AGG GAC AGA GGC CCA TTT ACT
Ala Leu His Asn His Tyr Thr Gln Lys Ser Leu Ser Leu Ser Pro Gly Lys ***>
```

Fig. 14A.

```
          10             20             30             40             50             60
           *              *              *              *              *              *
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu>

70             80             90            100            110            120
           *              *              *              *              *              *
ACA GGA TCT AGT TCC GGA GGT AGA CCT TTC GTA GAG ATG TAC AGT GAA ATC CCC GAA ATT
TGT CCT AGA TCA AGG CCT CCA TCT GGA AAG CAT CTC TAC ATG TCA CTT TAG GGG CTT TAA
Thr Gly Ser Ser Ser Gly Gly Arg Pro Phe Val Glu Met Tyr Ser Glu Ile Pro Glu Ile>

130            140            150            160            170            180
           *              *              *              *              *              *
ATA CAC ATG ACT GAA GGA AGG GAG CTC GTC ATT CCC TGC CGG GTT ACG TCA CCT AAC ATC
TAT GTG TAC TGA CTT CCT TCC CTC GAG CAG TAA GGG ACG GCC CAA TGC AGT GGA TTG TAG
Ile His Met Thr Glu Gly Arg Glu Leu Val Ile Pro Cys Arg Val Thr Ser Pro Asn Ile>

190            200            210            220            230            240
           *              *              *              *              *              *
ACT GTT ACT TTA AAA AAG TTT CCA CTT GAC ACT TTG ATC CCT GAT GGA AAA CGC ATA ATC
TGA CAA TGA AAT TTT TTC AAA GGT GAA CTG TGA AAC TAG GGA CTA CCT TTT GCG TAT TAG
Thr Val Thr Leu Lys Lys Phe Pro Leu Asp Thr Leu Ile Pro Asp Gly Lys Arg Ile Ile>

250            260            270            280            290            300
           *              *              *              *              *              *
TGG GAC AGT AGA AAG GGC TTC ATC ATA TCA AAT GCA ACG TAC AAA GAA ATA GGG CTT CTG
ACC CTG TCA TCT TTC CCG AAG TAG TAT AGT TTA CGT TGC ATG TTT CTT TAT CCC GAA GAC
Trp Asp Ser Arg Lys Gly Phe Ile Ile Ser Asn Ala Thr Tyr Lys Glu Ile Gly Leu Leu>

310            320            330            340            350            360
           *              *              *              *              *              *
ACC TGT GAA GCA ACA GTC AAT GGG CAT TTG TAT AAG ACA AAC TAT CTC ACA CAT CGA CAA
TGG ACA CTT CGT TGT CAG TTA CCC GTA AAC ATA TTC TGT TTG ATA GAG TGT GTA GCT GTT
Thr Cys Glu Ala Thr Val Asn Gly His Leu Tyr Lys Thr Asn Tyr Leu Thr His Arg Gln>

370            380            390            400            410            420
           *              *              *              *              *              *
ACC AAT ACA ATC ATA GAT GTC CAA ATA AGC ACA CCA CGC CCA GTC AAA TTA CTT AGA GGC
TGG TTA TGT TAG TAT CTA CAG GTT TAT TCG TGT GGT GCG GGT CAG TTT AAT GAA TCT CCG
Thr Asn Thr Ile Ile Asp Val Gln Ile Ser Thr Pro Arg Pro Val Lys Leu Leu Arg Gly>

430            440            450            460            470            480
           *              *              *              *              *              *
CAT ACT CTT GTC CTC AAT TGT ACT GCT ACC ACT CCC TTG AAC ACG AGA GTT CAA ATG ACC
GTA TGA GAA CAG GAG TTA ACA TGA CGA TGG TGA GGG AAC TTG TGC TCT CAA GTT TAC TGG
His Thr Leu Val Leu Asn Cys Thr Ala Thr Thr Pro Leu Asn Thr Arg Val Gln Met Thr>

490            500            510            520            530            540
           *              *              *              *              *              *
TGG AGT TAC CCT GAT GAA ATT GAC CAA AGC AAT TCC CAT GCC AAC ATA TTC TAC AGT GTT
ACC TCA ATG GGA CTA CTT TAA CTG GTT TCG TTA AGG GTA CGG TTG TAT AAG ATG TCA CAA
Trp Ser Tyr Pro Asp Glu Ile Asp Gln Ser Asn Ser His Ala Asn Ile Phe Tyr Ser Val>
```

Fig.14B.

```
        550         560         570         580         590         600
         *           *           *           *           *           *
CTT ACT ATT GAC AAA ATG CAG AAC AAA GAC AAA GGA CTT TAT ACT TGT CGT GTA AGG AGT
GAA TGA TAA CTG TTT TAC GTC TTG TTT CTG TTT CCT GAA ATA TGA ACA GCA CAT TCC TCA
Leu Thr Ile Asp Lys Met Gln Asn Lys Asp Lys Gly Leu Tyr Thr Cys Arg Val Arg Ser>

610         620         630         640         650         660
         *           *           *           *           *           *
GGA CCA TCA TTC AAA TCT GTT AAC ACC TCA GTG CAT ATA TAT GAT AAA GCA GGC CCG GGC
CCT GGT AGT AAG TTT AGA CAA TTG TGG AGT CAC GTA TAT ATA CTA TTT CGT CCG GGC CCG
Gly Pro Ser Phe Lys Ser Val Asn Thr Ser Val His Ile Tyr Asp Lys Ala Gly Pro Gly>

670         680         690         700         710         720
         *           *           *           *           *           *
GAG CCC AAA TCT TGT GAC AAA ACT CAC ACA TGC CCA CCG TGC CCA GCA CCT GAA CTC CTG
CTC GGG TTT AGA ACA CTG TTT TGA GTG TGT ACG GGT GGC ACG GGT CGT GGA CTT GAG GAC
Glu Pro Lys Ser Cys Asp Lys Thr His Thr Cys Pro Pro Cys Pro Ala Pro Glu Leu Leu>

730         740         750         760         770         780
         *           *           *           *           *           *
GGG GGA CCG TCA GTC TTC CTC TTC CCC CCA AAA CCC AAG GAC ACC CTC ATG ATC TCC CGG
CCC CCT GGC AGT CAG AAG GAG AAG GGG GGT TTT GGG TTC CTG TGG GAG TAC TAG AGG GCC
Gly Gly Pro Ser Val Phe Leu Phe Pro Pro Lys Pro Lys Asp Thr Leu Met Ile Ser Arg>

790         800         810         820         830         840
         *           *           *           *           *           *
ACC CCT GAG GTC ACA TGC GTG GTG GTG GAC GTG AGC CAC GAA GAC CCT GAG GTC AAG TTC
TGG GGA CTC CAG TGT ACG CAC CAC CAC CTG CAC TCG GTG CTT CTG GGA CTC CAG TTC AAG
Thr Pro Glu Val Thr Cys Val Val Val Asp Val Ser His Glu Asp Pro Glu Val Lys Phe>

850         860         870         880         890         900
         *           *           *           *           *           *
AAC TGG TAC GTG GAC GGC GTG GAG GTG CAT AAT GCC AAG ACA AAG CCG CGG GAG GAG CAG
TTG ACC ATG CAC CTG CCG CAC CTC CAC GTA TTA CGG TTC TGT TTC GGC GCC CTC CTC GTC
Asn Trp Tyr Val Asp Gly Val Glu Val His Asn Ala Lys Thr Lys Pro Arg Glu Glu Gln>

910         920         930         940         950         960
         *           *           *           *           *           *
TAC AAC AGC ACG TAC CGT GTG GTC AGC GTC CTC ACC GTC CTG CAC CAG GAC TGG CTG AAT
ATG TTG TCG TGC ATG GCA CAC CAG TCG CAG GAG TGG CAG GAC GTG GTC CTG ACC GAC TTA
Tyr Asn Ser Thr Tyr Arg Val Val Ser Val Leu Thr Val Leu His Gln Asp Trp Leu Asn>

970         980         990        1000        1010        1020
         *           *           *           *           *           *
GGC AAG GAG TAC AAG TGC AAG GTC TCC AAC AAA GCC CTC CCA GCC CCC ATC GAG AAA ACC
CCG TTC CTC ATG TTC ACG TTC CAG AGG TTG TTT CGG GAG GGT CGG GGG TAG CTC TTT TGG
Gly Lys Glu Tyr Lys Cys Lys Val Ser Asn Lys Ala Leu Pro Ala Pro Ile Glu Lys Thr>

1030        1040        1050        1060        1070        1080
         *           *           *           *           *           *
ATC TCC AAA GCC AAA GGG CAG CCC CGA GAA CCA CAG GTG TAC ACC CTG CCC CCA TCC CGG
TAG AGG TTT CGG TTT CCC GTC GGG GCT CTT GGT GTC CAC ATG TGG GAC GGG GGT AGG GCC
Ile Ser Lys Ala Lys Gly Gln Pro Arg Glu Pro Gln Val Tyr Thr Leu Pro Pro Ser Arg>
```

Fig.14C.

```
         1090         1100        1110        1120        1130        1140
           *           *            *           *           *           *
GAT GAG CTG ACC AAG AAC CAG GTC AGC CTG ACC TGC CTG GTC AAA GGC TTC TAT CCC AGC
CTA CTC GAC TGG TTC TTG GTC CAG TCG GAC TGG ACG GAC CAG TTT CCG AAG ATA GGG TCG
Asp Glu Leu Thr Lys Asn Gln Val Ser Leu Thr Cys Leu Val Lys Gly Phe Tyr Pro Ser>

1150         1160        1170        1180        1190        1200
           *           *            *           *           *           *
GAC ATC GCC GTG GAG TGG GAG AGC AAT GGG CAG CCG GAG AAC AAC TAC AAG ACC ACG CCT
CTG TAG CGG CAC CTC ACC CTC TCG TTA CCC GTC GGC CTC TTG TTG ATG TTC TGG TGC GGA
Asp Ile Ala Val Glu Trp Glu Ser Asn Gly Gln Pro Glu Asn Asn Tyr Lys Thr Thr Pro>

1210         1220        1230        1240        1250        1260
           *           *            *           *           *           *
CCC GTG CTG GAC TCC GAC GGC TCC TTC TTC CTC TAC AGC AAG CTC ACC GTG GAC AAG AGC
GGG CAC GAC CTG AGG CTG CCG AGG AAG AAG GAG ATG TCG TTC GAG TGG CAC CTG TTC TCG
Pro Val Leu Asp Ser Asp Gly Ser Phe Phe Leu Tyr Ser Lys Leu Thr Val Asp Lys Ser>

1270         1280        1290        1300        1310        1320
           *           *            *           *           *           *
AGG TGG CAG CAG GGG AAC GTC TTC TCA TGC TCC GTG ATG CAT GAG GCT CTG CAC AAC CAC
TCC ACC GTC GTC CCC TTG CAG AAG AGT ACG AGG CAC TAC GTA CTC CGA GAC GTG TTG GTG
Arg Trp Gln Gln Gly Asn Val Phe Ser Cys Ser Val Met His Glu Ala Leu His Asn His>

1330         1340        1350
           *           *            *           *
TAC ACG CAG AAG AGC CTC TCC CTG TCT CCG GGT AAA TGA
ATG TGC GTC TTC TCG GAG AGG GAC AGA GGC CCA TTT ACT
Tyr Thr Gln Lys Ser Leu Ser Leu Ser Pro Gly Lys ***>
```

Fig.15A.

```
            10          20          30          40          50          60
             *           *           *           *           *           *
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu>

70          80          90         100         110         120
             *           *           *           *           *           *
ACA GGA TCT AGT TCC GGA GGT AGA CCT TTC GTA GAG ATG TAC AGT GAA ATC CCC GAA ATT
TGT CCT AGA TCA AGG CCT CCA TCT GGA AAG CAT CTC TAC ATG TCA CTT TAG GGG CTT TAA
Thr Gly Ser Ser Ser Gly Gly Arg Pro Phe Val Glu Met Tyr Ser Glu Ile Pro Glu Ile>

130         140         150         160         170         180
             *           *           *           *           *           *
ATA CAC ATG ACT GAA GGA AGG GAG CTC GTC ATT CCC TGC CGG GTT ACG TCA CCT AAC ATC
TAT GTG TAC TGA CTT CCT TCC CTC GAG CAG TAA GGG ACG GCC CAA TGC AGT GGA TTG TAG
Ile His Met Thr Glu Gly Arg Glu Leu Val Ile Pro Cys Arg Val Thr Ser Pro Asn Ile>

190         200         210         220         230         240
             *           *           *           *           *           *
ACT GTT ACT TTA AAA AAG TTT CCA CTT GAC ACT TTG ATC CCT GAT GGA AAA CGC ATA ATC
TGA CAA TGA AAT TTT TTC AAA GGT GAA CTG TGA AAC TAG GGA CTA CCT TTT GCG TAT TAG
Thr Val Thr Leu Lys Lys Phe Pro Leu Asp Thr Leu Ile Pro Asp Gly Lys Arg Ile Ile>

250         260         270         280         290         300
             *           *           *           *           *           *
TGG GAC AGT AGA AAG GGC TTC ATC ATA TCA AAT GCA ACG TAC AAA GAA ATA GGG CTT CTG
ACC CTG TCA TCT TTC CCG AAG TAG TAT AGT TTA CGT TGC ATG TTT CTT TAT CCC GAA GAC
Trp Asp Ser Arg Lys Gly Phe Ile Ile Ser Asn Ala Thr Tyr Lys Glu Ile Gly Leu Leu>

310         320         330         340         350         360
             *           *           *           *           *           *
ACC TGT GAA GCA ACA GTC AAT GGG CAT TTG TAT AAG ACA AAC TAT CTC ACA CAT CGA CAA
TGG ACA CTT CGT TGT CAG TTA CCC GTA AAC ATA TTC TGT TTG ATA GAG TGT GTA GCT GTT
Thr Cys Glu Ala Thr Val Asn Gly His Leu Tyr Lys Thr Asn Tyr Leu Thr His Arg Gln>

370         380         390         400         410         420
             *           *           *           *           *           *
ACC AAT ACA ATC ATA GAT GTC CAA ATA AGC ACA CCA CGC CTA GTC AAA TTA CTT AGA GGC
TGG TTA TGT TAG TAT CTA CAG GTT TAT TCG TGT GGT GCG GAT CAG TTT AAT GAA TCT CCG
Thr Asn Thr Ile Ile Asp Val Gln Ile Ser Thr Pro Arg Pro Val Lys Leu Leu Arg Gly>

430         440         450         460         470         480
             *           *           *           *           *           *
CAT ACT CTT GTC CTC AAT TGT ACT GCT ACC ACT CCC TTG AAC ACG AGA GTT CAA ATG ACC
GTA TGA GAA CAG GAG TTA ACA TGA CGA TGG TGA GGG AAC TTG TGC TCT CAA GTT TAC TGG
His Thr Leu Val Leu Asn Cys Thr Ala Thr Thr Pro Leu Asn Thr Arg Val Gln Met Thr>

490         500         510         520         530         540
             *           *           *           *           *           *
TGG AGT TAC CCT GAT GAA AAA AAT AAG AGA GCT TCC GTA AGG CGA CGA ATT GAC CAA AGC
ACC TCA ATG GGA CTA CTT TTT TTA TTC TCT CGA AGG CAT TCC GCT GCT TAA CTG GTT TCG
Trp Ser Tyr Pro Asp Glu Lys Asn Lys Arg Ala Ser Val Arg Arg Arg Ile Asp Gln Ser>
```

Fig.15B.

```
         550         560         570         580         590         600
          *           *           *           *           *           *
AAT TCC CAT GCC AAC ATA TTC TAC AGT GTT CTT ACT ATT GAC AAA ATG CAG AAC AAA GAC
TTA AGG GTA CGG TTG TAT AAG ATG TCA CAA GAA TGA TAA CTG TTT TAC GTC TTG TTT CTG
Asn Ser His Ala Asn Ile Phe Tyr Ser Val Leu Thr Ile Asp Lys Met Gln Asn Lys Asp>

610         620         630         640         650         660
          *           *           *           *           *           *
AAA GGA CTT TAT ACT TGT CGT GTA AGG AGT GGA CCA TCA TTC AAA TCT GTT AAC ACC TCA
TTT CCT GAA ATA TGA ACA GCA CAT TCC TCA CCT GGT AGT AAG TTT AGA CAA TTG TGG AGT
Lys Gly Leu Tyr Thr Cys Arg Val Arg Ser Gly Pro Ser Phe Lys Ser Val Asn Thr Ser>

670         680         690         700         710         720
          *           *           *           *           *           *
GTG CAT ATA TAT GAT AAA GCA GGC CCG GGC GAG CCC AAA TCT TGT GAC AAA ACT CAC ACA
CAC GTA TAT ATA CTA TTT CGT CCG GGC CCG CTC GGG TTT AGA ACA CTG TTT TGA GTG TGT
Val His Ile Tyr Asp Lys Ala Gly Pro Gly Glu Pro Lys Ser Cys Asp Lys Thr His Thr>

730         740         750         760         770         780
          *           *           *           *           *           *
TGC CCA CCG TGC CCA GCA CCT GAA CTC CTG GGG GGA CCG TCA GTC TTC CTC TTC CCC CCA
ACG GGT GGC ACG GGT CGT GGA CTT GAG GAC CCC CCT GGC AGT CAG AAG GAG AAG GGG GGT
Cys Pro Pro Cys Pro Ala Pro Glu Leu Leu Gly Gly Pro Ser Val Phe Leu Phe Pro Pro>

790         800         810         820         830         840
          *           *           *           *           *           *
AAA CCC AAG GAC ACC CTC ATG ATC TCC CGG ACC CCT GAG GTC ACA TGC GTG GTG GTG GAC
TTT GGG TTC CTG TGG GAG TAC TAG AGG GCC TGG GGA CTC CAG TGT ACG CAC CAC CAC CTG
Lys Pro Lys Asp Thr Leu Met Ile Ser Arg Thr Pro Glu Val Thr Cys Val Val Val Asp>

850         860         870         880         890         900
          *           *           *           *           *           *
GTG AGC CAC GAA GAC CCT GAG GTC AAG TTC AAC TGG TAC GTG GAC GGC GTG GAG GTG CAT
CAC TCG GTG CTT CTG GGA CTC CAG TTC AAG TTG ACC ATG CAC CTG CCG CAC CTC CAC GTA
Val Ser His Glu Asp Pro Glu Val Lys Phe Asn Trp Tyr Val Asp Gly Val Glu Val His>

910         920         930         940         950         960
          *           *           *           *           *           *
AAT GCC AAG ACA AAG CCG CGG GAG GAG CAG TAC AAC AGC ACG TAC CGT GTG GTC AGC GTC
TTA CGG TTC TGT TTC GGC GCC CTC CTC GTC ATG TTG TCG TGC ATG GCA CAC CAG TCG CAG
Asn Ala Lys Thr Lys Pro Arg Glu Glu Gln Tyr Asn Ser Thr Tyr Arg Val Val Ser Val>

970         980         990        1000        1010        1020
          *           *           *           *           *           *
CTC ACC GTC CTG CAC CAG GAC TGG CTG AAT GGC AAG GAG TAC AAG TGC AAG GTC TCC AAC
GAG TGG CAG GAC GTG GTC CTG ACC GAC TTA CCG TTC CTC ATG TTC ACG TTC CAG AGG TTG
Leu Thr Val Leu His Gln Asp Trp Leu Asn Gly Lys Glu Tyr Lys Cys Lys Val Ser Asn>

1030        1040        1050        1060        1070        1080
          *           *           *           *           *           *
AAA GCC CTC CCA GCC CCC ATC GAG AAA ACC ATC TCC AAA GCC AAA GGG CAG CCC CGA GAA
TTT CGG GAG GGT CGG GGG TAG CTC TTT TGG TAG AGG TTT CGG TTT CCC GTC GGG GCT CTT
Lys Ala Leu Pro Ala Pro Ile Glu Lys Thr Ile Ser Lys Ala Lys Gly Gln Pro Arg Glu>
```

Fig.15C.

```
       1090           1100           1110           1120           1130           1140
         *      *       *      *       *      *       *      *       *      *       *      *
CCA CAG GTG TAC ACC CTG CCC CCA TCC CGG GAT GAG CTG ACC AAG AAC CAG GTC AGC CTG
GGT GTC CAC ATG TGG GAC GGG GGT AGG GCC CTA CTC GAC TGG TTC TTG GTC CAG TCG GAC
Pro Gln Val Tyr Thr Leu Pro Pro Ser Arg Asp Glu Leu Thr Lys Asn Gln Val Ser Leu>

1150           1160           1170           1180           1190           1200
         *      *       *      *       *      *       *      *       *      *       *      *
ACC TGC CTG GTC AAA GGC TTC TAT CCC AGC GAC ATC GCC GTG GAG TGG GAG AGC AAT GGG
TGG ACG GAC CAG TTT CCG AAG ATA GGG TCG CTG TAG CGG CAC CTC ACC CTC TCG TTA CCC
Thr Cys Leu Val Lys Gly Phe Tyr Pro Ser Asp Ile Ala Val Glu Trp Glu Ser Asn Gly>

1210           1220           1230           1240           1250           1260
         *      *       *      *       *      *       *      *       *      *       *      *
CAG CCG GAG AAC AAC TAC AAG ACC ACG CCT CCC GTG CTG GAC TCC GAC GGC TCC TTC TTC
GTC GGC CTC TTG TTG ATG TTC TGG TGC GGA GGG CAC GAC CTG AGG CTG CCG AGG AAG AAG
Gln Pro Glu Asn Asn Tyr Lys Thr Thr Pro Pro Val Leu Asp Ser Asp Gly Ser Phe Phe>

1270           1280           1290           1300           1310           1320
         *      *       *      *       *      *       *      *       *      *       *      *
CTC TAC AGC AAG CTC ACC GTG GAC AAG AGC AGG TGG CAG CAG GGG AAC GTC TTC TCA TGC
GAG ATG TCG TTC GAG TGG CAC CTG TTC TCG TCC ACC GTC GTC CCC TTG CAG AAG AGT ACG
Leu Tyr Ser Lys Leu Thr Val Asp Lys Ser Arg Trp Gln Gln Gly Asn Val Phe Ser Cys>

1330           1340           1350           1360           1370           1380
         *      *       *      *       *      *       *      *       *      *       *      *
TCC GTG ATG CAT GAG GCT CTG CAC AAC CAC TAC ACG CAG AAG AGC CTC TCC CTG TCT CCG
AGG CAC TAC GTA CTC CGA GAC GTG TTG GTG ATG TGC GTC TTC TCG GAG AGG GAC AGA GGC
Ser Val Met His Glu Ala Leu His Asn His Tyr Thr Gln Lys Ser Leu Ser Leu Ser Pro>

*
GGT AAA TGA
CCA TTT ACT
Gly Lys ***>
```

Fig.16A.

```
           10          20          30          40          50          60
            *           *           *           *           *           *
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu>

70          80          90         100         110         120
            *           *           *           *           *           *
ACA GGA TCT AGT TCA GGT TCA AAA TTA AAA GAT CCT GAA CTG AGT TTA AAA GGC ACC CAG
TGT CCT AGA TCA AGT CCA AGT TTT AAT TTT CTA GGA CTT GAC TCA AAT TTT CCG TGG GTC
Thr Gly Ser Ser Ser Gly Ser Lys Leu Lys Asp Pro Glu Leu Ser Leu Lys Gly Thr Gln>

130         140         150         160         170         180
            *           *           *           *           *           *
CAC ATC ATG CAA GCA GGC CAG ACA CTG CAT CTC CAA TGC AGG GGG GAA GCA GCC CAT AAA
GTG TAG TAC GTT CGT CCG GTC TGT GAC GTA GAG GTT ACG TCC CCC CTT CGT CGG GTA TTT
His Ile Met Gln Ala Gly Gln Thr Leu His Leu Gln Cys Arg Gly Glu Ala Ala His Lys>

190         200         210         220         230         240
            *           *           *           *           *           *
TGG TCT TTG CCT GAA ATG GTG AGT AAG GAA AGC GAA AGG CTG AGC ATA ACT AAA TCT GCC
ACC AGA AAC GGA CTT TAC CAC TCA TTC CTT TCG CTT TCC GAC TCG TAT TGA TTT AGA CGG
Trp Ser Leu Pro Glu Met Val Ser Lys Glu Ser Glu Arg Leu Ser Ile Thr Lys Ser Ala>

250         260         270         280         290         300
            *           *           *           *           *           *
TGT GGA AGA AAT GGC AAA CAA TTC TGC AGT ACT TTA ACC TTG AAC ACA GCT CAA GCA AAC
ACA CCT TCT TTA CCG TTT GTT AAG ACG TCA TGA AAT TGG AAC TTG TGT CGA GTT CGT TTG
Cys Gly Arg Asn Gly Lys Gln Phe Cys Ser Thr Leu Thr Leu Asn Thr Ala Gln Ala Asn>

310         320         330         340         350         360
            *           *           *           *           *           *
CAC ACT GGC TTC TAC AGC TGC AAA TAT CTA GCT GTA CCT ACT TCA AAG AAG AAG GAA ACA
GTG TGA CCG AAG ATG TCG ACG TTT ATA GAT CGA CAT GGA TGA AGT TTC TTC CTT CTT TGT
His Thr Gly Phe Tyr Ser Cys Lys Tyr Leu Ala Val Pro Thr Ser Lys Lys Lys Glu Thr>

370         380         390         400         410         420
            *           *           *           *           *           *
GAA TCT GCA ATC TAT ATA TTT ATT AGT GAT ACA GGT AGA CCT TTC GTA GAG ATG TAC AGT
CTT AGA CGT TAG ATA TAT AAA TAA TCA CTA TGT CCA TCT GGA AAG CAT CTC TAC ATG TCA
Glu Ser Ala Ile Tyr Ile Phe Ile Ser Asp Thr Gly Arg Pro Phe Val Glu Met Tyr Ser>

430         440         450         460         470         480
            *           *           *           *           *           *
GAA ATC CCC GAA ATT ATA CAC ATG ACT GAA GGA AGG GAG CTC GTC ATT CCC TGC CGG GTT
CTT TAG GGG CTT TAA TAT GTG TAC TGA CTT CCT TCC CTC GAG CAG TAA GGG ACG GCC CAA
Glu Ile Pro Glu Ile Ile His Met Thr Glu Gly Arg Glu Leu Val Ile Pro Cys Arg Val>

490         500         510         520         530         540
            *           *           *           *           *           *
ACG TCA CCT AAC ATC ACT GTT ACT TTA AAA AAG TTT CCA CTT GAC ACT TTG ATC CCT GAT
TGC AGT GGA TTG TAG TGA CAA TGA AAT TTT TTC AAA GGT GAA CTG TGA AAC TAG GGA CTA
Thr Ser Pro Asn Ile Thr Val Thr Leu Lys Lys Phe Pro Leu Asp Thr Leu Ile Pro Asp>
```

Fig.16B.

```
         550         560         570         580         590         600
          *           *           *           *           *           *
GGA AAA CGC ATA ATC TGG GAC AGT AGA AAG GGC TTC ATC ATA TCA AAT GCA ACG TAC AAA
CCT TTT GCG TAT TAG ACC CTG TCA TCT TTC CCG AAG TAG TAT AGT TTA CGT TGC ATG TTT
Gly Lys Arg Ile Ile Trp Asp Ser Arg Lys Gly Phe Ile Ile Ser Asn Ala Thr Tyr Lys>

610         620         630         640         650         660
          *           *           *           *           *           *
GAA ATA GGG CTT CTG ACC TGT GAA GCA ACA GTC AAT GGG CAT TTG TAT AAG ACA AAC TAT
CTT TAT CCC GAA GAC TGG ACA CTT CGT TGT CAG TTA CCC GTA AAC ATA TTC TGT TTG ATA
Glu Ile Gly Leu Leu Thr Cys Glu Ala Thr Val Asn Gly His Leu Tyr Lys Thr Asn Tyr>

670         680         690         700         710         720
          *           *           *           *           *           *
CTC ACA CAT CGA CAA ACC AAT ACA ATC ATA GAT GTC CAA ATA AGC ACA CCA CGC CCA GTC
GAG TGT GTA GCT GTT TGG TTA TGT TAG TAT CTA CAG GTT TAT TCG TGT GGT GCG GGT CAG
Leu Thr His Arg Gln Thr Asn Thr Ile Ile Asp Val Gln Ile Ser Thr Pro Arg Pro Val>

730         740         750         760         770         780
          *           *           *           *           *           *
AAA TTA CTT AGA GGC CAT ACT CTT GTC CTC AAT TGT ACT GCT ACC ACT CCC TTG AAC ACG
TTT AAT GAA TCT CCG GTA TGA GAA CAG GAG TTA ACA TGA CGA TGG TGA GGG AAC TTG TGC
Lys Leu Leu Arg Gly His Thr Leu Val Leu Asn Cys Thr Ala Thr Thr Pro Leu Asn Thr>

790         800         810         820         830         840
          *           *           *           *           *           *
AGA GTT CAA ATG ACC TGG AGT TAC CCT GAT GAA AAA AAT AAG AAC GCT TCC GTA AGG CGA
TCT CAA GTT TAC TGG ACC TCA ATG GGA CTA CTT TTT TTA TTC TTG CGA AGG CAT TCC GCT
Arg Val Gln Met Thr Trp Ser Tyr Pro Asp Glu Lys Asn Lys Asn Ala Ser Val Arg Arg>

850         860         870         880         890         900
          *           *           *           *           *           *
CGA ATT GAC CAA AGC AAT TCC CAT GCC AAC ATA TTC TAC AGT GTT CTT ACT ATT GAC AAA
GCT TAA CTG GTT TCG TTA AGG GTA CGG TTG TAT AAG ATG TCA CAA GAA TGA TAA CTG TTT
Arg Ile Asp Gln Ser Asn Ser His Ala Asn Ile Phe Tyr Ser Val Leu Thr Ile Asp Lys>

910         920         930         940         950         960
          *           *           *           *           *           *
ATG CAG AAC AAA GAC AAA GGA CTT TAT ACT TGT CGT GTA AGG AGT GGA CCA TCA TTC AAA
TAC GTC TTG TTT CTG TTT CCT GAA ATA TGA ACA GCA CAT TCC TCA CCT GGT AGT AAG TTT
Met Gln Asn Lys Asp Lys Gly Leu Tyr Thr Cys Arg Val Arg Ser Gly Pro Ser Phe Lys>

970         980         990        1000        1010        1020
          *           *           *           *           *           *
TCT GTT AAC ACC TCA GTG CAT ATA TAT GAT AAA GCA GGC CCG GGC GAG CCC AAA TCT TGT
AGA CAA TTG TGG AGT CAC GTA TAT ATA CTA TTT CGT CCG GGC CCG CTC GGG TTT AGA ACA
Ser Val Asn Thr Ser Val His Ile Tyr Asp Lys Ala Gly Pro Gly Glu Pro Lys Ser Cys>

1030        1040        1050        1060        1070        1080
          *           *           *           *           *           *
GAC AAA ACT CAC ACA TGC CCA CCG TGC CCA GCA CCT GAA CTC CTG GGG GGA CCG TCA GTC
CTG TTT TGA GTG TGT ACG GGT GGC ACG GGT CGT GGA CTT GAG GAC CCC CCT GGC AGT CAG
Asp Lys Thr His Thr Cys Pro Pro Cys Pro Ala Pro Glu Leu Leu Gly Gly Pro Ser Val>
```

Fig.16C.

```
         1090        1100        1110        1120        1130        1140
           *     *     *     *     *     *     *     *     *     *     *     *
         TTC CTC TTC CCC CCA AAA CCC AAG GAC ACC CTC ATG ATC TCG CGG ACC CCT GAG GTC ACA
         AAG GAG AAG GGG GGT TTT GGG TTC CTG TGG GAG TAC TAG AGG GCC TGG GGA CTC CAG TGT
         Phe Leu Phe Pro Pro Lys Pro Lys Asp Thr Leu Met Ile Ser Arg Thr Pro Glu Val Thr>

1150        1160        1170        1180        1190        1200
           *     *     *     *     *     *     *     *     *     *     *     *
         TGC GTG GTG GTG GAC GTG AGC CAC GAA GAC CCT GAG GTC AAG TTC AAC TGG TAC GTG GAC
         ACG CAC CAC CAC CTG CAC TCG GTG CTT CTG GGA CTC CAG TTC AAG TTG ACC ATG CAC CTG
         Cys Val Val Val Asp Val Ser His Glu Asp Pro Glu Val Lys Phe Asn Trp Tyr Val Asp>

1210        1220        1230        1240        1250        1260
           *     *     *     *     *     *     *     *     *     *     *     *
         GGC GTG GAG GTG CAT AAT GCC AAG ACA AAG CCG CGG GAG GAG CAG TAC AAC AGC ACG TAC
         CCG CAC CTC CAC GTA TTA CGG TTC TGT TTC GGC GCC CTC CTC GTC ATG TTG TCG TGC ATG
         Gly Val Glu Val His Asn Ala Lys Thr Lys Pro Arg Glu Glu Gln Tyr Asn Ser Thr Tyr>

1270        1280        1290        1300        1310        1320
           *     *     *     *     *     *     *     *     *     *     *     *
         CGT GTG GTC AGC GTC CTC ACC GTC CTG CAC CAG GAC TGG CTG AAT GGC AAG GAG TAC AAG
         GCA CAC CAG TCG CAG GAG TGG CAG GAC GTG GTC CTG ACC GAC TTA CCG TTC CTC ATG TTC
         Arg Val Val Ser Val Leu Thr Val Leu His Gln Asp Trp Leu Asn Gly Lys Glu Tyr Lys>

1330        1340        1350        1360        1370        1380
           *     *     *     *     *     *     *     *     *     *     *     *
         TGC AAG GTC TCC AAC AAA GCC CTC CCA GCC CCC ATC GAG AAA ACC ATC TCC AAA GCC AAA
         ACG TTC CAG AGG TTG TTT CGG GAG GGT CGG GGG TAG CTC TTT TGG TAG AGG TTT CGG TTT
         Cys Lys Val Ser Asn Lys Ala Leu Pro Ala Pro Ile Glu Lys Thr Ile Ser Lys Ala Lys>

1390        1400        1410        1420        1430        1440
           *     *     *     *     *     *     *     *     *     *     *     *
         GGG CAG CCC CGA GAA CCA CAG GTG TAC ACC CTG CCC CCA TCC CGG GAT GAG CTG ACC AAG
         CCC GTC GGG GCT CTT GGT GTC CAC ATG TGG GAC GGG GGT AGG GCC CTA CTC GAC TGG TTC
         Gly Gln Pro Arg Glu Pro Gln Val Tyr Thr Leu Pro Pro Ser Arg Asp Glu Leu Thr Lys>

1450        1460        1470        1480        1490        1500
           *     *     *     *     *     *     *     *     *     *     *     *
         AAC CAG GTC AGC CTG ACC TGC CTG GTC AAA GGC TTC TAT CCC AGC GAC ATC GCC GTG GAG
         TTG GTC CAG TCG GAC TGG ACG GAC CAG TTT CCG AAG ATA GGG TCG CTG TAG CGG CAC CTC
         Asn Gln Val Ser Leu Thr Cys Leu Val Lys Gly Phe Tyr Pro Ser Asp Ile Ala Val Glu>

1510        1520        1530        1540        1550        1560
           *     *     *     *     *     *     *     *     *     *     *     *
         TGG GAG AGC AAT GGG CAG CCG GAG AAC AAC TAC AAG ACC ACG CCT CCC GTG CTG GAC TCC
         ACC CTC TCG TTA CCC GTC GGC CTC TTG TTG ATG TTC TGG TGC GGA GGG CAC GAC CTG AGG
         Trp Glu Ser Asn Gly Gln Pro Glu Asn Asn Tyr Lys Thr Thr Pro Pro Val Leu Asp Ser>

1570        1580        1590        1600        1610        1620
           *     *     *     *     *     *     *     *     *     *     *     *
         GAC GGC TCC TTC TTC CTC TAC AGC AAG CTC ACC GTG GAC AAG AGC AGG TGG CAG CAG GGG
         CTG CCG AGG AAG AAG GAG ATG TCG TTC GAG TGG CAC CTG TTC TCG TCC ACC GTC GTC CCC
         Asp Gly Ser Phe Phe Leu Tyr Ser Lys Leu Thr Val Asp Lys Ser Arg Trp Gln Gln Gly>
```

Fig.16D.

```
          1630          1640          1650          1660          1670          1680
      *       *       *       *       *       *       *       *       *       *       *       *
AAC GTC TTC TCA TGC TCC GTG ATG CAT GAG GCT CTG CAC AAC CAC TAC ACG CAG AAG AGC
TTG CAG AAG AGT ACG AGG CAC TAC GTA CTC CGA GAC GTG TTG GTG ATG TGC GTC TTC TCG
Asn Val Phe Ser Cys Ser Val Met His Glu Ala Leu His Asn His Tyr Thr Gln Lys Ser>

1690          1700
      *       *       *       *
CTC TCC CTG TCT CCG GGT AAA TGA
GAG AGG GAC AGA GGC CCA TTT ACT
Leu Ser Leu Ser Pro Gly Lys ***>
```

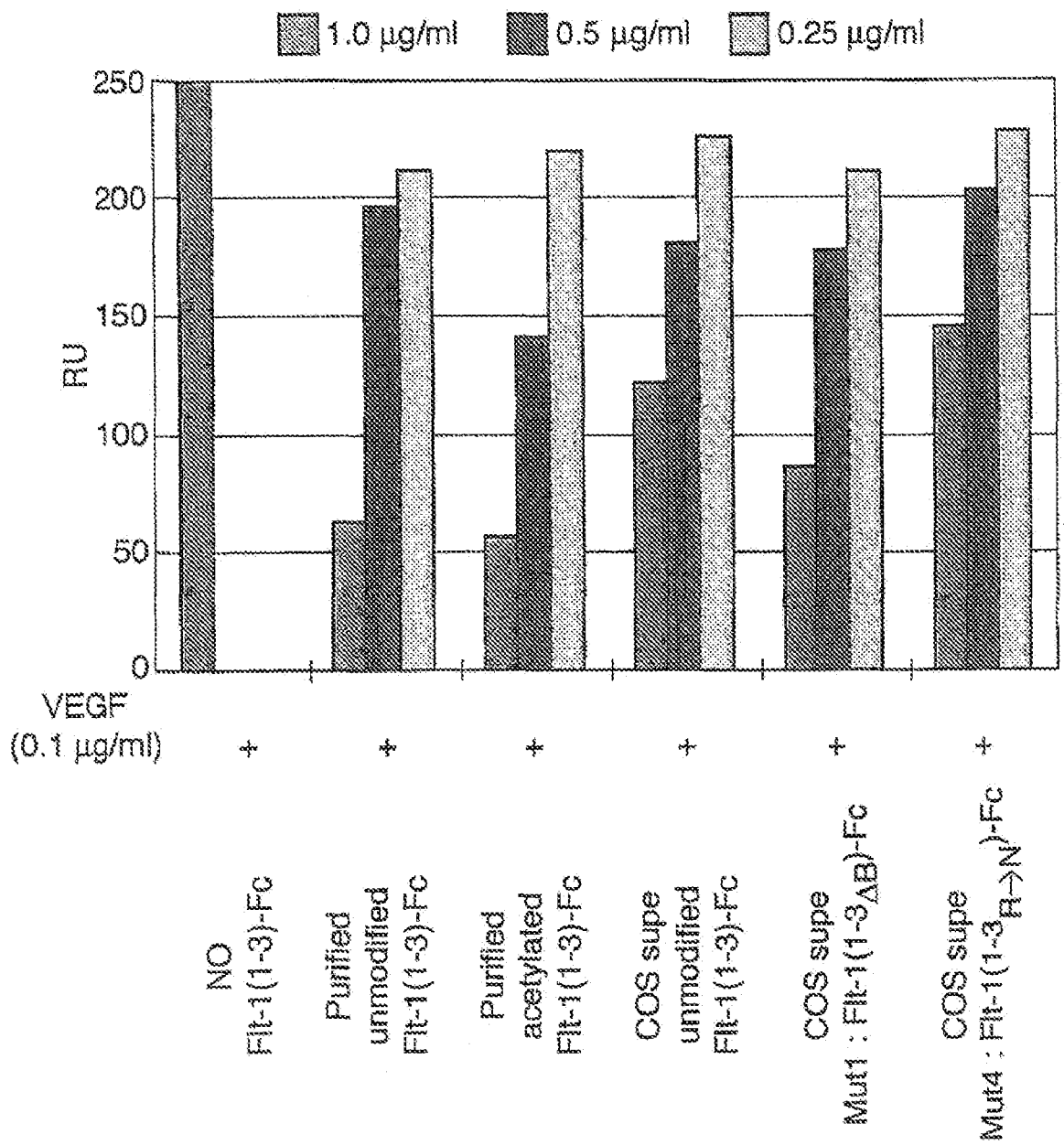

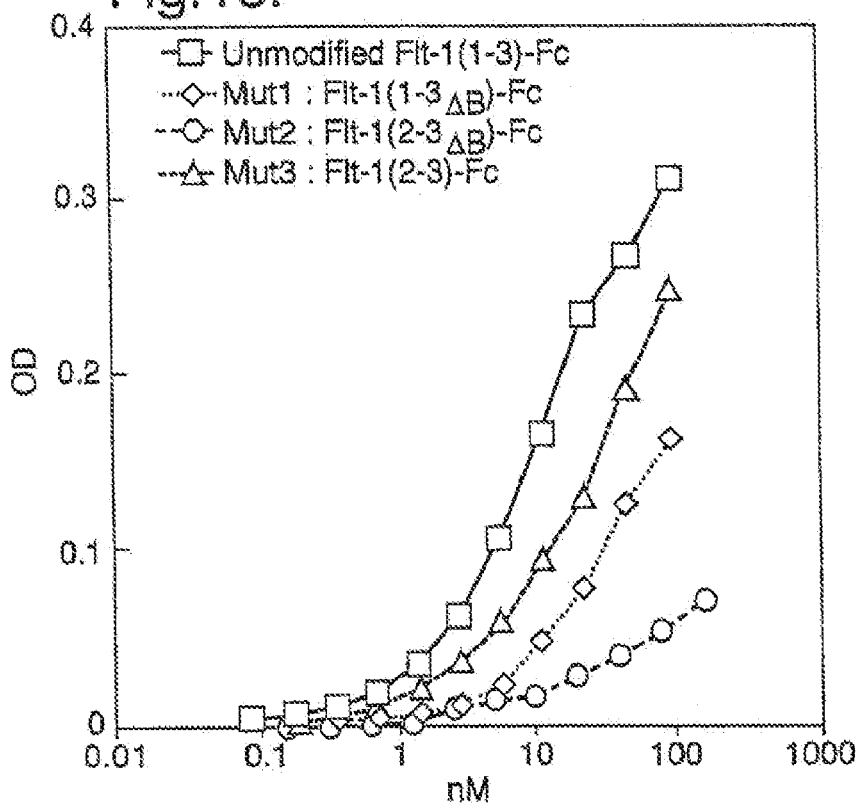
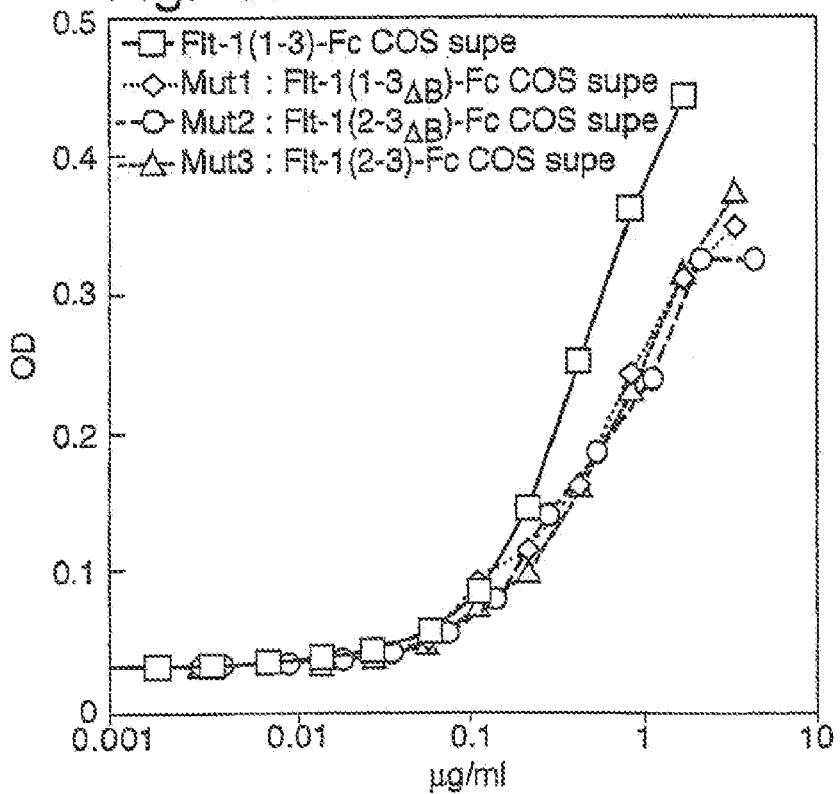

Fig.21A.

```
                                              >EcoRI_site
      10        20        30        40        50 |      60        70        80
AAGCTTGGGCTGCAGGTCGATCGACTCTAGAGGATCGATCCCCGGGCGAGCTCGAATTCGCAACCACCATGGTCAGCTAC
TTCGAACCCGACGTCCAGCTAGCTGAGATCTCCTAGCTAGGGGCCCGCTCGAGCTTAAGCGTTGGTGGTACCAGTCGATG
                                                            M   V   S   Y>
                                                            1           4
                                                            _____>

>BspEI_bridge
      90       100       110       120       130       140|      150       160
TGGGACACCGGGGTCCTGCTGTGCGCGCTGCTCAGCTGTCTGCTTCTCACAGGATCTAGTTCCGGAGGTAGACCTTTCGT
ACCCTGTGGCCCCAGGACGACACGCGCGACGAGTCGACAGACGAAGAGTGTCCTAGATCAAGGCCTCCATCTGGAAAGCA
 W   D   T   G   V   L   L   C   A   L   L   S   C   L   L   L   T   G   S   S>
 _____FLT1 SS_____>
                                                                  S   G>
                                                                  _____>
                                                                          G   R   P   F   V>
                                                                                          31
                                                                          _____>

170       180       190       200       210       220       230       240
AGAGATGTACAGTGAAATCCCCGAAATTATACACATGACTGAAGGAAGGGAGCTCGTCATTCCCTGCCGGGTTACGTCAC
TCTCTACATGTCACTTTAGGGGCTTTAATATGTGTACTGACTTCCTTCCCTCGAGCAGTAAGGGACGGCCCAATGCAGTG
 E   M   Y   S   E   I   P   E   I   I   H   M   T   E   G   R   E   L   V   I   P   C   R   V   T   S>
                                                                                                      57
 _____HFLT1 D2_____>

250       260       270       280       290       300       310       320
CTAACATCACTGTTACTTTAAAAAAGTTTCCACTTGACACTTTGATCCCTGATGGAAAACGCATAATCTGGGACAGTAGA
GATTGTAGTGACAATGAAATTTTTTCAAAGGTGAACTGTGAAACTAGGGACTACCTTTTGCGTATTAGACCCTGTCATCT
 P   N   I   T   V   T   L   K   K   F   P   L   D   T   L   I   P   D   G   K   R   I   I   W   D   S   R>
                                                                                                          84
 _____HFLT1 D2_____>

330       340       350       360       370       380       390       400
AAGGGCTTCATCATATCAAATGCAACGTACAAAGAAATAGGGCTTCTGACCTGTGAAGCAACAGTCAATGGGCATTTGTA
TTCCCGAAGTAGTATAGTTTACGTTGCATGTTTCTTTATCCCGAAGACTGGACACTTCGTTGTCAGTTACCCGTAAACAT
 K   G   F   I   I   S   N   A   T   Y   K   E   I   G   L   L   T   C   E   A   T   V   N   G   H   L   Y>
                                                                                                          111
 _____HFLT1 D2_____>

410       420       430       440       450       460       470       480
TAAGACAAACTATCTCACACATCGACAAACCAATACAATCATAGATGTGGTTCTGAGTCCGTCTCATGGAATTGAACTAT
ATTCTGTTTGATAGAGTGTGTAGCTGTTTGGTTATGTTAGTATCTACACCAAGACTCAGGCAGAGTACCTTAACTTGATA
 K   T   N   Y   L   T   H   R   Q   T   N   T   I   I   D>
 _____HFLT1 D2_____>
                                    V   V   L   S   P   S   H   G   I   E   L>
                                                                              137
                                    _____HFLT1 D3_____>
```

Fig. 21B.

```
      490        500        510        520        530        540        550        560
CTGTTGGAGAAAAGCTTGTCTTAAATTGTACAGCAAGAACTGAACTAAATGTGGGGATTGACTTCAACTGGGAATACCCT
GACAACCTCTTTTCGAACAGAATTTAACATGTCGTTCTTGACTTGATTTACACCCCTAACTGAAGTTGACCCTTATGGGA
 S  V  G  E  K  L  V  L  N  C  T  A  R  T  E  L  N  V  G  I  D  F  N  W  E  Y  P>
                                                                                 164
_____HFLK1 D3_____>

570        580        590        600        610        620        630        640
TCTTCGAAGCATCAGCATAAGAAACTTGTAAACCGAGACCTAAAAACCCAGTCTGGGAGTGAGATGAAGAAATTTTTGAG
AGAAGCTTCGTAGTCGTATTCTTTGAACATTTGGCTCTGGATTTTTGGGTCAGACCCTCACTCTACTTCTTTAAAAACTC
 S  S  K  H  Q  H  K  K  L  V  N  R  D  L  K  T  Q  S  G  S  E  M  K  K  F  L  S>
                                                                                 191
_____HFLK1 D3_____>

650        660        670        680        690        700        710        720
CACCTTAACTATAGATGGTGTAACCCGGAGTGACCAAGGATTGTACACCTGTGCAGCATCCAGTGGGCTGATGACCAAGA
GTGGAATTGATATCTACCACATTGGGCCTCACTGGTTCCTAACATGTGGACACGTCGTAGGTCACCCGACTACTGGTTCT
 T  L  T  I  D  G  V  T  R  S  D  Q  G  L  Y  T  C  A  A  S  S  G  L  M  T  K>
                                                                             217
_____HFLK1 D3_____>

>Srf_Bridge_
                              |
      730        740        750|       760        770        780        790        800
AGAACAGCACATTTGTCAGGGTCCATGAAAAGGGCCCGGGCGACAAAACTCACACATGCCCACCGTGCCCAGCACCTGAA
TCTTGTCGTGTAAACAGTCCCAGGTACTTTTCCCGGGCCCGCTGTTTTGAGTGTGTACGGGTGGCACGGGTCGTGGACTT
 K  N  S  T  F  V  R  V  H  E  K>
                                  G  P  G>
 _____HFLK1 D3_____>    _____>
                                      D  K  T  H  T  C  P  P  C  P  A  P  E>
                                                                            244
                                 _____FCΔC1(A)_____>

810        820        830        840        850        860        870        880
CTCCTGGGGGGACCGTCAGTCTTCCTCTTCCCCCCAAAACCCAAGGACACCCTCATGATCTCCCGGACCCCTGAGGTCAC
GAGGACCCCCCTGGCAGTCAGAAGGAGAAGGGGGGGTTTTGGGTTCCTGTGGGAGTACTAGAGGGCCTGGGGACTCCAGTG
 L  L  G  G  P  S  V  F  L  F  P  P  K  P  K  D  T  L  M  I  S  R  T  P  E  V  T>
                                                                                 271
_____FCΔC1(A)_____>

890        900        910        920        930        940        950        960
ATGCGTGGTGGTGGACGTGAGCCACGAAGACCCTGAGGTCAAGTTCAACTGGTACGTGGACGGCGTGGAGGTGCATAATG
TACGCACCACCACCTGCACTCGGTGCTTCTGGGACTCCAGTTCAAGTTGACCATGCACCTGCCGCACCTCCACGTATTAC
 C  V  V  V  D  V  S  H  E  D  P  E  V  K  F  N  W  Y  V  D  G  V  E  V  H  N>
                                                                             297
_____FCΔC1(A)_____>

970        980        990       1000       1010       1020       1030       1040
CCAAGACAAAGCCGCGGGAGGAGCAGTACAACAGCACGTACCGTGTGGTCAGCGTCCTCACCGTCCTGCACCAGGACTGG
GGTTCTGTTTCGGCGCCCTCCTCGTCATGTTGTCGTGCATGGCACACCAGTCGCAGGAGTGGCAGGACGTGGTCCTGACC
 A  K  T  K  P  R  E  E  Q  Y  N  S  T  Y  R  V  V  S  V  L  T  V  L  H  Q  D  W>
                                                                                 324
_____FCΔC1(A)_____>
```

Fig.21C.

```
            1050       1060       1070       1080       1090       1100       1110       1120
      CTGAATGGCAAGGAGTACAAGTGCAAGGTCTCCAACAAAGCCCTCCCAGCCCCCATCGAGAAAACCATCTCCAAAGCCAA
      GACTTACCGTTCCTCATGTTCACGTTCCAGAGGTTGTTTCGGGAGGGTCGGGGGTAGCTCTTTTGGTAGAGGTTTCGGTT
       L  N  G  K  E  Y  K  C  K  V  S  N  K  A  L  P  A  P  I  E  K  T  I  S  K  A  K>
                                                                                    351
      _____FCAC1(A)_____>

>A>C_A_allotype
                                                          |
                                                >G>T_A_allotype
                                                |         |
            1130       1140       1150       1160       1170 |     1180       1190       1200
      AGGGCAGCCCCGAGAACCACAGGTGTACACCCTGCCCCCATCCCGGGATGAGCTGACCAAGAACCAGGTCAGCCTGACCT
      TCCCGTCGGGGCTCTTGGTGTCCACATGTGGGACGGGGGTAGGGCCCTACTCGACTGGTTCTTGGTCCAGTCGGACTGGA
        G  Q  P  R  E  P  Q  V  Y  T  L  P  P  S  R  D  E  L  T  K  N  Q  V  S  L  T>
                                                                                    377
      _____FCAC1(A)_____>

1210       1220       1230       1240       1250       1260       1270       1280
      GCCTGGTCAAAGGCTTCTATCCCAGCGACATCGCCGTGGAGTGGGAGAGCAATGGGCAGCCGGAGAACAACTACAAGACC
      CGGACCAGTTTCCGAAGATAGGGTCGCTGTAGCGGCACCTCACCCTCTCGTTACCCGTCGGCCTCTTGTTGATGTTCTGG
        C  L  V  K  G  F  Y  P  S  D  I  A  V  E  W  E  S  N  G  Q  P  E  N  N  Y  K  T>
                                                                                    404
      _____FCAC1(A)_____>

>T>C
                                                    |
            1290       1300       1310       1320       1330       1340       1350       1360
      ACGCCTCCCGTGCTGGACTCCGACGGCTCCTTCTTCCTCTATAGCAAGCTCACCGTGGACAAGAGCAGGTGGCAGCAGGG
      TGCGGAGGGCACGACCTGAGGCTGCCGAGGAAGAAGGAGATATCGTTCGAGTGGCACCTGTTCTCGTCCACCGTCGTCCC
         T  P  P  V  L  D  S  D  G  S  F  F  L  Y  S  K  L  T  V  D  K  S  R  W  Q  Q  G>
                                                                                    431
      _____FCAC1(A)_____>

1370       1380       1390       1400       1410       1420       1430       1440
      GAACGTCTTCTCATGCTCCGTGATGCATGAGGCTCTGCACAACCACTACACGCAGAAGAGCCTCTCCCTGTCTCCGGGTA
      CTTGCAGAAGAGTACGAGGCACTACGTACTCCGAGACGTGTTGGTGATGTGCGTCTTCTCGGAGAGGGACAGAGGCCCAT
         N  V  F  S  C  S  V  M  H  E  A  L  H  N  H  Y  T  Q  K  S  L  S  L  S  P  G>
                                                                                    457
      _____FCAC1(A)_____>

>NotI_site
      |
      |1450
      AATGAGCGGCCGC
      TTACTCGCCGGCG
      K   *>
      458
      _____>
```

Fig.22A.

```
                                              >EcoRI_site
                                                   |
      10        20        30        40        50   |    60        70        80
AAGCTTGGGCTGCAGGTCGATCGACTCTAGAGGATCGATCCCCGGGCGAGCTCGAATTCGCAACCACCATGGTCAGCTAC
TTCGAACCCGACGTCCAGCTAGCTGAGATCTCCTAGCTAGGGGCCCGCTCGAGCTTAAGCGTTGGTGGTACCAGTCGATG
                                                             M  V  S  Y>
                                                             1        4
                                                             ──────────>

>BspEI_bridge
                                                        |
      90       100       110       120       130       140|      150       160
TGGGACACCGGGGTCCTGCTGTGCGCGCTGCTCAGCTGTCTGCTTCTCACAGGATCTAGTTCCGGAGGTAGACCTTTCGT
ACCCTGTGGCCCCAGGACGACACGCGCGACGAGTCGACAGACGAAGAGTGTCCTAGATCAAGGCCTCCATCTGGAAAGCA
    W  D  T  G  V  L  L  C  A  L  L  S  C  L  L  L  T  G  S  S>
    ─────────────FLT1 SIGNAL SEQUENCE──────────────────────────>
                                                        S  G>
                                                        ─────>
                                                              G  R  P  F  V>
                                                                          31
                                                              ──────────────>

170       180       190       200       210       220       230       240
AGAGATGTACAGTGAAATCCCCGAAATTATACACATGACTGAAGGAAGGGAGCTCGTCATTCCCTGCCGGGTTACGTCAC
TCTCTACATGTCACTTTAGGGGCTTTAATATGTGTACTGACTTCCTTCCCTCGAGCAGTAAGGGACGGCCCAATGCAGTG
    E  M  Y  S  E  I  P  E  I  I  H  M  T  E  G  R  E  L  V  I  P  C  R  V  T  S>
                                                                               57
    ─────────────FLT1 IG DOMAIN 2──────────────────────────────────────────────>

250       260       270       280       290       300       310       320
CTAACATCACTGTTACTTTAAAAAAGTTTCCACTTGACACTTTGATCCCTGATGGAAAACGCATAATCTGGGACAGTAGA
GATTGTAGTGACAATGAAATTTTTTCAAAGGTGAACTGTGAAACTAGGGACTACCTTTTGCGTATTAGACCCTGTCATCT
    P  N  I  T  V  T  L  K  K  F  P  L  D  T  L  I  P  D  G  K  R  I  I  W  D  S  R>
                                                                                  84
    ─────────────FLT1 IG DOMAIN 2──────────────────────────────────────────────────>

330       340       350       360       370       380       390       400
AAGGGCTTCATCATATCAAATGCAACGTACAAAGAAATAGGGCTTCTGACCTGTGAAGCAACAGTCAATGGGCATTTGTA
TTCCCGAAGTAGTATAGTTTACGTTGCATGTTTCTTTATCCCGAAGACTGGACACTTCGTTGTCAGTTACCCGTAAACAT
    K  G  F  I  I  S  N  A  T  Y  K  E  I  G  L  L  T  C  E  A  T  V  N  G  H  L  Y>
                                                                                  111
    ─────────────FLT1 IG DOMAIN 2──────────────────────────────────────────────────>

410       420       430       440       450       460       470       480
TAAGACAAACTATCTCACACAATCGACAAACCAATACAATCATAGATATCCAGCTGTTGCCCAGGAAGTCGCTGGAGCTGC
ATTCTGTTTGATAGAGTGTGTAGCTGTTTGGTTATGTTAGTATCTATAGGTCGACAACGGGTCCTTCAGCGACCTCGACG
    K  T  N  Y  L  T  H  R  Q  T  N  T  I  I  D>
    ─────FLT1 IG DOMAIN 2────────────────────────>
                                                  I  Q  L  L  P  R  K  S  L  E  L>
                                                                                137
                                                  ─────VEGFR3 (FLT4) IG DOMAIN 3─────>
```

Fig. 22B.

```
            490       500       510       520       530       540       550       560
TGGTAGGGGAGAAGCTGGTCCTCAACTGCACCGTGTGGGCTGAGTTTAACTCAGGTGTCACCTTTGACTGGGACTACCCA
ACCATCCCCTCTTCGACCAGGAGTTGACGTGGCACACCCGACTCAAATTGAGTCCACAGTGGAAACTGACCCTGATGGGT
     L  V  G  E  K  L  V  L  N  C  T  V  W  A  E  F  N  S  G  V  T  F  D  W  D  Y  P>
                                                                                  164
                  _____VEGFR3 (FLT4) IG DOMAIN 3_____>

570       580       590       600       610       620       630       640
GGGAAGCAGGCAGAGCGGGGTAAGTGGGTGCCCGAGCGACGCTCCCAACAGACCCACACAGAACTCTCCAGCATCCTGAC
CCCTTCGTCCGTCTCGCCCCATTCACCCACGGGCTCGCTGCGAGGGTTGTCTGGGTGTGTCTTGAGAGGTCGTAGGACTG
     G  K  Q  A  E  R  G  K  W  V  P  E  R  R  S  Q  Q  T  H  T  E  L  S  S  I  L  T>
                                                                                  191
                  _____VEGFR3 (FLT4) IG DOMAIN 3_____>

650       660       670       680       690       700       710       720
CATCCACAACGTCAGCCAGCACGACCTGGGCTCGTATGTGTGCAAGGCCAACAACGGCATCCAGCGATTTCGGGAGAGCA
GTAGGTGTTGCAGTCGGTCGTGCTGGACCCGAGCATACACACGTTCCGGTTGTTGCCGTAGGTCGCTAAAGCCCTCTCGT
     I  H  N  V  S  Q  H  D  L  G  S  Y  V  C  K  A  N  N  G  I  Q  R  F  R  E  S>
                                                                               217
                  _____VEGFR3 (FLT4) IG DOMAIN 3_____>

730       740       750       760       770       780       790       800
CCGAGGTCATTGTGCATGAAAATGGCCCGGGCGACAAAACTCACACATGCCCACCGTGCCCAGCACCTGAACTCCTGGGG
GGCTCCAGTAACACGTACTTTTACCGGGCCCGCTGTTTTGAGTGTGTACGGGTGGCACGGGTCGTGGACTTGAGGACCCC
     T  E  V  I  V  H  E  N>
     __VEGFR3 (FLT4) IG____>
                          G  P  G>
                          _____>
                                   D  K  T  H  T  C  P  P  C  P  A  P  E  L  L  G>
                                                                                244
                                   _____FCΔC1 - A ALLOTYPE_____>

810       820       830       840       850       860       870       880
GGACCGTCAGTCTTCCTCTTCCCCCCAAAACCCAAGGACACCCTCATGATCTCCCGGACCCCTGAGGTCACATGCGTGGT
CCTGGCAGTCAGAAGGAGAAGGGGGGTTTTGGGTTCCTGTGGGAGTACTAGAGGGCCTGGGGACTCCAGTGTACGCACCA
     G  P  S  V  F  L  F  P  P  K  P  K  D  T  L  M  I  S  R  T  P  E  V  T  C  V  V>
                                                                                    271
                  _____FCΔC1 - A ALLOTYPE_____>

890       900       910       920       930       940       950       960
GGTGGACGTGAGCCACGAAGACCCTGAGGTCAAGTTCAACTGGTACGTGGACGGCGTGGAGGTGCATAATGCCAAGACAA
CCACCTGCACTCGGTGCTTCTGGGACTCCAGTTCAAGTTGACCATGCACCTGCCGCACCTCCACGTATTACGGTTCTGTT
     V  D  V  S  H  E  D  P  E  V  K  F  N  W  Y  V  D  G  V  E  V  H  N  A  K  T>
                                                                                297
                  _____FCΔC1 - A ALLOTYPE_____>

970       980       990      1000      1010      1020      1030      1040
AGCCGCGGGAGGAGCAGTACAACAGCACGTACCGTGTGGTCAGCGTCCTCACCGTCCTGCACCAGGACTGGCTGAATGGC
TCGGCGCCCTCCTCGTCATGTTGTCGTGCATGGCACACCAGTCGCAGGAGTGGCAGGACGTGGTCCTGACCGACTTACCG
     K  P  R  E  E  Q  Y  N  S  T  Y  R  V  V  S  V  L  T  V  L  H  Q  D  W  L  N  G>
                                                                                    324
                  _____FCΔC1 - A ALLOTYPE_____>
```

Fig.22C.

```
          1050      1060      1070      1080      1090      1100      1110      1120
     AAGGAGTACAAGTGCAAGGTCTCCAACAAAGCCCTCCCAGCCCCCATCGAGAAAACCATCTCCAAAGCCAAAGGGCAGCC
     TTCCTCATGTTCACGTTCCAGAGGTTGTTTCGGGAGGGTCGGGGGTAGCTCTTTTGGTAGAGGTTTCGGTTTCCCGTCGG
       K  E  Y  K  C  K  V  S  N  K  A  L  P  A  P  I  E  K  T  I  S  K  A  K  G  Q  P>
                                                                                   351
     _____FCΔC1 - A ALLOTYPE_____>

>A>C_A_allotype
                                               |
                                         >G>T_A_allotype
                                          |    |
          1130      1140      1150      1160   |1170      1180      1190      1200
     CCGAGAACCACAGGTGTACACCCTGCCCCCATCCCGGGATGAGCTGACCAAGAACCAGGTCAGCCTGACCTGCCTGGTCA
     GGCTCTTGGTGTCCACATGTGGGACGGGGGTAGGGCCCTACTCGACTGGTTCTTGGTCCAGTCGGACTGGACGGACCAGT
       R  E  P  Q  V  Y  T  L  P  P  S  R  D  E  L  T  K  N  Q  V  S  L  T  C  L  V>
                                                                                   377
     _____FCΔC1 - A ALLOTYPE_____>

1210      1220      1230      1240      1250      1260      1270      1280
     AAGGCTTCTATCCCAGCGACATCGCCGTGGAGTGGGAGAGCAATGGGCAGCCGGAGAACAACTACAAGACCACGCCTCCC
     TTCCGAAGATAGGGTCGCTGTAGCGGCACCTCACCCTCTCGTTACCCGTCGGCCTCTTGTTGATGTTCTGGTGCGGAGGG
       K  G  F  Y  P  S  D  I  A  V  E  W  E  S  N  G  Q  P  E  N  N  Y  K  T  T  P>
                                                                                   404
     _____FCΔC1 - A ALLOTYPE_____>

>T>C
                                               |
          1290      1300      1310      1320   |1330      1340      1350      1360
     GTGCTGGACTCCGACGGCTCCTTCTTCCTCTATAGCAAGCTCACCGTGGACAAGAGCAGGTGGCAGCAGGGGAACGTCTT
     CACGACCTGAGGCTGCCGAGGAAGAAGGAGATATCGTTCGAGTGGCACCTGTTCTCGTCCACCGTCGTCCCCTTGCAGAA
       V  L  D  S  D  G  S  F  F  L  Y  S  K  L  T  V  D  K  S  R  W  Q  Q  G  N  V  F>
                                                                                   431
     _____FCΔC1 - A ALLOTYPE_____>

>NotI_site
                                                                               |
          1370      1380      1390      1400      1410      1420      1430    |1440
     CTCATGCTCCGTGATGCATGAGGCTCTGCACAACCACTACACGCAGAAGAGCCTCTCCCTGTCTCCGGGTAAATGAGCGG
     GAGTACGAGGCACTACGTACTCCGAGACGTGTTGGTGATGTGCGTCTTCTCGGAGAGGGACAGAGGCCCATTTACTCGCC
       S  C  S  V  M  H  E  A  L  H  N  H  Y  T  Q  K  S  L  S  L  S  P  G  K  *>
                                                                                   455
     _____FCΔC1 - A ALLOTYPE_____>

CCGC
     GGCG
```

Fig.24A.

```
            10             20             30             40             50             60
             *              *              *              *              *              *
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
 M   V   S   Y   W   D   T   G   V   L   L   C   A   L   L   S   C   L   L   L>
 1_____5_____hFLT1 SIGNAL SEQUENCE_____15_____20>

70             80             90            100            110            120
             *              *              *              *              *              *
ACA GGA TCT AGT TCC GGA AGT GAT ACC GGT AGA CCT TTC GTA GAG ATG TAC AGT GAA ATC
TGT CCT AGA TCA AGG CCT TCA CTA TGG CCA TCT GGA AAG CAT CTC TAC ATG TCA CTT TAG
 T   G   S   S   S   G>
21_hFLT1 SIGNAL SEQ_26>    S   D   T   G   R   P   F   V   E   M   Y   S   E   I>
                          _27_____30__hFLT1 IG DOMAIN 2_____40>

130            140            150            160            170            180
             *              *              *              *              *              *
CCC GAA ATT ATA CAC ATG ACT GAA GGA AGG GAG CTC GTC ATT CCC TGC CGG GTT ACG TCA
GGG CTT TAA TAT GTG TAC TGA CTT CCT TCC CTC GAG CAG TAA GGG ACG GCC CAA TGC AGT
 P   E   I   I   H   M   T   E   G   R   E   L   V   I   P   C   R   V   T   S>
41_____45_____hFLT1 IG DOMAIN 2_____55_____60>

190            200            210            220            230            240
             *              *              *              *              *              *
CCT AAC ATC ACT GTT ACT TTA AAA AAG TTT CCA CTT GAC ACT TTG ATC CCT GAT GGA AAA
GGA TTG TAG TGA CAA TGA AAT TTT TTC AAA GGT GAA CTG TGA AAC TAG GGA CTA CCT TTT
 P   N   I   T   V   T   L   K   K   F   P   L   D   T   L   I   P   D   G   K>
61_____65_____hFLT1 IG DOMAIN 2_____75_____80>

250            260            270            280            290            300
             *              *              *              *              *              *
CGC ATA ATC TGG GAC AGT AGA AAG GGC TTC ATC ATA TCA AAT GCA ACG TAC AAA GAA ATA
GCG TAT TAG ACC CTG TCA TCT TTC CCG AAG TAG TAT AGT TTA CGT TGC ATG TTT CTT TAT
 R   I   I   W   D   S   R   K   G   F   I   I   S   N   A   T   Y   K   E   I>
81_____85_____hFLT1 IG DOMAIN 2_____95_____100>

310            320            330            340            350            360
             *              *              *              *              *              *
GGG CTT CTG ACC TGT GAA GCA ACA GTC AAT GGG CAT TTG TAT AAG ACA AAC TAT CTC ACA
CCC GAA GAC TGG ACA CTT CGT TGT CAG TTA CCC GTA AAC ATA TTC TGT TTG ATA GAG TGT
 G   L   L   T   C   E   A   T   V   N   G   H   L   Y   K   T   N   Y   L   T>
101_____105_____hFLT1 IG DOMAIN 2_____115_____120>

370            380            390            400            410            420
             *              *              *              *              *              *
CAT CGA CAA ACC AAT ACA ATC ATA GAT GTG GTT CTG AGT CCG TCT CAT GGA ATT GAA CTA
GTA GCT GTT TGG TTA TGT TAG TAT CTA CAC CAA GAC TCA GGC AGA GTA CCT TAA CTT GAT
 H   R   Q   T   N   T   I   I   D>
121_____hFLT1 IG DOMAIN 2___129_>
                                        V   V   L   S   P   S   H   G   I   E   L>
                                       130_____hFLK1 IG DOMAIN 3_____140>
```

Fig.24B.

```
        430         440         450         460         470         480
         *           *           *           *           *           *
TCT GTT GGA GAA AAG CTT GTC TTA AAT TGT ACA GCA AGA ACT GAA CTA AAT GTG GGG ATT
AGA CAA CCT CTT TTC GAA CAG AAT TTA ACA TGT CGT TCT TGA CTT GAT TTA CAC CCC TAA
 S   V   G   E   K   L   V   L   N   C   T   A   R   T   E   L   N   V   G   I>
141_____145_____hFLK1 IG DOMAIN 3_____155_____160>

490         500         510         520         530         540
         *           *           *           *           *           *
GAC TTC AAC TGG GAA TAC CCT TCT TCG AAG CAT CAG CAT AAG AAA CTT GTA AAC CGA GAC
CTG AAG TTG ACC CTT ATG GGA AGA AGC TTC GTA GTC GTA TTC TTT GAA CAT TTG GCT CTG
 D   F   N   W   E   Y   P   S   S   K   H   Q   H   K   K   L   V   N   R   D>
161_____165_____hFLK1 IG DOMAIN 3_____175_____180>

550         560         570         580         590         600
         *           *           *           *           *           *
CTA AAA ACC CAG TCT GGG AGT GAG ATG AAG AAA TTT TTG AGC ACC TTA ACT ATA GAT GGT
GAT TTT TGG GTC AGA CCC TCA CTC TAC TTC TTT AAA AAC TCG TGG AAT TGA TAT CTA CCA
 L   K   T   Q   S   G   S   E   M   K   K   F   L   S   T   L   T   I   D   G>
181_____185_____hFLK1 IG DOMAIN 3_____195_____200>

610         620         630         640         650         660
         *           *           *           *           *           *
GTA ACC CGG AGT GAC CAA GGA TTG TAC ACC TGT GCA GCA TCC AGT GGG CTG ATG ACC AAG
CAT TGG GCC TCA CTG GTT CCT AAC ATG TGG ACA CGT CGT AGG TCA CCC GAC TAC TGG TTC
 V   T   R   S   D   Q   G   L   Y   T   C   A   A   S   S   G   L   M   T   K>
201_____205_____hFLK1 IG DOMAIN 3_____215_____220>

670         680         690         700         710         720
         *           *           *           *           *           *
AAG AAC AGC ACA TTT GTC AGG GTC CAT GAA AAG GAC AAA ACT CAC ACA TGC CCA CCG TGC
TTC TTG TCG TGT AAA CAG TCC CAG GTA CTT TTC CTG TTT TGA GTG TGT ACG GGT GGC ACG
 K   N   S   T   F   V   R   V   H   E   K>
221_____hFLK1 IG DOMAIN 3_____231>
                                            D   K   T   H   T   C   P   P   C>
                                        232_____hFCAC1 A _____240>

730         740         750         760         770         780
         *           *           *           *           *           *
CCA GCA CCT GAA CTC CTG GGG GGA CCG TCA GTC TTC CTC TTC CCC CCA AAA CCC AAG GAC
GGT CGT GGA CTT GAG GAC CCC CCT GGC AGT CAG AAG GAG AAG GGG GGT TTT GGG TTC CTG
 P   A   P   E   L   L   G   G   P   S   V   F   L   F   P   P   K   P   K   D>
241_____245_____hFCAC1 A _____255_____260>

790         800         810         820         830         840
         *           *           *           *           *           *
ACC CTC ATG ATC TCC CGG ACC CCT GAG GTC ACA TGC GTG GTG GTG GAC GTG AGC CAC GAA
TGG GAG TAC TAG AGG GCC TGG GGA CTC CAG TGT ACG CAC CAC CAC CTG CAC TCG GTG CTT
 T   L   M   I   S   R   T   P   E   V   T   C   V   V   V   D   V   S   H   E>
261_____265_____hFCAC1 A _____275_____280>

850         860         870         880         890         900
         *           *           *           *           *           *
GAC CCT GAG GTC AAG TTC AAC TGG TAC GTG GAC GGC GTG GAG GTG CAT AAT GCC AAG ACA
CTG GGA CTC CAG TTC AAG TTG ACC ATG CAC CTG CCG CAC CTC CAC GTA TTA CGG TTC TGT
 D   P   E   V   K   F   N   W   Y   V   D   G   V   E   V   H   N   A   K   T>
281_____285_____hFCAC1 A _____295_____300>
```

Fig.24C.

```
          910         920         930         940         950         960
           *           *           *           *           *           *
    AAG CCG CGG GAG GAG CAG TAC AAC AGC ACG TAC CGT GTG GTC AGC GTC CTC ACC GTC CTG
    TTC GGC GCC CTC CTC GTC ATG TTG TCG TGC ATG GCA CAC CAG TCG CAG GAG TGG CAG GAC
     K   P   R   E   E   Q   Y   N   S   T   Y   R   V   V   S   V   L   T   V   L>
    301_____305_____hFCAC1 A_____315_____320>

970         980         990        1000        1010        1020
           *           *           *           *           *           *
    CAC CAG GAC TGG CTG AAT GGC AAG GAG TAC AAG TGC AAG GTC TCC AAC AAA GCC CTC CCA
    GTG GTC CTG ACC GAC TTA CCG TTC CTC ATG TTC ACG TTC CAG AGG TTG TTT CGG GAG GGT
     H   Q   D   W   L   N   G   K   E   Y   K   C   K   V   S   N   K   A   L   P>
    321_____325_____hFCAC1 A_____335_____340>

1030        1040        1050        1060        1070        1080
           *           *           *           *           *           *
    GCC CCC ATC GAG AAA ACC ATC TCC AAA GCC AAA GGG CAG CCC CGA GAA CCA CAG GTG TAC
    CGG GGG TAG CTC TTT TGG TAG AGG TTT CGG TTT CCC GTC GGG GCT CTT GGT GTC CAC ATG
     A   P   I   E   K   T   I   S   K   A   K   G   Q   P   R   E   P   Q   V   Y>
    341_____345_____hFCAC1 A_____355_____360>

1090        1100        1110        1120        1130        1140
           *           *           *           *           *           *
    ACC CTG CCC CCA TCC CGG GAT GAG CTG ACC AAG AAC CAG GTC AGC CTG ACC TGC CTG GTC
    TGG GAC GGG GGT AGG GCC CTA CTC GAC TGG TTC TTG GTC CAG TCG GAC TGG ACG GAC CAG
     T   L   P   P   S   R   D   E   L   T   K   N   Q   V   S   L   T   C   L   V>
    361_____365_____hFCAC1 A_____375_____380>

1150        1160        1170        1180        1190        1200
           *           *           *           *           *           *
    AAA GGC TTC TAT CCC AGC GAC ATC GCC GTG GAG TGG GAG AGC AAT GGG CAG CCG GAG AAC
    TTT CCG AAG ATA GGG TCG CTG TAG CGG CAC CTC ACC CTC TCG TTA CCC GTC GGC CTC TTG
     K   G   F   Y   P   S   D   I   A   V   E   W   E   S   N   G   Q   P   E   N>
    381_____385_____hFCAC1 A_____395_____400>

1210        1220        1230        1240        1250        1260
           *           *           *           *           *           *
    AAC TAC AAG ACC ACG CCT CCC GTG CTG GAC TCC GAC GGC TCC TTC TTC CTC TAC AGC AAG
    TTG ATG TTC TGG TGC GGA GGG CAC GAC CTG AGG CTG CCG AGG AAG AAG GAG ATG TCG TTC
     N   Y   K   T   T   P   P   V   L   D   S   D   G   S   F   F   L   Y   S   K>
    401_____405_____hFCAC1 A_____415_____420>

1270        1280        1290        1300        1310        1320
           *           *           *           *           *           *
    CTC ACC GTG GAC AAG AGC AGG TGG CAG CAG GGG AAC GTC TTC TCA TGC TCC GTG ATG CAT
    GAG TGG CAC CTG TTC TCG TCC ACC GTC GTC CCC TTG CAG AAG AGT ACG AGG CAC TAC GTA
     L   T   V   D   K   S   R   W   Q   Q   G   N   V   F   S   C   S   V   M   H>
    421_____425_____hFCAC1 A_____435_____440>

1330        1340        1350        1360        1370
           *           *           *           *           *
    GAG GCT CTG CAC AAC CAC TAC ACG CAG AAG AGC CTC TCC CTG TCT CCG GGT AAA TGA
    CTC CGA GAC GTG TTG GTG ATG TGC GTC TTC TCG GAG AGG GAC AGA GGC CCA TTT ACT
     E   A   L   H   N   H   Y   T   Q   K   S   L   S   L   S   P   G   K   *>
    441_____445_____hFCAC1 A_____455_____458____>
```

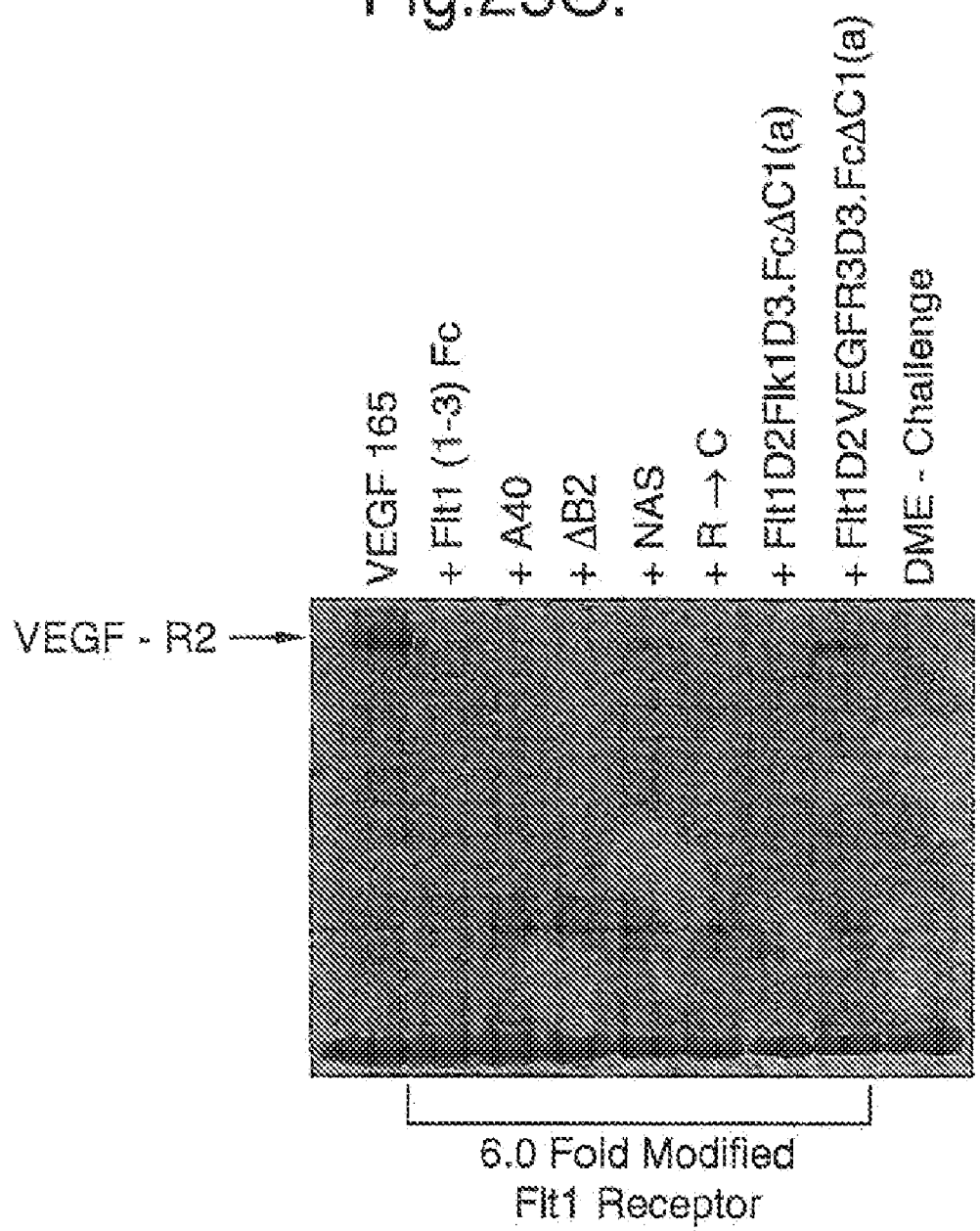

Fig. 28.

| hVEGF165 (nM) | Binding Stoichiometry of hVEGF165 to Flt1D2Flk1D3.FcΔC1(a) & VEGFR1R2-FcΔC1(a) | |
| --- | --- | --- |
| | VEGF/Flt1D2Flk1D3.FcΔC1(a) | VEGF/VEGFR1R2-FcΔC1(a) |
| 1 | 0.93 | 0.98 |
| 10 | 0.97 | 0.94 |
| 50 | 1 | 0.99 |
| Average ± StDev | 0.96 ± 0.03 | 0.97 ± 0.02 |

Fig. 36.

GRPFFVEMYSEIPEIHMTEGRELVIPCRVTSPNITVTLKKFPLDTLIPDG 50

KRIIWDSRKGFIISNATYKEIGLLTCEATVNGHLYKTNYLTHRQTNTIID 100

VVLSPSHIELSVGEKLVLNCTARTELNVGIDFNWEYPSSKHQHKKLVNR 150

DLKTQSGSEMKKFLSTLTIDGVTRSDQGLYTCAASSGLMTKKNSTFVRVH 200

EKGPGDKTHTCPPCPAPELLGGPSVFLFPPKPKDTLMISRTPEVTCVVVD 250

VSHEDPEVKFNWYVDGVEVHNAKTKPREEQYNSTYRVVSVLTVLHQDWLN 300

GKEYKCKVSNKALPAPIEKTISKAKGQPREPQVYTLPPSRDELTKNQVSL 350

TCLVKGFYPSDIAVEWESNGQPENNYKTTPPVLDSDGSFFLYSKLTVDKS 400

RWQQGNVFSCSVMHEALHNHYTQKSLSLSPGK

SEQUENCE LISTING

```
<160> NUMBER OF SEQ ID NOS: 38

<210> SEQ ID NO 1
<211> LENGTH: 1704
<212> TYPE: DNA
<213> ORGANISM: Homo sapiens
<220> FEATURE:
<221> NAME/KEY: CDS
<222> LOCATION: (1)...(1701)

<400> SEQUENCE: 1 atg gtc agc tac tgg gac acc ggg gtc ctg ctg tgc gcg ctg ctc agc      48
Met Val Ser Tyr Trp Asp Thr Gly Val Leu Leu Cys Ala Leu Leu Ser
 1               5                  10                  15 tgt ctg ctt ctc aca gga tct agt tca ggt tca aaa tta aaa gat cct      96
Cys Leu Leu Leu Thr Gly Ser Ser Ser Gly Ser Lys Leu Lys Asp Pro
             20                  25                  30 gaa ctg agt tta aaa ggc acc cag cac atc atg caa gca ggc cag aca     144
```

```
                Glu Leu Ser Leu Lys Gly Thr Gln His Ile Met Gln Ala Gly Gln Thr
                             35                  40                  45 ctg cat ctc caa tgc agg ggg gaa gca gcc cat aaa tgg tct ttg cct              192
Leu His Leu Gln Cys Arg Gly Glu Ala Ala His Lys Trp Ser Leu Pro
 50                  55                  60 gaa atg gtg agt aag gaa agc gaa agg ctg agc ata act aaa tct gcc              240
Glu Met Val Ser Lys Glu Ser Glu Arg Leu Ser Ile Thr Lys Ser Ala
 65                  70                  75                  80 tgt gga aga aat ggc aaa caa ttc tgc agt act tta acc ttg aac aca              288
Cys Gly Arg Asn Gly Lys Gln Phe Cys Ser Thr Leu Thr Leu Asn Thr
                 85                  90                  95 gct caa gca aac cac act ggc ttc tac agc tgc aaa tat cta gct gta              336
Ala Gln Ala Asn His Thr Gly Phe Tyr Ser Cys Lys Tyr Leu Ala Val
             100                 105                 110 cct act tca aag aag aag gaa aca gaa tct gca atc tat ata ttt att              384
Pro Thr Ser Lys Lys Lys Glu Thr Glu Ser Ala Ile Tyr Ile Phe Ile
         115                 120                 125 agt gat aca ggt aga cct ttc gta gag atg tac agt gaa atc ccc gaa              432
Ser Asp Thr Gly Arg Pro Phe Val Glu Met Tyr Ser Glu Ile Pro Glu
130                 135                 140 att ata cac atg act gaa gga agg gag ctc gtc att ccc tgc cgg gtt              480
Ile Ile His Met Thr Glu Gly Arg Glu Leu Val Ile Pro Cys Arg Val
145                 150                 155                 160 acg tca cct aac atc act gtt act tta aaa aag ttt cca ctt gac act              528
Thr Ser Pro Asn Ile Thr Val Thr Leu Lys Lys Phe Pro Leu Asp Thr
                165                 170                 175 ttg atc cct gat gga aaa cgc ata atc tgg gac agt aga aag ggc ttc              576
Leu Ile Pro Asp Gly Lys Arg Ile Ile Trp Asp Ser Arg Lys Gly Phe
            180                 185                 190 atc ata tca aat gca acg tac aaa gaa ata ggg ctt ctg acc tgt gaa              624
Ile Ile Ser Asn Ala Thr Tyr Lys Glu Ile Gly Leu Leu Thr Cys Glu
        195                 200                 205 gca aca gtc aat ggg cat ttg tat aag aca aac tat ctc aca cat cga              672
Ala Thr Val Asn Gly His Leu Tyr Lys Thr Asn Tyr Leu Thr His Arg
210                 215                 220 caa acc aat aca atc ata gat gtc caa ata agc aca cca cgc cca gtc              720
Gln Thr Asn Thr Ile Ile Asp Val Gln Ile Ser Thr Pro Arg Pro Val
225                 230                 235                 240 aaa tta ctt aga ggc cat act ctt gtc ctc aat tgt act gct acc act              768
Lys Leu Leu Arg Gly His Thr Leu Val Leu Asn Cys Thr Ala Thr Thr
                245                 250                 255 ccc ttg aac acg aga gtt caa atg acc tgg agt tac cct gat gaa aaa              816
Pro Leu Asn Thr Arg Val Gln Met Thr Trp Ser Tyr Pro Asp Glu Lys
            260                 265                 270 aat aag aga gct tcc gta agg cga cga att gac caa agc aat tcc cat              864
Asn Lys Arg Ala Ser Val Arg Arg Arg Ile Asp Gln Ser Asn Ser His
        275                 280                 285 gcc aac ata ttc tac agt gtt ctt act att gac aaa atg cag aac aaa              912
Ala Asn Ile Phe Tyr Ser Val Leu Thr Ile Asp Lys Met Gln Asn Lys
290                 295                 300 gac aaa gga ctt tat act tgt cgt gta agg agt gga cca tca ttc aaa              960
Asp Lys Gly Leu Tyr Thr Cys Arg Val Arg Ser Gly Pro Ser Phe Lys
305                 310                 315                 320 tct gtt aac acc tca gtg cat ata tat gat aaa gca ggc ccg ggc gag             1008
Ser Val Asn Thr Ser Val His Ile Tyr Asp Lys Ala Gly Pro Gly Glu
                325                 330                 335 ccc aaa tct tgt gac aaa act cac aca tgc cca ccg tgc cca gca cct             1056
Pro Lys Ser Cys Asp Lys Thr His Thr Cys Pro Pro Cys Pro Ala Pro
            340                 345                 350 gaa ctc ctg ggg gga ccg tca gtc ttc ctc ttc ccc cca aaa ccc aag             1104
```

-continued

```
Glu Leu Leu Gly Gly Pro Ser Val Phe Leu Phe Pro Pro Lys Pro Lys
            355                 360                 365 gac acc ctc atg atc tcc cgg acc cct gag gtc aca tgc gtg gtg gtg      1152
Asp Thr Leu Met Ile Ser Arg Thr Pro Glu Val Thr Cys Val Val Val
370                 375                 380 gac gtg agc cac gaa gac cct gag gtc aag ttc aac tgg tac gtg gac      1200
Asp Val Ser His Glu Asp Pro Glu Val Lys Phe Asn Trp Tyr Val Asp
385                 390                 395                 400 ggc gtg gag gtg cat aat gcc aag aca aag ccg cgg gag gag cag tac      1248
Gly Val Glu Val His Asn Ala Lys Thr Lys Pro Arg Glu Glu Gln Tyr
                405                 410                 415 aac agc acg tac cgt gtg gtc agc gtc ctc acc gtc ctg cac cag gac      1296
Asn Ser Thr Tyr Arg Val Val Ser Val Leu Thr Val Leu His Gln Asp
            420                 425                 430 tgg ctg aat ggc aag gag tac aag tgc aag gtc tcc aac aaa gcc ctc      1344
Trp Leu Asn Gly Lys Glu Tyr Lys Cys Lys Val Ser Asn Lys Ala Leu
        435                 440                 445 cca gcc ccc atc gag aaa acc atc tcc aaa gcc aaa ggg cag ccc cga      1392
Pro Ala Pro Ile Glu Lys Thr Ile Ser Lys Ala Lys Gly Gln Pro Arg
450                 455                 460 gaa cca cag gtg tac acc ctg ccc cca tcc cgg gat gag ctg acc aag      1440
Glu Pro Gln Val Tyr Thr Leu Pro Pro Ser Arg Asp Glu Leu Thr Lys
465                 470                 475                 480 aac cag gtc agc ctg acc tgc ctg gtc aaa ggc ttc tat ccc agc gac      1488
Asn Gln Val Ser Leu Thr Cys Leu Val Lys Gly Phe Tyr Pro Ser Asp
                485                 490                 495 atc gcc gtg gag tgg gag agc aat ggg cag ccg gag aac aac tac aag      1536
Ile Ala Val Glu Trp Glu Ser Asn Gly Gln Pro Glu Asn Asn Tyr Lys
            500                 505                 510 acc acg cct ccc gtg ctg gac tcc gac ggc tcc ttc ttc ctc tac agc      1584
Thr Thr Pro Pro Val Leu Asp Ser Asp Gly Ser Phe Phe Leu Tyr Ser
        515                 520                 525 aag ctc acc gtg gac aag agc agg tgg cag cag ggg aac gtc ttc tca      1632
Lys Leu Thr Val Asp Lys Ser Arg Trp Gln Gln Gly Asn Val Phe Ser
530                 535                 540 tgc tcc gtg atg cat gag gct ctg cac aac cac tac acg cag aag agc      1680
Cys Ser Val Met His Glu Ala Leu His Asn His Tyr Thr Gln Lys Ser
545                 550                 555                 560 ctc tcc ctg tct ccg ggt aaa tga                                      1704
Leu Ser Leu Ser Pro Gly Lys
                565

<210> SEQ ID NO 2
<211> LENGTH: 567
<212> TYPE: PRT
<213> ORGANISM: Homo sapiens

<400> SEQUENCE: 2

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95
```

```
Ala Gln Ala Asn His Thr Gly Phe Tyr Ser Cys Lys Tyr Leu Ala Val
            100                 105                 110
Pro Thr Ser Lys Lys Glu Thr Glu Ser Ala Ile Tyr Ile Phe Ile
        115                 120                 125
Ser Asp Thr Gly Arg Pro Phe Val Glu Met Tyr Ser Glu Ile Pro Glu
    130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
        195                 200                 205
Ala Thr Val Asn Gly His Leu Tyr Lys Thr Asn Tyr Leu Thr His Arg
    210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Gly Pro Gly Glu
                325                 330                 335
Pro Lys Ser Cys Asp Lys Thr His Thr Cys Pro Pro Cys Pro Ala Pro
            340                 345                 350
Glu Leu Leu Gly Gly Pro Ser Val Phe Leu Phe Pro Pro Lys Pro Lys
        355                 360                 365
Asp Thr Leu Met Ile Ser Arg Thr Pro Glu Val Thr Cys Val Val Val
    370                 375                 380
Asp Val Ser His Glu Asp Pro Glu Val Lys Phe Asn Trp Tyr Val Asp
385                 390                 395                 400
Gly Val Glu Val His Asn Ala Lys Thr Lys Pro Arg Glu Glu Gln Tyr
                405                 410                 415
Asn Ser Thr Tyr Arg Val Val Ser Val Leu Thr Val Leu His Gln Asp
            420                 425                 430
Trp Leu Asn Gly Lys Glu Tyr Lys Cys Lys Val Ser Asn Lys Ala Leu
        435                 440                 445
Pro Ala Pro Ile Glu Lys Thr Ile Ser Lys Ala Lys Gly Gln Pro Arg
    450                 455                 460
Glu Pro Gln Val Tyr Thr Leu Pro Pro Ser Arg Asp Glu Leu Thr Lys
465                 470                 475                 480
Asn Gln Val Ser Leu Thr Cys Leu Val Lys Gly Phe Tyr Pro Ser Asp
                485                 490                 495
Ile Ala Val Glu Trp Glu Ser Asn Gly Gln Pro Glu Asn Asn Tyr Lys
            500                 505                 510
Thr Thr Pro Pro Val Leu Asp Ser Asp Gly Ser Phe Phe Leu Tyr Ser
```

-continued

```
                515                 520                 525
Lys Leu Thr Val Asp Lys Ser Arg Trp Gln Gln Gly Asn Val Phe Ser
        530                 535                 540

Cys Ser Val Met His Glu Ala Leu His Asn His Tyr Thr Gln Lys Ser
545                 550                 555                 560

Leu Ser Leu Ser Pro Gly Lys
                565

<210> SEQ ID NO 3
<211> LENGTH: 1674
<212> TYPE: DNA
<213> ORGANISM: Homo sapiens
<220> FEATURE:
<221> NAME/KEY: CDS
<222> LOCATION: (1)...(1671)

<400> SEQUENCE: 3 atg gtc agc tac tgg gac acc ggg gtc ctg ctg tgc gcg ctg ctc agc     48
Met Val Ser Tyr Trp Asp Thr Gly Val Leu Leu Cys Ala Leu Leu Ser
  1               5                  10                  15 tgt ctg ctt ctc aca gga tct agt tca ggt tca aaa tta aaa gat cct     96
Cys Leu Leu Leu Thr Gly Ser Ser Ser Gly Ser Lys Leu Lys Asp Pro
                 20                  25                  30 gaa ctg agt tta aaa ggc acc cag cac atc atg caa gca ggc cag aca    144
Glu Leu Ser Leu Lys Gly Thr Gln His Ile Met Gln Ala Gly Gln Thr
             35                  40                  45 ctg cat ctc caa tgc agg ggg gaa gca gcc cat aaa tgg tct ttg cct    192
Leu His Leu Gln Cys Arg Gly Glu Ala Ala His Lys Trp Ser Leu Pro
         50                  55                  60 gaa atg gtg agt aag gaa agc gaa agg ctg agc ata act aaa tct gcc    240
Glu Met Val Ser Lys Glu Ser Glu Arg Leu Ser Ile Thr Lys Ser Ala
 65                  70                  75                  80 tgt gga aga aat ggc aaa caa ttc tgc agt act tta acc ttg aac aca    288
Cys Gly Arg Asn Gly Lys Gln Phe Cys Ser Thr Leu Thr Leu Asn Thr
                 85                  90                  95 gct caa gca aac cac act ggc ttc tac agc tgc aaa tat cta gct gta    336
Ala Gln Ala Asn His Thr Gly Phe Tyr Ser Cys Lys Tyr Leu Ala Val
                100                 105                 110 cct act tca aag aag aag gaa aca gaa tct gca atc tat ata ttt att    384
Pro Thr Ser Lys Lys Lys Glu Thr Glu Ser Ala Ile Tyr Ile Phe Ile
            115                 120                 125 agt gat aca ggt aga cct ttc gta gag atg tac agt gaa atc ccc gaa    432
Ser Asp Thr Gly Arg Pro Phe Val Glu Met Tyr Ser Glu Ile Pro Glu
        130                 135                 140 att ata cac atg act gaa gga agg gag ctc gtc att ccc tgc cgg gtt    480
Ile Ile His Met Thr Glu Gly Arg Glu Leu Val Ile Pro Cys Arg Val
145                 150                 155                 160 acg tca cct aac atc act gtt act tta aaa aag ttt cca ctt gac act    528
Thr Ser Pro Asn Ile Thr Val Thr Leu Lys Lys Phe Pro Leu Asp Thr
                165                 170                 175 ttg atc cct gat gga aaa cgc ata atc tgg gac agt aga aag ggc ttc    576
Leu Ile Pro Asp Gly Lys Arg Ile Ile Trp Asp Ser Arg Lys Gly Phe
            180                 185                 190 atc ata tca aat gca acg tac aaa gaa ata ggg ctt ctg acc tgt gaa    624
Ile Ile Ser Asn Ala Thr Tyr Lys Glu Ile Gly Leu Leu Thr Cys Glu
        195                 200                 205 gca aca gtc aat ggg cat ttg tat aag aca aac tat ctc aca cat cga    672
Ala Thr Val Asn Gly His Leu Tyr Lys Thr Asn Tyr Leu Thr His Arg
    210                 215                 220 caa acc aat aca atc ata gat gtc caa ata agc aca cca cgc cca gtc    720
Gln Thr Asn Thr Ile Ile Asp Val Gln Ile Ser Thr Pro Arg Pro Val
```

```
                    225                 230                 235                 240
aaa tta ctt aga ggc cat act ctt gtc ctc aat tgt act gct acc act        768
Lys Leu Leu Arg Gly His Thr Leu Val Leu Asn Cys Thr Ala Thr Thr
                245                 250                 255 ccc ttg aac acg aga gtt caa atg acc tgg agt tac cct gat gaa att        816
Pro Leu Asn Thr Arg Val Gln Met Thr Trp Ser Tyr Pro Asp Glu Ile
            260                 265                 270 gac caa agc aat tcc cat gcc aac ata ttc tac agt gtt ctt act att        864
Asp Gln Ser Asn Ser His Ala Asn Ile Phe Tyr Ser Val Leu Thr Ile
            275                 280                 285 gac aaa atg cag aac aaa gac aaa gga ctt tat act tgt cgt gta agg        912
Asp Lys Met Gln Asn Lys Asp Lys Gly Leu Tyr Thr Cys Arg Val Arg
        290                 295                 300 agt gga cca tca ttc aaa tct gtt aac acc tca gtg cat ata tat gat        960
Ser Gly Pro Ser Phe Lys Ser Val Asn Thr Ser Val His Ile Tyr Asp
305                 310                 315                 320 aaa gca ggc ccg ggc gag ccc aaa tct tgt gac aaa act cac aca tgc       1008
Lys Ala Gly Pro Gly Glu Pro Lys Ser Cys Asp Lys Thr His Thr Cys
                325                 330                 335 cca ccg tgc cca gca cct gaa ctc ctg ggg gga ccg tca gtc ttc ctc       1056
Pro Pro Cys Pro Ala Pro Glu Leu Leu Gly Gly Pro Ser Val Phe Leu
            340                 345                 350 ttc ccc cca aaa ccc aag gac acc ctc atg atc tcc cgg acc cct gag       1104
Phe Pro Pro Lys Pro Lys Asp Thr Leu Met Ile Ser Arg Thr Pro Glu
        355                 360                 365 gtc aca tgc gtg gtg gtg gac gtg agc cac gaa gac cct gag gtc aag       1152
Val Thr Cys Val Val Val Asp Val Ser His Glu Asp Pro Glu Val Lys
    370                 375                 380 ttc aac tgg tac gtg gac ggc gtg gag gtg cat aat gcc aag aca aag       1200
Phe Asn Trp Tyr Val Asp Gly Val Glu Val His Asn Ala Lys Thr Lys
385                 390                 395                 400 ccg cgg gag gag cag tac aac agc acg tac cgt gtg gtc agc gtc ctc       1248
Pro Arg Glu Glu Gln Tyr Asn Ser Thr Tyr Arg Val Val Ser Val Leu
                405                 410                 415 acc gtc ctg cac cag gac tgg ctg aat ggc aag gag tac aag tgc aag       1296
Thr Val Leu His Gln Asp Trp Leu Asn Gly Lys Glu Tyr Lys Cys Lys
            420                 425                 430 gtc tcc aac aaa gcc ctc cca gcc ccc atc gag aaa acc atc tcc aaa       1344
Val Ser Asn Lys Ala Leu Pro Ala Pro Ile Glu Lys Thr Ile Ser Lys
        435                 440                 445 gcc aaa ggg cag ccc cga gaa cca cag gtg tac acc ctg ccc cca tcc       1392
Ala Lys Gly Gln Pro Arg Glu Pro Gln Val Tyr Thr Leu Pro Pro Ser
    450                 455                 460 cgg gat gag ctg acc aag aac cag gtc agc ctg acc tgc ctg gtc aaa       1440
Arg Asp Glu Leu Thr Lys Asn Gln Val Ser Leu Thr Cys Leu Val Lys
465                 470                 475                 480 ggc ttc tat ccc agc gac atc gcc gtg gag tgg gag agc aat ggg cag       1488
Gly Phe Tyr Pro Ser Asp Ile Ala Val Glu Trp Glu Ser Asn Gly Gln
                485                 490                 495 ccg gag aac aac tac aag acc acg cct ccc gtg ctg gac tcc gac ggc       1536
Pro Glu Asn Asn Tyr Lys Thr Thr Pro Pro Val Leu Asp Ser Asp Gly
            500                 505                 510 tcc ttc ttc ctc tac agc aag ctc acc gtg gac aag agc agg tgg cag       1584
Ser Phe Phe Leu Tyr Ser Lys Leu Thr Val Asp Lys Ser Arg Trp Gln
        515                 520                 525 cag ggg aac gtc ttc tca tgc tcc gtg atg cat gag gct ctg cac aac       1632
Gln Gly Asn Val Phe Ser Cys Ser Val Met His Glu Ala Leu His Asn
    530                 535                 540 cac tac acg cag aag agc ctc tcc ctg tct ccg ggt aaa tga              1674
His Tyr Thr Gln Lys Ser Leu Ser Leu Ser Pro Gly Lys
```

545            550            555

<210> SEQ ID NO 4
<211> LENGTH: 557
<212> TYPE: PRT
<213> ORGANISM: Homo sapiens

<400> SEQUENCE: 4

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
             20                  25                  30

Glu Leu Ser Leu Lys Gly Thr Gln His Ile Met Gln Ala Gly Gln Thr
         35                  40                  45

Leu His Leu Gln Cys Arg Gly Glu Ala Ala His Lys Trp Ser Leu Pro
     50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Ile
            260                 265                 270

Asp Gln Ser Asn Ser His Ala Asn Ile Phe Tyr Ser Val Leu Thr Ile
        275                 280                 285

Asp Lys Met Gln Asn Lys Asp Lys Gly Leu Tyr Thr Cys Arg Val Arg
    290                 295                 300

Ser Gly Pro Ser Phe Lys Ser Val Asn Thr Ser Val His Ile Tyr Asp
305                 310                 315                 320

Lys Ala Gly Pro Gly Glu Pro Lys Ser Cys Asp Lys Thr His Thr Cys
                325                 330                 335

Pro Pro Cys Pro Ala Pro Glu Leu Leu Gly Gly Pro Ser Val Phe Leu
            340                 345                 350

Phe Pro Pro Lys Pro Lys Asp Thr Leu Met Ile Ser Arg Thr Pro Glu
        355                 360                 365

Val Thr Cys Val Val Val Asp Val Ser His Glu Asp Pro Glu Val Lys

```
                    370                 375                 380
Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
                405                 410                 415

Thr Val Leu His Gln Asp Trp Leu Asn Gly Lys Glu Tyr Lys Cys Lys
            420                 425                 430

Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
    450                 455                 460

Arg Asp Glu Leu Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540

His Tyr Thr Gln Lys Ser Leu Ser Leu Ser Pro Gly Lys
545                 550                 555

<210> SEQ ID NO 5
<211> LENGTH: 1359
<212> TYPE: DNA
<213> ORGANISM: Homo sapiens
<220> FEATURE:
<221> NAME/KEY: CDS
<222> LOCATION: (1)...(1356)

<400> SEQUENCE: 5 atg gtc agc tac tgg gac acc ggg gtc ctg ctg tgc gcg ctg ctc agc    48
Met Val Ser Tyr Trp Asp Thr Gly Val Leu Leu Cys Ala Leu Leu Ser
1               5                   10                  15 tgt ctg ctt ctc aca gga tct agt tcc gga ggt aga cct ttc gta gag    96
Cys Leu Leu Leu Thr Gly Ser Ser Ser Gly Gly Arg Pro Phe Val Glu
            20                  25                  30 atg tac agt gaa atc ccc gaa att ata cac atg act gaa gga agg gag   144
Met Tyr Ser Glu Ile Pro Glu Ile Ile His Met Thr Glu Gly Arg Glu
        35                  40                  45 ctc gtc att ccc tgc cgg gtt acg tca cct aac atc act gtt act tta   192
Leu Val Ile Pro Cys Arg Val Thr Ser Pro Asn Ile Thr Val Thr Leu
    50                  55                  60 aaa aag ttt cca ctt gac act ttg atc cct gat gga aaa cgc ata atc   240
Lys Lys Phe Pro Leu Asp Thr Leu Ile Pro Asp Gly Lys Arg Ile Ile
65                  70                  75                  80 tgg gac agt aga aag ggc ttc atc ata tca aat gca acg tac aaa gaa   288
Trp Asp Ser Arg Lys Gly Phe Ile Ile Ser Asn Ala Thr Tyr Lys Glu
                85                  90                  95 ata ggg ctt ctg acc tgt gaa gca aca gtc aat ggg cat ttg tat aag   336
Ile Gly Leu Leu Thr Cys Glu Ala Thr Val Asn Gly His Leu Tyr Lys
            100                 105                 110 aca aac tat ctc aca cat cga caa acc aat aca atc ata gat gtc caa   384
Thr Asn Tyr Leu Thr His Arg Gln Thr Asn Thr Ile Ile Asp Val Gln
        115                 120                 125 ata agc aca cca cgc cca gtc aaa tta ctt aga ggc cat act ctt gtc   432
Ile Ser Thr Pro Arg Pro Val Lys Leu Leu Arg Gly His Thr Leu Val
```

-continued

|     |     |     |     |     | 130 |     |     |     | 135 |     |     |     |     | 140 |     |      |
|-----|-----|-----|-----|-----|-----|-----|-----|-----|-----|-----|-----|-----|-----|-----|-----|------|
| ctc | aat | tgt | act | gct | acc | act | ccc | ttg | aac | acg | aga | gtt | caa | atg | acc | 480  |
| Leu | Asn | Cys | Thr | Ala | Thr | Thr | Pro | Leu | Asn | Thr | Arg | Val | Gln | Met | Thr |      |
| 145 |     |     |     |     | 150 |     |     |     | 155 |     |     |     |     | 160 |     |      |

| tgg | agt | tac | cct | gat | gaa | att | gac | caa | agc | aat | tcc | cat | gcc | aac | ata | 528 |
| Trp | Ser | Tyr | Pro | Asp | Glu | Ile | Asp | Gln | Ser | Asn | Ser | His | Ala | Asn | Ile |     |
|     |     |     |     | 165 |     |     |     |     | 170 |     |     |     |     | 175 |     |     |

| ttc | tac | agt | gtt | ctt | act | att | gac | aaa | atg | cag | aac | aaa | gac | aaa | gga | 576 |
| Phe | Tyr | Ser | Val | Leu | Thr | Ile | Asp | Lys | Met | Gln | Asn | Lys | Asp | Lys | Gly |     |
|     |     |     | 180 |     |     |     |     | 185 |     |     |     |     | 190 |     |     |     |

| ctt | tat | act | tgt | cgt | gta | agg | agt | gga | cca | tca | ttc | aaa | tct | gtt | aac | 624 |
| Leu | Tyr | Thr | Cys | Arg | Val | Arg | Ser | Gly | Pro | Ser | Phe | Lys | Ser | Val | Asn |     |
|     |     | 195 |     |     |     |     | 200 |     |     |     |     | 205 |     |     |     |     |

| acc | tca | gtg | cat | ata | tat | gat | aaa | gca | ggc | ccg | ggc | gag | ccc | aaa | tct | 672 |
| Thr | Ser | Val | His | Ile | Tyr | Asp | Lys | Ala | Gly | Pro | Gly | Glu | Pro | Lys | Ser |     |
| 210 |     |     |     |     | 215 |     |     |     |     | 220 |     |     |     |     |     |     |

| tgt | gac | aaa | act | cac | aca | tgc | cca | ccg | tgc | cca | gca | cct | gaa | ctc | ctg | 720 |
| Cys | Asp | Lys | Thr | His | Thr | Cys | Pro | Pro | Cys | Pro | Ala | Pro | Glu | Leu | Leu |     |
| 225 |     |     |     |     | 230 |     |     |     |     | 235 |     |     |     |     | 240 |     |

| ggg | gga | ccg | tca | gtc | ttc | ctc | ttc | ccc | cca | aaa | ccc | aag | gac | acc | ctc | 768 |
| Gly | Gly | Pro | Ser | Val | Phe | Leu | Phe | Pro | Pro | Lys | Pro | Lys | Asp | Thr | Leu |     |
|     |     |     |     | 245 |     |     |     |     | 250 |     |     |     |     | 255 |     |     |

| atg | atc | tcc | cgg | acc | cct | gag | gtc | aca | tgc | gtg | gtg | gtg | gac | gtg | agc | 816 |
| Met | Ile | Ser | Arg | Thr | Pro | Glu | Val | Thr | Cys | Val | Val | Val | Asp | Val | Ser |     |
|     |     |     | 260 |     |     |     |     | 265 |     |     |     |     | 270 |     |     |     |

| cac | gaa | gac | cct | gag | gtc | aag | ttc | aac | tgg | tac | gtg | gac | ggc | gtg | gag | 864 |
| His | Glu | Asp | Pro | Glu | Val | Lys | Phe | Asn | Trp | Tyr | Val | Asp | Gly | Val | Glu |     |
|     |     | 275 |     |     |     |     | 280 |     |     |     |     | 285 |     |     |     |     |

| gtg | cat | aat | gcc | aag | aca | aag | ccg | cgg | gag | gag | cag | tac | aac | agc | acg | 912 |
| Val | His | Asn | Ala | Lys | Thr | Lys | Pro | Arg | Glu | Glu | Gln | Tyr | Asn | Ser | Thr |     |
| 290 |     |     |     |     | 295 |     |     |     |     | 300 |     |     |     |     |     |     |

| tac | cgt | gtg | gtc | agc | gtc | ctc | acc | gtc | ctg | cac | cag | gac | tgg | ctg | aat | 960 |
| Tyr | Arg | Val | Val | Ser | Val | Leu | Thr | Val | Leu | His | Gln | Asp | Trp | Leu | Asn |     |
| 305 |     |     |     |     | 310 |     |     |     |     | 315 |     |     |     |     | 320 |     |

| ggc | aag | gag | tac | aag | tgc | aag | gtc | tcc | aac | aaa | gcc | ctc | cca | gcc | ccc | 1008 |
| Gly | Lys | Glu | Tyr | Lys | Cys | Lys | Val | Ser | Asn | Lys | Ala | Leu | Pro | Ala | Pro |      |
|     |     |     |     | 325 |     |     |     |     | 330 |     |     |     |     | 335 |     |      |

| atc | gag | aaa | acc | atc | tcc | aaa | gcc | aaa | ggg | cag | ccc | cga | gaa | cca | cag | 1056 |
| Ile | Glu | Lys | Thr | Ile | Ser | Lys | Ala | Lys | Gly | Gln | Pro | Arg | Glu | Pro | Gln |      |
|     |     |     | 340 |     |     |     |     | 345 |     |     |     |     | 350 |     |     |      |

| gtg | tac | acc | ctg | ccc | cca | tcc | cgg | gat | gag | ctg | acc | aag | aac | cag | gtc | 1104 |
| Val | Tyr | Thr | Leu | Pro | Pro | Ser | Arg | Asp | Glu | Leu | Thr | Lys | Asn | Gln | Val |      |
|     |     | 355 |     |     |     |     | 360 |     |     |     |     | 365 |     |     |     |      |

| agc | ctg | acc | tgc | ctg | gtc | aaa | ggc | ttc | tat | ccc | agc | gac | atc | gcc | gtg | 1152 |
| Ser | Leu | Thr | Cys | Leu | Val | Lys | Gly | Phe | Tyr | Pro | Ser | Asp | Ile | Ala | Val |      |
| 370 |     |     |     |     | 375 |     |     |     |     | 380 |     |     |     |     |     |      |

| gag | tgg | gag | agc | aat | ggg | cag | ccg | gag | aac | aac | tac | aag | acc | acg | cct | 1200 |
| Glu | Trp | Glu | Ser | Asn | Gly | Gln | Pro | Glu | Asn | Asn | Tyr | Lys | Thr | Thr | Pro |      |
| 385 |     |     |     |     | 390 |     |     |     |     | 395 |     |     |     |     | 400 |      |

| ccc | gtg | ctg | gac | tcc | gac | ggc | tcc | ttc | ttc | ctc | tac | agc | aag | ctc | acc | 1248 |
| Pro | Val | Leu | Asp | Ser | Asp | Gly | Ser | Phe | Phe | Leu | Tyr | Ser | Lys | Leu | Thr |      |
|     |     |     |     | 405 |     |     |     |     | 410 |     |     |     |     | 415 |     |      |

| gtg | gac | aag | agc | agg | tgg | cag | cag | ggg | aac | gtc | ttc | tca | tgc | tcc | gtg | 1296 |
| Val | Asp | Lys | Ser | Arg | Trp | Gln | Gln | Gly | Asn | Val | Phe | Ser | Cys | Ser | Val |      |
|     |     |     | 420 |     |     |     |     | 425 |     |     |     |     | 430 |     |     |      |

| atg | cat | gag | gct | ctg | cac | aac | cac | tac | acg | cag | aag | agc | ctc | tcc | ctg | 1344 |
| Met | His | Glu | Ala | Leu | His | Asn | His | Tyr | Thr | Gln | Lys | Ser | Leu | Ser | Leu |      |
|     |     | 435 |     |     |     |     | 440 |     |     |     |     | 445 |     |     |     |      |

| tct | ccg | ggt | aaa | tga |     |     |     |     |     |     |     |     |     |     |     | 1359 |
| Ser | Pro | Gly | Lys |     |     |     |     |     |     |     |     |     |     |     |     |      |

450

<210> SEQ ID NO 6
<211> LENGTH: 452
<212> TYPE: PRT
<213> ORGANISM: Homo sapiens

<400> SEQUENCE: 6

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
                20                  25                  30

Met Tyr Ser Glu Ile Pro Glu Ile Ile His Met Thr Glu Gly Arg Glu
             35                  40                  45

Leu Val Ile Pro Cys Arg Val Thr Ser Pro Asn Ile Thr Val Thr Leu
         50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Gln
        115                 120                 125

Ile Ser Thr Pro Arg Pro Val Lys Leu Leu Arg Gly His Thr Leu Val
    130                 135                 140

Leu Asn Cys Thr Ala Thr Thr Pro Leu Asn Thr Arg Val Gln Met Thr
145                 150                 155                 160

Trp Ser Tyr Pro Asp Glu Ile Asp Gln Ser Asn Ser His Ala Asn Ile
                165                 170                 175

Phe Tyr Ser Val Leu Thr Ile Asp Lys Met Gln Asn Lys Asp Lys Gly
            180                 185                 190

Leu Tyr Thr Cys Arg Val Arg Ser Gly Pro Ser Phe Lys Ser Val Asn
        195                 200                 205

Thr Ser Val His Ile Tyr Asp Lys Ala Gly Pro Gly Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
```

```
                370               375                 380
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
        450

<210> SEQ ID NO 7
<211> LENGTH: 1389
<212> TYPE: DNA
<213> ORGANISM: Homo sapiens
<220> FEATURE:
<221> NAME/KEY: CDS
<222> LOCATION: (1)...(1386)

<400> SEQUENCE: 7 atg gtc agc tac tgg gac acc ggg gtc ctg ctg tgc gcg ctg ctc agc      48
Met Val Ser Tyr Trp Asp Thr Gly Val Leu Leu Cys Ala Leu Leu Ser
  1               5                  10                  15 tgt ctg ctt ctc aca gga tct agt tcc gga ggt aga cct ttc gta gag      96
Cys Leu Leu Leu Thr Gly Ser Ser Ser Gly Gly Arg Pro Phe Val Glu
                 20                  25                  30 atg tac agt gaa atc ccc gaa att ata cac atg act gaa gga agg gag     144
Met Tyr Ser Glu Ile Pro Glu Ile Ile His Met Thr Glu Gly Arg Glu
             35                  40                  45 ctc gtc att ccc tgc cgg gtt acg tca cct aac atc act gtt act tta     192
Leu Val Ile Pro Cys Arg Val Thr Ser Pro Asn Ile Thr Val Thr Leu
         50                  55                  60 aaa aag ttt cca ctt gac act ttg atc cct gat gga aaa cgc ata atc     240
Lys Lys Phe Pro Leu Asp Thr Leu Ile Pro Asp Gly Lys Arg Ile Ile
 65                  70                  75                  80 tgg gac agt aga aag ggc ttc atc ata tca aat gca acg tac aaa gaa     288
Trp Asp Ser Arg Lys Gly Phe Ile Ile Ser Asn Ala Thr Tyr Lys Glu
                 85                  90                  95 ata ggg ctt ctg acc tgt gaa gca aca gtc aat ggg cat ttg tat aag     336
Ile Gly Leu Leu Thr Cys Glu Ala Thr Val Asn Gly His Leu Tyr Lys
            100                 105                 110 aca aac tat ctc aca cat cga caa acc aat aca atc ata gat gtc caa     384
Thr Asn Tyr Leu Thr His Arg Gln Thr Asn Thr Ile Ile Asp Val Gln
        115                 120                 125 ata agc aca cca cgc cca gtc aaa tta ctt aga ggc cat act ctt gtc     432
Ile Ser Thr Pro Arg Pro Val Lys Leu Leu Arg Gly His Thr Leu Val
    130                 135                 140 ctc aat tgt act gct acc act ccc ttg aac acg aga gtt caa atg acc     480
Leu Asn Cys Thr Ala Thr Thr Pro Leu Asn Thr Arg Val Gln Met Thr
145                 150                 155                 160 tgg agt tac cct gat gaa aaa aat aag aga gct tcc gta agg cga cga     528
Trp Ser Tyr Pro Asp Glu Lys Asn Lys Arg Ala Ser Val Arg Arg Arg
                165                 170                 175 att gac caa agc aat tcc cat gcc aac ata ttc tac agt gtt ctt act     576
Ile Asp Gln Ser Asn Ser His Ala Asn Ile Phe Tyr Ser Val Leu Thr
            180                 185                 190 att gac aaa atg cag aac aaa gac aaa gga ctt tat act tgt cgt gta     624
Ile Asp Lys Met Gln Asn Lys Asp Lys Gly Leu Tyr Thr Cys Arg Val
        195                 200                 205
```

```
agg agt gga cca tca ttc aaa tct gtt aac acc tca gtg cat ata tat      672
Arg Ser Gly Pro Ser Phe Lys Ser Val Asn Thr Ser Val His Ile Tyr
    210                 215                 220 gat aaa gca ggc ccg ggc gag ccc aaa tct tgt gac aaa act cac aca      720
Asp Lys Ala Gly Pro Gly Glu Pro Lys Ser Cys Asp Lys Thr His Thr
225                 230                 235                 240 tgc cca ccg tgc cca gca cct gaa ctc ctg ggg gga ccg tca gtc ttc      768
Cys Pro Pro Cys Pro Ala Pro Glu Leu Leu Gly Gly Pro Ser Val Phe
                245                 250                 255 ctc ttc ccc cca aaa ccc aag gac acc ctc atg atc tcc cgg acc cct      816
Leu Phe Pro Pro Lys Pro Lys Asp Thr Leu Met Ile Ser Arg Thr Pro
                260                 265                 270 gag gtc aca tgc gtg gtg gtg gac gtg agc cac gaa gac cct gag gtc      864
Glu Val Thr Cys Val Val Val Asp Val Ser His Glu Asp Pro Glu Val
            275                 280                 285 aag ttc aac tgg tac gtg gac ggc gtg gag gtg cat aat gcc aag aca      912
Lys Phe Asn Trp Tyr Val Asp Gly Val Glu Val His Asn Ala Lys Thr
        290                 295                 300 aag ccg cgg gag gag cag tac aac agc acg tac cgt gtg gtc agc gtc      960
Lys Pro Arg Glu Glu Gln Tyr Asn Ser Thr Tyr Arg Val Val Ser Val
305                 310                 315                 320 ctc acc gtc ctg cac cag gac tgg ctg aat ggc aag gag tac aag tgc     1008
Leu Thr Val Leu His Gln Asp Trp Leu Asn Gly Lys Glu Tyr Lys Cys
                325                 330                 335 aag gtc tcc aac aaa gcc ctc cca gcc ccc atc gag aaa acc atc tcc     1056
Lys Val Ser Asn Lys Ala Leu Pro Ala Pro Ile Glu Lys Thr Ile Ser
                340                 345                 350 aaa gcc aaa ggg cag ccc cga gaa cca cag gtg tac acc ctg ccc cca     1104
Lys Ala Lys Gly Gln Pro Arg Glu Pro Gln Val Tyr Thr Leu Pro Pro
            355                 360                 365 tcc cgg gat gag ctg acc aag aac cag gtc agc ctg acc tgc ctg gtc     1152
Ser Arg Asp Glu Leu Thr Lys Asn Gln Val Ser Leu Thr Cys Leu Val
        370                 375                 380 aaa ggc ttc tat ccc agc gac atc gcc gtg gag tgg gag agc aat ggg     1200
Lys Gly Phe Tyr Pro Ser Asp Ile Ala Val Glu Trp Glu Ser Asn Gly
385                 390                 395                 400 cag ccg gag aac aac tac aag acc acg cct ccc gtg ctg gac tcc gac     1248
Gln Pro Glu Asn Asn Tyr Lys Thr Thr Pro Pro Val Leu Asp Ser Asp
                405                 410                 415 ggc tcc ttc ttc ctc tac agc aag ctc acc gtg gac aag agc agg tgg     1296
Gly Ser Phe Phe Leu Tyr Ser Lys Leu Thr Val Asp Lys Ser Arg Trp
                420                 425                 430 cag cag ggg aac gtc ttc tca tgc tcc gtg atg cat gag gct ctg cac     1344
Gln Gln Gly Asn Val Phe Ser Cys Ser Val Met His Glu Ala Leu His
            435                 440                 445 aac cac tac acg cag aag agc ctc tcc ctg tct ccg ggt aaa              1386
Asn His Tyr Thr Gln Lys Ser Leu Ser Leu Ser Pro Gly Lys
        450                 455                 460 tga                                                                  1389

<210> SEQ ID NO 8
<211> LENGTH: 462
<212> TYPE: PRT
<213> ORGANISM: Homo sapiens

<400> SEQUENCE: 8

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30
```

```
Met Tyr Ser Glu Ile Pro Glu Ile His Met Thr Glu Gly Arg Glu
            35                  40                  45

Leu Val Ile Pro Cys Arg Val Thr Ser Pro Asn Ile Thr Val Thr Leu
 50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
                100                 105                 110

Thr Asn Tyr Leu Thr His Arg Gln Thr Asn Thr Ile Ile Asp Val Gln
            115                 120                 125

Ile Ser Thr Pro Arg Pro Val Lys Leu Leu Arg Gly His Thr Leu Val
130                 135                 140

Leu Asn Cys Thr Ala Thr Thr Pro Leu Asn Thr Arg Val Gln Met Thr
145                 150                 155                 160

Trp Ser Tyr Pro Asp Glu Lys Asn Lys Arg Ala Ser Val Arg Arg Arg
                165                 170                 175

Ile Asp Gln Ser Asn Ser His Ala Asn Ile Phe Tyr Ser Val Leu Thr
                180                 185                 190

Ile Asp Lys Met Gln Asn Lys Asp Lys Gly Leu Tyr Thr Cys Arg Val
                195                 200                 205

Arg Ser Gly Pro Ser Phe Lys Ser Val Asn Thr Ser Val His Ile Tyr
210                 215                 220

Asp Lys Ala Gly Pro Gly Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
                355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460
```

-continued

```
<210> SEQ ID NO 9
<211> LENGTH: 1704
<212> TYPE: DNA
<213> ORGANISM: Homo sapiens
<220> FEATURE:
<221> NAME/KEY: CDS
<222> LOCATION: (1)...(1701)

<400> SEQUENCE: 9 atg gtc agc tac tgg gac acc ggg gtc ctg ctg tgc gcg ctg ctc agc      48
Met Val Ser Tyr Trp Asp Thr Gly Val Leu Leu Cys Ala Leu Leu Ser
1               5                   10                  15 tgt ctg ctt ctc aca gga tct agt tca ggt tca aaa tta aaa gat cct      96
Cys Leu Leu Leu Thr Gly Ser Ser Ser Gly Ser Lys Leu Lys Asp Pro
            20                  25                  30 gaa ctg agt tta aaa ggc acc cag cac atc atg caa gca ggc cag aca     144
Glu Leu Ser Leu Lys Gly Thr Gln His Ile Met Gln Ala Gly Gln Thr
        35                  40                  45 ctg cat ctc caa tgc agg ggg gaa gca gcc cat aaa tgg tct ttg cct     192
Leu His Leu Gln Cys Arg Gly Glu Ala Ala His Lys Trp Ser Leu Pro
    50                  55                  60 gaa atg gtg agt aag gaa agc gaa agg ctg agc ata act aaa tct gcc     240
Glu Met Val Ser Lys Glu Ser Glu Arg Leu Ser Ile Thr Lys Ser Ala
65                  70                  75                  80 tgt gga aga aat ggc aaa caa ttc tgc agt act tta acc ttg aac aca     288
Cys Gly Arg Asn Gly Lys Gln Phe Cys Ser Thr Leu Thr Leu Asn Thr
                85                  90                  95 gct caa gca aac cac act ggc ttc tac agc tgc aaa tat cta gct gta     336
Ala Gln Ala Asn His Thr Gly Phe Tyr Ser Cys Lys Tyr Leu Ala Val
            100                 105                 110 cct act tca aag aag aag gaa aca gaa tct gca atc tat ata ttt att     384
Pro Thr Ser Lys Lys Lys Glu Thr Glu Ser Ala Ile Tyr Ile Phe Ile
        115                 120                 125 agt gat aca ggt aga cct ttc gta gag atg tac agt gaa atc ccc gaa     432
Ser Asp Thr Gly Arg Pro Phe Val Glu Met Tyr Ser Glu Ile Pro Glu
    130                 135                 140 att ata cac atg act gaa gga agg gag ctc gtc att ccc tgc cgg gtt     480
Ile Ile His Met Thr Glu Gly Arg Glu Leu Val Ile Pro Cys Arg Val
145                 150                 155                 160 acg tca cct aac atc act gtt act tta aaa aag ttt cca ctt gac act     528
Thr Ser Pro Asn Ile Thr Val Thr Leu Lys Lys Phe Pro Leu Asp Thr
                165                 170                 175 ttg atc cct gat gga aaa cgc ata atc tgg gac agt aga aag ggc ttc     576
Leu Ile Pro Asp Gly Lys Arg Ile Ile Trp Asp Ser Arg Lys Gly Phe
            180                 185                 190 atc ata tca aat gca acg tac aaa gaa ata ggg ctt ctg acc tgt gaa     624
Ile Ile Ser Asn Ala Thr Tyr Lys Glu Ile Gly Leu Leu Thr Cys Glu
        195                 200                 205 gca aca gtc aat ggg cat ttg tat aag aca aac tat ctc aca cat cga     672
Ala Thr Val Asn Gly His Leu Tyr Lys Thr Asn Tyr Leu Thr His Arg
    210                 215                 220 caa acc aat aca atc ata gat gtc caa ata agc aca cca cgc cca gtc     720
Gln Thr Asn Thr Ile Ile Asp Val Gln Ile Ser Thr Pro Arg Pro Val
225                 230                 235                 240 aaa tta ctt aga ggc cat act ctt gtc ctc aat tgt act gct acc act     768
Lys Leu Leu Arg Gly His Thr Leu Val Leu Asn Cys Thr Ala Thr Thr
                245                 250                 255 ccc ttg aac acg aga gtt caa atg acc tgg agt tac cct gat gaa aaa     816
Pro Leu Asn Thr Arg Val Gln Met Thr Trp Ser Tyr Pro Asp Glu Lys
            260                 265                 270
```

| | | |
|---|---|---|
| aat aag aac gct tcc gta agg cga cga att gac caa agc aat tcc cat<br>Asn Lys Asn Ala Ser Val Arg Arg Arg Ile Asp Gln Ser Asn Ser His<br>    275                              280                          285 | 864 |
| gcc aac ata ttc tac agt gtt ctt act att gac aaa atg cag aac aaa<br>Ala Asn Ile Phe Tyr Ser Val Leu Thr Ile Asp Lys Met Gln Asn Lys<br>290                          295                          300 | 912 |
| gac aaa gga ctt tat act tgt cgt gta agg agt gga cca tca ttc aaa<br>Asp Lys Gly Leu Tyr Thr Cys Arg Val Arg Ser Gly Pro Ser Phe Lys<br>305                          310                          315                320 | 960 |
| tct gtt aac acc tca gtg cat ata tat gat aaa gca ggc ccg ggc gag<br>Ser Val Asn Thr Ser Val His Ile Tyr Asp Lys Ala Gly Pro Gly Glu<br>                        325                          330                          335 | 1008 |
| ccc aaa tct tgt gac aaa act cac aca tgc cca ccg tgc cca gca cct<br>Pro Lys Ser Cys Asp Lys Thr His Thr Cys Pro Pro Cys Pro Ala Pro<br>                        340                          345                          350 | 1056 |
| gaa ctc ctg ggg gga ccg tca gtc ttc ctc ttc ccc cca aaa ccc aag<br>Glu Leu Leu Gly Gly Pro Ser Val Phe Leu Phe Pro Pro Lys Pro Lys<br>                        355                          360                          365 | 1104 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>        370                        375                          380 | 1152 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>385                          390                          395                400 | 1200 |
| ggc gtg gag gtg cat aat gcc aag aca aag ccg cgg gag gag cag tac<br>Gly Val Glu Val His Asn Ala Lys Thr Lys Pro Arg Glu Glu Gln Tyr<br>                        405                          410                          415 | 1248 |
| aac agc acg tac cgt gtg gtc agc gtc ctc acc gtc ctg cac cag gac<br>Asn Ser Thr Tyr Arg Val Val Ser Val Leu Thr Val Leu His Gln Asp<br>                    420                          425                          430 | 1296 |
| tgg ctg aat ggc aag gag tac aag tgc aag gtc tcc aac aaa gcc ctc<br>Trp Leu Asn Gly Lys Glu Tyr Lys Cys Lys Val Ser Asn Lys Ala Leu<br>                435                          440                          445 | 1344 |
| cca gcc ccc atc gag aaa acc atc tcc aaa gcc aaa ggg cag ccc cga<br>Pro Ala Pro Ile Glu Lys Thr Ile Ser Lys Ala Lys Gly Gln Pro Arg<br>450                          455                          460 | 1392 |
| gaa cca cag gtg tac acc ctg ccc cca tcc cgg gat gag ctg acc aag<br>Glu Pro Gln Val Tyr Thr Leu Pro Pro Ser Arg Asp Glu Leu Thr Lys<br>465                          470                          475                480 | 1440 |
| aac cag gtc agc ctg acc tgc ctg gtc aaa ggc ttc tat ccc agc gac<br>Asn Gln Val Ser Leu Thr Cys Leu Val Lys Gly Phe Tyr Pro Ser Asp<br>                        485                          490                          495 | 1488 |
| atc gcc gtg gag tgg gag agc aat ggg cag ccg gag aac aac tac aag<br>Ile Ala Val Glu Trp Glu Ser Asn Gly Gln Pro Glu Asn Asn Tyr Lys<br>                          500                          505                        510 | 1536 |
| acc acg cct ccc gtg ctg gac tcc gac ggc tcc ttc ttc ctc tac agc<br>Thr Thr Pro Pro Val Leu Asp Ser Asp Gly Ser Phe Phe Leu Tyr Ser<br>              515                          520                          525 | 1584 |
| aag ctc acc gtg gac aag agc agg tgg cag cag ggg aac gtc ttc tca<br>Lys Leu Thr Val Asp Lys Ser Arg Trp Gln Gln Gly Asn Val Phe Ser<br>              530                          535                          540 | 1632 |
| tgc tcc gtg atg cat gag gct ctg cac aac cac tac acg cag aag agc<br>Cys Ser Val Met His Glu Ala Leu His Asn His Tyr Thr Gln Lys Ser<br>545                          550                          555                560 | 1680 |
| ctc tcc ctg tct ccg ggt aaa tga<br>Leu Ser Leu Ser Pro Gly Lys<br>                        565 | 1704 |

<210> SEQ ID NO 10
<211> LENGTH: 567
<212> TYPE: PRT

<213> ORGANISM: Homo sapiens

<400> SEQUENCE: 10

```
Met Val Ser Tyr Trp Asp Thr Gly Val Leu Leu Cys Ala Leu Leu Ser
  1               5                  10                  15
Cys Leu Leu Leu Thr Gly Ser Ser Ser Gly Ser Lys Leu Lys Asp Pro
             20                  25                  30
Glu Leu Ser Leu Lys Gly Thr Gln His Ile Met Gln Ala Gly Gln Thr
         35                  40                  45
Leu His Leu Gln Cys Arg Gly Glu Ala Ala His Lys Trp Ser Leu Pro
     50                  55                  60
Glu Met Val Ser Lys Glu Ser Glu Arg Leu Ser Ile Thr Lys Ser Ala
 65                  70                  75                  80
Cys Gly Arg Asn Gly Lys Gln Phe Cys Ser Thr Leu Thr Leu Asn Thr
                 85                  90                  95
Ala Gln Ala Asn His Thr Gly Phe Tyr Ser Cys Lys Tyr Leu Ala Val
            100                 105                 110
Pro Thr Ser Lys Lys Lys Glu Thr Glu Ser Ala Ile Tyr Ile Phe Ile
        115                 120                 125
Ser Asp Thr Gly Arg Pro Phe Val Glu Met Tyr Ser Glu Ile Pro Glu
    130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
        195                 200                 205
Ala Thr Val Asn Gly His Leu Tyr Lys Thr Asn Tyr Leu Thr His Arg
    210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Asn Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Gly Pro Gly Glu
                325                 330                 335
Pro Lys Ser Cys Asp Lys Thr His Thr Cys Pro Pro Cys Pro Ala Pro
            340                 345                 350
Glu Leu Leu Gly Gly Pro Ser Val Phe Leu Phe Pro Pro Lys Pro Lys
        355                 360                 365
Asp Thr Leu Met Ile Ser Arg Thr Pro Glu Val Thr Cys Val Val Val
    370                 375                 380
Asp Val Ser His Glu Asp Pro Glu Val Lys Phe Asn Trp Tyr Val Asp
385                 390                 395                 400
Gly Val Glu Val His Asn Ala Lys Thr Lys Pro Arg Glu Glu Gln Tyr
```

```
                       405                 410                 415
Asn Ser Thr Tyr Arg Val Val Ser Val Leu Thr Val Leu His Gln Asp
                420                 425                 430

Trp Leu Asn Gly Lys Glu Tyr Lys Cys Lys Val Ser Asn Lys Ala Leu
            435                 440                 445

Pro Ala Pro Ile Glu Lys Thr Ile Ser Lys Ala Lys Gly Gln Pro Arg
450                 455                 460

Glu Pro Gln Val Tyr Thr Leu Pro Pro Ser Arg Asp Glu Leu Thr Lys
465                 470                 475                 480

Asn Gln Val Ser Leu Thr Cys Leu Val Lys Gly Phe Tyr Pro Ser Asp
                485                 490                 495

Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
        515                 520                 525

Lys Leu Thr Val Asp Lys Ser Arg Trp Gln Gln Gly Asn Val Phe Ser
    530                 535                 540

Cys Ser Val Met His Glu Ala Leu His Asn His Tyr Thr Gln Lys Ser
545                 550                 555                 560

Leu Ser Leu Ser Pro Gly Lys
                565

<210> SEQ ID NO 11
<211> LENGTH: 1453
<212> TYPE: DNA
<213> ORGANISM: Homo sapiens
<220> FEATURE:
<221> NAME/KEY: CDS
<222> LOCATION: (69)...(1442)

<400> SEQUENCE: 11
aagcttgggc tgcaggtcga tcgactctag aggatcgatc cccgggcgag ctcgaattcg      60 caaccacc atg gtc agc tac tgg gac acc ggg gtc ctg ctg tgc gcg ctg     110
         Met Val Ser Tyr Trp Asp Thr Gly Val Leu Leu Cys Ala Leu
           1               5                  10 ctc agc tgt ctg ctt ctc aca gga tct agt tcc gga ggt aga cct ttc     158
Leu Ser Cys Leu Leu Leu Thr Gly Ser Ser Ser Gly Gly Arg Pro Phe
 15                  20                  25                  30 gta gag atg tac agt gaa atc ccc gaa att ata cac atg act gaa gga     206
Val Glu Met Tyr Ser Glu Ile Pro Glu Ile Ile His Met Thr Glu Gly
                 35                  40                  45 agg gag ctc gtc att ccc tgc cgg gtt acg tca cct aac atc act gtt     254
Arg Glu Leu Val Ile Pro Cys Arg Val Thr Ser Pro Asn Ile Thr Val
             50                  55                  60 act tta aaa aag ttt cca ctt gac act ttg atc cct gat gga aaa cgc     302
Thr Leu Lys Lys Phe Pro Leu Asp Thr Leu Ile Pro Asp Gly Lys Arg
         65                  70                  75 ata atc tgg gac agt aga aag ggc ttc atc ata tca aat gca acg tac     350
Ile Ile Trp Asp Ser Arg Lys Gly Phe Ile Ile Ser Asn Ala Thr Tyr
     80                  85                  90 aaa gaa ata ggg ctt ctg acc tgt gaa gca aca gtc aat ggg cat ttg     398
Lys Glu Ile Gly Leu Leu Thr Cys Glu Ala Thr Val Asn Gly His Leu
 95                 100                 105                 110 tat aag aca aac tat ctc aca cat cga caa acc aat aca atc ata gat     446
Tyr Lys Thr Asn Tyr Leu Thr His Arg Gln Thr Asn Thr Ile Ile Asp
                115                 120                 125 gtg gtt ctg agt ccg tct cat gga att gaa cta tct gtt gga gaa aag     494
Val Val Leu Ser Pro Ser His Gly Ile Glu Leu Ser Val Gly Glu Lys
            130                 135                 140
```

```
                                        -continued ctt gtc tta aat tgt aca gca aga act gaa cta aat gtg ggg att gac        542
Leu Val Leu Asn Cys Thr Ala Arg Thr Glu Leu Asn Val Gly Ile Asp
            145                 150                 155 ttc aac tgg gaa tac cct tct tcg aag cat cag cat aag aaa ctt gta        590
Phe Asn Trp Glu Tyr Pro Ser Ser Lys His Gln His Lys Lys Leu Val
160                 165                 170 aac cga gac cta aaa acc cag tct ggg agt gag atg aag aaa ttt ttg        638
Asn Arg Asp Leu Lys Thr Gln Ser Gly Ser Glu Met Lys Lys Phe Leu
175                 180                 185                 190 agc acc tta act ata gat ggt gta acc cgg agt gac caa gga ttg tac        686
Ser Thr Leu Thr Ile Asp Gly Val Thr Arg Ser Asp Gln Gly Leu Tyr
                195                 200                 205 acc tgt gca gca tcc agt ggg ctg atg acc aag aag aac agc aca ttt        734
Thr Cys Ala Ala Ser Ser Gly Leu Met Thr Lys Lys Asn Ser Thr Phe
            210                 215                 220 gtc agg gtc cat gaa aag ggc ccg ggc gac aaa act cac aca tgc cca        782
Val Arg Val His Glu Lys Gly Pro Gly Asp Lys Thr His Thr Cys Pro
        225                 230                 235 ccg tgc cca gca cct gaa ctc ctg ggg gga ccg tca gtc ttc ctc ttc        830
Pro Cys Pro Ala Pro Glu Leu Leu Gly Gly Pro Ser Val Phe Leu Phe
240                 245                 250 ccc cca aaa ccc aag gac acc ctc atg atc tcc cgg acc cct gag gtc        878
Pro Pro Lys Pro Lys Asp Thr Leu Met Ile Ser Arg Thr Pro Glu Val
255                 260                 265                 270 aca tgc gtg gtg gtg gac gtg agc cac gaa gac cct gag gtc aag ttc        926
Thr Cys Val Val Val Asp Val Ser His Glu Asp Pro Glu Val Lys Phe
                275                 280                 285 aac tgg tac gtg gac ggc gtg gag gtg cat aat gcc aag aca aag ccg        974
Asn Trp Tyr Val Asp Gly Val Glu Val His Asn Ala Lys Thr Lys Pro
            290                 295                 300 cgg gag gag cag tac aac agc acg tac cgt gtg gtc agc gtc ctc acc       1022
Arg Glu Glu Gln Tyr Asn Ser Thr Tyr Arg Val Val Ser Val Leu Thr
        305                 310                 315 gtc ctg cac cag gac tgg ctg aat ggc aag gag tac aag tgc aag gtc       1070
Val Leu His Gln Asp Trp Leu Asn Gly Lys Glu Tyr Lys Cys Lys Val
320                 325                 330 tcc aac aaa gcc ctc cca gcc ccc atc gag aaa acc atc tcc aaa gcc       1118
Ser Asn Lys Ala Leu Pro Ala Pro Ile Glu Lys Thr Ile Ser Lys Ala
335                 340                 345                 350 aaa ggg cag ccc cga gaa cca cag gtg tac acc ctg ccc cca tcc cgg       1166
Lys Gly Gln Pro Arg Glu Pro Gln Val Tyr Thr Leu Pro Pro Ser Arg
                355                 360                 365 gat gag ctg acc aag aac cag gtc agc ctg acc tgc ctg gtc aaa ggc       1214
Asp Glu Leu Thr Lys Asn Gln Val Ser Leu Thr Cys Leu Val Lys Gly
            370                 375                 380 ttc tat ccc agc gac atc gcc gtg gag tgg gag agc aat ggg cag ccg       1262
Phe Tyr Pro Ser Asp Ile Ala Val Glu Trp Glu Ser Asn Gly Gln Pro
        385                 390                 395 gag aac aac tac aag acc acg cct ccc gtg ctg gac tcc gac ggc tcc       1310
Glu Asn Asn Tyr Lys Thr Thr Pro Pro Val Leu Asp Ser Asp Gly Ser
400                 405                 410 ttc ttc ctc tat agc aag ctc acc gtg gac aag agc agg tgg cag cag       1358
Phe Phe Leu Tyr Ser Lys Leu Thr Val Asp Lys Ser Arg Trp Gln Gln
415                 420                 425                 430 ggg aac gtc ttc tca tgc tcc gtg atg cat gag gct ctg cac aac cac       1406
Gly Asn Val Phe Ser Cys Ser Val Met His Glu Ala Leu His Asn His
                435                 440                 445 tac acg cag aag agc ctc tcc ctg tct ccg ggt aaa tgagcggccg            1452
Tyr Thr Gln Lys Ser Leu Ser Leu Ser Pro Gly Lys
            450                 455
```

| | | | | | | | | | | | | |
|---|---|---|---|---|---|---|---|---|---|---|---|---|
| c | | | | | | | | | | | | 1453 |

<210> SEQ ID NO 12
<211> LENGTH: 458
<212> TYPE: PRT
<213> ORGANISM: Homo sapiens

<400> SEQUENCE: 12

Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Gly Pro Gly Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

-continued

```
Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 13
<211> LENGTH: 1444
<212> TYPE: DNA
<213> ORGANISM: Homo sapiens
<220> FEATURE:
<221> NAME/KEY: CDS
<222> LOCATION: (69)...(1433)

<400> SEQUENCE: 13

```
aagcttgggc tgcaggtcga tcgactctag aggatcgatc cccgggcgag ctcgaattcg     60 caaccacc atg gtc agc tac tgg gac acc ggg gtc ctg ctg tgc gcg ctg    110
         Met Val Ser Tyr Trp Asp Thr Gly Val Leu Leu Cys Ala Leu
           1               5                  10 ctc agc tgt ctg ctt ctc aca gga tct agt tcc gga ggt aga cct ttc    158
Leu Ser Cys Leu Leu Leu Thr Gly Ser Ser Ser Gly Gly Arg Pro Phe
 15                  20                  25                  30 gta gag atg tac agt gaa atc ccc gaa att ata cac atg act gaa gga    206
Val Glu Met Tyr Ser Glu Ile Pro Glu Ile Ile His Met Thr Glu Gly
                 35                  40                  45 agg gag ctc gtc att ccc tgc cgg gtt acg tca cct aac atc act gtt    254
Arg Glu Leu Val Ile Pro Cys Arg Val Thr Ser Pro Asn Ile Thr Val
             50                  55                  60 act tta aaa aag ttt cca ctt gac act ttg atc cct gat gga aaa cgc    302
Thr Leu Lys Lys Phe Pro Leu Asp Thr Leu Ile Pro Asp Gly Lys Arg
         65                  70                  75 ata atc tgg gac agt aga aag ggc ttc atc ata tca aat gca acg tac    350
Ile Ile Trp Asp Ser Arg Lys Gly Phe Ile Ile Ser Asn Ala Thr Tyr
     80                  85                  90 aaa gaa ata ggg ctt ctg acc tgt gaa gca aca gtc aat ggg cat ttg    398
Lys Glu Ile Gly Leu Leu Thr Cys Glu Ala Thr Val Asn Gly His Leu
 95                 100                 105                 110 tat aag aca aac tat ctc aca cat cga caa acc aat aca atc ata gat    446
Tyr Lys Thr Asn Tyr Leu Thr His Arg Gln Thr Asn Thr Ile Ile Asp
                115                 120                 125 atc cag ctg ttg ccc agg aag tcg ctg gag ctg ctg gta ggg gag aag    494
Ile Gln Leu Leu Pro Arg Lys Ser Leu Glu Leu Leu Val Gly Glu Lys
            130                 135                 140 ctg gtc ctc aac tgc acc gtg tgg gct gag ttt aac tca ggt gtc acc    542
Leu Val Leu Asn Cys Thr Val Trp Ala Glu Phe Asn Ser Gly Val Thr
        145                 150                 155 ttt gac tgg gac tac cca ggg aag cag gca gag cgg ggt aag tgg gtg    590
Phe Asp Trp Asp Tyr Pro Gly Lys Gln Ala Glu Arg Gly Lys Trp Val
    160                 165                 170 ccc gag cga cgc tcc caa cag acc cac aca gaa ctc tcc agc atc ctg    638
Pro Glu Arg Arg Ser Gln Gln Thr His Thr Glu Leu Ser Ser Ile Leu
175                 180                 185                 190 acc atc cac aac gtc agc cag cac gac ctg ggc tcg tat gtg tgc aag    686
```

```
Thr Ile His Asn Val Ser Gln His Asp Leu Gly Ser Tyr Val Cys Lys
                195                 200                 205 gcc aac aac ggc atc cag cga ttt cgg gag agc acc gag gtc att gtg      734
Ala Asn Asn Gly Ile Gln Arg Phe Arg Glu Ser Thr Glu Val Ile Val
            210                 215                 220 cat gaa aat ggc ccg ggc gac aaa act cac aca tgc cca ccg tgc cca      782
His Glu Asn Gly Pro Gly Asp Lys Thr His Thr Cys Pro Pro Cys Pro
225                 230                 235 gca cct gaa ctc ctg ggg gga ccg tca gtc ttc ctc ttc ccc cca aaa      830
Ala Pro Glu Leu Leu Gly Gly Pro Ser Val Phe Leu Phe Pro Pro Lys
        240                 245                 250 ccc aag gac acc ctc atg atc tcc cgg acc cct gag gtc aca tgc gtg      878
Pro Lys Asp Thr Leu Met Ile Ser Arg Thr Pro Glu Val Thr Cys Val
255                 260                 265                 270 gtg gtg gac gtg agc cac gaa gac cct gag gtc aag ttc aac tgg tac      926
Val Val Asp Val Ser His Glu Asp Pro Glu Val Lys Phe Asn Trp Tyr
                275                 280                 285 gtg gac ggc gtg gag gtg cat aat gcc aag aca aag ccg cgg gag gag      974
Val Asp Gly Val Glu Val His Asn Ala Lys Thr Lys Pro Arg Glu Glu
            290                 295                 300 cag tac aac agc acg tac cgt gtg gtc agc gtc ctc acc gtc ctg cac     1022
Gln Tyr Asn Ser Thr Tyr Arg Val Val Ser Val Leu Thr Val Leu His
305                 310                 315 cag gac tgg ctg aat ggc aag gag tac aag tgc aag gtc tcc aac aaa     1070
Gln Asp Trp Leu Asn Gly Lys Glu Tyr Lys Cys Lys Val Ser Asn Lys
        320                 325                 330 gcc ctc cca gcc ccc atc gag aaa acc atc tcc aaa gcc aaa ggg cag     1118
Ala Leu Pro Ala Pro Ile Glu Lys Thr Ile Ser Lys Ala Lys Gly Gln
335                 340                 345                 350 ccc cga gaa cca cag gtg tac acc ctg ccc cca tcc cgg gat gag ctg     1166
Pro Arg Glu Pro Gln Val Tyr Thr Leu Pro Pro Ser Arg Asp Glu Leu
                355                 360                 365 acc aag aac cag gtc agc ctg acc tgc ctg gtc aaa ggc ttc tat ccc     1214
Thr Lys Asn Gln Val Ser Leu Thr Cys Leu Val Lys Gly Phe Tyr Pro
            370                 375                 380 agc gac atc gcc gtg gag tgg gag agc aat ggg cag ccg gag aac aac     1262
Ser Asp Ile Ala Val Glu Trp Glu Ser Asn Gly Gln Pro Glu Asn Asn
385                 390                 395 tac aag acc acg cct ccc gtg ctg gac tcc gac ggc tcc ttc ttc ctc     1310
Tyr Lys Thr Thr Pro Pro Val Leu Asp Ser Asp Gly Ser Phe Phe Leu
        400                 405                 410 tat agc aag ctc acc gtg gac aag agc agg tgg cag cag ggg aac gtc     1358
Tyr Ser Lys Leu Thr Val Asp Lys Ser Arg Trp Gln Gln Gly Asn Val
415                 420                 425                 430 ttc tca tgc tcc gtg atg cat gag gct ctg cac aac cac tac acg cag     1406
Phe Ser Cys Ser Val Met His Glu Ala Leu His Asn His Tyr Thr Gln
                435                 440                 445 aag agc ctc tcc ctg tct ccg ggt aaa tgagcggccg c                     1444
Lys Ser Leu Ser Leu Ser Pro Gly Lys
            450                 455

<210> SEQ ID NO 14
<211> LENGTH: 455
<212> TYPE: PRT
<213> ORGANISM: Homo sapiens

<400> SEQUENCE: 14

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30
```

```
Met Tyr Ser Glu Ile Pro Glu Ile His Met Thr Glu Gly Arg Glu
         35                  40                  45
Leu Val Ile Pro Cys Arg Val Thr Ser Pro Asn Ile Thr Val Thr Leu
 50                  55                  60
Lys Lys Phe Pro Leu Asp Thr Leu Ile Pro Asp Gly Lys Arg Ile Ile
 65                  70                  75                  80
Trp Asp Ser Arg Lys Gly Phe Ile Ile Ser Asn Ala Thr Tyr Lys Glu
                 85                  90                  95
Ile Gly Leu Leu Thr Cys Glu Ala Thr Val Asn Gly His Leu Tyr Lys
                100                 105                 110
Thr Asn Tyr Leu Thr His Arg Gln Thr Asn Thr Ile Ile Asp Ile Gln
            115                 120                 125
Leu Leu Pro Arg Lys Ser Leu Glu Leu Leu Val Gly Glu Lys Leu Val
        130                 135                 140
Leu Asn Cys Thr Val Trp Ala Glu Phe Asn Ser Gly Val Thr Phe Asp
145                 150                 155                 160
Trp Asp Tyr Pro Gly Lys Gln Ala Glu Arg Gly Lys Trp Val Pro Glu
                165                 170                 175
Arg Arg Ser Gln Gln Thr His Thr Glu Leu Ser Ser Ile Leu Thr Ile
            180                 185                 190
His Asn Val Ser Gln His Asp Leu Gly Ser Tyr Val Cys Lys Ala Asn
        195                 200                 205
Asn Gly Ile Gln Arg Phe Arg Glu Ser Thr Glu Val Ile Val His Glu
210                 215                 220
Asn Gly Pro Gly Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
            260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro Gly Lys
```

<210> SEQ ID NO 15
<211> LENGTH: 1377
<212> TYPE: DNA
<213> ORGANISM: Homo sapiens
<220> FEATURE:
<221> NAME/KEY: CDS
<222> LOCATION: (1)...(1374)

<400> SEQUENCE: 15

| | | | | | | | | | | | | | | | | |
|---|---|---|---|---|---|---|---|---|---|---|---|---|---|---|---|---|
| atg | gtc | agc | tac | tgg | gac | acc | ggg | gtc | ctg | ctg | tgc | gcg | ctg | ctc | agc | 48 |
| Met | Val | Ser | Tyr | Trp | Asp | Thr | Gly | Val | Leu | Leu | Cys | Ala | Leu | Leu | Ser | |
| 1 | | | | 5 | | | | | 10 | | | | | 15 | | |
| tgt | ctg | ctt | ctc | aca | gga | tct | agt | tcc | gga | agt | gat | acc | ggt | aga | cct | 96 |
| Cys | Leu | Leu | Leu | Thr | Gly | Ser | Ser | Ser | Gly | Ser | Asp | Thr | Gly | Arg | Pro | |
| | | | 20 | | | | | 25 | | | | | 30 | | | |
| ttc | gta | gag | atg | tac | agt | gaa | atc | ccc | gaa | att | ata | cac | atg | act | gaa | 144 |
| Phe | Val | Glu | Met | Tyr | Ser | Glu | Ile | Pro | Glu | Ile | Ile | His | Met | Thr | Glu | |
| | | 35 | | | | | 40 | | | | | 45 | | | | |
| gga | agg | gag | ctc | gtc | att | ccc | tgc | cgg | gtt | acg | tca | cct | aac | atc | act | 192 |
| Gly | Arg | Glu | Leu | Val | Ile | Pro | Cys | Arg | Val | Thr | Ser | Pro | Asn | Ile | Thr | |
| | 50 | | | | | 55 | | | | | 60 | | | | | |
| gtt | act | tta | aaa | aag | ttt | cca | ctt | gac | act | ttg | atc | cct | gat | gga | aaa | 240 |
| Val | Thr | Leu | Lys | Lys | Phe | Pro | Leu | Asp | Thr | Leu | Ile | Pro | Asp | Gly | Lys | |
| 65 | | | | | 70 | | | | | 75 | | | | | 80 | |
| cgc | ata | atc | tgg | gac | agt | aga | aag | ggc | ttc | atc | ata | tca | aat | gca | acg | 288 |
| Arg | Ile | Ile | Trp | Asp | Ser | Arg | Lys | Gly | Phe | Ile | Ile | Ser | Asn | Ala | Thr | |
| | | | | 85 | | | | | 90 | | | | | 95 | | |
| tac | aaa | gaa | ata | ggg | ctt | ctg | acc | tgt | gaa | gca | aca | gtc | aat | ggg | cat | 336 |
| Tyr | Lys | Glu | Ile | Gly | Leu | Leu | Thr | Cys | Glu | Ala | Thr | Val | Asn | Gly | His | |
| | | | 100 | | | | | 105 | | | | | 110 | | | |
| ttg | tat | aag | aca | aac | tat | ctc | aca | cat | cga | caa | acc | aat | aca | atc | ata | 384 |
| Leu | Tyr | Lys | Thr | Asn | Tyr | Leu | Thr | His | Arg | Gln | Thr | Asn | Thr | Ile | Ile | |
| | | 115 | | | | | 120 | | | | | 125 | | | | |
| gat | gtg | gtt | ctg | agt | ccg | tct | cat | gga | att | gaa | cta | tct | gtt | gga | gaa | 432 |
| Asp | Val | Val | Leu | Ser | Pro | Ser | His | Gly | Ile | Glu | Leu | Ser | Val | Gly | Glu | |
| | 130 | | | | | 135 | | | | | 140 | | | | | |
| aag | ctt | gtc | tta | aat | tgt | aca | gca | aga | act | gaa | cta | aat | gtg | ggg | att | 480 |
| Lys | Leu | Val | Leu | Asn | Cys | Thr | Ala | Arg | Thr | Glu | Leu | Asn | Val | Gly | Ile | |
| 145 | | | | | 150 | | | | | 155 | | | | | 160 | |
| gac | ttc | aac | tgg | gaa | tac | cct | tct | tcg | aag | cat | cag | cat | aag | aaa | ctt | 528 |
| Asp | Phe | Asn | Trp | Glu | Tyr | Pro | Ser | Ser | Lys | His | Gln | His | Lys | Lys | Leu | |
| | | | | 165 | | | | | 170 | | | | | 175 | | |
| gta | aac | cga | gac | cta | aaa | acc | cag | tct | ggg | agt | gag | atg | aag | aaa | ttt | 576 |
| Val | Asn | Arg | Asp | Leu | Lys | Thr | Gln | Ser | Gly | Ser | Glu | Met | Lys | Lys | Phe | |
| | | | 180 | | | | | 185 | | | | | 190 | | | |
| ttg | agc | acc | tta | act | ata | gat | ggt | gta | acc | cgg | agt | gac | caa | gga | ttg | 624 |
| Leu | Ser | Thr | Leu | Thr | Ile | Asp | Gly | Val | Thr | Arg | Ser | Asp | Gln | Gly | Leu | |
| | | 195 | | | | | 200 | | | | | 205 | | | | |
| tac | acc | tgt | gca | gca | tcc | agt | ggg | ctg | atg | acc | aag | aag | aac | agc | aca | 672 |
| Tyr | Thr | Cys | Ala | Ala | Ser | Ser | Gly | Leu | Met | Thr | Lys | Lys | Asn | Ser | Thr | |
| | 210 | | | | | 215 | | | | | 220 | | | | | |
| ttt | gtc | agg | gtc | cat | gaa | aag | gac | aaa | act | cac | aca | tgc | cca | ccg | tgc | 720 |
| Phe | Val | Arg | Val | His | Glu | Lys | Asp | Lys | Thr | His | Thr | Cys | Pro | Pro | Cys | |
| 225 | | | | | 230 | | | | | 235 | | | | | 240 | |
| cca | gca | cct | gaa | ctc | ctg | ggg | gga | ccg | tca | gtc | ttc | ctc | ttc | ccc | cca | 768 |
| Pro | Ala | Pro | Glu | Leu | Leu | Gly | Gly | Pro | Ser | Val | Phe | Leu | Phe | Pro | Pro | |
| | | | | 245 | | | | | 250 | | | | | 255 | | |
| aaa | ccc | aag | gac | acc | ctc | atg | atc | tcc | cgg | acc | cct | gag | gtc | aca | tgc | 816 |
| Lys | Pro | Lys | Asp | Thr | Leu | Met | Ile | Ser | Arg | Thr | Pro | Glu | Val | Thr | Cys | |
| | | | 260 | | | | | 265 | | | | | 270 | | | |

-continued

```
gtg gtg gtg gac gtg agc cac gaa gac cct gag gtc aag ttc aac tgg      864
Val Val Val Asp Val Ser His Glu Asp Pro Glu Val Lys Phe Asn Trp
            275                 280                 285 tac gtg gac ggc gtg gag gtg cat aat gcc aag aca aag ccg cgg gag      912
Tyr Val Asp Gly Val Glu Val His Asn Ala Lys Thr Lys Pro Arg Glu
        290                 295                 300 gag cag tac aac agc acg tac cgt gtg gtc agc gtc ctc acc gtc ctg      960
Glu Gln Tyr Asn Ser Thr Tyr Arg Val Val Ser Val Leu Thr Val Leu
305                 310                 315                 320 cac cag gac tgg ctg aat ggc aag gag tac aag tgc aag gtc tcc aac     1008
His Gln Asp Trp Leu Asn Gly Lys Glu Tyr Lys Cys Lys Val Ser Asn
                325                 330                 335 aaa gcc ctc cca gcc ccc atc gag aaa acc atc tcc aaa gcc aaa ggg     1056
Lys Ala Leu Pro Ala Pro Ile Glu Lys Thr Ile Ser Lys Ala Lys Gly
            340                 345                 350 cag ccc cga gaa cca cag gtg tac acc ctg ccc cca tcc cgg gat gag     1104
Gln Pro Arg Glu Pro Gln Val Tyr Thr Leu Pro Pro Ser Arg Asp Glu
        355                 360                 365 ctg acc aag aac cag gtc agc ctg acc tgc ctg gtc aaa ggc ttc tat     1152
Leu Thr Lys Asn Gln Val Ser Leu Thr Cys Leu Val Lys Gly Phe Tyr
370                 375                 380 ccc agc gac atc gcc gtg gag tgg gag agc aat ggg cag ccg gag aac     1200
Pro Ser Asp Ile Ala Val Glu Trp Glu Ser Asn Gly Gln Pro Glu Asn
385                 390                 395                 400 aac tac aag acc acg cct ccc gtg ctg gac tcc gac ggc tcc ttc ttc     1248
Asn Tyr Lys Thr Thr Pro Pro Val Leu Asp Ser Asp Gly Ser Phe Phe
            405                 410                 415 ctc tac agc aag ctc acc gtg gac aag agc agg tgg cag cag ggg aac     1296
Leu Tyr Ser Lys Leu Thr Val Asp Lys Ser Arg Trp Gln Gln Gly Asn
        420                 425                 430 gtc ttc tca tgc tcc gtg atg cat gag gct ctg cac aac cac tac acg     1344
Val Phe Ser Cys Ser Val Met His Glu Ala Leu His Asn His Tyr Thr
    435                 440                 445 cag aag agc ctc tcc ctg tct ccg ggt aaa tga                         1377
Gln Lys Ser Leu Ser Leu Ser Pro Gly Lys
450                 455
```

<210> SEQ ID NO 16
<211> LENGTH: 458
<212> TYPE: PRT
<213> ORGANISM: Homo sapiens

<400> SEQUENCE: 16

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125
```

```
Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 17
<211> LENGTH: 430
<212> TYPE: PRT
<213> ORGANISM: Homo sapiens

<400> SEQUENCE: 17

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45
```

```
Asp Gly Lys Arg Ile Ile Trp Asp Ser Arg Lys Gly Phe Ile Ile Ser
     50                  55                  60

Asn Ala Thr Tyr Lys Glu Ile Gly Leu Leu Thr Cys Glu Ala Thr Val
 65                  70                  75                  80

Asn Gly His Leu Tyr Lys Thr Asn Tyr Leu Thr His Arg Gln Thr Asn
                 85                  90                  95

Thr Ile Ile Asp Val Val Leu Ser Pro Ser His Gly Ile Glu Leu Ser
                100                 105                 110

Val Gly Glu Lys Leu Val Leu Asn Cys Thr Ala Arg Thr Glu Leu Asn
            115                 120                 125

Val Gly Ile Asp Phe Asn Trp Glu Tyr Pro Ser Ser Lys His Gln His
        130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Gly Pro Gly Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Pro Gly Lys
            420                 425                 430

<210> SEQ ID NO 18
<211> LENGTH: 36
<212> TYPE: DNA
<213> ORGANISM: Artificial Sequence
<220> FEATURE:
<223> OTHER INFORMATION: primer
```

```
<400> SEQUENCE: 18
gactagcagt ccggaggtag acctttcgta gagatg                              36

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
cggactcaga accacatcta tgattgtatt ggt                                 33

<210> SEQ ID NO 20
<211> LENGTH: 7
<212> TYPE: PRT
<213> ORGANISM: Homo sapiens

<400> SEQUENCE: 20

Gly Arg Pro Phe Val Glu Met
 1               5

<210> SEQ ID NO 21
<211> LENGTH: 35
<212> TYPE: DNA
<213> ORGANISM: Artificial Sequence
<220> FEATURE:
<223> OTHER INFORMATION: primer

<400> SEQUENCE: 21
acaatcatag atgtggttct gagtccgtct catgg                               35

<210> SEQ ID NO 22
<211> LENGTH: 38
<212> TYPE: DNA
<213> ORGANISM: Artificial Sequence
<220> FEATURE:
<223> OTHER INFORMATION: primer

<400> SEQUENCE: 22
gataatgccc gggccctttt catggaccct gacaaatg                            38

<210> SEQ ID NO 23
<211> LENGTH: 6
<212> TYPE: PRT
<213> ORGANISM: Homo sapiens

<400> SEQUENCE: 23

Val Arg Val His Glu Lys
 1               5

<210> SEQ ID NO 24
<211> LENGTH: 36
<212> TYPE: DNA
<213> ORGANISM: Artificial Sequence
<220> FEATURE:
<223> OTHER INFORMATION: primer

<400> SEQUENCE: 24
gactagcagt ccggaggtag acctttcgta gagatg                              36

<210> SEQ ID NO 25
<211> LENGTH: 38
<212> TYPE: DNA
<213> ORGANISM: Artificial Sequence
```

```
<220> FEATURE:
<223> OTHER INFORMATION: primer

<400> SEQUENCE: 25
ttcctgggca acagctggat atctatgatt gtattggt                              38

<210> SEQ ID NO 26
<211> LENGTH: 4
<212> TYPE: PRT
<213> ORGANISM: Homo sapiens

<400> SEQUENCE: 26

Ile Gln Leu Leu
 1

<210> SEQ ID NO 27
<211> LENGTH: 39
<212> TYPE: DNA
<213> ORGANISM: Artificial Sequence
<220> FEATURE:
<223> OTHER INFORMATION: primer

<400> SEQUENCE: 27
atccagctgt tgcccaggaa gtcgctggag ctgctggta                             39

<210> SEQ ID NO 28
<211> LENGTH: 39
<212> TYPE: DNA
<213> ORGANISM: Artificial Sequence
<220> FEATURE:
<223> OTHER INFORMATION: primer

<400> SEQUENCE: 28
attttcatgc acaatgacct cggtgctctc ccgaaatcg                             39

<210> SEQ ID NO 29
<211> LENGTH: 38
<212> TYPE: DNA
<213> ORGANISM: Artificial Sequence
<220> FEATURE:
<223> OTHER INFORMATION: primer

<400> SEQUENCE: 29
tcatagatat ccagctgttg cccaggaagt cgctggag                              38

<210> SEQ ID NO 30
<211> LENGTH: 39
<212> TYPE: DNA
<213> ORGANISM: Artificial Sequence
<220> FEATURE:
<223> OTHER INFORMATION: primer

<400> SEQUENCE: 30
gataatgccc gggccatttt catgcacaat gacctcggt                             39

<210> SEQ ID NO 31
<211> LENGTH: 6
<212> TYPE: PRT
<213> ORGANISM: Homo sapiens

<400> SEQUENCE: 31

Val Ile Val His Glu Asn
 1               5

<210> SEQ ID NO 32
<211> LENGTH: 10
```

```
<212> TYPE: PRT
<213> ORGANISM: Artificial Sequence
<220> FEATURE:
<223> OTHER INFORMATION: modified Flt1 receptor

<400> SEQUENCE: 32

Lys Asn Lys Arg Ala Ser Val Arg Arg Arg
 1               5                  10

<210> SEQ ID NO 33
<211> LENGTH: 8
<212> TYPE: PRT
<213> ORGANISM: Artificial Sequence
<220> FEATURE:
<223> OTHER INFORMATION: modified Flt1 receptor

<400> SEQUENCE: 33

Asn Ala Ser Val Asn Gly Ser Arg
 1               5

<210> SEQ ID NO 34
<211> LENGTH: 10
<212> TYPE: PRT
<213> ORGANISM: Artificial Sequence
<220> FEATURE:
<223> OTHER INFORMATION: modified Flt1 receptor

<400> SEQUENCE: 34

Lys Asn Lys Cys Ala Ser Val Arg Arg Arg
 1               5                  10

<210> SEQ ID NO 35
<211> LENGTH: 4
<212> TYPE: PRT
<213> ORGANISM: Homo sapiens

<400> SEQUENCE: 35

Ser Lys Leu Lys
 1

<210> SEQ ID NO 36
<211> LENGTH: 9
<212> TYPE: PRT
<213> ORGANISM: Homo sapiens

<400> SEQUENCE: 36

Lys Asn Lys Arg Ala Ser Val Arg Arg
 1               5

<210> SEQ ID NO 37
<211> LENGTH: 4
<212> TYPE: PRT
<213> ORGANISM: Homo sapiens

<400> SEQUENCE: 37

Thr Ile Ile Asp
 1

<210> SEQ ID NO 38
<211> LENGTH: 4
<212> TYPE: PRT
<213> ORGANISM: Homo sapiens

<400> SEQUENCE: 38

Val Val Leu Ser
 1
```

CELL CULTURE COMPOSITIONS CAPABLE OF PRODUCING A VEGF-BINDING FUSION POLYPEPTIDE

This application is a continuation of U.S. patent application Ser. No. 12/334,927, filed Dec. 15, 2008, now U.S. Pat. No. 7,964,377, which is a continuation of U.S. patent application Ser. No. 12/102,648, filed Apr. 14, 2008, now U.S. Pat. No. 7,524,499, which is a divisional of U.S. patent application Ser. No. 11/016,097, filed Dec. 17, 2004, now U.S. Pat. No. 7,374,757, which is a divisional of U.S. patent application Ser. No. 10/009,852, filed Dec. 6, 2001, now U.S. Pat. No. 7,070,959, which is a national stage application of international Application No. PCT/US00/14142, filed May 23, 2000, which claims priority of U.S. Provisional Application No. 60/138,133, filed Jun. 8, 1999. The disclosures of these publications in their entireties are hereby incorporated by reference into this application.

INTRODUCTION

The field of this invention is modified polypeptides with improved pharmacokinetics. Specifically, the field of this invention relates to Flt1 receptor polypeptides that have been modified in such away as to improve their pharmacokinetic profile. The field of this invention also relates to methods of making and using the modified polypeptides including but not limited to using the modified polypeptides to decrease or inhibit plasma leakage and/or vascular permeability in a mammal.

BACKGROUND

The ability of polypeptide ligands to bind to cells and thereby elicit a phenotypic response such as cell growth, survival, cell product secretion, or differentiation is often mediated through transmembrane receptors on the cells. The extracellular domain of such receptors (i.e. that portion of the receptor that is displayed on the surface of the cell) is generally the most distinctive portion of the molecule, as it provides the protein with its ligand binding characteristic. Binding of a ligand to the extracellular domain generally results in signal transduction which transmits a biological signal to intracellular targets. Often, this signal transduction acts via a catalytic intracellular domain. The particular array of sequence motifs of this catalytic intracellular domain determines its access to potential kinase substrates (Mohammadi, et al., 1990, Mol. Cell. Biol. 11:5068-5078; Fantl, et al., 1992, Cell 69:413-413). Examples of receptors that transduce signals via catalytic intracellular domains include the receptor tyrosine kinases (RTKs) such as the Trk family of receptors which are generally limited to cells of the nervous system, the cytokine family of receptors including the tripartate CNTF receptor complex (Stahl & Yancopoulos, 1994, J. Neurobio. 25:1454-1466) which is also generally limited to the cells of the nervous system, G-protein coupled receptors such as the $\beta_2$-adrenergic receptor found on, for instance, cardiac muscle cells, and the multimeric IgE high affinity receptor FcεRI which is localized, for the most part, on mast cells and basophils (Sutton & Gould, 1993, Nature 366:421-428).

All receptors identified so far appear to undergo dimerization, multimerization, or some related conformational change following ligand binding (Schlessinger, J., 1988, Trend Biochem. Sci. 13:443-447; Ullrich & Schlessinger, 1990, Cell 61:203-212; Schlessinger & Ullrich, 1992, Neuron 9:383-391) and molecular interactions between dimerizing intracellular domains lead to activation of catalytic function. In some instances, such platelet-derived, growth factor (PDGF), the ligand is a dimer that binds two receptor molecules (Hart, et al., 1988, Science, 240:1529-1531; Heldin, 1989, J. Biol. Chem. 264:8905-8912) while, for example, in the case of epidermal growth factor (EGF), the ligand is a monomer (Weber, et al., 1984, J. Biol. Chem. 259:14631-14636). In the case of the FcεRI receptor ligand, IgE, exists bound to FcεRI in a monomeric fashion and only becomes activated when antigen binds to the IgE/FcεRI complex and cross-links adjacent IgE molecules (Sutton & Gould, 1993, Nature 366:421-428).

Often, the tissue distribution of a particular receptor within higher organisms provides insight into the biological function of the receptor. The RTKs for some growth and differentiation factors, such as fibroblast growth factor (FGF), are widely expressed and therefore appear to play some general role in tissue growth and maintenance. Members of the Trk RTK family (Glass & Yancopoulos, 1993, Trends in Cell Biol. 3:262-268) of receptors are more generally limited to cells of the nervous system, and the Nerve Growth Factor family consisting of nerve, growth factor (NGF), brain-derived, neurotrophic factor (BDNF), neurotrophin-3 (NT-3) and neurotrophin-4/5 (NT-4/5), which bind the Trk RTK family receptors, promote the differentiation of diverse groups of neuronsons the brain and periphery (Lindsay, R. M, 1993, in Neurotrophic Factors, S. E. Loughlin & J. H. Fallon, eds., pp. 257-1284, San Diego, Calif., Academic Press). FcεRI is localized to a very limited number of types of cells such as mast cells and basophilis. Mast cells derive from bone marrow pluripotent hematopoietic stem cell lineage, but complete there maturation in the tissue following migration from the blood stream (See Janeway & Travers, 1996, in Immunobiology, 2d. Edition, M. Robertson & E. Lawrence, eds., pp. 1:3-1:4, Current Biology Ltd., London, UK; Publisher) and are involved in the allergic response.

Many studies have demonstrated that the extracellular domain of a receptor provides the specific ligand binding characteristic. Furthermore, the cellular environment in which a receptor is expressed may influence the biological response exhibited upon binding of a ligand to the receptor. For example, when a neuronal cell expressing a Trk receptor is exposed to a neurotrophin which binds to that receptor, neuronal survival and differentiation results. When the same receptor is expressed by a fibroblast, exposure to the neurotrophin results in proliferation of the fibroblast (Glass, et al., 1991, Cell 66:405-413).

A class of cell-derived dimeric mitogens with selectivity for vascular endothelial cells has been identified and designated vascular endothelial cell growth factor (VEGF). VEGF has been purified from conditioned growth media of rat glioma cells (Conn et al., 1990, Proc. Natl. Acad. Sci. U.S.A., 87. pp 2628-2632); and conditioned growth media of bovine pituitary follicle stellate cells (Ferrara and Henzel, 1989, Biochem. Biophys. Res. Comm., 161, pp. 851-858; Gozpadorowicz et al., 1989, Proc. Natl. Acad. Sci. U.S.A., 86, pp. 7311-7315 and conditioned growth medium from human U937 cells (Connolly, D. T. et al. 1989, Science, 246, pp. 1309-1312). VEGF is a dimer with an apparent molecular mass of about 46 kDa with each subunit having an apparent molecular mass of about 23 kDa. VEGF has some structural similarities to platelet derived growth factor (PDGF), which is a mitogen for connective tissue cells but not mitogenic for vascular endothelial cells from large vessels.

The membrane-bound tyrosine kinase receptor, known as Flt, was shown to be a VEGF receptor (DeVries, C. et al., 1992, Science, 255, pp. 989-991). The Flt receptor specifically binds VEGF which induces mitogenesis. Another form of the VEGF receptor, designated KDR, is also known to, bind VEGF and induce mitogenesis. The partial cDNA sequence and nearly full length protein sequence of KDR is known as well (Terman, B. I. at al., 1991 Oncogene 6, pp. 1677-1683; Terman, B. I. et al., 1992 Biochem. Biophys. Res. Comm. 187, pp. 1579-1586).

Persistent angiogenesis may cause or exacerbate certain diseases such as psoriasis, rheumatoid arthritis, hemangiomas, angiofibromas, diabetic retinopathy, and neovascular glaucoma. An inhibitor of VEGF activity would be useful as a treatment for such diseases and other VEGF-induced pathological angiogenesis and vascular permeability conditions, such as tumor vascularization. The present invention relates to a VEGF inhibitor that is based on the VEGF receptor Flt1.

Plasma leakage, a key component of inflammation, occurs in a distinct subset of microvessels. In particular, in most organs plasma leakage occurs specifically in the venules. Unlike arterioles and capillaries, venules become leaky in response to numerous inflammatory mediators including histamine, bradykinin, and serotonin. One characteristic of inflammation is the plasma leakage that results from intercellular gaps that form in the endothelium olvenules. Most experimental models of inflammation indicate that these intercellular gaps occur between the endothelial cells of post-capillary and collecting venules (Baluk, P., et al., Am. J. Pathol., 1998, 152:1463-76). It has been shown that certain lectins may be used to reveal features of focal sites of plasma leakage, endothelial gaps, and finger-like processes at endothelial cell borders in inflamed venules (Thurston, G., et al., Am. J. Physiol., 1996, 271: H2547-62). In particular, plant lectins have been used to visualize morphological changes at endothelial cell borders in inflamed venules of, for example, the rat trachea. Lectins, such as conconavalin A and ricin, that bind focally to inflamed venules reveal regions of the subendothelial vessel wall exposed by gaps that correspond to sites of plasma leakage (Thurston, G., et al., Am J Physiol., 1996; 271: H2547-62).

The properties of the microvessels are, dynamic. Chronic inflammatory diseases, for example, are associated with microvascular remodeling, including angiogenesis and microvessel enlargement. Microvessels can also remodel by acquiring abnormal phenotypic properties. In a murine model of chronic airway inflammation, airway capillaries acquire properties of venules, including widened vessel diameter, increased immunoreactivity for von Willebrand factor, and increased immunoreactivity for P-selectin. In addition, these remodeled vessels leak in response to inflammatory mediators, whereas vessels in the same position in the airways of normal mice do not.

Certain substances have been shown to decrease or inhibit vascular permeability and/or plasma leakage. For example, mystixins are synthetic polypeptides that have been reported to inhibit plasma leakage without blocking endothelial gap formation (Baluk, P., et al., J. Pharmacol. Exp. Ther., 1998, 284: 693-9). Also, the beta 2-adrenergic receptor agonist formoterol reduces microvascular leakage by inhibiting endothelial gap formation (Baluk, P. and McDonald, D. M., Am. J. Physiol., 1994, 266:L461-8).

The angiopoietins and members of the vascular endothelial growth factor (VEGF) family are the only growth factors thought to be largely specific for vascular endothelial, cells. Targeted gene inactivation studies in mice have shown that VEGF is necessary for the early stages of vascular development and that Ang-1 is required for later stages of vascular remodeling.

U.S. Pat. No. 6,011,003, issued Jan. 4, 2000, in the name of Metris Therapeutics Limited, discloses an altered, soluble form of FLT polypeptide being capable of binding to VEGF and thereby exerting an inhibitory effect thereon, the polypeptide comprising five or fewer complete immunoglobulin domains.

U.S. Pat. No. 5,712,380, issued Jan. 27, 1998 and assigned to Merck & Co., discloses vascularendothelial cell growth factor (VEGF), inhibitors that are naturally occurring or recombinantly engineered soluble forms with or without a C-terminal transmembrane region of the receptor for VEGF.

Also assigned to Merck & Co. is PCT Publication No. WO 98/13071, published Apr. 2, 1998, which discloses gene therapy methodology for inhibition of primary tumor growth and metastasis by gene transfer of a nucleotide sequence encoding a soluble receptor protein which binds to VEGF.

PCT Publication No. WO 97/44453, published Nov. 27, 1997, in the name of Genentech, Inc., discloses novel chimeric VEGF receptor proteins comprising amino acid sequences derived from the vascular endothelial growth factor (VEGF) receptors Flt1 and KDR, including the murine homologue to the human KDR receptor FLK1, wherein said chimeric VEGF receptor protein's bind to VEGF and antagonize the endothelial cell proliferative and angiogenic activity thereof.

PCT Publication No. WO 97/13787, published Apr. 17, 1997, in the name of Toa Gosei Co., LTD., discloses a low molecular weight VEGF inhibitor usable in the treatment of diseases accompanied by neovascularization such as solid tumors. A polypeptide containing the first immunoglobulin-like domain and the second immunoglobulin-like domain in the extracellular region of a VEGF receptor FLT but not containing the sixth immunoglobulin-like domain and the seventh immunoglobulin-like domain thereof shows a VEGF inhibitory activity.

Sharifi, J. et al., 1998, The Quarterly Jour. of Nucl. Med. 42:242-249, disclose that because monoclonal antibodies (MAbs) are basic, positively charged proteins, and mammalian cells are negatively charged, the electrostatic interactions between the two can create higher levels of background binding resulting in low tumor to normal organ ratios. To overcome this effect, the investigators attempted to improve MAb clearance by using various methods such as secondary agents as well as, chemical and charge modifications of the MAb itself.

Jensen-Pippo, et al., 1996, Pharmaceutical Research 13:102-107, disclose that pegylation of a therapeutic protein, recombinant human granulocyte colony stimulating factor (PEG-G-CSF), results in an increase in stability and in retention of in vivo bioactivity when administered by the intraduodenal route.

Tsutsumi, et al., 1997, Thromb Haemost. 77:168-73, disclose experiments wherein the in vivo thrombopoietic activity of polyethylene glycol-modified interleukin-6 (MPEG-IL-6), in which 54% of the 14 lysine amino groups of IL-6 were coupled with PEG, was compared to that of native IL-6.

Yang, et al., 1995, Cancer 76:687-94, disclose that conjugation of polyethylene glycol to recombinant human interleukin-2 (IL-2) results in a compound, polyethylene glycol-modified IL-2 (PEG-IL-2) that retains the in vitro and in vivo activity of IL-2, but exhibits a markedly prolonged circulating half-life.

R. Duncan and F. Spreafico, Clin. Pharmatokinet. 27: 290-306, 296 (1994) review efforts to improve the plasma half-life of asparaginase by conjugating polyethylene glycol.

PCT International Publication No. WO 99/03996 published Jan. 28, 1999 in the name of Regeneron Pharmaceuticals, Inc. and The Regents of The University of California describes modified human noggin polypeptides having deletions of regions of basic amino acids. The modified human noggin polypeptides are described as retaining biological activity while having reduced affinity for heparin and superior pharmacokinetics in animal sera as compared to the unmodified human noggin.

SUMMARY OF THE INVENTION

The present invention is directed to VEGF antagonists with improved pharmacokinetic properties. A preferred embodiment is an isolated nucleic acid molecule encoding a fusion polypeptide capable of binding a VEGF polypeptide comprising (a) a nucleotide sequence encoding a VEGF receptor component operatively linked to (b) a nucleotide sequence encoding a multimerizing component, wherein the VEGF receptor component is the only VEGF receptor component of the fusion polypeptide and wherein the nucleotide sequence of (a) consists essentially of a nucleotide sequence encoding the amino acid sequence of Ig domain 2 of the extracellular domain of a first VEGF receptor and a nucleotide sequence encoding the amino acid, sequence of Ig domain 3 of the extracellular domain of a second VEGF receptor.

In a further embodiment, the isolated nucleic acid of the first VEGF receptor is Flt1.

In a further embodiment, the isolated nucleic acid of the second VEGF receptor is, Flk1.

In yet another embodiment; the isolated nucleic acid of the second VEGF receptor is Flt4.

In another preferred embodiment, the nucleotide sequence encoding Ig domain 2 of the extracellular domain of the first VEGF receptor is upstream of than nucleotide sequence encoding domain 3 of the extracellular domain of the second VEGF receptor.

In still another preferred embodiment, the nucleotide sequence encoding Ig domain 2 of the extracellular domain or the first VEGF receptor is downstream of the nucleotide a sequence encoding Ig domain 3 of the extracellular domain of the second VEGF receptor.

In a preferred of the invention the multimerizing component comprises an immunoglobulin domain.

In another embodiment, the immunoglobulin domain is selected from the group consisting of the Fc domain of the heavy chain of IgG, and the light chain of IgG.

Preferred embodiments include an isolated nucleic acid molecule comprising a nucleotide sequence encoding a modified Flt1 receptor fusion polypeptide, wherein the coding region of the nucleic acid molecule consists of a nucleotide sequence selected from the group consisting of (a) the nucleotide sequence set forth in FIG. 13A-13D (SEQ ID No:3); (b) the nucleotide sequence set forth in FIG. 14A-14C (SEQ ID NO:5); (c) the nucleotide sequence set forth in FIG. 15A-15C (SEQ ID NO:7); (d) the nucleotide sequence set forth in FIG. 16A-16D (SEQ ID NO:9); (e) the nucleotide sequence set forth in FIG. 21A-21C (SEQ ID NO:11); (f) the nucleotide sequence set forth in FIG. 22A-22C (SEQ ID NO:13); (g) the nucleotide sequence set forth in FIG. 24A-24C; and (SEQ ID NO:15); and (h) a nucleotide sequence which, as a result of the degeneracy of the genetic code, differs from the nucleotide sequence of (a), (b), (c), (d), (e), (f), or (g) and which encodes a fusion polypeptide molecule having the biological activity or the modified Flt1 receptor fusion polypeptide.

In a further embodiment of the invention, a fusion polypeptide is encoded by the isolated nucleic acid molecules described above.

A preferred embodiment is a composition capable of binding a VEGF molecule to form a nonfunctional complex comprising a multimer of the fusion polypeptide.

Also preferred is a composition wherein the multimer is a dimer.

In yet another embodiment, the composition is in a carrier.

Another embodiment is a vector, which comprises the acid molecules described above, including an expression vector comprising a the nucleic acid molecules described wherein the nucleic acid molecule is operatively linked to an expression control sequence.

Other included embodiments area host-vector system for the production of a fusion polypeptide which comprises the expression vector, in a suitable host cell; the host-vector system wherein the suitable host cell is a bacterial cell, yeast cell, insect cell, or mammalian cell; the host-vector system wherein the suitable host cell is *E. coli*, the host-vector system wherein the suitable host cell is a COS cell; the host-vector system wherein the suitable host cell is a CHO cell.

Another embodiment of the invention is a method of producing a fusion polypeptide which comprises growing cells of the host-vector system under conditions permitting production of the fusion polypeptide and recovering the fusion polypeptide so produced.

Additional embodiments include a fusion polypeptide encoded by the nucleic acid sequence set forth in FIG. 10A-10D (SEQ ID NO:1) or FIG. 24A-24C (SEQ ID NO:15), which has been modified by acetylation or pegylation wherein the acetylation is accomplished with at least about a 100 fold molar excess of acetylation reagent or wherein acetylation is accomplished with a molar excess of acetylation reagent ranging from at least about a 10 fold molar excess to about a 100 fold molar excess or wherein the pegylation is 10K or 20K PEG.

A Preferred embodiment includes a method of decreasing or inhibiting plasma leakage in a mammal comprising administering to the mammal the fusion polypeptide described above, including embodiments wherein the mammal is a human, the fusion polypeptide is acetylated or the fusion polypeptide is pegylated.

A further embodiments is a fusion polypeptide which specifically binds the VEGF receptor ligand VEGF.

A preferred embodiment of the invention is a method of blocking blood vessel growth in a human comprising administering an effective amount of the fusion polypeptide described above.

Also preferred is a method of inhibiting VEGF receptor ligand activity in a mammal comprising administering to the mammal an effective amount of the fusion polypeptide described above.

Preferred embodiments of these methods are wherein the mammal is a human.

Further embodiments of the methods of the invention include attenuation or prevention of tumor growth in a human; attenuation or prevention of edema in a human, especially wherein the edema is brain edema; attenuation or prevention of ascites formation in a human, especially wherein the ascites is ovarian cancer-associated ascites.

Preferred embodiments of the invention include a fusion polypeptide capable of binding a VEGF polypeptide comprising (a) a VEGF receptor component operatively linked to (b) a multimerizing component, wherein the VEGF receptor component is the only VEGF receptor component in the fusion polypeptide and consists essentially of the amino acid sequence of Ig domain 2 of the extracellular domain of a first VEGF receptor and the amino acid sequence of Ig domain 3 of the extracellular domain of a second VEGF receptor.

In a further embodiment of the fusion polypeptide the first VEGF receptor is Flk1.

In yet a further embodiment of the fusion polypeptide, the second VEGF receptor Flk1.

Still another embodiment of the fusion polypeptide is one in which the second VEGF receptor is Flt4.

Preferred embodiments include a fusion polypeptide wherein amino acid sequence of Ig domain 2 of the extracellular domain of the first VEGF receptor is upstream of the amino acid sequence of Ig domain 3 of the extracellular domain of the second VEGF receptor and a fusion polypeptide wherein the amino acid sequence of Ig domain 2 of the extracellular domain of the first VEGF receptor is downstream of the amino acid sequence of Ig domain 3 of the extracellular domain of the second VEGF receptor.

In yet another embodiment, the fusion polypeptide multimerizing component comprises an immunoglobulin domain including an embodiment wherein the immunoglobulin domain is selected from the group consisting of the Fc domain of IgG, the heavy chain of IgG, and the light chain of IgG.

Preferred embodiments include a fusion polypeptide comprising an amino acid sequence of a modified Flt1 receptor, wherein the amino acid sequence selected from the group consisting of (a) the amino acid sequence set forth in FIG. 13A-13D (SEQ ID NO:4); (b) the amino acid sequence set forth in FIG. 14A-14C (SEQ ID NO:6); (c) the amino acid sequence set forth in FIG. 15A-15C (SEQ ID NO:8); (d) the amino acid sequence set forth in FIG. 16A-16D (SEQ ID NO:10); (e) the amino acid sequence set forth in FIG. 21A-21C (SEQ ID NO:12); (f) the amino acid sequence set forth in FIG. 22A-22C (SEQ ID NO:14); and (g) the amino acid sequence set forth in FIG. 24A-24C (SEQ ID NO:16).

Another preferred embodiment is a method of decreasing or inhibiting plasma leakage in a mammal comprising administering to the mammal the fusion polypeptide described above.

An alternative preferred embodiment is a method of inhibiting VEGF receptor ligand activity in a mammal comprising administering to the mammal an effective amount of the fusion polypeptide described above.

BRIEF DESCRIPTION OF THE FIGURES

FIG. 7. Binding of unmodified Flt1(1-3)-Fc and step-acetylated Flt1(1-3)-Fc proteins to MATRIGEL® coated plates. As with the irrelevant control protein, rTie2-Fc, step-acetylated Flt1(1-3)-Fc (20 and 30 fold excess samples) does not exhibit any binding to the MATRIGEL® coated plate, whereas the non-acetylated Flt1(1-3)-Fc protein exhibits significant binding. The 10 fold excess sample shows reduced binding, but the degree, of acetylation is not enough to completely block to extracellular matrix components.

FIG. 8. Binding of unmodified Flt1(1-3)-Fc and step-acetylated Flt1(1-3)-Fc in a BIACORE™-bated assay. At a sub-stoichiometric ratio (0.5 µg/ml of either unmodified Flt1 (1-3) or step-acetylated Flt1(1-3)-Fc vs. 0.2 µg/ml VEGF), there is not enough Flt1(1-3)-Fc (either unmodified or step-acetylated) in the solution to completely bind the VEGF. At 1.0 µg/ml, which approximates a 1:1 stoichiometric ratio, the both unmodified and step-acetylated Flt1(1-3)-Fc are better able to compete for VEGF binding, but there is still insufficient Flt1(13)-Ft protein (either unmodified or step-acetylated) to completely saturate the available VEGF. However, at 5.0 µg/ml which is several times greater a 1:1 stoichiometric ratio, both the Flt1(1-3)-Fc and the step-acetylated Flt1(1-3)-Fc proteins are able to saturated the VEGF, regardless of the degree of acetylation.

FIG. 10A-10D. Nucleic acid (SEQ ID NO:1) and deduced amino acid sequence (SEQ ID NO:2) of Flt1(1-3)-Fc.

FIG. 11. Schematic diagram of the structure

FIGS. 12A and 12B. Hydrophilicity analysis of the amino acid sequences of Ig domain 2 and Ig domain 3 of Flt1.

FIG. 13A-13D. Nucleic-acid (SEQ ID NO:3) and deduced amino acid sequence (SEQ ID NO:4) of Mut1: Flt1(1-3$_{\Delta B}$)-Fc.

FIG. 14A-14C. Nucleic acid (SEQ ID NO:5) and deduced amino acid sequence (SEQ ID NO:6) of Mut2: Flt1(2-3$_{AB}$)-Fc.

FIG. 15A-15C. Nucleic acid (SEQ ID NO:7) and deduced amino acid sequence (SEQ ID NO:8) of Mut3: Flt1(2-3)-Fc.

FIG. 16A-16D. Nucleic acid (SEQ ID NO:9) and deduced amino acid sequence (SEQ ID NO:10) of Mut4: Flt1(1-3$_{R \to N}$)-Fc.

FIG. 17. Binding, of unmodified Flt1(1-3)-Fc, bait region deletion mutant Flt1(1-3)-Fc, and Flt1(1-3)$_{R \to N}$ mutant proteins in a BIACORE™-based assay. At the sub-stoichiometric ratio (0.25 μg/ml Flt1(1-3)-Fc of unmodified, acetylated or genetically modified samples vs. 01. μg/ml VEGF), there is insufficient Flt1(1-3)-Fc protein to block binding of VEGF to the Flt1(1-3)-Fc immobilized on the BIACORE™ chip. At 0.5 μg/ml of unmodified, acetylated or genetically Modified Flt1(1-3)-Fc, proteins, the stoichiometric ratio approximates 1:1 and there is an increased ability to block VEGF binding to the BIACORE™ chip. At 1.0 μg/ml of unmodified, acetylated or genetically modified Flt1(1-3)-Fc proteins, which is approximately a 10:1 stoichiometric ratio, the Flt1(1-3)-Fc proteins are able to block binding of VEGF to the BIACORE™ chip, but they are not equivalent. Unmodified, acetylated, and Mut1: Flt1(1-3$_{AB}$)-Fc are essentially equal in their ability to block VEGF binding, whereas Mut4: Flt1(1-3$_{R \to N}$)-Fc is somewhat less efficient at blocking binding.

FIG. 18. Binding of unmodified Flt1(1-3)-Fc, Mut1. Flt1 (1-3$_{AB}$)-Fc, Mut2: Flt1(2-3$_{AB}$)-Fc, and Flt1(2-3) mutant proteins to MATRIGEL® coated plates. Unmodified Flt1(1-3)-Fc protein binds avidly to these wells, the Mut3: Flt1(2-3)-Fc protein binds somewhat more weakly, the Mut1: Flt1(1-3$_{AB}$)-Fc protein binds more weakly still and the Mut2: Flt1(2-3$_{AB}$)-Fc protein shows the best profile, binding more weakly than any of these other mutant proteins. The Mut4: Flt1(1-3$_{R \to N}$)-Fc glycosylation mutant protein shows only marginal benefit on the MATRIGEL® assay.

FIG. 19. Binding of unmodified Flt1(1-3)-Fc, Mut1: Flt1 (1-3$_{AB}$)-Fc, Mut2: Flt1(2-3$_{AB}$)-Fc, and Flt1(2-3) mutant proteins in an ELISA-based assay. At the concentrations tested, unmodified Flt1(1-3)-Fc, Mut1: Flt1(1-3$_{AB}$)-Fc, Mut2: Flt1 (2-3$_{AB}$)-Fc, and Flt1(2-3) mutant proteins bind VEGF similarly.

FIG. 21A-21C. Nucleotide (SEQ ID NO:11) and deduced amino acid sequence (SEQ ID NO:12) of the modified Flt1 receptor termed Flt1D2.Flk1D3.FcΔC1(a).

FIG. 22A-22C. Nucleotide (SEQ ID NO:13) and deduced amino acid sequence (SEQ ID NO:14) of the modified Flt1 receptor termed Flt1D2.VEGFR3D3.FcΔC1(a).

FIG. 24A-24C. Nucleotide (SEQ ID NO:15) and deduced amino acid sequence (SEQ ID NO:16) of the modified Flt1 receptor termed VEGFR1R2-FcΔC1(a).

FIG. 25A-25C. Phosphorylation assay. At a 1.5 molar excess of either Flt1(1-3)-Fc, Flt1(1-3)-Fc (A40) or transient Flt1D2Flk1D3.FcΔC1(a) there is complete blockage of receptor stimulation by these three modified Flt1 receptors as compared to control media challenge. In contrast, transient Flt1D2VEGFR3D3.FcΔC1(a) does not show significant blockage at this molar excess, as compared with VEGF positive control challenge. Similar results are seen in FIG. 25B, where the modified Flt receptors are in a 3-fold molar excess to VEGF165 ligand. In FIG. 25C, where the modified Flt1 receptors are in a 6-fold molar excess to VEGF165 ligand, transient Flt1D2VEGFR3D3.FcΔC1(a) can now be shown to be partially blocking VEGF165-induced stimulation of cell-surface receptors.

FIG. 28. BIACORE™ analysis of Binding Stoichiometry. Binding Stoichiometry was calculated as a molar ratio of bound VEGF165 to the immobilized Flt1D2Flk1D3.FcΔC1 (a) or VEGFR1R2-FcΔC1(a), listing the conversion factor of 1000 RU equivalent to 1 ng/ml. The results indicated binding stoichiometry of one VEGF165 dimeric molecule per one Flt1D2Flk1D3.FcΔC1(a) or VEGFR1R2-FcΔ1(a) molecule.

As shown in FIG. 33, the elution profile shows two peaks. Peak #1 represents the receptor-ligand complex and, peak #2 represents the unbound VEGF165. MW was calculated from LS and RI signals. The same procedure was used to determine MW of the individual components of the receptor-ligand complex. The results of these determinations are as follows: MW of the Flt1D2Flk1D3.FcΔC1(a)/VEGF165 complex at the peak position is 157 300 (FIG. 33), the MW of VEGF165 at the peak position is 44 390 (FIG. 34) and the MW of the mW of R1R2 at the peak is 113 300 (FIG. 35).

FIG. 36. Peptide mapping and glycosylation analysis. The disulfide structures and glycosylation sites in Flt1D2.Flk1D3.FcΔC1(6) (SEQ ID NO:12) were determined by a peptide mapping method. There are a total of ten cysteines in Flt1D2.Flk1D3.FcΔC1(a), six of them belong to the Fc region. Cys27 is disulfide bonded to Cys76. Cys121 is disulfide bonded to Cys182. The first two cysteines in the Fc region (Cys211 and Cys214) form an intermolecular disulfide bond with the same two cysteines in another Fc chain. However, it can not be determined whether disulfide bonding is occurring between same cysteines (Cys211 to Cys211, for example) or between Cys211 and Cys214. Cys216 is disulfide bonded to Cys306. Cys352 is disulfide bonded to Cys410. There are five possible N-linked glycosylation sites in Flt1D2.Flk1D3.FcΔC1(a) (SEQ ID NO:12) and are found to be glycosylated to varying degrees. Complete glycosylation is observed at Asn33, Asn193, and Asn282. Partial glycosylation is observed on Atn65 and Atn120. Sites of glycosylation are highlighted by underline in the figure.

DETAILED DESCRIPTION OF THE INVENTION

Figure 1:
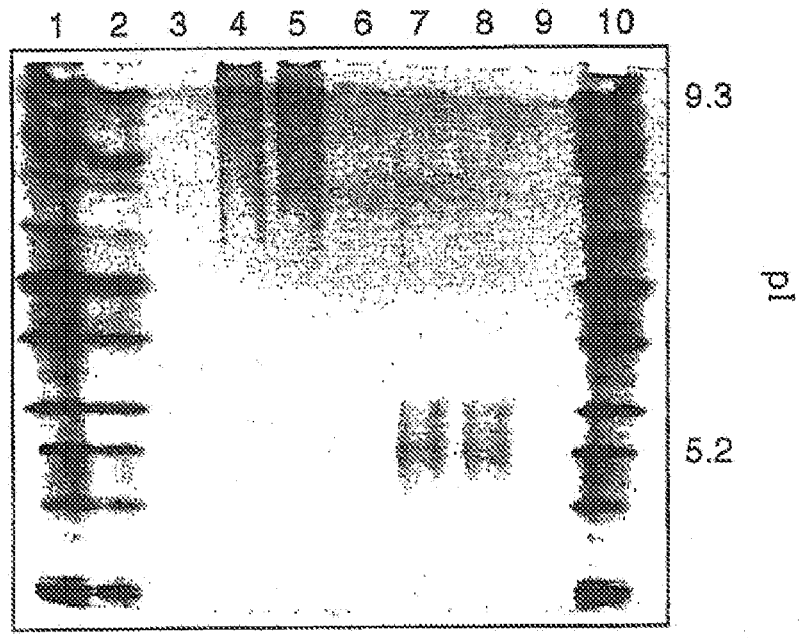
FIG. 1. IEF gel analysis of unmodified and acetylated Flt1(1-3)-Fc proteins. Unmodified Flt1(1-3)-Fc protein is unable to enter the gel due to its >9.3 pI, whereas acetylated Flt1(1-3)-Fc is able to enter the gel and equilibrate at pI 52.

It has been a long standing problem in the art to produce a receptor based VEGF antagonist that has a pharmacokinetic profile that is appropriate for consideration of the antagonist as a therapeutic candidate. Applicants describe herein, for the first time, a chimeric polypeptide molecule, capable of antagonizing VEGF activity, that exhibits improved pharmacokinetic properties as compared to other known receptor-based VEGF antagonists. The chimeric polypeptide molecules described herein thus provide for the first time appropriate molecules for use in therapies in which antagonism of VEGF is a desired result.

The present invention provides for novel chimeric polypeptide molecules formed by fusing a modified extracellular ligand binding domain of the Flt1 receptor to the Fc region of IgG.

The extracellular ligand binding domain is defined as the portion of a receptor that, in its native conformation in the cell membrane, is oriented extracellularly where it can contact with its cognate ligand. The extracellular ligand binding domain does not include the hydrophobic amino acids associated with the receptor's transmembrane domain or any amino acids associated with the receptor's intracellular domain. Generally, the intracellular or cytoplasmic domain of a receptor is usually composed of positively charged or polar amino acids (i.e. lysine, arginine, histidine, glutamic acid, aspartic acid). The preceding 15-30, predominantly hydrophobic or apolar amino acids (i.e. leucine, valine, isoleucine, and phenylalanine) comprise the transmembrane domain. The extracellular domain comprises the amino acids that precede the hydrophobic transmembrane stretch of amino acids. Usually the transmembrane domain is flanked by positively charged or polar amino acids such as lysine or arginine. von Heijne has published detailed rules that are commonly referred to by skilled artisans when determining which amino acids of a given receptor belong to the extracellular, transmembrane, or intracellular domains (See von Heijne, 1995, BioEssays 17:25-30). Alternatively, websites on the Internet have become available to provide protein chemists with information about making predictions about protein domains.

The present invention provides for the construction of nucleic acid molecules encoding chimeric polypeptide molecules that are inserted into a vector that is able to express the chimeric polypeptide molecules when introduced into an appropriate host cell. Appropriate host cells include, but are not limited to, bacterial cells, yeast cells, insect cells, and mammalian cells. Any of the methods known to one skilled in the art for the insertion of DNA fragments into a vector may be used to construct expression vectors encoding the chimeric polypeptide molecules under control of transcriptional/translational control signals. These methods may include in vitro recombinant DNA and synthetic techniques and in vivo recombinations (genetic recombination) (See Sambrook, et al., Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Expression of nucleic acid molecules encoding the chimeric polypeptide molecules may be regulated by a second nucleic acid sequence so that the chimeric polypeptide molecule is expressed in a host transformed with the recombinant DNA molecule. For example, expression of the chimeric polypeptide molecules described herein may be controlled by any promoter/enhancer element known in the art. Promoters which may be used to control expression of the chimeric polypeptide molecules include, but are not limited to, the long terminal repeat as described in Squinto et al., (1991, Cell 65:1-20); the SV40 early promoter region (Bernoist and Chambon, 1981, Nature, 290:304-310), the CMV promoter, the M-MuLV 5'-terminal repeat the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionine gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25, see also "Useful proteins from recombinant bacteria" in Scientific American, 1980, 242:74-94); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring, Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al. 1986, Cell 45:485-495), albumin gene control region which is active in liver (Pinkert et al., 1987, Genes and Devel. 1:268-270), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising chimeric polypeptide molecule-encoding nucleic acid as described herein, are used to transfect the host and thereby direct expression of such nucleic acids to produce the chimeric polypeptide molecules, which may then be recovered in a biologically active form. As used herein, a biologically active form includes a form capable of binding to VEGF.

Expression vectors containing the chimeric nucleic acid molecules described herein can be identified by three general approaches: (a) DNA-DNA hybridization, (b) presence or absence of "marker" gene functions, and (c) expression of inserted sequences. In the first approach, the presence of a foreign gene inserted, in an expression vector can be detected by DNA-DNA hybridization using probes comprising sequences that are homologous to the inserted chimeric polypeptide molecule sequences. In the second approach, the recombinant vector/host system can be identified and selected bated upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the chimeric polypeptide molecule DNA sequence is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of the chimeric polypeptide molecules.

Cells of the present invention may transiently or, preferably, constitutively and permanently express the chimeric polypeptide molecules.

The chimeric polypeptide molecules may be purified by any technique which allows for the subsequent formation of a stable, biologically active chimeric polypeptide molecule. For example, and not by way of limitation, the factors may be recovered from cells either as soluble proteins or as inclusion bodies, from which they may be extracted quantitatively by 8 M guanidinium hydrochloride and dialysis (see, for example, Builder, et al., U.S. Pat. No. 5,888,304). In order to further purify the factors, conventional ion exchange chromatography, hydrophobic interaction chromatography, reverse phase chromatography or gel filtration may be used.

In one embodiment of the invention, the nucleotide sequence encoding the first component is upstream of the nucleotide sequence encoding the second component. In another embodiment of the invention, the nucleotide sequence encoding the first component is downstream of the nucleotide sequence encoding the second component. Further embodiments of the invention may be prepared in which the order of the first, second and third fusion polypeptide components are rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

The present invention also has diagnostic and therapeutic utilities. In particular embodiments of the invention, methods of detecting aberrancies in the function or expression of the chimeric polypeptide molecules described herein may be used in the diagnosis of disorders. In other embodiments, manipulation of the chimeric polypeptide molecules or agonists or antagonists which bind the chimeric polypeptide molecules may be used in the treatment of diseases. In further embodiments, the chimeric polypeptide molecule is utilized as an agent to block the binding of a binding agent to its target.

By way of example, but not limitation, the method of the invention may be useful in treating clinical conditions that are characterized by vascular permeability, edema, or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

An amino acid sequence analysis of Flt1(1-3)-Fc revealed the presence of an unusually high number (46) of the basic amino acid residue lysine. An IEF analysis of Flt1(1-3)-Fc showed that this protein has pI greater than 9.3, confirming the prediction that the protein is very basic. It was hypothesized that the basic nature of Flt1(1-3)-Fc protein was causing it to bind to extracellular matrix components and that this interaction might be the cause of the extremely short detectable circulating serum half-life exhibited by Flt1(1-3)-Fc when injected into mice. In order to test this hypothesis, Flt1(1-3)-Fc protein was acetylated at the lysine residues to reduce the basic charge. Acetylated Flt1(1-3)-Fc was then tested in the assays described infra.

The following examples are offered by way of illustration and not by way of limitation.

EXAMPLES

Example 1

Expression of Flt1(1-3)-Fc Protein in CHO K1 Cells

Using standard molecular biology techniques (see e.g., Molecular Cloning, A Laboratory Manual (Sambrook, et al., Cold Spring Harbor Laboratory), Current Protocols in Molecular Biology (Eds. Ausubel, et al., Greene Publ. Assoc., Wiley-Interscience, NY), the gene encoding Flt1 (1-3)-Fc was inserted into the expression vector pEE14.1 (Lonza Biologics, plc) at a multiple cloning site downstream of the CMV promoter. CHO K1 cells were transfected with the pEE14.1/Flt1(1-3)-Fc DNA construct using lipofectamine (Gaithersburg, Md.). The transfected CHO K1 cells were grown in glutamine-free DMEM (JRH, Kansas City, Mo.) containing 25 µM methionine sulfoximine (MSX) from Sigma Inc., St. Louis, Mo., and high recombinant protein expressors were obtained by screening the CHO K1 cell supernatants from over 100 hand-picked colony isolates using a standard immunoassay which captures and detects human Fc. The selected hand-picked clone was amplified in the presence of 100 µM MSX followed by a second round of screening of the amplified clones. The highest producing clone had a specific productivity of recombinant Flt1(1-3)-Fc protein of 55 µg/cell/day.

The selected clone was expanded in 225 $cm^2$ T-flasks (Corning, Acton, Mass.) and then into 8.5 L roller bottles (Corning, Acton, Mass.) using the cell culture media described supra. Cells were removed from the roller bottles by standard trypsinization and put into 3.5 L of suspension medium. The suspension medium is comprised of glutamine free ISCHO medium (Irvine Scientific, Santa Ana, Calif.) containing 5% fetal bovine serum (FBS from HYCLONE™ Labs, Logan, Utah), 100 µM MSX and GS supplement (JRH Scientific, Kansas City, Mo.) in a 5 L Celligen bioreactor (New Brunswick Scientific, New Brunswick, N.J.) at a density of $0.3\times10^6$ cells/mL. After the cells reached a density of $3.6\times10^6$/mL and were adapted to suspension they were transferred to a 60 L bioreactor (ABEC, Allentown, Pa.) at a density of $0.5\times10^6$ cells/mL in 20 L of ISCHO medium with 5% fetal bovine serum. After two days an additional 20 L of ISCHO+5% fetal bovine serum was added to the bioreactor. The cells were allowed to grow for an additional two days reaching a final density of $3.1\times10^6$ cells/mL, and a final Flt1 (1-3)-Fc concentration at harvest was 95 mg/L. At harvest the cells were removed by tangential flow filtration using 0.45 µm Prostak Filters (Millipore, Inc., Bedford, Mass.).

Example 2

Purification of Flt1(1-3)-Fc Protein Obtained from CHO K1 Cells

Flt1(1-3)-Fc protein was initially purified by affinity chromatography. A Protein A column was used to bind, with high specificity, the Fc portion of the molecule. This affinity-purified protein was then concentrated and passed over a SEC column. The protein was then eluted into the formulation buffer. The following describes these procedures in detail.

Materials and Methods. All chemicals were obtained from J. T. Baker, Phillipsburg, N.J. with the exception of PBS, which was obtained as a 10× concentrate from Life Technologies, Gaithersburg, Md. Protein A Fast Flow and SUPERDEX™ 200 preparation grade resins were obtained from Pharmacia, Piscataway, N.J. Equipment and membranes for protein concentration were obtained from Millipore, Bedford, Mass.

Approximately 40 L of 0.45 µm-filtered CHO conditioned media containing Flt1(1-3)-Fc protein was applied to a 290 mL Protein A Fast Flow column (10 cm diameter) that had been equilibrated with PBS. The column was washed with PBS containing 350 mM NaCl and 0.02% CHAPS and the bound protein was eluted with 20 mM Citric Acid containing 10 mM $Na_2HPO_4$. The single peak in the elution was collected and its pH was raised to neutrality with 1 M NaOH. The eluate fractions was concentrated to approximately 9, mg/mL using 10K regenerated cellulose membranes by both tangential flow filtration and by stirred cell concentration. To remove aggregates and other contaminants, the concentrated protein was applied to a column packed with SUPERDEX™ 200 preparation grade resin (10 cm×55 cm) and run in PBS containing 5% glycerol. The main peak fractions were pooled, sterile filtered, aliquoted and stored at −80° C.

Example 3

Acetylation of Flt1(1-3)-Fc Protein

Two milligrams of Flt1(1-3)-Fc protein were acetylated as described in the instruction manual provided with the sulfo-NHS-acetate modification kit (Pierce Chemical Co., Rockford, Ill., Cat. #26777).

Example 4

Characterization of Acetylated Flt1(1-3)-Fc Protein

IEF Flt1(1-3)-Fc and acetylated Flt1(1-3)-Fc were analyzed by Standard IEF analysis. As shown in FIG. 1, Flt1(1-3)-Fc protein is not able to migrate into the gel and therefore must have a pI greater than 9.3, the highest pI in the standard. However, acetylated Flt1(1-3)-Fc is able to migrate into the gel and equilibrate at a pI of approximately 5.2. This result demonstrates that acetylation reduces the net positive charge of the protein and therefore its pI considerably.

Figure 2:
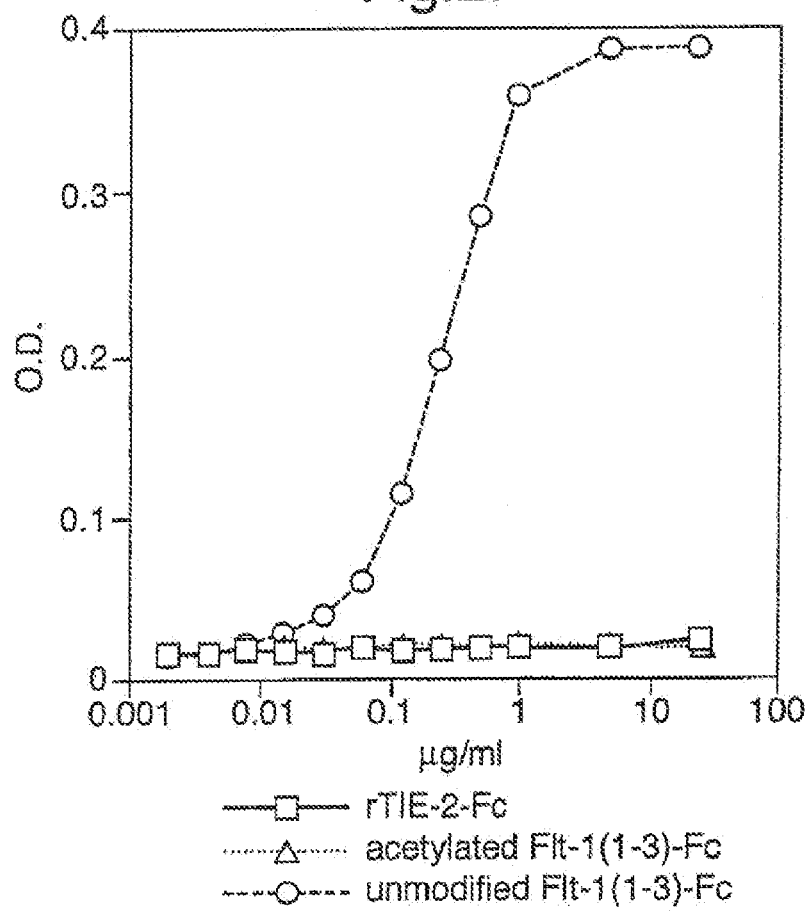
FIG. 2. Binding of unmodified Flt1(1-3)-Fc and acetylated Flt1(1-3)-Fc proteins to MATRIGEL® coated plates. Unmodified Flt1(1-3)-Fc proteins binds extensive to extracellular matrix components in MATRIGEL®, whereas acetylated Flt1(1-3)-Fc does not bind.

Binding to extracellular matrix components. To test for binding to extracellular matrix components, Flt1(1-3)-Fc and acetylated Flt1(1-3)-Fc where tested in an assay designed to mimic the interaction with extracellular matrix components. In this assay, 96-well tissue culture plates are coated with MATRIGEL® (Biocoat MATRIGEL® matrix thin layer 96 well plate, Catalog #40607, Becton Dickinson Labware, Bedford, Mass.). The plates are incubated with varying concentrations of either Flt1(1-3)-Fc; acetylated Flt1(1-3)-Fc, or rTie2-Fc (an irrelevant control) protein are added to the wells. The plates are incubated for 1-2 hours at either room temperature or 37° C. degrees and then detection of bound proteins is accomplished by adding a secondary alkaline phosphatase-conjugated anti-human Fc antibody to the wells. Finally, alkaline phosphatase substrate is added to the wells and optical density is measured. FIG. 2 shows the results of this assay. Like the irrelevant control protein rTie2-Fc, acetylated Flt1(1-3)-Fc does not exhibit any binding to the MATRIGEL® coated plate, whereas the non-acetylated Flt1(1-3)-Fc protein exhibits significant binding. This result indicates that acetylation of basic amino acid residues is an effective way to interfere with the charge interactions that exist between positively charged proteins and the negatively charged extracellular matrix components they are exposed to in vivo.

Example 5

Pegylation of Flt1(1-3)-Fc Protein

Although pegylation (polyethylene glycol—PEG) of proteins has been shown to increase their in vivo potency by enhancing stability and bioavailability while minimizing immunogenicity (see references cited supra), it is counterintuitive that pegylating molecules that are too large to be filtered by the kidney glomeruli would improve their pharmacokinetic properties. Without being bound by theory, Applicants postulated that pegylation of the Flt1(1-3)-Fc molecules could improve the pharmacokinetic properties, possibly not by altering the positive charge or by decreasing the pI of Flt1(1-3)-Fc, but rather by physically shielding the positive charges from interacting with the extracellular matrix. Applicants decided to attempt to improve the pharmacokinetic properties of Flt1(1-3)-Fc molecules by attaching strands of 20K PEGs as described infra.

Materials and Methods. Purified Flt1(1-3)-Fc derived from CHO cells (see supra) was used in the following pegylation experiments. Functionalized PEGs were obtained from Shearwater Polymers, Huntsville, Ala.; Bicine from Sigma, St Louis, Mo.; SUPEROSE™ 6 column from Pharmacia, Piscataway, N.J.; PBS as a 10× concentrate from Life Technologies, Gaithersburg, Md.; Glycerol from J. T. Baker, Phillipsburg, N.J.; and Bis-Tris precast gels from Novex, Calif.

20K PEG strands functionalized with amine-specific terminal moieties were used in small-scale reaction studies that were set-up to evaluate different reaction conditions in which the PEG:protein stoichiometry was varied. Based on these reaction's and the analyses of samples on standard SDS-PAGE, Flt1(1-3)-Fc at a concentration of 1.5 mg/mL was reacted at pH 8.1 with 20K SPA-PEG (PEG succinimidyl propionate) molecules at a PEG-to-Flt1(1-3)-Fc monomer molar ratio of 1:6. The reaction was allowed to proceed at 8° C. overnight. For initial purification, the reaction products were applied to a 10 mm×30 cm SUPEROSE™ 6 column equilibrated with PBS containing 5% Glycerol. The column appeared to separate pegylated Flt1(1-3)-Fc molecules based on the extent of pegylation. Fractions corresponding to what appeared to be primarily mono-pegylated and di-pegylated dimeric Flt1(1-3)-Fc, as judged by banding patterns on reducing and non-reducing SDS-PAGE gels were pooled. The protein concentration was determined by measuring absorbance at 280 nm. The pegylated Flt1(1-3)-Fc protein was sterile filtered, aliquoted and stored at −40° C.

Example 6

Figure 3:
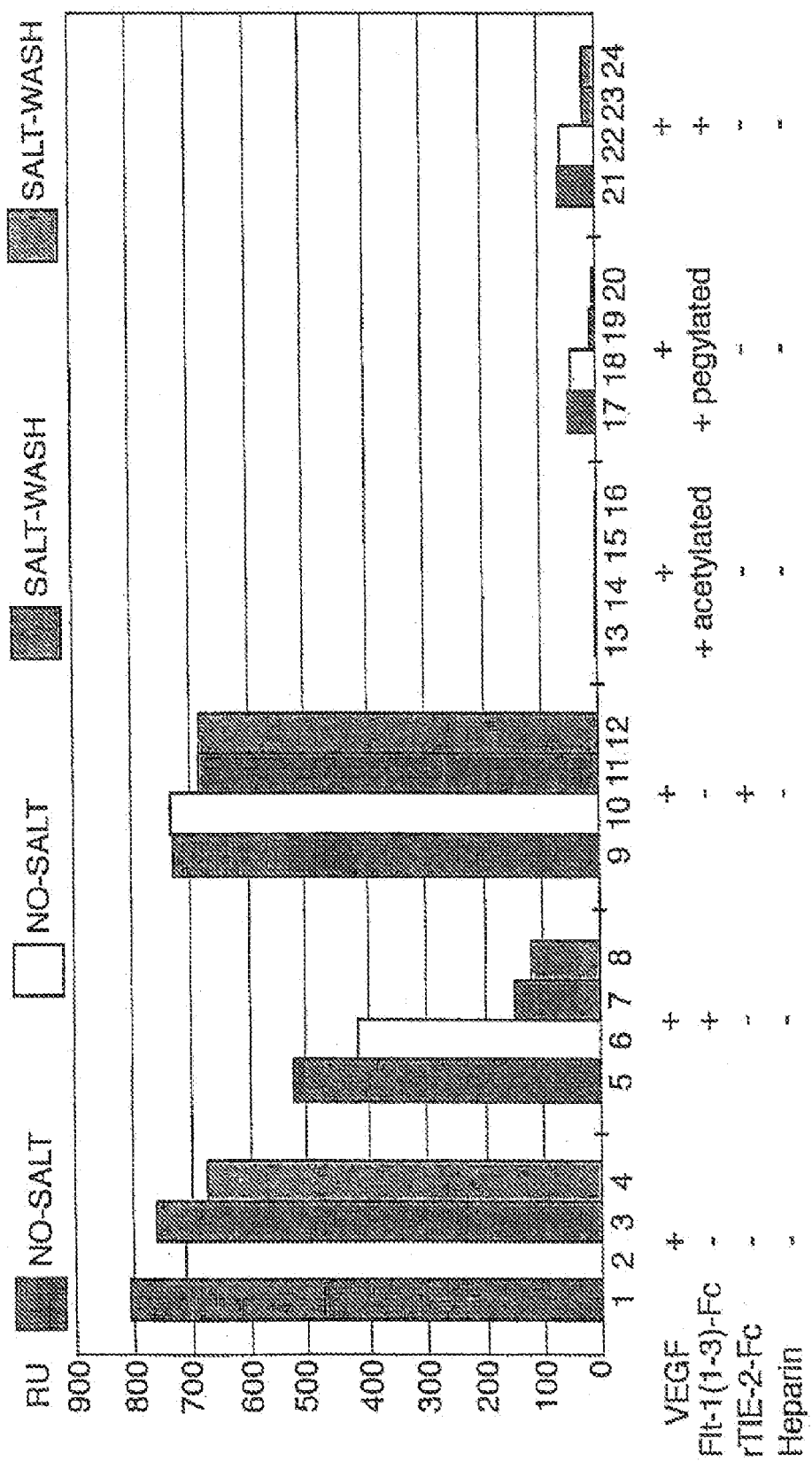
FIG. 3. Binding of unmodified Flt1(1-3)-Fc, acetylated Flt1(1-3)-Fc, and pegylated Flt1(1-3)-Fc in a BIACORE™-based assay. Acetylated (columns 13-16), pegylated (columns 17-20), and heparin-treated Flt1(1-3)-Fc (columns 21-24) are each able to completely compete with the BIACORE™ chip-bound Flt1(1-3)-Fc for VEGF binding as compared to control (columns 1-4) and irrelevant protein (columns 5-8). Unmodified Flt1(1-3)-Fc (columns 5-6) appears to only partially compete with BIACORE™ chip-bound Flt1(1-3)-Fc for VEGF binding. However, washing the bound samples with 0.5 M NaCl (columns 7-8) results in a binding profile similar to the modified forms of Flt1(1-3)-Fc, indicating that the unmodified protein is exhibiting non-specific binding to the chip that can be eliminated by the salt wash.

Binding of Unmodified, Acetylated, and Pegylated Flt1(1-3)-Fc in a BIACORE™-Based Assay Unmodified, acetylated, and pegylated Flt1(1-3)-Fc proteins were tested in a BIACORE™-based assay to evaluate their ability to bind to the Flt1 ligand, VEGF. In this assay, unmodified Flt1(1-3)-Fc protein was immobilized on the surface of a BIACORE™ chip (see BIACORE™ Instruction Manual, Pharmacia, Inc., Piscataway, N.J., for standard procedures) and a sample containing 0.2 µg/ml VEGF and either unmodified Flt1(1-3)-Fc, acetylated Flt1(1-3)-Fc or pegylated Flt1(1-3)-Fc (each at 25 µg/ml) was passed over the Flt1(1-3)-Fc coated chip. To minimize the effects of non-specific binding, the bound samples were washed with a 0.5 M NaCl wash. In one sample, unmodified Flt1(1-3)-Fc was mixed with heparin. Heparin is a negatively charged molecule and the Flt1(1-3)-Fc protein is a positively charged molecule, so when the two molecules are mixed together, they should interact through their respective charges. This essentially neutralizes Flt1(1-3)-Fc's inherent positive charge making the molecule behave as if it has been chemically or genetically modified so as to reduce its charge and its tendency to bind via charge interactions. As shown in FIG. 3, acetylated (columns 13-16), pegylated (columns 17-20), and heparin-treated Flt1(1-3)-Fc (columns 21-24) are each able to completely compete with the BIACORE™ chip-bound Flt1(1-3)-Fc for VEGF binding at compared to control (columns 1-4) and irrelevant protein (columns 5-8). Unmodified Flt1(1-3)-Fc (columns 5-6) appeared to only partially compete with BIACORE™ chip-bound Flt1(1-3)-Fc for VEGF binding. However, washing the bound samples with 0.5 M NaCl (columns 7-8) resulted in a binding profile similar to the modified forms of Flt1(1-3)-Fc, indicating that the unmodified proteins was exhibiting non-specific binding to the chip that could be eliminated by the salt wash.

Example 7

Figure 4:
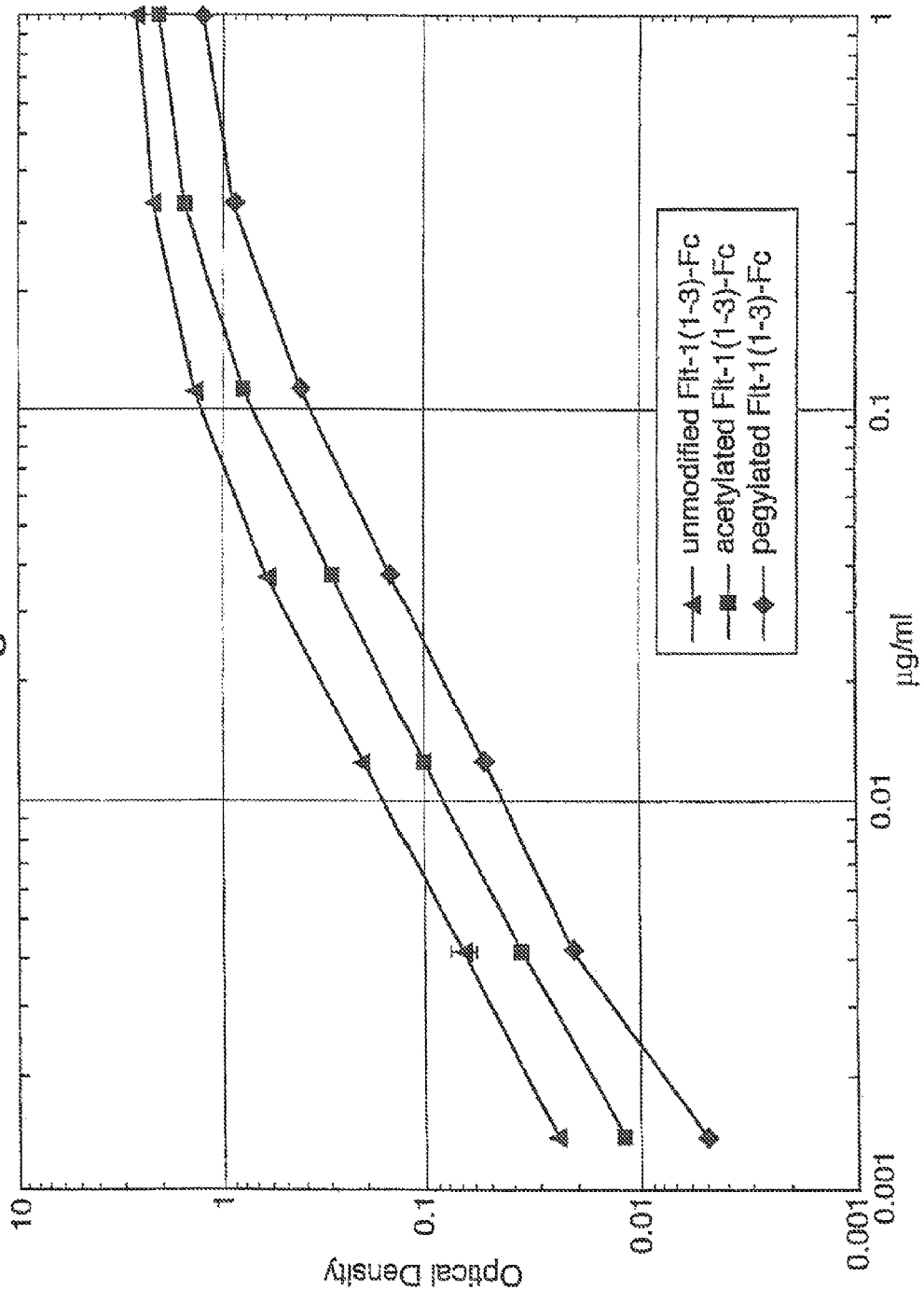
FIG. 4. Binding of unmodified Flt1(1-3)-Fc, acetylated Flt1(1-3)-Fc, and pegylated Flt1(1-3)-Fc, and Fc to VEGF in an ELISA-based assay. Both pegylated and acetylated Flt1 (1-3)-Fc proteins bind to VEGF with affinities approaching that of unmodified Flt1(1-3)-Fc.

Binding of Unmodified, Acetylated, and Pegylated Flt1(1-3)-Fc in an ELISA-Based Assay Unmodified, acetylated, and pegylated Flt1(1-3)-Fc proteins were tested in a standard ELISA-based assay to evaluate their ability to bind the Flt1 receptor ligand VEGF. As shown in FIG. 4, both pegylated and acetylated Flt1(1-3)-Fc proteins are capable of binding to VEGF, demonstrating that modifying the protein either by pegylation or acetylation does not destroy its ability to bind its ligand.

Example 8

Figure 5:
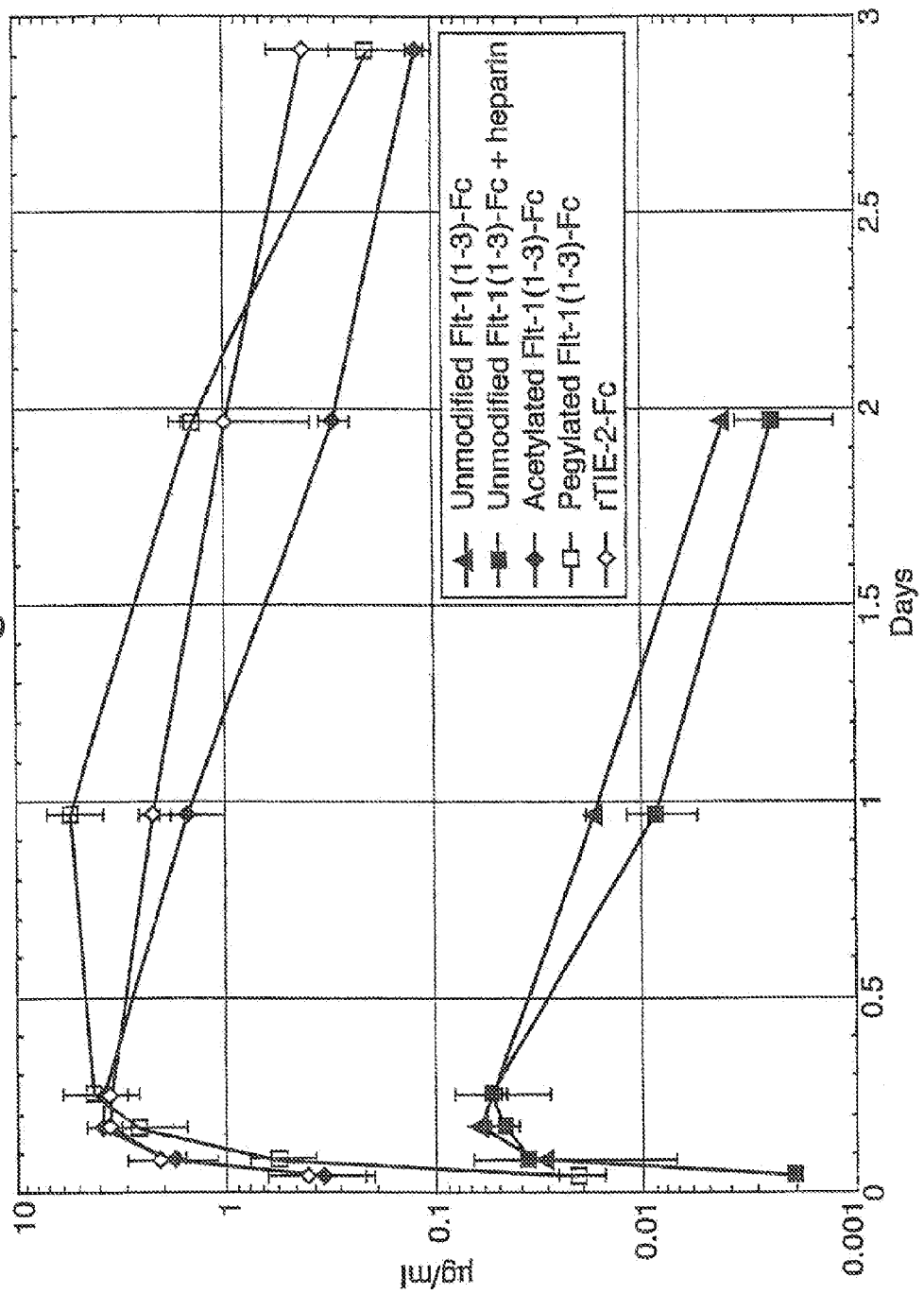
FIG. 5. Pharmacokinetic profiles of unmodified Flt1(1-3)-Fc, acetylated Flt1(1-3)-Fc, and pegylated Flt1(1-3)-Fc. Balb/c mice (23-28 g) were injected subcutaneously with 4 mg/kg of unmodified, acetylated, or pegylated Flt1(1-3)-Fc. The mice were tail bled at 1, 2, 4, 6, 24 hours, 2 days, and 3 days after injection of protein and the sera were assayed in a standard ELISA-based assay designed to detect Flt1(1-3)-Fc protein. The $T_{max}$ for all of the Flt1(1-3)-Fc proteins was between the 6 hour and 24 hour time points. The $C_{max}$ for the different proteins was as follows: Unmodified: 0.06 µg/ml-0.15 µg/ml; acetylated: 1.5 µg/ml-4.0 µg/ml; and pegylated: approximately 5 µg/ml.

Pharmacokinetic Analysis of Unmodified Flt1(1-3)-Fc, Acetylated Flt1(1-3)-Fc, and Pegylated Flt1(1-3)-Fc In vivo experiments were designed to assess the pharmacokinetic profiles of unmodified Flt1(1-3)-Fc, acetylated Flt1 (1-3)-Fc, and pegylated Flt1(1-3)-Fc protein. Balb/c mice (23-28 g; 3 mice/group) were injected subcutaneously with 4 mg/kg of unmodified, acetylated, or pegylated Flt1(1-3)-Fc. The mice were tail bled at 1, 2, 4, 6, 24 hours, 2 days, and 3 days after injection of protein. The sera were assayed in a standard ELISA-based assay designed to detect Flt1(1-3)-Fc protein. Briefly, the assay involves coating an ELISA plate with VEGF, binding the unmodified, acetylated, or pegylated Flt1(1-3)-Fc-containing sera, and reporting with an anti-Fc antibody linked to alkaline phosphatase. As shown in FIG. 5, the $T_{max}$ for all of the Flt1(1-3)-Fc proteins was between the 6 hour and 24 hour time points. The $C_{max}$ for the different proteins was as follows: Unmodified: 0.06 μ/ml-0.15 μg/ml; acetylated: 1.5 μg/ml-4.0 μg/ml; and pegylated: approximately 5 μg/ml.

Example 9

Step-Acetylation of Flt1(1-3)-Fc

To determine what minimal amount of acetylation is necessary to eliminate binding to extracellular matrix components, an experiment was designed that acetylated the Flt1(1-3)-Fc protein in a step-wise fashion by using increasing amounts of molar excess of acetylation reagent in the acetylation reaction mixture. The range of molar excess was as follows: 0, 10, 20, 30, 40, 50, 60, 70, 80, 90, and 100 moles of acetylation reagent per 1 mole of Flt1(1-3)-Fc monomer. The reactions were performed as detailed in the instruction manual provided with the sulfo-NHS-Acetate modification kit (Pierce Chemical Co., Rockford, Ill., Cat. #26777).

Example 10

Characterization of Step-Acetylated Flt1(13)-Fc

Figure 6A:
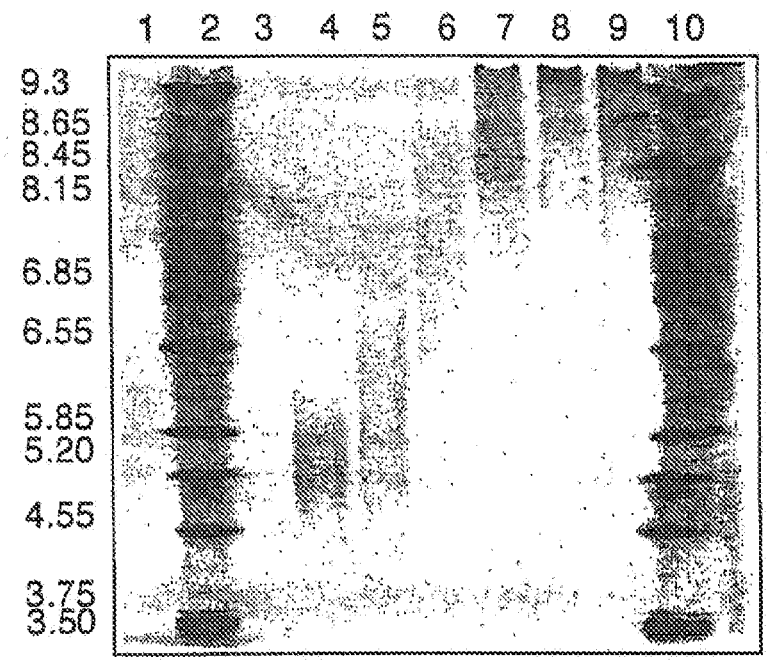
FIG. 6A-6B. IEF gel analysis of unmodified and step-acetylated Flt1(1-3)-Fc proteins. Unmodified Flt1(1-3)-Fc protein is unable to enter the gel due to its >9.3 pI, whereas most of the step-acetylated Flt1(1-3)-Fc samples (30-100 fold excess samples) were able to migrate into the gel and equilibrate at pIs ranging between 4.55-8.43, depending on the degree of acetylation.
Figure 6B:
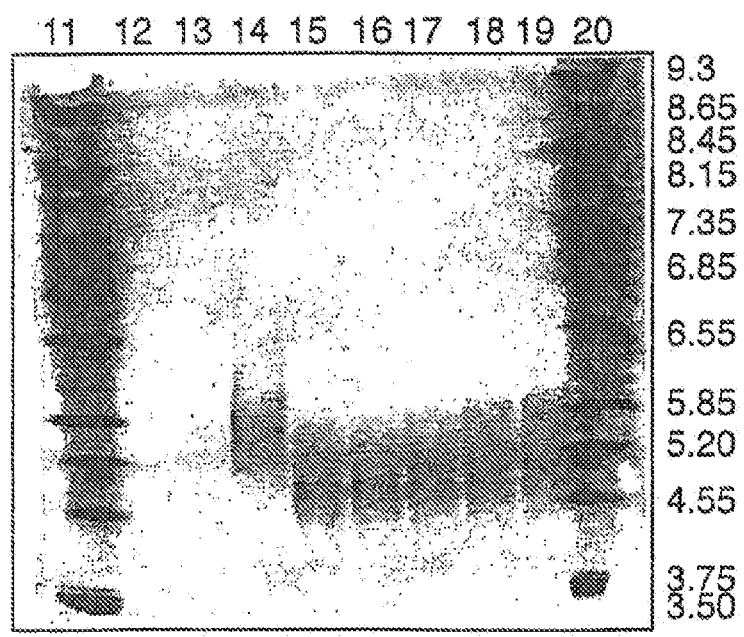

IEF analysis Unmodified Flt1(1-3)-Fc and step-acetylated Flt1(1-3)-Fc proteins were analyzed by standard IEF analysis. As shown in FIG. 6A-6B, unmodified Flt1(1-3)-Fc protein was not able to migrate into the gel due to its extremely high pI (greater than 9.3). However, most of the step-acetylated Flt1(1-3)-Fc samples (30-100 fold molar excess samples) were able to migrate into the gel and equilibrate at pIs ranging between 4.55-8.43, depending on the degree of acetylation of the protein. This result demonstrates that acetylation can change the positive charge of the protein in a dose-dependent manner and that reduction of the pI can be controlled by controlling the degree of acetylation.

Figure 9:
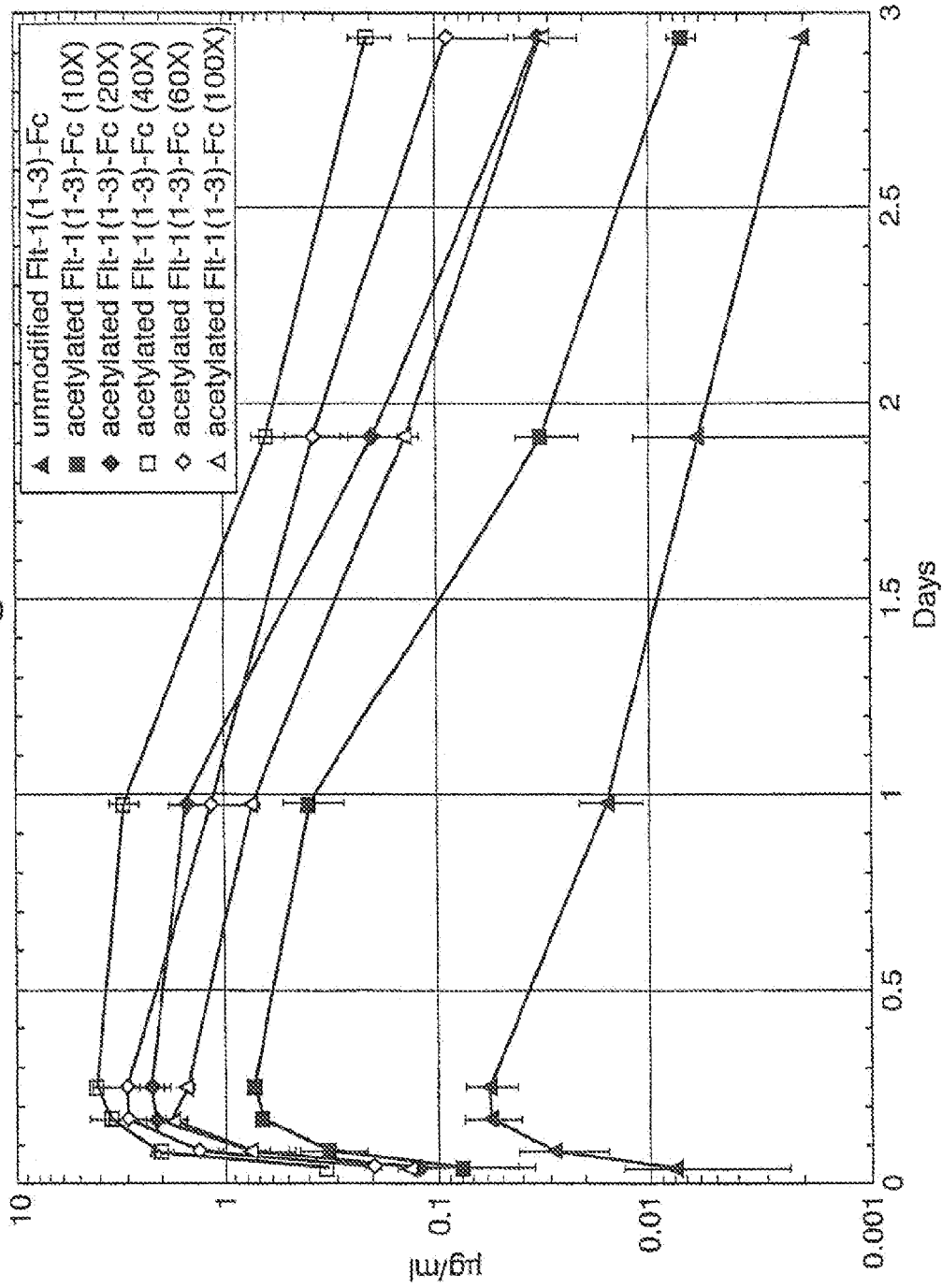
FIG. 9. Pharmacokinetic profiles of unmodified Flt1(1-3)-Fc and step-acetylated Flt1(1-3)-Fc. Balb/mice (23-28 g) were injected with 4 mg/kg of unmodified or 10, 20, 40, 60 and 100 fold excess samples of step-acetylated Flt1(1-3)-Fc (3 mice for unmodified, 10, 20 and 40 fold excess samples and 2 mice for 60 and 100 fold excess samples). The mice were tail bled at 1, 2, 4, 6, 24 hours, 2 days and 3 days after injection. The sera were assayed in an ELISA-based assay designed to detect Flt1(1-3)-Fc. The $T_{max}$ for all of the Flt1 (1-3)-Fc proteins tested was at the 6 hour time point but the $C_{max}$ was as follows. Unmodified Flt1(1-3)-Fc: 0.06 µg/ml; 10 fold excess sample: ~0.7 µg/ml, 20 fold excess sample—2 µg/ml, 40 fold excess sample—4 µg/ml, 60 fold excess sample—2 µg/ml, 100 fold excess sample—1 µg/ml.

Binding of step-acetylated Flt1(1-3)-Fc to extracellular matrix components. To test for binding to extracellular matrix components, Flt1(1-3)-Fc and step-acetylated Flt1(1-3)-Fc where tested in the above-described assay designed to mimic the interaction with extracellular matrix components. Varying concentrations of either unmodified Flt1(1-3)-Fc, step-acetylated Flt1(1-3)-Fc (10, 20, and 30 fold molar excess samples), or rTie2-Fc (an irrelevant control) protein were added to the wells. The plates were incubated for 1-2 hours at room temperature or 37° C. and then detection of bound proteins was accomplished by adding a secondary alkaline phosphatase-conjugated anti-human Fc antibody to the wells. Alkaline phosphatase substrate was subsequently added to the wells and optical density measured. FIG. 7 shows the results of this assay. Like the irrelevant control protein rTie2-Fc, step-acetylated Flt1(1-3)-Fc (20 and 30 fold molar excess samples) did not exhibit any significant binding to the MATRIGEL® coated plate, whereas the non-acetylated Flt1(1-3)-Fc protein exhibited significant binding. The binding is saturable, indicating that the Flt1(1-3)-Fc protein may be binding to specific sites, rather than a more general charge-mediated interaction that might not be saturable. The 10 fold molar excess sample showed reduced binding, but the degree of acetylation was not enough to completely block binding to extracellular matrix components. The 20 fold molar excess and higher samples displayed no detectable binding, despite the fact that by IEF analysis (FIGS. 6A and 6B) the lower molar excess samples still had a large net positive charge. This result demonstrates that it is not necessary to completely acetylate all available basic amino acids in order to eliminate binding to extracellular matrix components.

Binding of step-acetylated Flt1(1-3)-Fc in a BIACORE™-based assay. Unmodified and step-acetylated Flt1(1-3)-Fc proteins where tested in a BIACORE™-based assay to evaluate their ability to bind to the Flt1 ligand, VEGF. In this assay, unmodified Flt1(1-3)-Fc protein (0.5, 1.0, or 5.0 μg/ml) was immobilized on the surface of a BIACORE™ chip (see BIACORE™ Instruction Manual, Pharmacia, Inc., Piscataway, N.J., for standard procedures) and a solution containing 0.2 μg/ml VEGF and either unmodified Flt1(1-3)-Fc (at either 0.5, 1.0, or 5.0 μg/ml) or 10 different step-acetylated Flt1(1-3)-Fc samples (at 0.5, 1.0, or 5.0 μg/ml each) were passed over the Flt1(1-3)-Fc-coated chip. As shown in FIG. 8, at a sub-stoichiometric ratio (0.5 μg/ml of either unmodified Flt1 (1-3) or step-acetylated Flt1(1-3)-Fc vs. 0.2 μg/ml VEGF), there is not enough Flt1(1-3)-Fc (either unmodified or step-acetylated) in the solution to completely bind the VEGF. At 1.0 μg/ml, which approximates a 1:1 stoichiometric ratio, both unmodified and step-acetylated Flt1(1-3)-Fc are better able to compete for VEGF binding, but there is still insufficient Flt1(1-3)-Fc protein (either unmodified or step-acetylated) to completely bind the available VEGF. However, at 5.0 μg/ml, which is several times greater than a 1:1 stoichiometric ratio, both the Flt1(1-3)-Fc and the step-acetylated Flt1(1-3)-Fc proteins are able to bind the VEGF, regardless of the degree of acetylation. This clearly demonstrates that acetylation does not alter Flt1(1-3)-Fc's ability to bind VEGF.

Pharmacokinetic analysis of step-acetylated Flt1(1-3)-Fc. In vivo experiments were designed to assess the pharmacokinetic profiles of unmodified Flt1(1-3)-Fc and step-acetylated Flt1(1-3)-Fc protein. Balb/c mice (23-28 g) were injected subcutaneously with 4 mg/kg of unmodified or 10, 20, 40, 60 and 100 fold molar excess samples of step-acetylated Flt1(1-3)-Fc (3 mice for unmodified, 10, 20 and 40 fold molar excess samples and 2 mice for 60 and 100 fold molar excess samples). The mice were tail bled at 1, 2, 4, 6, 24 hours, 2 days and 3 days after injection. The sera were assayed in an ELISA-based assay designed to detect Flt1(1-3)-Fc (described supra). FIG. 9 details the results of this study. The $T_{max}$ for all of the Flt1(1-3)-Fc proteins tested was at the 6 hour time point but the $C_{max}$ was as follows: Unmodified Flt1(1-3)-Fc: 0.06 μg/ml; 10 fold molar excess sample: ~0.7 μg/ml, 20 fold molar excess sample—2 μg/ml, 40 fold molar excess sample—4 μg/ml, 60 fold molar excess sample—2 μg/ml, 100 fold molar excess sample—1 μg/ml. This results demonstrates that acetylation or pegylation of Flt1(1-3)-Fc significantly improves its pharmacokinetic profile.

Example 11

Construction of Flt1(1-3)-Fc Basic Region Deletion Mutant Designated Mut1: Flt1(1-3$_{AB}$)-Fc Based on the observation that acetylated Flt1(1-3)-Fc, which has a pI below 6, has much better pharmacokinetics than the highly positive unmodified Flt1(1-3)-Fc (pI>9.3), it was asked whether the difference in pharmacokinetics could be attributed to the net charge of the protein, which made it stick to negatively charged extracellular matrix components, or whether there were perhaps specific locations on the surface of the Flt1(1-3)-Fc protein that constituted specific binding sites for extracellular matrix components. For example, many proteins are known to have heparin binding sites, often consisting of a cluster of basic residues. Sometimes these residues are found in a cluster on the primary sequence of the protein; some of the literature has identified "consensus sequences" for such heparin binding sites (see for example Hileman, et al., 1998, Bioessays 20(2):156-67). In other cases, the known crystal structure of a protein reveals a cluster of positively charged residues on the surface of a protein, but the residues come from different regions of the primary sequence and are only brought together when the protein folds into its tertiary structure. Thus it is difficult to deduce whether an isolated amino acid residue forms part of a cluster of basic residues on the surface of the protein. However, if there is a cluster of positively charged amino acid residues in the primary sequence, it is not unreasonable to surmise that the residues are spatially close to one another and might therefore be part of an extracellular matrix component binding site. Flt1 receptor has been studied extensively and various domains have been described (see for example Tanaka et al., 1997, Jpn. J. Cancer Res. 88:867-876). Referring to the nucleic acid and amino acid sequence set forth in FIG. 10A-10D of this application, one can identify the signal sequence for secretion which is located at the beginning of the sequence and extends to the glycine coded for by nucleotides 76-78. The mature protein begins with Ser-Lys-Leu-Lys, starting at nucleotide 79 of the nucleic acid sequence. Flt1 Ig domain 1 extends from nucleotide 79 to 393, ending with the amino acids Ser-Asp-Thr. Flt1 Ig domain 2 extends from nucleotide 394 to 687 (encoding Gly-Arg-Pro to Asn-Thr-Ile), and Flt1 Ig domain 3 extends from nucleotides 688 to 996 (encoding Ile-Asp-Val to Asp-Lys-Ala). There is a bridging amino acid sequence, Gly-Pro-Gly, encoded by nucleotides 997-1005, followed by the nucleotide sequence encoding human Fc (nucleotides 1006-1701 or amino acids. Glu-Pro-Lys to Pro-Gly-Lys-stop).

A more detailed analysis of the Flt1 amino acid sequence reveals that there is a cluster, namely, amino acid residues 272-281 (KNKRASVRR) of FIG. 10A-10D, in which 6 out of 10 amino acid residues are basic. This sequence is located in Flt1 Ig domain 3 of the receptor (see FIG. 11), which is not itself essential for binding of VEGF ligand, but which confers a higher affinity binding to ligand. An alignment of the sequence of Ig domain 3 with that of Ig domain 2 reveals that in this region, there is very poor alignment between the two Ig domains, and that there are about 10 additional amino acids in Ig domain 3. An analysis of the hydrophilicity profiles (MACVECTOR™ computer software) of these two domains clearly indicates the presence of a hydrophilic region in the protein (FIG. 12A-12B). These observations raised the possibility that the actual three dimensional conformation of Flt1 Ig domain 3 allowed for some type of protrusion that is not in Flt1 Ig domain 2. To test this hypothesis, the 10 additional amino acids were deleted and the resulting protein was tested to see whether the deletion would affect the pharmacokinetics favorably without seriously compromising the affinity of the receptor for VEGF. This DNA construct, which was constructed using standard molecular biology techniques (see e.g., Molecular Cloning, A Laboratory Manual (Sambrook, et al., Cold Spring Harbor Laboratory), Current Protocols in Molecular Biology (Eds. Ausubel, et al., Greene Publ. Assoc., Wiley-Interscience, NY) in the mammalian expression vector pMT21 (Genetics Institute, Inc., Cambridge, Mass.), is referred to as Mut1: Flt1(1-3$_{AB}$)-Fc. The Mut1: Flt1(1-3$_{AB}$)-Fc construct was derived from Flt1(1-3)-Fc by deletion of nucleotides 814-843 (set forth in FIG. 10A-10D), which deletes the highly basic 10-amino acid residue sequence Lys-Asn-Lys-Arg-Ala-Ser-Val-Arg-Arg-Arg from Flt1 Ig domain 3.

The final DNA construct was sequence-verified using an ABI 373A DNA sequencer and Taq Dideoxy Terminator Cycle Sequencing Kit (Applied Biosystems, Inc., Foster City, Calif.). The sequence of Mut1: Flt1(1-3$_{AB}$)-Fc is set forth in FIG. 13A-13D.

Example 12

Construction of Flt1(1-3)-Fc Basic Region Deletion Mutant Designated Mut2: Flt1(2-3$_{AB}$)-Fc A second deletion mutant construct, designated Mut2: Flt1(2-3$_{AB}$)-Fc, was derived from the Mut1: Flt1(1-3$_{AB}$)-Fc construct by deletion of Flt1 Ig domain 1 encoded by nucleotides 79-393 (see FIG. 10A-10D); for convenience, nucleotides 73-78 (TCA GGT) were changed to TCC GGA. This introduced a restriction site (BspEI) without altering the associated amino acid sequence, Ser-Gly. This DNA construct, which was constructed using standard molecular biology techniques (see e.g., Molecular Cloning, A Laboratory Manual (Sambrook, et al., Cold Spring Harbor Laboratory), Current Protocols in Molecular Biology (Eds. Ausubel, et al., Greene Publ. Assoc., Wiley-Interscience, NY)) in the mammalian expression vector pMT21 (Genetic's Institute, Inc., Cambridge, Mass.), was also sequence-verified using an ABI 373A DNA sequencer and Taq Dideoxy Terminator Cycle Sequencing Kit (Applied Biosystems, Inc., Foster City, Calif.). The sequence of Mut2: Flt1(2-3$_{AB}$)-Fc is set forth in FIG. 14A-14C.

Example 13

Construction of Flt1(1-3)-Fc Deletion Mutant Designated Mut3: Flt1(2-3)-Fc

A third deletion mutate construct, designated Mut3: Flt1(2-3)-Fc, was constructed the same way as the Mut2: Flt1(2-

$3_{AB}$)-Fc construct, except that Flt1 Ig domain 3 was left intact (the basic region amino acids were not deleted). The construct was constructed using standard molecular biology techniques and the final construct was sequence-verified as described supra. The sequence of Mut3: Flt1(2-3)-Fc is set forth in FIG. 15A-15C.

Example 14

Construction of Flt1-3)-Fc Basic Region N-glycosylation Mutant Designated Mut4: Flt1(1-3$_{R→N}$)-Fc A final construct was made in which a N-glycosylation site was introduced into the middle of the basic region of Flt1 Ig domain 3. This construct was designated Mut4: Flt1(1-3$_{R→N}$)-Fc and was made by changing nucleotides 824-825 from GA to AC, consequently changing the coded Arg residue (AGA) into an Asn residue (AAC) (see FIG. 10A-10D). The resulting amino acid sequence is therefore changed from Arg-Ala-Ser to Asn-Ala-Ser; which matches the canonical signal (Asn-Xxx-Ser/Thr) for the addition of a N-glycosylation site at the Asn residue. The sequence of Mut4: Flt1(1-3$_{R→N}$)-Fc is set forth in FIG. 16A-16D.

Example 15

Characterization of Acetylated Flt1(1-3)-Fc, Mut1: Flt1(1-3$_{AB}$)-Fc, and Mut4: Flt1(1-3$_{R→N}$)-Fc Mutants Binding to extracellular matrix components. To determine whether the three modified proteins were more or less likely to have improved pharmacokinetic properties, MATRIGEL® coated 96-well dishes (as described supra) were incubated with varying concentrations of the mutant proteins and detected with anti-human Fc/alkaline-phosphatase conjugated antibodies. As shown in FIG. 18, this experiment showed that while the unmodified Flt1(1-3)-Fc protein could bind avidly to these wells, the Mut3: Flt1(2-3)-Fc protein bound somewhat more weakly, the Mut1: Flt1(1-3$_{AB}$)-Fc protein bound more weakly still, and the Mut2: Flt1(2-3$_{AB}$)-Fc protein showed the best profile, binding more weakly than any of the other mutant proteins. The Mut4: Flt1(1-3$_{R→N}$)-Fc glycosylation mutant protein showed only marginal benefit on the MATRIGEL® assay. These results confirm the hypothesis that a linear sequence of positive amino acids can be deleted from the primary sequence resulting in a decrease in charge interaction with extracellular matrix components.

Binding of Mut1: Flt1(1-3$_{AB}$)-Fc and Mut4: Flt1(1-3$_{R→N}$)-Fc in a BIACORE™-Based Assay. Unmodified and acetylated Flt1(1-3)-Fc and genetically modified Mut1: Flt1(1-3$_{AB}$)-Fc and Mut4: Flt1(1-3$_{R→N}$)-Fc proteins where tested in a BIACORE™-based assay to evaluate their ability to bind to the Flt1 ligand, VEGF. In this assay, unmodified Flt1(1-3)-Fc protein (0.25, 0.5, or 1.0 µg/ml) was immobilized on the surface of a BIACORE™ chip (see BIACORE™ Instruction Manual, Pharmacia, Inc., Piscataway, N.J., for standard procedures) and a solution containing 0.1 µg/ml VEGF and either purified or COS cell supernatant containing unmodified Flt1(1-3)-Fc (at approximately (0.25, 0.5, or 1.0 µg/ml), purified acetylated Flt1(1-3)-Fc (at (0.25, 0.5, or 1.0 µg/ml), COS cell supernatant containing Mut1; Flt1(1-3$_{AB}$)-Fc (at approximately (0.25, 0.5, or 1.0 µg/ml), or COS cell supernatant containing Mut4 Flt1(1-3$_{R→N}$)-Fc (at approximately (0.25, 0.5, or 1.0 µg/ml) were passed over the Flt1(1-3)-Fc coated chip. As shown in FIG. 17, at the sub-stoichiometric ratio (0.25 µg/ml Flt1(1-3)-Fc of unmodified, acetylated or genetically modified samples vs. 0.1 µg/ml VEGF), there is insufficient Flt1(1-3)-Fc protein to block binding of VEGF to the Flt1(1-3)-Fc immobilized on the BIACORE™ chip. At 0.5 µg/ml of unmodified, acetylated or genetically modified Flt1(1-3)-Fc proteins, the stoichiometric ratio approximates 1:1 and there is an increased ability to block VEGF binding to the BIACORE™ chip. At 1.0 µg/ml of unmodified, acetylated or genetically modified Flt1(1-3)-Fc proteins, which is approximately a 10:1 stoichiometric ratio, the Flt1(1-3)-Fc proteins are able to block binding of VEGF to the BIACORE™ chip, but they are not equivalent. Unmodified, acetylated, and Mut1: Flt1(1-3$_{AB}$)-Fc are essentially equal in their ability to block VEGF binding, whereas Mut4: Flt1(1-3$_{R→N}$)-Fc is somewhat less efficient blocking binding. These results confirm the hypothesis that it is possible to reduce the non-specific binding of a positively charged molecule by genetically removing a linear sequence of predominantly negatively charged amino acids.

Binding of Mut1: Flt1(1-3$_{AB}$)-Fc, Mut2: Flt1(2-3$_{AB}$)-Fc, Mut3: Flt1(2-3-Fc, and in an ELISA-based assay. To determine whether the three mutant proteins could bind the Flt1 ligand VEGF, binding experiments were done in which 96-well plates coated with VEGF were incubated with varying concentrations of the respective mutant protein, and after washing, the amount bound was detected by incubating with an alkaline phosphatase conjugated anti-human Fc antibody and quantitated colorimetrically by the addition of an appropriate alkaline phosphatase substrate. As shown in FIG. 19, this experiment showed that all the mutant proteins could bind VEGF similarly, at the concentrations tested.

Example 16

Figure 20:
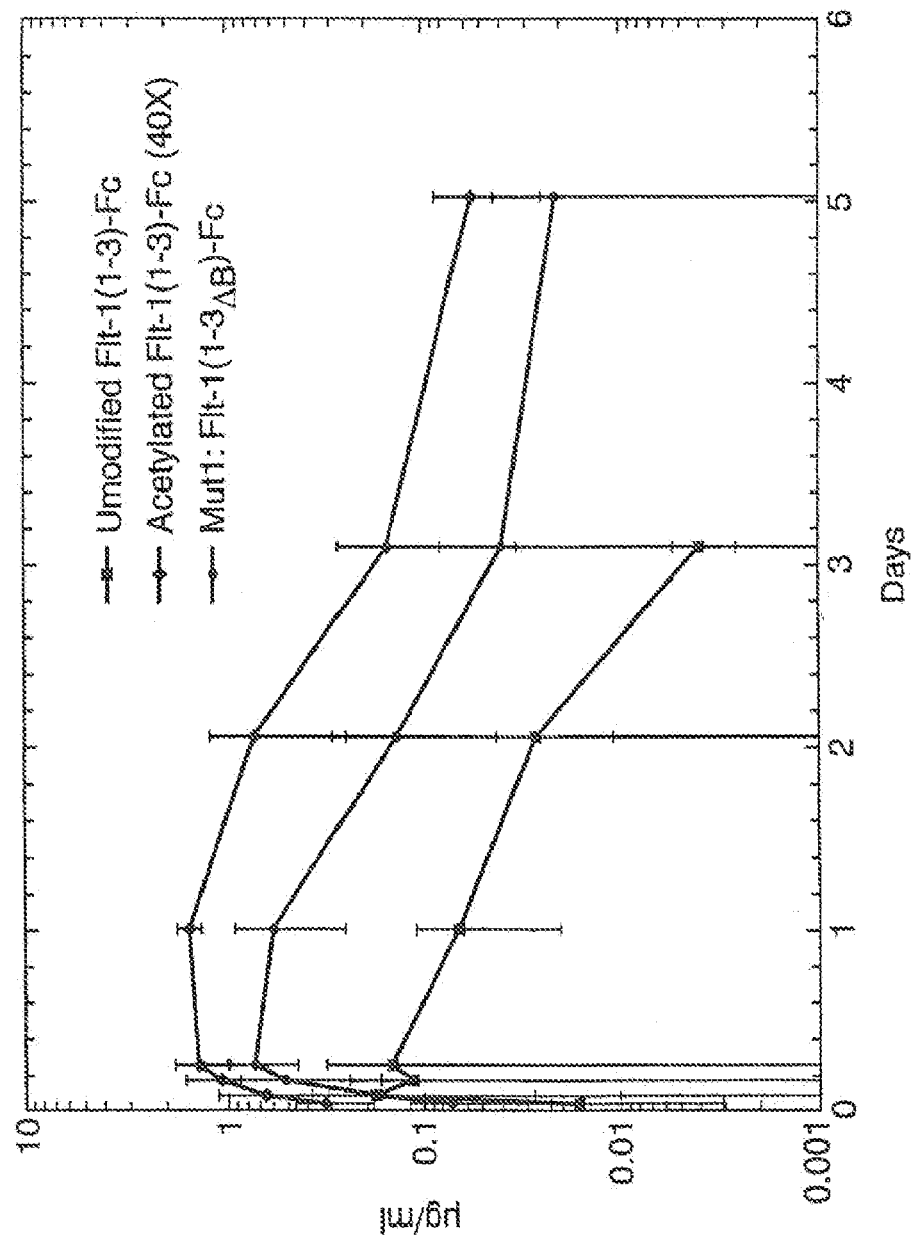
FIG. 20. Pharmacokinetic profiles of unmodified Flt1(1-3)-Fc, Mut1: Flt1-3$_{AB}$)-Fc, Mut2; Flt1(2-3$_{AB}$)-Fc, and Flt1(2-3) mutant proteins, the $C_{max}$ for these reagents was as follows: Unmodified Flt1(1-3)-Fc-0.15 μg/ml; 40 fold molar excess acetylated Flt1(1-3)-Fc-1.5 μg/ml; and Mut1: Flt1(1-3$_{A3}$)-Fc-0.7 μg/ml.

Pharmacokinetic Analysis of Acetylated Flt1(1-3)-Fc, Mutt Flt1(1-3$_{AB}$)-Fc, and Unmodified Flt1(1-3)-Fc In vivo experiments were designed to assess the pharmacokinetic profiles of unmodified Flt1(1-3)-Fc, Mut1: Flt1(1-3$_{AB}$)-Fc, and 40 fold molar excess acetylated Flt1(1-3)-Fc protein. Balb/c mice (25-30 g) were injected subcutaneously with 4 mg/kg of unmodified Flt1(1-3)-Fc, 40 fold molar excess acetylated Flt1(1-3)-Fc, and Mut1: Flt1(1-3$_{AB}$)-Fc proteins (4 mice each). These mice were tail bled at 1, 2, 4, 6, 24 hours, 2 days, 3 days, and 5 days after injection. The sera were assayed in an ELISA designed to detect Flt1(1-3)-Fc protein which involves coating an ELISA plate with VEGF, binding the Flt1(1-3)-Fc and reporting with an anti-Fc antibody linked to alkaline phosphatase. As shown in FIG. 20, the $C_{max}$ for these reagents was as follows: Unmodified Flt1(1-3)-Fc—0.15 µg/ml; 40 fold molar excess acetylated Flt1(1-3)-Fc—1.5 µg/ml; and Mut1: Flt1(1-3$_{AB}$)-Fc—0.7 µg/ml.

Example 17

Modified Flt1 Receptor Vector Construction

The rationale for constructing modified versions of the Flt1 receptor (also known as VEGFR1) was based on the observation that the protein sequence of Flt1 was highly basic, and was therefore likely to stick to extracellular matrix (ECM). The highly basic nature of Flt1 probably explains why unmodified Flt1(1-3)-Fc (described supra) has poor pharmacokinetics that make it difficult to use as a therapeutic agent. As described supra, the chemically modified form of 40 fold molar excess acetylated Flt1(1-3)-Fc, hereinafter termed A40, exhibited a greatly improved pharmacokinetic (PK) profile over the non-acetylated Flt1(1-3)-Fc. Therefore, attempts were made to engineer DNA molecules that could be used to recombinantly express modified forms of a Flt1 receptor molecule that would possess the improved PK profile exhibited by A40 and still maintain the ability to bind tightly to VEGF.

It is known in the literature that the first Ig domain of Flt1 (which has a net charge of +5 at neutral pH) is not essential for tight binding to VEGF, so this domain was deleted. The third Ig domain (having a netcharge of +11) is not essential for binding, but confers higher affinity for VEGF than the second 14 domain, so instead of deleting it entirely, it was replaced with the equivalent domains of the Flt1 receptor relatives Flk1 (also known as VEGFR2) and Flt4 (also known as VEGFR3). These chimeric molecules (denoted R1R2 (Flt1D2.Flk1D3.FcΔC1(a) and VEGFR1R2-FcΔC1(a)) and R1R3 (Flt1D2.VEGFR3D3-FcΔC1(a) and VEGFR1R3-FcΔC1(a)) respectively, wherein R1 and Flt1D2=Ig domain 2 of Flt1 (VEGFR1); R2 and Flk1D3=Ig domain 3 of Flk1 (VEGFR2); and R3 and VEGFR3D3=Ig domain 3 of Flt4 (VEGFR3)) were much less sticky to ECM, as judged by an in vitro ECM binding assay as described infra, had greatly improved PK as described infra. In addition, these molecules were able to bind VEGF tightly as described infra and block phosphorylation of the native Flk1 receptor expressed in endothelial cells as described infra.

Construction of the expression plasmid pFlt1D2.Flk1D3.FcΔC1(a). Expression plasmids pMT21.Flt1(1-3).Fc (6519 bp) and pMT21.Flk-1(1-3).Fc (5230 bp) are plasmids that encode ampicillin resistance and Fc-tagged versions of Ig domains 1-3 of human Flt1 and human Flk1, respectively. These plasmids were used to construct a DNA fragment consisting of a fusion of Ig domain 2 of Flt1 with Ig domain 3 of Flk1, using PCR amplification of the respective Ig domains followed by further rounds of PCR to achieve fusion of the two domains into a single fragment. For Ig domain 2 of Flt1, the 5' and 3' amplification primers were as follows:

```
5': bsp/flt1D2
                                       (SEQ ID NO: 18)
(5'-GACTAGCAGTCCGGAGGTAGACCTTTCGTAGAGATG-3')

3': Flt1D2-Flk1D3.as
                                       (SEQ ID NO: 19)
(5'-CGGACTCAGAACCACATCTATGATTGTATTGGT-3')
```

The 5' amplification primer encodes a BspE1 restriction enzyme site, upstream of Ig domain 2 of Flt1, defined by the amino acid, sequence GRPFVEM (SEQ ID NO:20) (corresponding to amino acids 27-33 of FIG. 21A-21C). The 3' primer encodes the reverse complement of the 3' end of Flt1 Ig domain 2 fused directly to the 5' beginning of Flk1 Ig domain 3, with fusion point defined as TIID (SEQ ID NO:37) of Flt1 (corresponding to amino acids 123-126 of FIG. 21A-21C) an continuing into VVLS (SEQ ID NO:38) (corresponding to amino acids 127-130 of FIG. 21A-21C) of Flk1.

For Ig domain 3 of Flk1, the 5' and 3' amplification primers were as follows:

```
5': Flt1D2-Flk1D3.s
                                       (SEQ ID NO: 21)
(5'-ACAATCATAGATGTGGTTCTGAGTCCGTCTCATGG-3')

3': Flk1D3/apa/srf.as
                                       (SEQ ID NO: 22)
(5'-GATAATGCCCGGGCCCTTTTCATGGACCCTGACAAATG-3')
```

The 5' amplification primer encodes the end of Flt1 Ig domain 2 fused directly to the beginning of Flk1 Ig domain 3, as described above. The 3' amplification primer encodes the end of Flk1 Ig domain 3, defined by the amino acids VRVHEK (SEQ ID NO:23) (corresponding to amino acids 223-228 of FIG. 21A-21C), followed by a bridging sequence that includes a recognition sequence for the restriction enzyme Srf1, and encodes the amino acids GPG. The bridging sequence corresponds to amino acids 229-231 of FIG. 21A-21C.

After a round of PCR amplification to produce the individual domains, the products were combined in a tube and subjected to a further round of PCR with the primers bsp/flt1D2 and Flk1D3/apa/srf as (described supra) to produce the fusion product. This PCR product was subsequently digested with the restriction enzymes BspEI and SmaI and the resulting 614 bp fragment was subcloned into the BspEI to SrfI restriction sites of the vector pMT21/ΔB2.Fc, to create the plasmid pMT21/Flt1D2.Flk1D3.Fc. The nucleotide sequence of the Flt1D2-Flk1D3 gene fusion insert was verified by standard sequence analysis. This plasmid was then digested with the restriction enzymes EcoRI and SrfI and the resulting 702 bp fragment was transferred into the EcoRI to SrfI restriction sites of the plasmid pFlt1(1-3)B2-FcΔC1(a) to produce the plasmid pFlt1D2.Flk1D3.FcΔC1(e). The complete DNA and deduced amino acid sequences of the Flt1D2.Flk1D3.FcΔC1(a) chimeric molecule is set forth in FIG. 21A-21C.

Construction of the expression plasmid pFlt1D2VEGFR3D3FcΔC1(a). The expression plasmid pMT21.Flt1(1-3).Fc (6519 bp) encodes ampicillin resistance and an Fc-tagged version of Ig domains 1-3 of human Flt1 receptor. This plasmid was used to produce a DNA fragment containing Ig domain 2 of Flt1 by PCR. RNA from the cell line HEL921.7 was used to produce Ig domain 3 of Flk1, using standard RT-PCR methodology. A further round of PCR amplification was used to achieve fusion of the two Ig domains into a single fused fragment. For Ig domain 2 of Flt1, the 5' and 3' amplification primers were as follows:

```
5': bsp/flt1D2
                                       (SEQ ID NO: 24)
(5'-GACTAGCAGTCCGGAGGTAGACCTTTCGTAGAGATG-3')

3': Flt1D2.VEGFR3D3.as
                                       (SEQ ID NO: 25)
(TTCCTGGGCAACAGCTGGATATCTATGATTGTATTGGT)
```

The 5' amplification primer encodes a BspE1 restriction site upstream of Ig domain 2 of Flt1, defined by the amino acid sequence, GRPFVEM (SEQ ID NO:20) (corresponding to amino acids 27-33 of FIG. 22A-22C). The 3' amplification primer encodes the reverse complement of the end of Flt1 Ig domain 2 fused directly to the beginning, of VEGFR3, Ig domain 3, with the fusion point defined as TIID (SEQ ID NO:37) of Flt1 (corresponding to amino acids 123-126 of FIG. 22A-22C) and continuing into IQLL (SEQ ID NO:26) of VEGFR3 (Corresponding to amino acids 127-130 of FIG. 22A-22C).

For Ig domain 3 of VEGFR3, the 5' and 3' primers used for RT-PCR were as follows:

```
5': R3D3.s
                                        (SEQ ID NO: 27)
(ATCCAGCTGTTGCCCAGGAAGTCGCTGGAGCTGCTGGTA)

3': R3D3.as
                                        (SEQ ID NO: 28)
(ATTTTCATGCACAATGACCTCGGTGCTCTCCCGAAATCG)
```

Both the 5' and 3' amplification primers match the sequence of VEGFR3. The 296 bp amplification product of this RT-PCR reaction was isolated by standard techniques and subjected to a second round of PCR to add suitable sequences to allow for fusion of the Flt1D2 with the Flk1D3 domains and fusion of the Flk1D3 and Fc domains via a GPG bridge (see below). The amplification primers were as follows:

```
5':Flt1D2.VEGFR3D3.s
                                        (SEQ ID NO: 29)
(TCATAGATATCCAGCTGTTGCCCAGGAAGTCGCTGGAG)

3': VEGFR3D3/srf.as
                                        (SEQ ID NO: 30)
(GATAATGCCCGGGCCATTTTCATGCACAATGACCTCGGT)
```

The 5' amplification primer encodes the 3' end of Flt1 Ig domain 2 fused directly to the beginning (5' end) of VEGFR3 Ig domain 3, as described above. The 3' amplification primer encodes the 3' end of VEGFR3. Ig domain 3, defined by the amino acids VIVHEN (SEQ ID NO:31) (corresponding to amino acids 221-226 of FIG. 22A-22C), followed by a bridging sequence that includes a recognition sequence for Srf1, and encodes the amino acids GPG. The bridging sequence corresponds to amino acids 227-229 of FIG. 22A-22C.

After one round (for Flt1 Ig domain 2) or two rounds (for Flt4 Ig domain 3) of PCR to produce the individual Ig domains, the PCR products were combined in a tube and subjected to a further round of PCR amplification with the amplification primers bsp/flt1D2 and VEGFR3D3/srf as described supra, to produce the fusion product. This PCR product was subsequently digested with the restriction enzymes BspEI and SmaI and the resulting 625 bp fragment was subcloned into the BspEI to SrfI restriction sites of the vector pMT21/Flt1ΔB2.Fc (described supra), to create the plasmid pMT21/Flt1D2 VEGFR3D3.Fc. The sequence of the Flt1D2-VEGFR3D3 gene fusion insert was verified by standard sequence analysis. This plasmid was then digested with the restriction enzyme EcoRI and SrfI and the resulting 693 bp fragment was subcloned into the EcoRI to SrfI restriction sites of the plasmid pFlt1(1-3)ΔB2-FcΔC1(a) to produce the plasmid designated pFlt1D2.VEGFR3D3.FCΔC1(a). The complete DNA deduced amino acid sequence of the Flt1D2.VEGFR3D3. EcΔC1(a) chimeric molecule is set forth in FIG. 22A-22C.

Example 18

Extracellular Matrix Binding (ECM) Binding Assay

Figure 23:
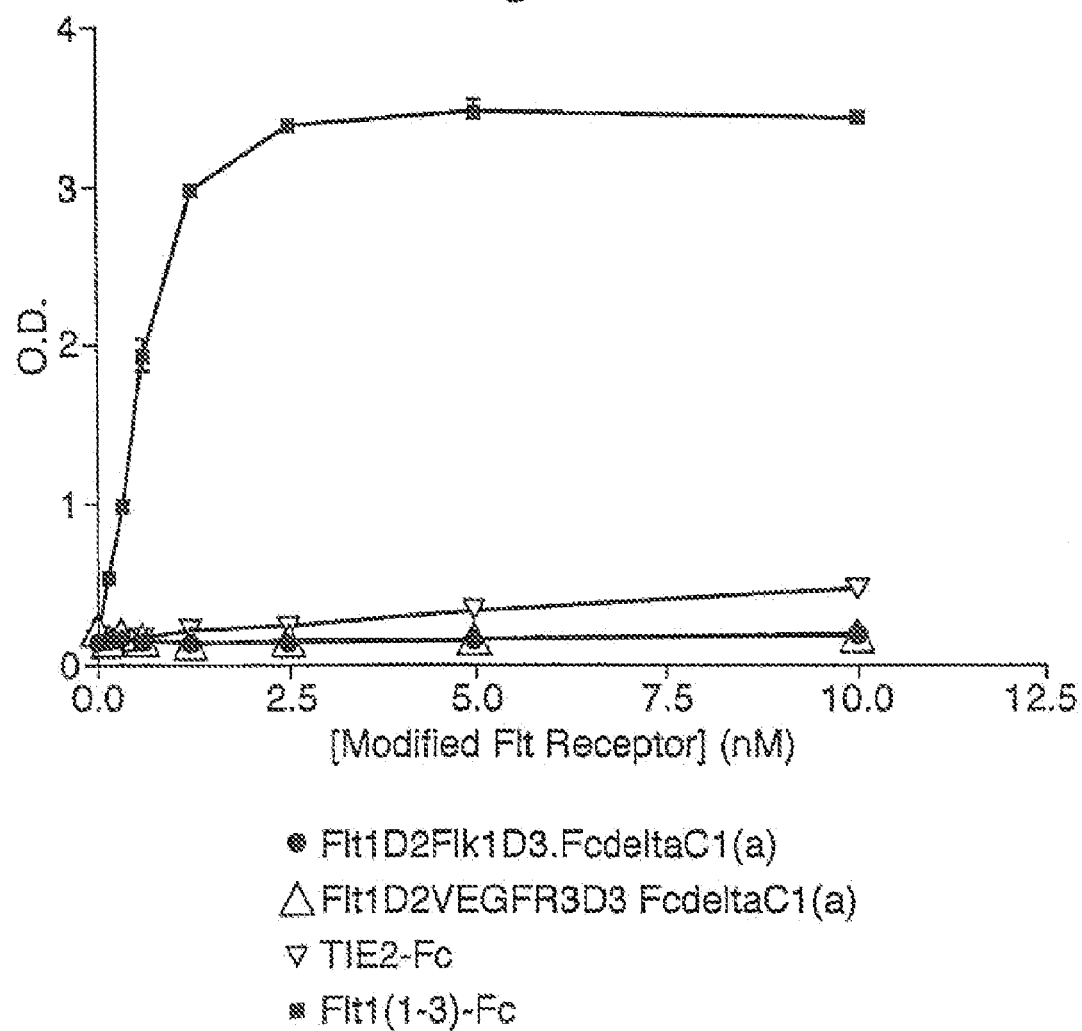
FIG. 23. Extracellular Matrix (ECM) Assay. The results of this assay demonstrate that the Flt1D2.Flk1D3.FcΔC1(a) and Flt1D2.VEGFR3D3.FcΔC1(a) proteins are considerably less sticky to the ECM as compared to the Flt1(1-3)-Fc protein.

ECM-coated plates (Becton Dickinson catalog #35-4607) were rehydrated with warm DME supplemented with glutamine (2 mM), 100 U penicillin, 100 U streptomycin, and 10% BCS for at least 1 hr before adding samples. The plates were then incubated for 1 hr at room temperature with varying concentrations of Flt1D2.Flk1D3.FCΔC1(a) and Flt1D2 VEGFR3D3.FcΔC1(a) starting at 10 nM with subsequent 2-fold dilutions in PBS plus 10% BCS. The plates were then washed 3 times with PBS plus 0.1% Triton-X and incubated with alkaline phosphatase-conjugated anti-human Fc antibody (Promega, 1:4000 in, PBS plus 10% BCS) for 1 hr at room temperature. The plates were then washed 4 times with PBS 0.1% Triton-X and alkaline phosphatase buffer/pNPP solution (Sigma) was added for color development. Plates were read at I=405-570 nm. The results of this experiment are shown in FIG. 23 and demonstrate that the Flt1D2.Flk1D3.FcΔC1(a) and Flt1D2.VEGFR3D3.FcΔC1 (a) proteins are considerably less sticky to the ECM as compared to the Flt1(1-3)-Fc protein.

Example 19

Transient Expression of pFlt1D2.Flk1D3.FcΔC1(a) in CHO-K1 (E1A) Cells

A large scale (2 L) culture of *E. coli* DH10B cells carrying the pFlt1D2.Flk1D3.FcΔC1(a) plasmid described supra in Example 17 was grown overnight in Terrific Broth (TB) plus 100 μg/ml ampicillin. The next day, the plasmid DNA was extracted using a QIAgen ENDOFREE™ Megaprep kit following the manufacturer's protocol. The concentration of the purified plasmid DNA was determined by standard techniques using a UV spectrophotometer and fluorometer. The plasmid DNA was verified by standard restriction enzyme digestion of aliquots using the restriction enzymes EcoRI plus NotI and AseI. All restriction enzyme digest fragments corresponded to the predicted sizes when analyzed on a 1% agarose gel.

Forty 15 cm petri plates were seeded with CHO-K1/E1A cells at a density of $4 \times 10^6$ cells/plate. Plating media was Gibco Ham's F-12 supplemented with 10% HYCLONE™ Fetal Bovine Serum (FBS), 100 U penicillin/100 U streptomycin and glutamine (2 mM). The following day each plate of cells was transfected with 6 μg of the pFlt1D2.Flk1D3.FcΔC1 (a) plasmid DNA using Gibco Optimem, and Gibco Lipofectamine in 12 ml volume, following the manufacturer's protocol. Four hours after adding the transfection mix to the cells, 12 ml/plate of Optimem supplemented with 10% FBS was added. Plates were incubated at 37° C. in a 5% $CO_2$ incubator overnight. The following day the media was removed from each plate and 25 ml expression media (Gibco CHO-S-SFM II supplemented with glutamine (2 mM) and 1 mM sodium butyrate) was added. The plates were incubated at 37° C. for 3 days. After 3 days of incubation, the media was aspirated from each plate and centrifuged at 400 rpm in a swinging bucket rotor to pellet cells. The supernatant was decanted into sterile 1 L bottles and purification of the expressed protein was performed as described infra.

Example 20

Construction pVEGFR1R2-FcΔC1(a) Expression Vector

The pVEGFR1R2.FcΔC1(a) expression plasmid was constructed by insertion of DNA encoding amino acids. SDT (corresponding to amino acids 27-29 of FIG. 24A-24C) between Flt1d2-Flk1d3-FcΔC1(a) amino acids 26 and 27 of FIG. 21A-21C (GG) and removal of DNA encoding amino acids GPG corresponding to amino acids 229-231. The SDT amino acid sequence is native to the Flt1 receptor and was added back in to decrease the likelihood of heterogeneous N-terminal processing. The GPG (bridging sequence) was removed so that the Flt1 and Flk1 Ig domains were fused directly to one another. The complete DNA and deduced amino acid sequences of the pVEGFR1R2.FcΔC1(a) chimeric molecule is set forth in FIG. 24A-24C.

Example 21

Cell Culture Process Used to Produce Modified Flt1 Receptors

Cell Culture Process Used to Produce Flt1D2.Flk1D3.FcΔC1(a). The process for production of Flt1D2.Flk1D3.FcΔC1(a) protein using the expression plasmid pFlt1D2.Flk1D3.FcΔC1(a) described supra in Example 1 involves suspension culture of recombinant Chinese hamster ovary (CHO K1/E1A) cells with constitutively express the protein product. The cells are grown in bioreactors and the protein product is isolated and purified by affinity and size exclusion chromatography. The process is provided in greater detail below.

Cell Expansion. Two confluent T-225 cm² flasks containing the Flt1D2.Flk1D3.FcΔC1(a) expressing cell line were expanded by passaging cells into eight T-225 cm² flasks in medium (GMEM+10% serum, GIBCO) and incubated at 37° C. and 5% $CO_2$. When the flasks approached confluence (approximately 3 to 4 days) the cells were detached using trypsin. Fresh medium was added to protect the cells from further exposure to the trypsin. The cells were centrifuged and resuspended in fresh medium then transferred to eight 850 cm² roller bottles and incubated at 37° C. and 5% $CO_2$ until confluent.

Suspension Culture in Bioreactors. Cells grown in, roller bottles were trypsinized to detach them from the surface and washed with suspension culture medium. The cells are aseptically transferred, to a 5 L bioreactor (New Brunswick Celligen Plus) where the cells are grown in 3.5 L of suspension culture. The suspension culture medium was a glutamine-free low glucose modification of IS-CHO (Irvine Scientific) to which 5% fetal bovine serum (HYCLONE™), GS supplement (Life Technologies) and 25 μM methionine, sulfoximine (Sigma) was added. The pH was controlled at 7.2 by addition of carbon dioxide to the inlet gas or by addition of a liquid solution of sodium carbonate to the bioreactor. Dissolved oxygen level was maintained at 30% of saturation by addition of oxygen or nitrogen to the inlet gas and temperature controlled at 37° C. When a density of 4×10⁶ cells/mL was reached the cells were transferred to a 40 L bioreactor containing the same medium and setpoints for controlling the bioreactor. The temperature setpoint was reduced to 34° C. to slow cell growth and increase the relative rate of protein expression.

Cell Culture. Process Used to Produce Flt1D2.VEGFR3D3.FcΔC1(a). The same methodologies as described supra for Flt1D2.Flk1D3.FcΔC1(a) were used to produce Flt1D2.VEGFR3D3.FcΔC1(a).

Example 22

Harvest and Purification of Modified Flt1 Receptors

Harvest and Purification of Flt1D2.Flk1D3.FcΔC1(a). The product protein was aseptically harvested from the bioreactor while retaining cells using millipore Prostak, tangential-flow filtration modules and a low-shear mechanical pump (Fristam). Fresh medium was added to the bioreactor to replace that removed during the harvest filtration. Approximately 40 L of harvest filtrate was then loaded onto a 400 mL column containing Protein A SEPHAROSE™ resin (Amersham Pharmacia). After loading the resin was washed With buffer Containing 10 mM sodium phosphate, 500 mM sodium chloride, pH 7.2 to remove any unbound contaminating proteins. Flt1D2.Flk1D3.FcΔC1(a) protein was eluted with a pH 3.0 citrate buffer. The eluted protein was neutralized by addition of Tris base and frozen at −20° C.

Several frozen lots of Flt1D2.Flk1D3.FcΔC1(a) protein from the Protein A step above were thawed, pooled and concentrated using a Millipore 30 kD nominal molecular weight cutoff (NMWCO) tangential flow filtration membrane. The protein was transferred to a stirred cell concentrator (Millipore) and further concentrated to 30 mg/mL using a 30 kD NMWCO membrane. The concentrated protein was loaded onto a size exclusion column packed with SUPERDEX™ 200 resin (Amersham Pharmacia) that was equilibrated with phosphate buffered saline plus 5% glycerol. The same buffer was used to run the column. The fractions corresponding to Flt1D2.Flk1D3.FcΔC1(a) dimer were pooled, sterile filtered through a 0.22 micron filter, aliquoted and frozen.

Harvest and Purification of Flt1D2.VEGFR3D3.FcΔC1 (a). The same methodologies as described supra for Flt1D2.Flk1D3.FcΔC1(a) were used to harvest and purify Flt1D2.VEGFR3D3.FcΔC1(a).

Example 23

Phosphorylation Assay for Transiently Expressed VEGFR2

Figure 25A:
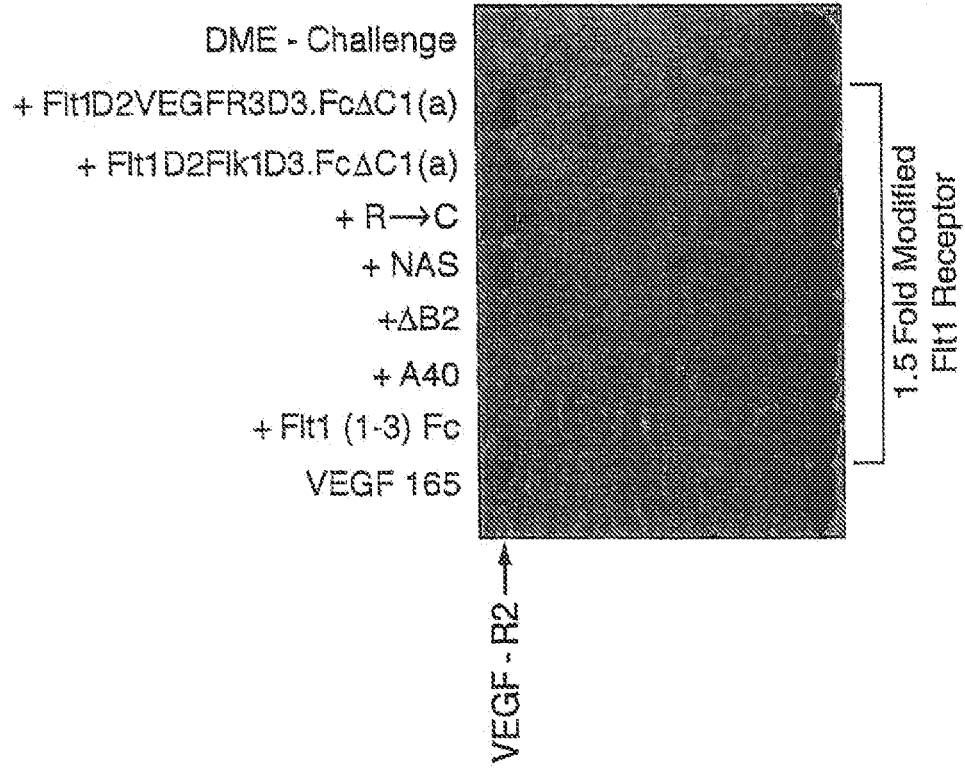
Figure 25B:
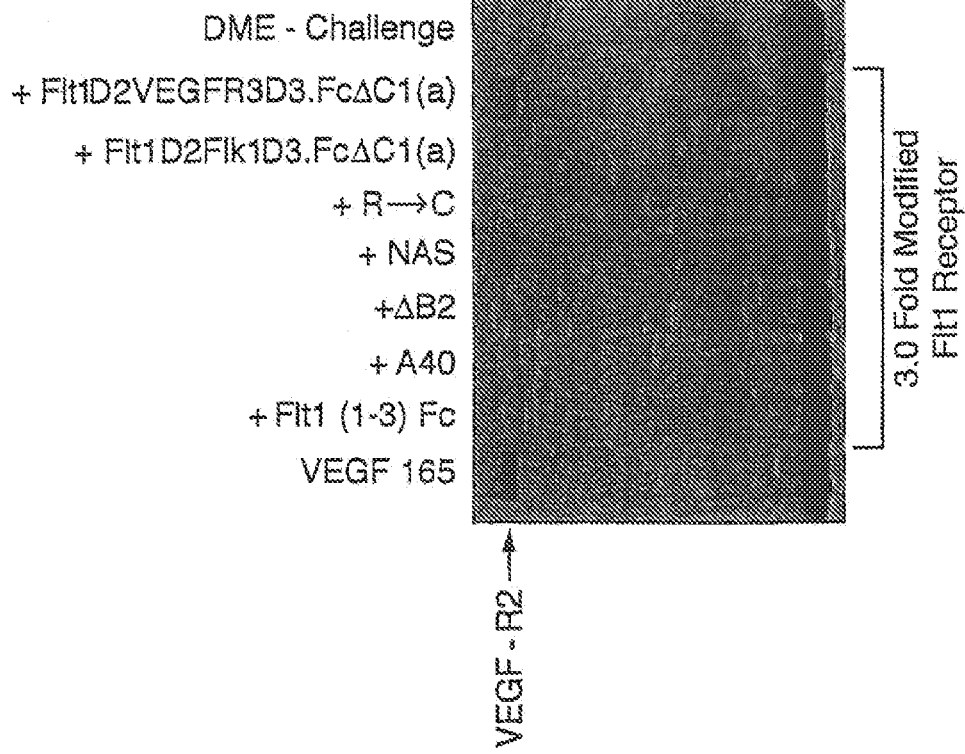

Primary human umbilical vein endothelial cells (HUVECs), passage 4-6, were starved for 2 hrs in serum-free DME high glucose media. Samples containing 40 ng/ml (1 nM) human VEGF165, which is a ligand for the VEGF receptors Flt1, Flk-1 and Flt4(VEGFR3) were prepared and were preincubated for 1 hr at room temperature with varying amounts of the modified Flt1 receptors Flt1(1-3)-Fc; Flt1(1-3)-Fc (A40), Flt1D2Flk1D3.FcΔC1(a) and Flt1D2VEGFR3D3.FcΔC1(a) in serum-free DME-high glucose media containing 0.1% BSA. Cells were challenged for 5 minutes with the samples prepared above +/− VEGF165, followed by whole cell lysis using complete lysis buffer. Cell lysates were immunoprecipitated with an antibody directed against the C=terminus of VEGFR2 receptor. The immunoprecipitated lysates were loaded onto 4-12% SDS-PAGE Novex gel and then transferred to PVDF membrane using standard transfer methodologies. Detection of phosphorylated VEGFR2 was done by immunoblotting with the anti-phospho Tyrosine mAb called 4G10 (UBI) and developed using ECL-reagent (Amersham). FIGS. 25A-25 and 26A-26B show the results of this experiment. FIG. 25A-25C reveals that detection by Western blot of tyrosine phosphorylated VEGFR2(Flk1) by VEGF165 ligand stimulation shows that cell-Surface receptors 'are' phosphorylated to varying levels depending on which modified Flt1 receptor is used during the preincubations with VEGF. As is seen in FIG. 25A, at a 1.5 molar excess of either Flt1(1-3)=Fc, Flt1(1-3)-Fc (A40) or transient Flt1D2Flk1D3.FcΔC1(a) there is complete blockage of receptor stimulation by these three modified Flt receptors as compared to control media challenge. In contrast, transient Flt1D2VEGFR3D3.FcΔC1(a) does not show significant blockage at this molar excess, as compared with VEGF positive control challenge. Similar results are seen in FIG. 25B, where the modified Flt receptors are in a 3-fold molar excess to VEGF165 ligand. In FIG. 25C, where the modified Flt1 receptors are in a 6-fold molar excess to VEGF165 ligand, transient Flt1D2VEGFR3D3.FcΔC1(a)

can how be shown to be partially blocking VEGF165-induced stimulation of cell-surface receptors.

Figure 26A:
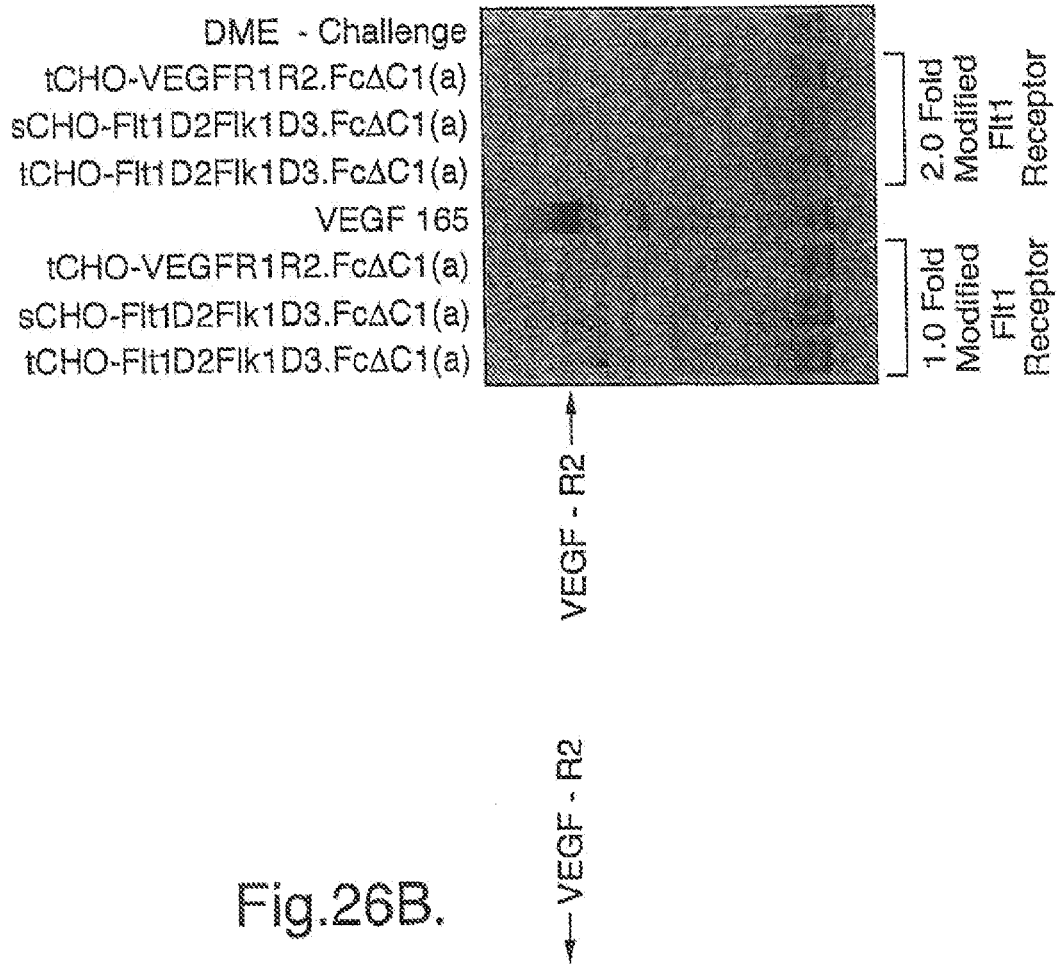
FIG. 26A-26B. Phosphorylation assay. Detection by Western blot of tyrosine phosphorylated VEGFR2(Flk1) by VEGF165 ligand stimulation shows cell-surface receptors are not phosphorylated by challenge samples which have VEGF165 preincubated with 1 and 2 fold molar excess (FIG. 26A) or 3 and 4 fold molar excess (FIG. 26B) of either transient Flt1D2Flk1D3.FcΔC1(a), stable Flt1D2Flk1D3.FcΔC1(a), or transient VEGFR1R2-FcΔC1 (a). At all modified Flt1 receptor concentrations tested there is complete binding of VEGF165 ligand during the preincubation, resulting in no detectable stimulation of cell-surface receptors by unbound VEGF165 as compared to Control, media challenge.
Figure 26B:
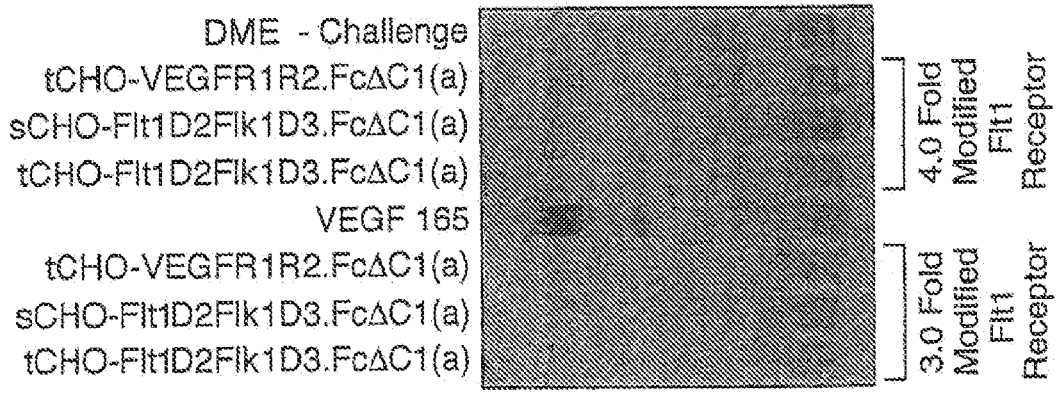

In FIG. 26A-26B, detection by Western blot of tyrosine phosphorylated VEGFR2(Flk1) by VEGF165 ligand stimulation shows that cell-surface receptors are not phosphorylated by challenge samples which have VEGF165 preincubated with 1 and 2 fold molar excess (FIG. 26A) or 3 and 4 fold molar excess (FIG. 26B) of either transient Flt1D2Flk1D3.FcΔC1(a), stable Flt1D2Flk1D3.FcΔC1(a), or transient VEGFR1R2-FcΔC1(a). At all modified Flt1 receptor concentrations tested there is complete binding of VEGF165 ligand during the preincubation, resulting in no detectable stimulation of cell-surface receptors by unbound VEGF165 as compared to control media challenge.

Example 24

Cell Proliferation Bioassay

The test cell population is MG87 cells that have been stably transfected with a expression plasmid that contains a DNA insert encoding the VEGFR2(Flk1) extracellular domain fused to the TrkB intracellular kinase domain, thus producing a chimeric molecule. The reason the TrkB intracellular kinase domain was used rather than the native VEGFR2(Flk1) intracellular kinase domain is that the intracellular kinase domain of VEGFR2(Flk1) does not cause a strong proliferative response when stimulated by VEGF165 in these cells. It is known that MG87 cells containing full length TrkB receptor give a robust proliferative response when stimulated with BDNF, so the TrkB intracellular kinase domain was engineered to replace the intracellular kinase domain of VEGFR2 (Flk1) to take advantage of this proliferative response capability.

Figure 27:
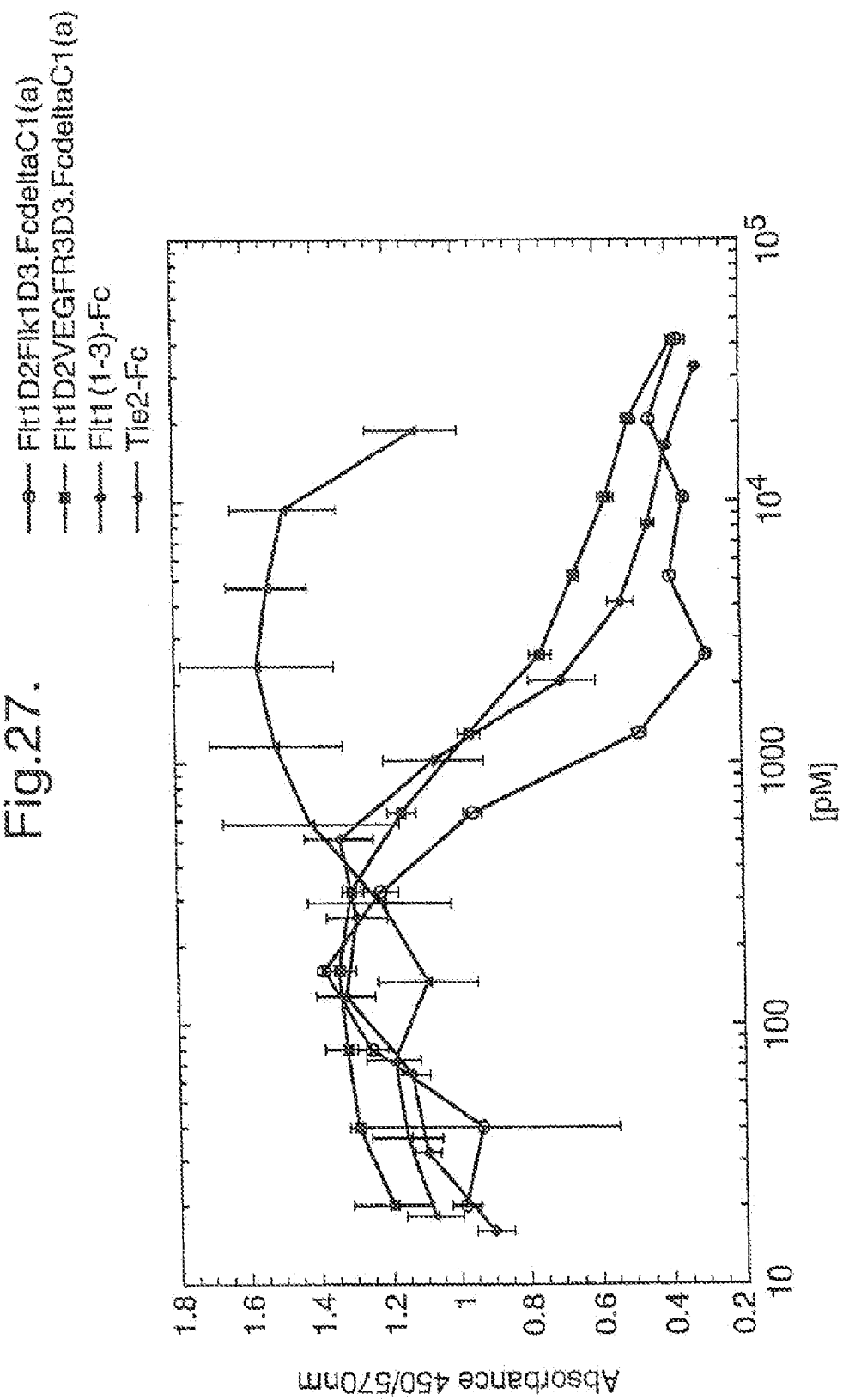
FIG. 27. MG/R2 Cell proliferation assay. The following modified Flt receptors Flt1(1-3)-Fc, Flt1D2.Flk1D3.FcΔC1 (a) and Flt1D2.VEGFR3D3.FcΔC1(a), plus an irrelevant receptor learned Tie2-Fc as a negative control, were titrated from 40 nM to 20 pM and incubated on the cells for 1 hr at 37° C. Human recombinant VEGF165 in defined media was then added to all the wells at a concentration of 1.56 nM. The negative control receptor Tie2-Fc does not block VEGF165-induced cell proliferation at any concentration whereas Flt1D2.Flk1D3.FcΔC1(a) blocks 1.56 nM VEGF165 with a half maximal dose of 0.8 nM. Flt1(1-3)-Fc and Flt1D2VEGFR3D3FcΔC1(a) are less effective in blocking VEGF165 in this assay with a half maximal dose of ~2 nM. VEGF165 alone gives a reading of 1.2 absorbance units and the background unit 0.38 absorbance units.

Five thousand cells/well were plated in a 96 well plate and allowed to settle for 2 hrs at 37° C. The following modified Flt receptors Flt1(1-3)-Fc, Flt1D2.Flk1D3.FcΔC1(a) and Flt1D2.VEGFR3D3.FcΔC1(a), plus an irrelevant receptor termed Tie2-Fc as a negative control, were titrated from 40 nM to 20 pM and incubated on the cells for 1 hr at 37° C. Human recombinant VEGF165 in defined media was then added to all the wells at a concentration of 1.56 nM. The plates were incubated for 72 hrs. at 37° C. end then MTS (Owen's reagent, Promega) added and the plates were incubated for an additional for 4 hrs. Finally, the plates were read on a spectrophotometer at 450/570 nm. The results of this experiment are shown in FIG. 27. The control receptor Tie2-Fc does not block VEGF165-induced cell proliferation at any concentration whereas Flt1D2.Flk1D3.FcΔC1(a) block's 1.56 nM VEGF165 with a half maximal dose of 0.8 nM. Flt1(1-3)-Fc and Flt1D2.VEGFR3D3.FcΔC1(a) are less effective in blocking VEGF165 in this assay with the half maximal dose of ~2 nM. VEGF165 alone gives a reading of 1.2 absorbance units and the background is 0.38 absorbance units.

Example 25

Binding Stoichiometry of Modified Flt Receptors to VEGF165

BIACORE™ Analysis. The stoichiometry of Flt1D2Flk1D3.FcΔC1(a) and VEGFR1R2-FcΔC1(a) interaction with human VEGF165 was determined by measuring either the level of VEGF saturation binding to the Flt1D2Flk1D3.FcΔC1(a) or VEGFR1R2-FcΔC1(a) surfaces or measuring concentration of VEGF165 needed to completely prevent binding of Flt1D2Flk1D3.FcΔC1(a) or VEGFR1R2-FcΔC1(a) to VEGF BIACORE™ chip surface.

Modified Flt receptors Flt1D2Flk1D3.FcΔC1(a) and VEGFR1R2-FcΔC1(a), were capture with an anti-Fc specific antibody that was first immobilized on a BIACORE™ chip using amine-coupling chemistry. A blank antibody surface was used as a negative control. VEGF165 was injected at a concentration of 1 nM, 10 nM, and 50 nM over the Flt1D2Flk1D3.FcΔC1(a) and VEGFR1R2-FcΔC1(a) surfaces at 10 μl/min for one hour. A real-time binding signal was recorded and saturation binding was achieved at end of each infection. Binding stoichiometry was calculated as a molar ratio of bound VEGF165 to the immobilized Flt1D2Flk1D3.FcΔC1(a) or VEGFR1R2-FcΔC1(a), using the conversion factor of 1000 RU equivalent to 1 ng/ml. The results indicated binding stoichiometry of one VEGF165 dimeric molecule per one Flt1D2Flk1D3.FcΔC1(a) or VEGFR1R2-FcΔC1(a) molecule (FIG. 28).

Figure 29:
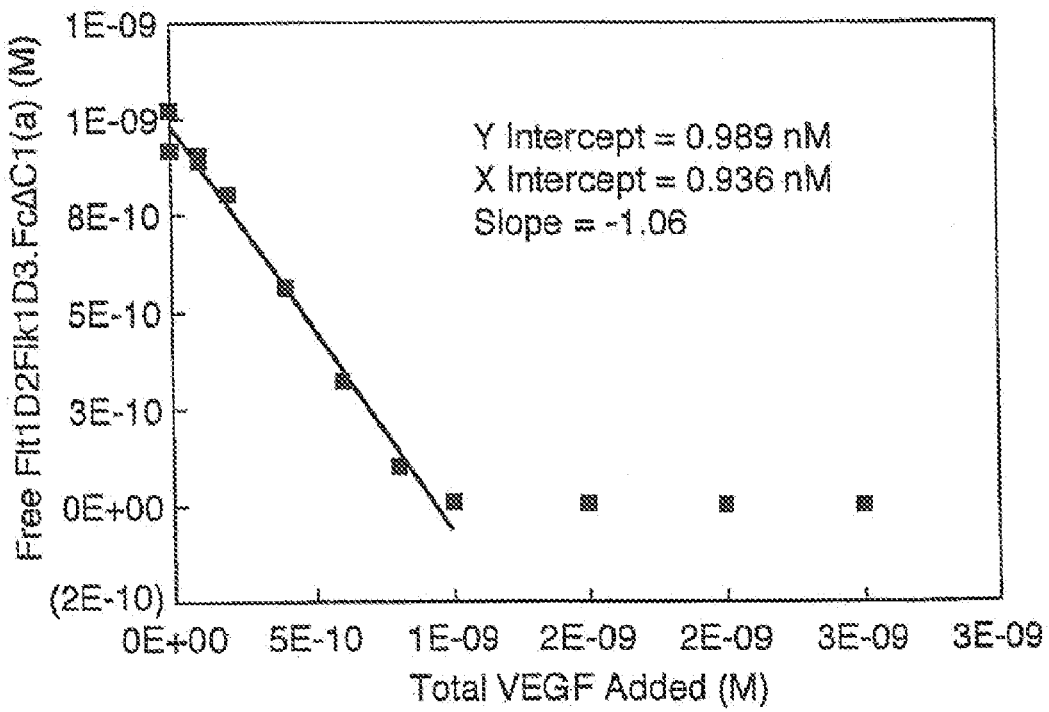
FIGS. 29-30. Size Exclusion Chromatography Stoichiometry. Flt1D2Flk1D3.FcΔC1(a) or VEGFR1R2-FcΔC1(a) at a concentration of 1 nM (estimated to be 1000 times higher than the KD, of the Flt1D2Flk1D3.FcΔC1(a) or VEGFR1R2-FcΔC1(a)/VEGF165 interaction) were mixed with varied concentrations of VEGF165. After incubation, concentrations of the free Flt1D2Flk1D3.FcΔC1(a) in solution were measured. The data shows that the addition of 1 nM VEGF165 into the Flt1D2Flk1D3.FcΔC1(a) solution completely blocks Flt1D2Flk1D3.FcΔC1(a) binding to the VEGF165 surface. This result suggested the binding stoichiometry of one VEGF165 molecule per one Flt1D2Flk1D3.FcΔC1(a) molecule.
Figure 30:
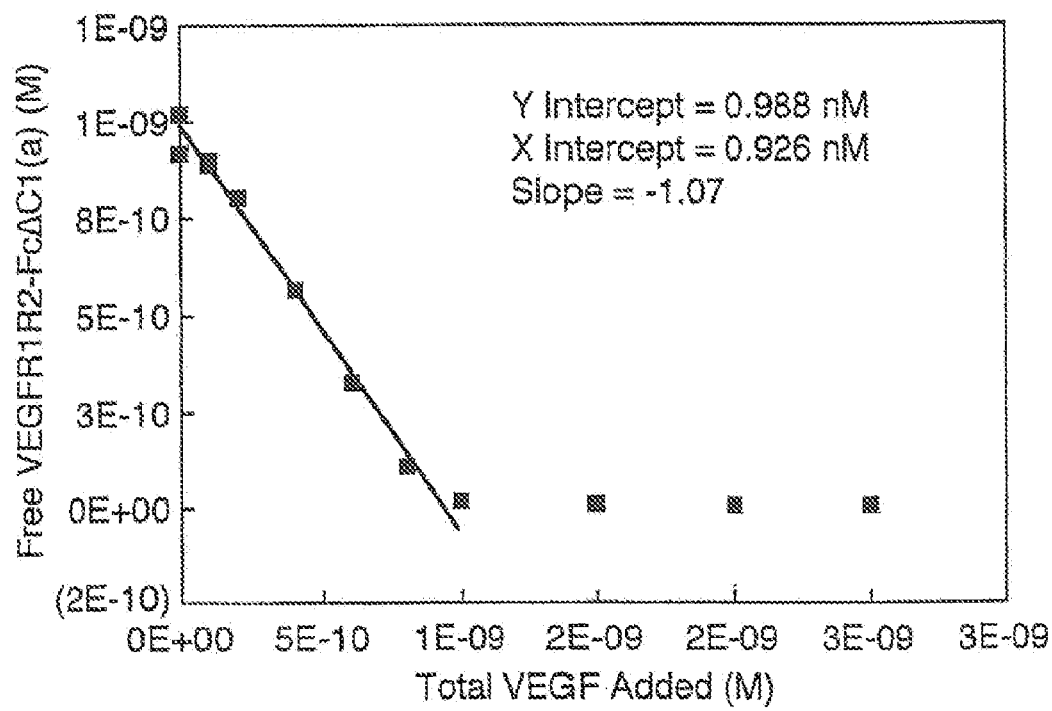

In solution, Flt1D2Flk1D3.FcΔC1(a) or VEGFR1R2-FcΔC1(a) at a concentration of 1 nM (estimated to be 1000 times higher than the KD of the Flt1D2Flk-1D3.FcΔC1(a) or VEGFR1R2-FcΔC1(a)/VEGF-165 interaction) were-mixed with varied concentrations of VEGF165. After one hour incubation, concentrations of the free Flt1D2Flk1D3.FcΔC1(a) in solution were measured as a binding signal to an amine-coupled VEGF165 surface. A calibration curve was used to convert the Flt1D2Flk1D3.FcΔC1(a) BIACORE™ binding signal to its molar concentration. The data showed that the addition of 1 nM VEGF165 into the Flt1D2Flk1D3.FcΔC1(a) solution completely blocked Flt1D2Flk1D3.FcΔC1(a) binding to the VEGF165 surface. This result suggested the binding stoichiometry of one VEGF165 molecule per one Flt1D2Flk1D3.FcΔC1(a) molecule (FIG. 29 and FIG. 30). When the concentration of Flt1D2Flk1D3.FcΔC1(a) was plotted as a function of added concentration of VEGF165, the slope of the linear portion was −1.06 for Flt1D2Flk1D3.FcΔC1(a) and −1.07 for VEGFR1R2-FcΔC1(a). The magnitude of the slope, very close to negative one, was indicative that one molecule of VEGF165 bound to one molecule of either Flt1D2Flk1D3.FcΔC1(a) or VEGFR1R2-FcΔC1(a).

Size Exclusion Chromatography. Flt1D2Flk1D3.FcΔC1 (a) was mixed with a 3-fold excess of VEGF165 and the receptor-ligand complex was purified using a Pharmacia SUPEROSE™ 6 size exclusion chromatography column. The receptor-ligand complex was then incubated in a buffer containing 6 M guanidine hydrochloride in order to dissociate it into its component proteins. Flt1D2Flk1D3.FcΔC1(a) was separated from VEGF165 using SUPEROSE™ 6 size exclusion chromatography column run in 6 M guanidium chloride. In order to determine complex stoichiometry, several injections of Flt1D2Flk1D3.FcΔC1(a) and VEGF165 were made and peak height or peak integrated intensity was plotted as a function of the concentration of injected protein. The calibration was done under condition identical to one used in separating components of Flt1D2Flk1D3.FcΔC1(a)/VEGF complex. Quantification of the Flt1D2Flk1D3.FcAC1(a)/VEGF complex composition was based on the calibration curves. The results of this experiment are set forth in FIG. 28, which shows the ratio of VEGF165 to Flt1D2Flk1D3.FcΔC1(a) in a complex to be 1:1.

Example 26

Determination of the Binding Stoichiometry of Flt1D2Flk1D3.FcΔC1(a)/VEGF165 Complex by Size Exclusion Chromatography Flt1D2Flk1D3.FcΔC1(a)/VEGF165 Complex Preparation. VEGF165 (concentration=3.61 mg/ml) was mixed with CHO cell transiently expressed Flt1D2.Flk1D3.FcΔC1(a) (concentration=mg/ml) in molar ratio of 3:1 (VEGF165: Flt1D2.Flk1D3.FcΔC1(a)) and incubated overnight at 4° C.

Figure 31:
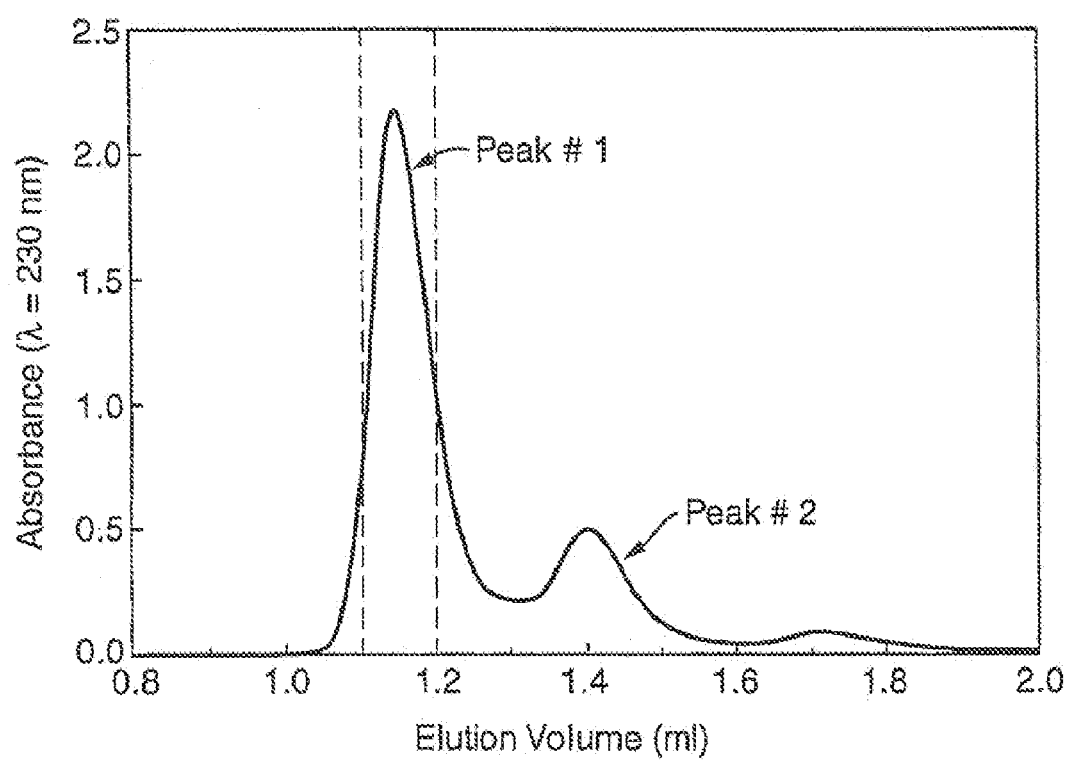
FIG. 31. Size Exclusion Chromatography (SEC) under native conditions. Peak #1 represents the Flt1D2Flk1D3.FcΔC1 (a)/VEGF165 complex and peak #2 represents unbound VEGF165. Fractions eluted between 1.1 and 1.2 ml were combined and guanidinium hydrochloride (GuHCl) was added to a final concentration 4.5 M to dissociate the complex.

Size Exclusion Chromatography (SEC) under native conditions. To separate the complex from excess of unbound VEGF165, 50 µl of the complex was loaded on a Pharmacia SUPEROSE™ 12 PC 3.2/30 which was equilibrated in PBS buffer. The sample was eluted with the same buffer at flow rate 40 µl/min. at room temperature. The results of this SEC are shown in FIG. 31. Peak #1 represents the complex and peak #2 represents unbound VEGF165. Fractions eluted between 1.1 and 1.2 ml were combined and guanidinium hydrochloride (GuHCl) was added to a final concentration 4.5 M to dissociate the complex.

Figure 32:
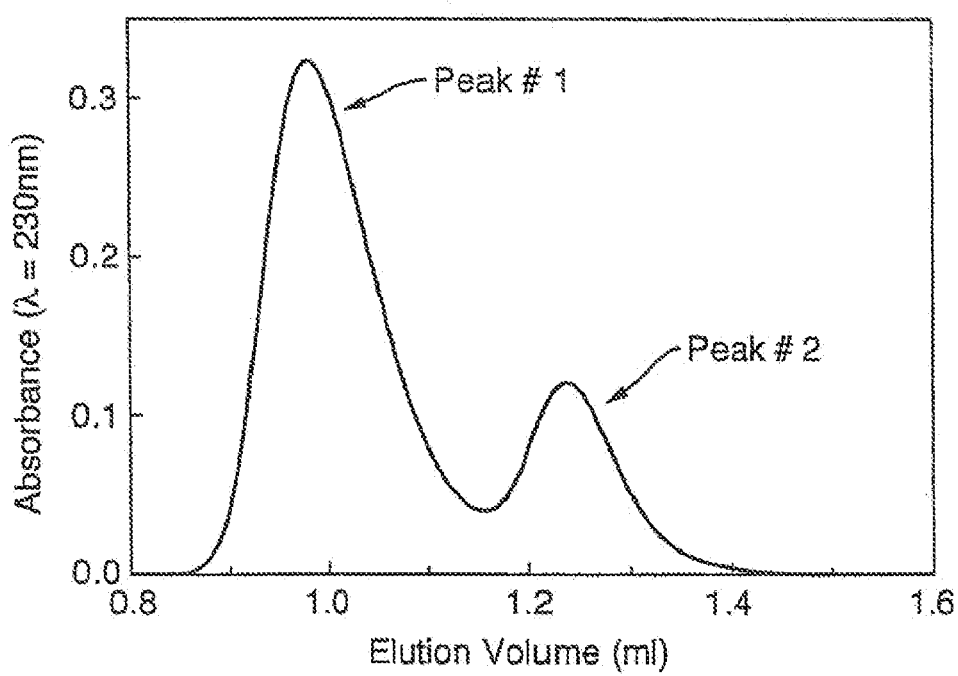
FIG. 32. Size Exclusion Chromatography (SEC) under dissociative conditions. To separate the components of the receptor-ligand complex and to determine their molar ratio, 50 μl of dissociated complex was loaded Onto a SUPER- OSE™ 12 PC.3.2/30 equilibrated in 6 M GuHCl and eluted. Peak #1 represents Flt1D2Flk1D3.FcΔC1(a) and peak #2 represents VEGF165.

Size Exclusion Chromatography (SEC) under dissociative conditions. To separate the components of the receptor-ligand complex and to determine their molar ratio, 50 µl of dissociated complex as, described supra was loaded onto a SUPEROSE™ 12 PC 3.2/30 equilibrated in 6 M GuHCl and eluted with; the same solution at a flow rate 40 µl/min at room temperature. The results of this SEC are shown in FIG. 32. Peak #1 represents Flt1D2Flk1D3.FcΔC1(a) and peak #2 represents VEGF165.

Calculation of Flt1D2Flk1D3.FcΔC1(a) VEGF165 Complex Stoichiometry. The stoichiometry of the receptor-ligand complex was determined from the peak area or the peak height of the components. Concentrations of VEGF165 and Flt1D2Flk1D3.FcΔC1(a), corresponding to the peak height or peak area, respectively, were obtained from the standard curves for VEGF165, and Flt1D2Flk1D3.FcΔC1(a). To obtain a standard curve, four different concentrations (0.04 mg/ml-0.3 mg/ml) of either component were injected onto a Pharmacia SUPEROSE™ 12 PC 3.2/30 column equilibrated in 6 M guanidinium chloride and eluted with the same solution at flow rate 40 µl/min at room temperature. The standard curve was obtained by plotting peak area or peak height vs protein concentration. The molar ratio of VEGF165: Flt1D2Flk1D3.FcΔC1(a) determined from the peak area of the components was 1.16. The molar ratio of VEGF165: Flt1D2Flk1D3.FcΔC1(a) determined from the peak height of the components was 1.10.

Example 27

Determination of the Stoichiometry of the Flt1D2Flk1D3.FcΔC1(a)/VEGF165 Complex by Size Exclusion Chromatography with On-Line Light Scattering Complex preparation. VEGF165 was mixed with CHO transiently expressed Flt1D2.Flk1D3.FcΔC1(a) protein in molar ratio of 3:1 (VEGF165:Flt1D2Flk1D3.FcΔC1(a)) and incubated overnight at 4° C.

Figure 33:
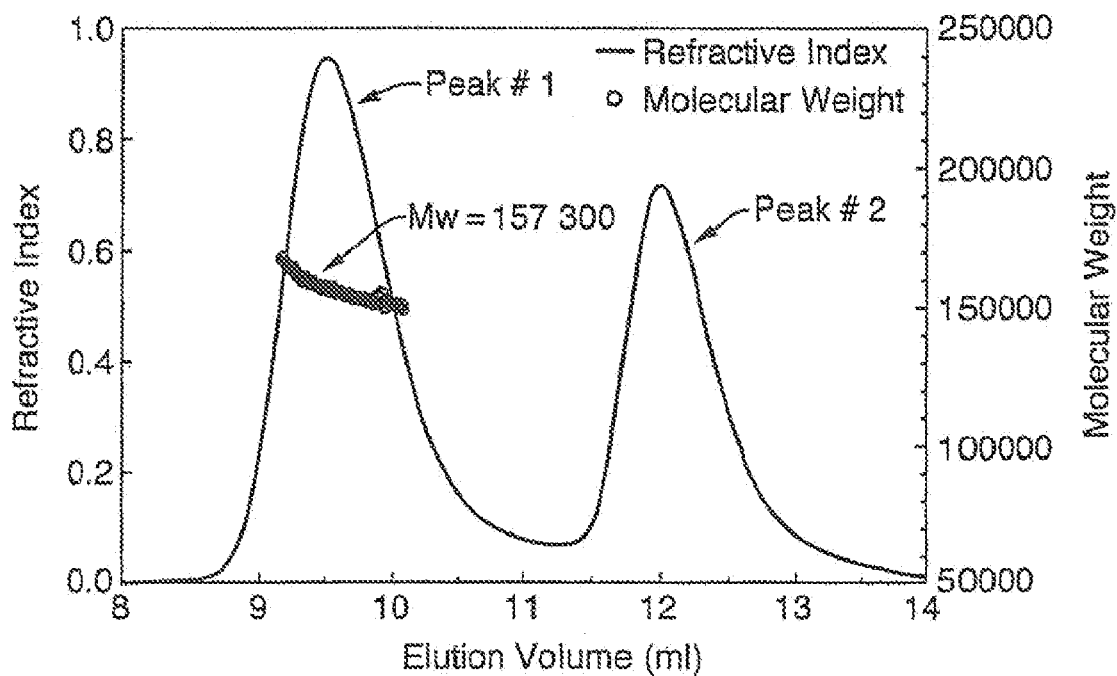
FIGS. 33-35. Size Exclusion Chromatography (SEC) with On-Line Light Scattering. Size exclusion chromatography column with a MiniDawn on-line light scattering detector (Wyatt Technology, Santa Barbara, Calif.) and refractive index (RI) detectors (Shimadzu, Kyoto, Japan) was used to determine the molecular weight (MW) of the receptor-ligand complex.
Figure 34:
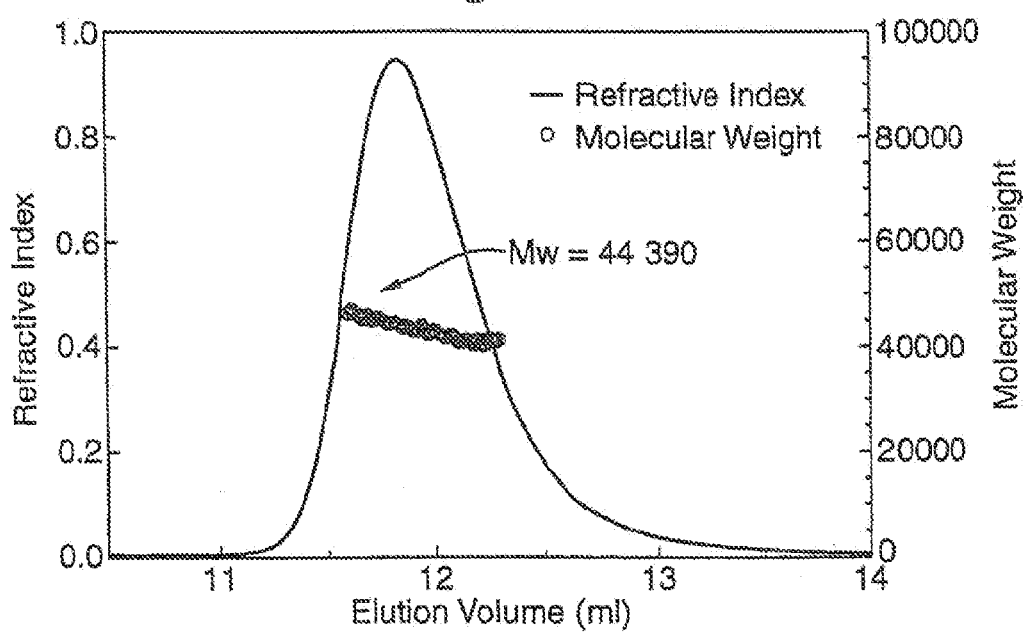
Figure 35:
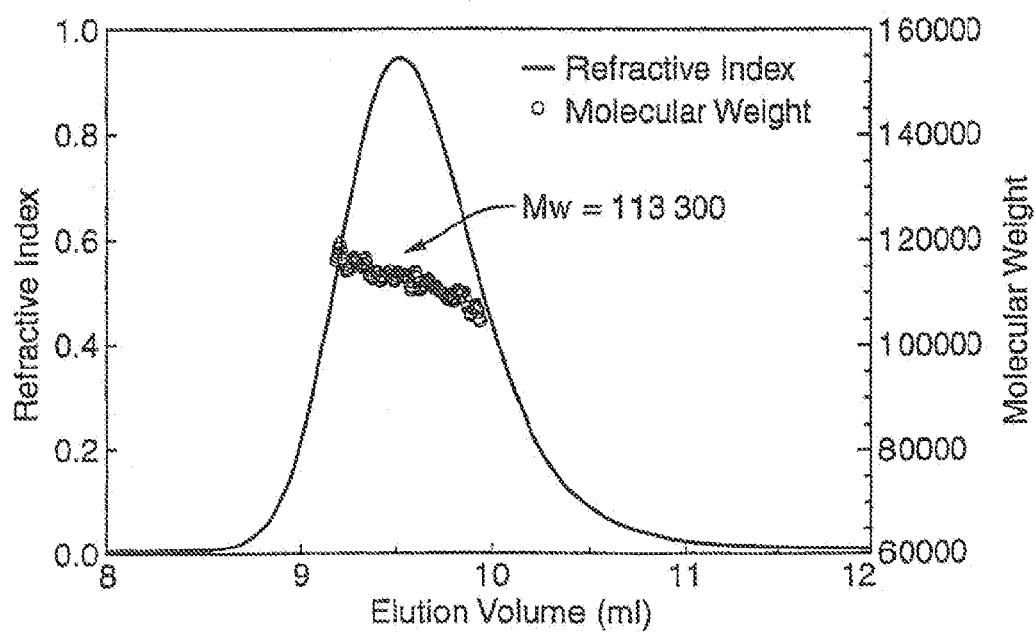

Size Exclusion Chromatography (SEC) with On-Line Light Scattering. Size exclusion chromatography column with a MiniDawn on-line light scattering detector (Wyatt Technology, Santa Barbara, Calif.) and refractive index (RI) detectors (Shimadzu, Kyoto, Japan) was used to determine the molecular weight (MW) of the receptor-ligand complex. Samples were injected onto a SUPEROSE™ 12 HR 10/30 column (Pharmacia) equilibrated in PBS buffer and eluted with the dame buffer at flow rate 0.5 ml/min. at room temperature. As shown in FIG. 33, the elution profile shows two peaks. Peak #1 represents the receptor-ligand complex and peak #2 represents the unbound VEGF165. MW was calculated from LS and RI signals. The same procedure was used to determine MW of the individual components of the receptor-ligand complex. The results of these determinations are as follows: MW of the Flt1D2Flk1D3.FcΔC1(a)/VEGF165 complex at the peak position is 157 300 (FIG. 33), the MW of VEGF165 at the peak position is 44 390 (FIG. 34) and the MW of R1R2 at the peak is 113 300 (FIG. 35).

These data indicated that the stoichiometry of the Flt1D2Flk1D3.FcΔC1(a)/VEGF complex is 1:1 as its corresponds to the sum of molecular weights for Flt1D2Flk1D3.FcΔC1(a) and VEGF165. Importantly, this method conclusively proved that the Flt1D2Flk1D3.FcΔC1(a)/VEGF165 complex was indeed composed of only one molecule of VEGF165 ligand and only one molecule of the Flt1D2Flk1D3.FcΔC1(a).

Example 28

Peptide Mapping of Flt1D2.Flk163.FcΔC1(a)

The disulfide structures and glycosylation sites in Flt1D2.Flk1D3.FcΔC1(a) were determined by a peptide mapping method. In this method, the protein was first cleaved with trypsin. Tryptic fragments were analyzed and identified by HPLC coupled with mass spectrometry, in addition to an N-terminal sequencing technique. Reduction of the tryptic digest was employed to help identify disulfide-bond-containing fragments. Treatment of the tryptic digest with PNGase F (Glyko, Novato, Calif.) was employed, to help identify fragments with N-linked glycosylation sites. The results are summarized in the accompanying FIG. 36.

There are a total of ten cysteines in Flt1D2.Flk1D3.FcΔC1(a); six of them belong to the Fc region. Cys27 has been confirmed to be disulfide bonded to Cys76. Cys121 is confirmed to be disulfide bonded to Cys182. The first two cysteines in the Fc region (Cys211 and Cys214) form an intermolecular disulfide bond with the same two cysteines in another Fc chain. However, because these two cysteines can not be separated enzymatically from each other, it can not be determined whether disulfide bonding is occurring between same cysteines (Cys211 to Cys211, for example) or between Cys211 and Cys214. Cys216 is confirmed to be disulfide bonded to Cys306. Cys352 is confirmed to be disulfide bonded to Cys410.

There are five possible N-linked glycosylation sites in Flt1D2.Flk1D3.FcΔC1(a). All five of them are found to be glycosylated to varying degrees. Complete glycosylation was observed at Asn33 (amino acid sequence NIT). Asn193 (amino acid sequence NST), and Asn282 (amino acid sequence NST). In addition, partial glycosylation is observed on Asn65 and Asn120. Sites of glycosylation are highlighted by underline in the FIG. 36.

Example 29

Pharmacokinetic Analysis of Modified Flt Receptors

Figure 37:
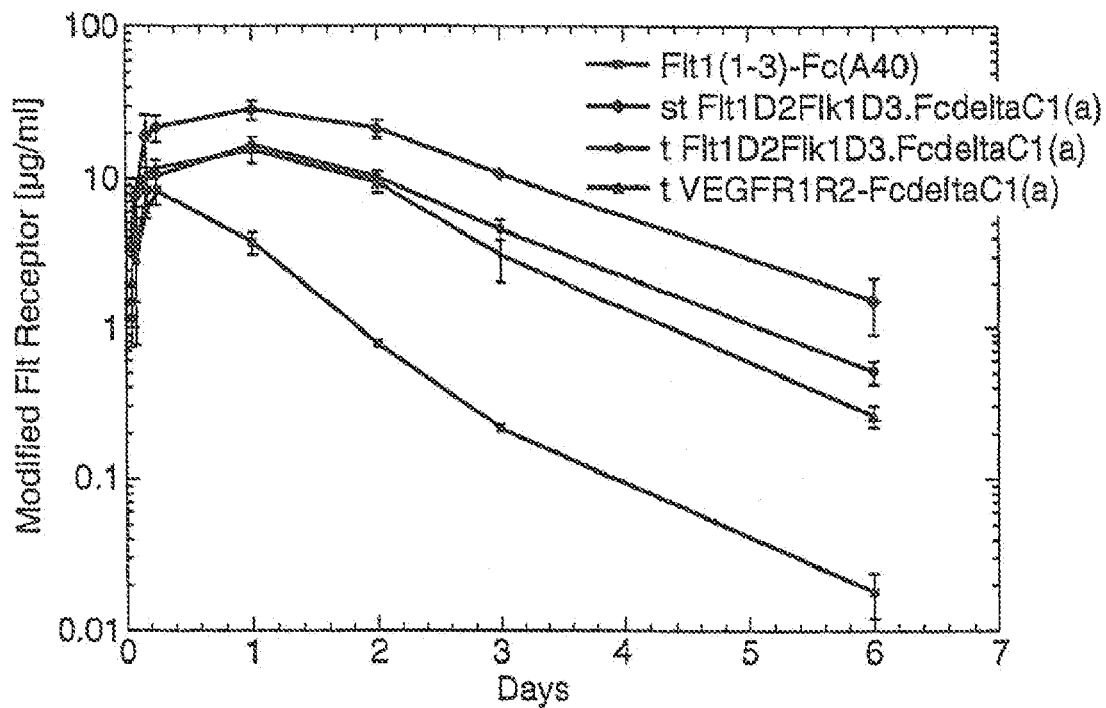
FIG. 37. Pharmacokinetics of Flt1(1-3)-Fc (A40), Flt1D2.Flk1D3.FcΔC1(a) and VEGFR1R2-FcΔC1 (a). Balb/c mice were injected subcutaneously with 4 mg/kg of Flt1(1-3)-Fc (A40), CHO transiently expressed Flt1D2.Flk1D3.FcΔC1(a), CHO stably expressed Flt1D2.Flk1D3.FcΔC1(a), and CHO transiently expressed VEGFR1R2-FcΔC1(a). The mice were tail bled at 1, 4, 6, 24 hrs; 2 days 3 days and 6 days after injection. The sera were assayed, in an ELISA designed to detect Flt1(1-3)-Fc Flt1D2.Flk1D3.FcΔC1(a) or VEGFR1R2-FcΔC1(a). The $T_{max}$ for Flt1(1-3)-Fc (A40) was at 6 hrs while the $T_{max}$ for the transient and stable Flt1D2.Flk1D3.FcΔC1(a) and the transient VEGFR1R2-FcΔC1(a) was 24 hrs. The $C_{max}$ Flt1(1-3)-Fc (A40) was 8 µg/ml. For both transients (Flt1D2.Flk1D3.FcΔC1(a) and VEGFR1R2-FcΔC1(a)) the $C_{max}$ was 18 µg/ml and the $C_{max}$ for the stable VEGFR1R2-FcΔC1(a) was 30 µg/ml.

Pharmacokinetic analysis of Flt1(1-3)-Fc (A40), Flt1D2.Flk1D3.FcΔC1(a) and VEGFR1R2-FcΔC1(a). Balb/c mice (25-30 g) were injected subcutaneously with 4 mg/kg of Flt1(1-3)-Fc (A40), CHO transiently expressed Flt1D2.Flk1D3.FcΔt1(a), CHO stably expressed Flt1D2.Flk1D3.FcΔC1(a), and CHO transiently expressed VEGFR1R2-FcΔC1(a). The mice were tail bled at 1, 2, 4, 6, 24 hrs, 2 days, 3 days and 6 days after injection. The sera were assayed in an ELISA designed to detect Flt1(1-3)-Fc (A40), Flt1D2.Flk1D3.FcΔC1(a) or VEGFR1R2-FcΔC1(a). The ELISA involves coating an ELISA plate with VEGF165, binding the detect Flt1(1-3)-Fc (A40), Flt1D2.Flk1D3.FcΔC1(a) or VEGFR1R2-FcΔC1(a) and reporting with an anti-Fc antibody linked to horse radish peroxidase. The results of this experiments are shown in FIG. 37. The $T_{max}$ for Flt1(1-3)-Fc (A40) was at 6 hrs while the $T_{max}$ for the transient and stable Flt1D2.Flk1D3.FcΔC1(a) and the transient VEGFR1R2-FcΔC1(a) was 24 hrs. The $C_{max}$ for Flt1(1-3)-Fc (A40) was 8 µg/ml. For both transients (Flt1D2.Flk1D3.FcΔC1(a) and VEGER1R2-FcΔC1(a)) the $C_{max}$ was 18 µg/ml and the $C_{max}$ for the stable VEGFR1R2-FcΔC1(a) was 30 µg/ml.

Figure 38:
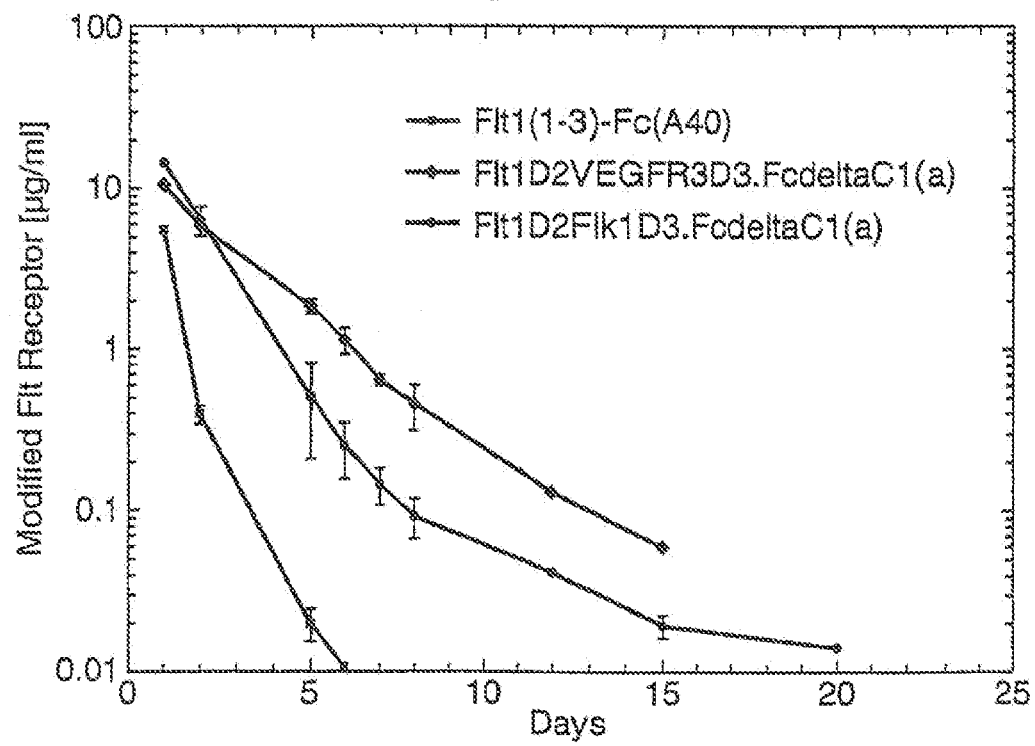
FIG. 38. Pharmacokinetics of Flt1(1-3)-Fc (A40), Flt1D2.Flk1D3.FcΔC1(a) and Flt1D2.VEGFR3D3.FcΔC1 (a). Balb/c mice were injected subcutaneoutly with 4 mg/kg of Flt1-3)-Fc (A40), CHO transiently expressed Flt1D2.Flk1D3.FcΔC1(a) and CHO transiently expressed Flt1D2.VEGFR3D3.FcΔC1(a). The mice were tail bled at 1, 2, 6, 7, 8, 12, 15 and 20 days after injection. The sera were assayed in an ELISA designed to detect Flt1(1-3)-Fc, Flt1D2.Flk1D3.FcΔC1(a) and Flt1D2. VEGFR3D3. FcΔC1 (a). Flt1(1-3)-Fc (A40) could no longer be detected in the serum after day 5 whereas Flt1D2.Flk1D3.FcΔC1(a) and Flt1D2.VEGFR3D3.FcΔC1(a) were detectable for 15 days or more.

Pharmacokinetic analysis of Flt1(1-3)-Fc (A40), Flt1D2.Flk1D3.FcΔC1(a) and Flt1D2.VEGFR3D3.FcΔC1(a). Balb/c mice (25-30 g) were injected subcutaneously with 4 mg/kg of Flt1(1-3)-Fc (A40), CHO transiently expressed Flt1D2.Flk1D3.FcΔC1(a) and CHO transiently expressed Flt1D2.VEGFR3D3.FcΔC1(a). The mice were tail bled at 1, 2, 5, 6, 7, 8, 12, 15 and 20 days after injection. The sera were assayed in an ELISA designed to detect Flt1(1-3)-Fc, Flt1D2.Flk1D3.FcΔC1(a) and Flt1D2.VEGFR3D3.FcΔC1(a). The ELISA involves coating an ELISA plate with VEGF 165, binding the Flt1(1-3)-Fc; Flt1D2.Flk1D3.FcΔC1(a) or Flt1D2.VEGFR3D3.FcΔC1(a) and reporting with an anti-Fc antibody linked to horse radish peroxidase. Flt1(1-3)-Fc (A40) could no longer be detected in the serum after day 5 whereas, Flt1D2.Flk1D3.FcΔC1(a) and Flt1D2.VEGFR3D3.FcΔC1(a) were detectable for 15 days of more. The results of this experiment are shown in FIG. 38.

Example 30

Figure 39:
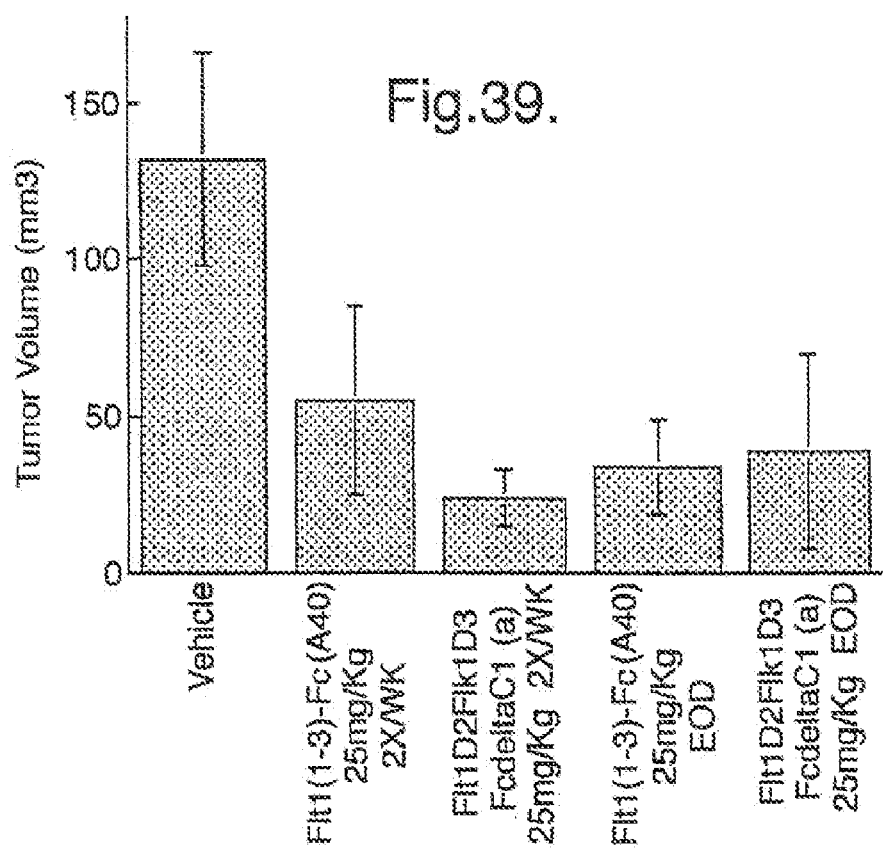
FIG. 39. The Ability of Flt1D2.Flk1D3.FcΔC1(a) to inhibit HT-1080 Fibrosarcoma Tumor Growth In Vivo. Every other day or 2 times per week treatment of SCID mice with Flt1D2.Flk1D3.FcΔC1(a) at 25 mg/Kg significantly decreases the growth of subcutaneous HT-1080 fibrosarcoma tumors.
Figure 40:
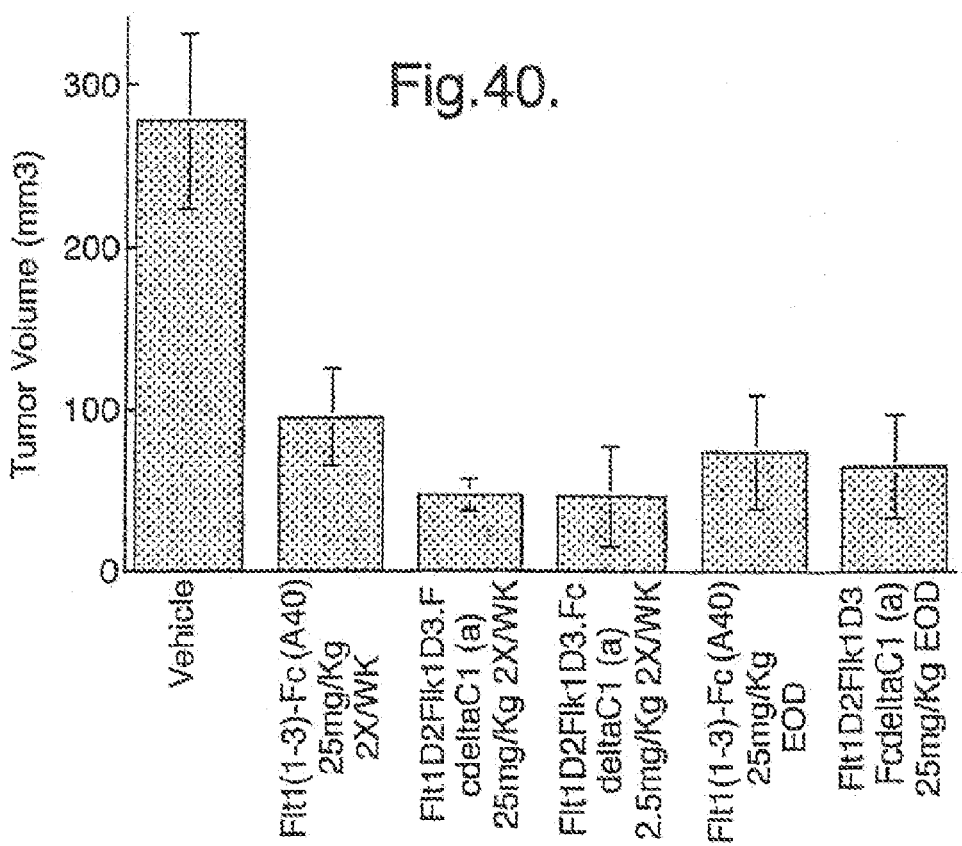
FIG. 40. The Ability of Flt1D2.Flk1D3.FcΔC1(a) to inhibit C6 Glioma Tumor Growth In Vivo. Every other day or 2 times a week treatment of SCID mice with Flt1D2.Flk1D3.FcΔC1 (a) significantly, decreases the growth of subcutaneous C6 glioma tumors at doses as low as 2.5 mg/Kg.

Evaluation of the Ability of Flt1D2.Flk1D3.FcΔC1(a) to Inhibit Tumor Growth In Vivo To evaluate the ability of Flt1D2.Flk1D3.FcΔC1(a) to inhibit tumor growth in vivo a model in which tumor cell suspensions are implanted subcutaneously on the right flank of male severe combined immunodeficiency (SCID) mice was employed. Two cell lines, the human HT-1080 fibrosarcoma cell line (ATCC accession no. CCL-121) and the rat C6 glioma cell line (ATCC accession no. CCL-107), each of which exhibit distinctly different morphologies and growth characteristics, were used in the assay. The first dose of Flt1D2.Flk1D3.FcΔC1(a) (at 25 mg/Kg or as indicated in FIGS. 39 and 40) was, given on the clay of tumor implantation. Animals subsequently received subcutaneous injections of Flt1(1-3)-Fc (A40), Flt1D2.Flk1D3.FcΔC1(a) or vehicle either every other day (EOD) or two times per week (2×/wk) for a period of 2 weeks. After 2 weeks, animals were perfused with fixative, tumors were removed and samples were blinded. Tumor volume was determined by measuring the length and width of visible subcutaneous tumors. Both of Flt1(1-3)-Fc (A40) and Flt1D2.Flk1D3.FcΔC1(a) significantly reduced the growth of tumors formed by HT-1080 and C6 cells. The results of these experiments are shown in FIG. 39 and FIG. 40.

Example 31

The Effect of VEGF165 and Modified Flt Receptors in Female Reproductive System

The stereotypic pattern of vascular remodeling which occur in the uterus and ovary over the course of the reproductive cycle has been well characterized, making these tissues particularly well suited to the study of mechanisms which regulate angiogenesis vascular remodeling and vascular regression. Indeed, in situ hybridization studies in the reproductive tissues provided the first clear evidence that VEGF acts as a mediator of physiological engiogenesis in mature rodents, as well as humans and non-human primates (Phillips et al., 1990; Ravindranath et al., 1992; Shweiki et al., 1993, Kamat et al., 1995). As cyclic angiogenesis and vascular remodeling are prominent features of the normal ovary and uterus, it is not surprising that abnormal blood vessel growth and/or vascular have been found to characterize many pathological conditions which affect these organs. Furthermore, these pathogenic vascular abnormalities are thought to be caused or perpetuated by the dysregulated expression of one or more angiogenic or anti-angiogenic factors, most prominently VEGF.

For example, abnormal angiogenesis is characteristic of polycystic ovary disease, endometriosis and endometrial carcinoma, and in each case VEGF is over-expressed in the affected tissue (Kamat al., 1995; Shifren et al., 1996; Guidi et at, 1996; Donnez et al., 1998). Overexpression of VEGF is also thought to play a pathogenic role in the establishment of systemic vascular hyperpermeability in ovarian hyperstimulation syndrome (McClure et al, 1994; Levin et al., 1998) and preeclampsia (Baker et al., 1995; Sharkey et al., 1996). In addition, VEGF has been implicated as the permeability factor responsible for the production of ascites associated with ovarian carcinoma and other tumors (Senger et al., 1983; Boocock et al, 1995). Agents which effectively neutralize the biological actions of VEGF can reasonably be anticipated to be of therapeutic benefit in the above and related conditions.

Angiogenesis and vascular remodeling are also hallmarks of blastocyst implantation and placental development (Findlay, 1986). VEGF is strongly expressed both in the maternal decidua and in embryonic trophoblasts, where it is thought to first stimulate expansion and hyperpermeability of the uterine vasculature during the peri-implantation period and subsequently mediate formation of both the maternal and embryonic components of the placental vasculature (Shweiki et al., 1993; Cullinan-Bove and Koos, 1993; Chakraborty et al., 1995; Das et al., 1997). VEGF is also required for luteal angiogenesis and associated progesterone secretion necessary to prepare the uterus for implantation (Ferrara et al., 1998). Thus, agents which inhibit the biological actions of VEGF may prove to be useful as contraceptive agents (by preventing implantation), or as an abortifacients in the early stages of station, latter application might find particular use, as a non-surgical intervention for the termination of ectopic pregnancies.

While the expression of VEGF receptors is largely confined to the vascular endothelium in normal reproductive tissues, Flt1 is also expressed by trophoblasts in the placenta in both humans and animals (Clark et al., 1996; He et al., 1999) where it has been proposed to play a role in trophoblast invasion. Interestingly, both Flt1 and KDR (Flk1) are expressed by choriocarcinoma cell line BeWo (Charnock-Jones, et al., 1994), and VEGF has been shown to promote DNA synthesis and tyrosine phosphorylation of MAP kinase in these cells. Furthermore, primary and metastatic ovarian carcinomas not only to express high levels of VEGF, but—in addition to the vascular endothelium—the tumor cells themselves express KDR and/or Flt1 (Boocock et al., 1995). These findings suggest that VEGF may not only be critically involved in the generation and maintenance of tumor vasculature, but that at least in some tumors of reproductive origin VEGF may subserve an autocrine role, directly supporting the survival and proliferation of the tumor cells. Thus agents which block the actions of VEGF may have particularly beneficial applications to the treatment of tumors of reproductive origin.

Figure 41:
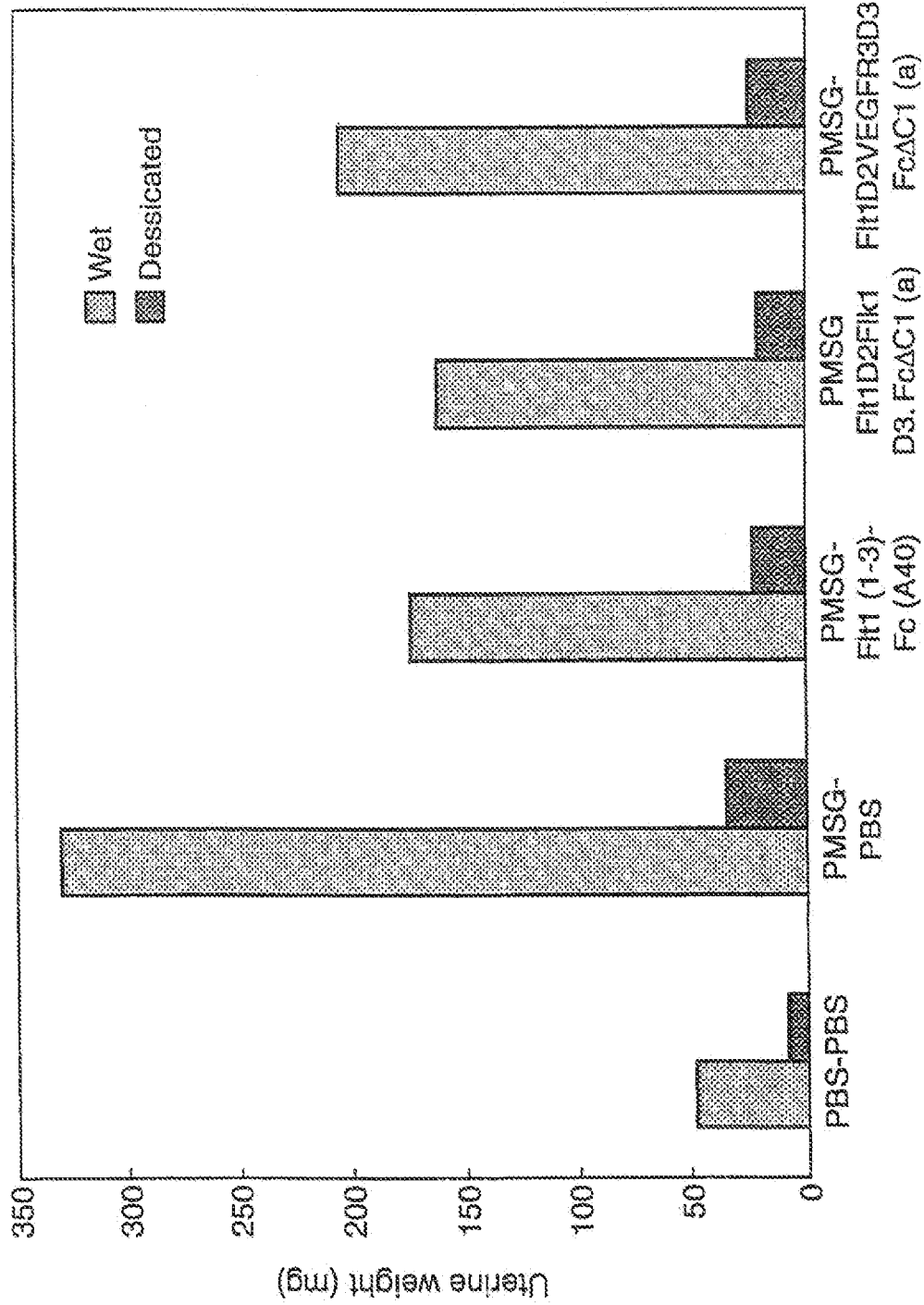
FIG. 41. VEGF-Induced Uterine Hyperpermeability Pregnant mare's serum gonadotrophin (PMSG) injected subcutaneously (5 IU) to induce ovulation in prepubertal female rats results in a surge of estradiol after-2 days which in turn causes an induction of VEGF in the uterus. This induction results in hyperpermeability of the uterus and an increase in uterine wet. Subcutaneous injection of Flt1(1-3)-Fc (A40), Flt1D2.Flk1D3.FcΔC1(a) and Flt1D2.VEGFR3D3.FcΔC1 (a) at 25 mg/kg at 1 hr after PMSG injection results in about a 50% inhibition of the increase in uterine wet weight.

Assessment of VEGF-Induced Uterine Hyperpermeability. Pregnant mare's serum gonadotrophin (PMSG) was injected subcutaneously (5 IU) to induce ovulation in prepubertal female rats. This results in a surge of estradiol after 2 days which in turn causes an induction of VEGF in the uterus. It is reported that this induction results in hyperpermeability of the uterus and an increase in uterine wet weight 6 hrs. later and, therefore, could potentially be blocked by the modified Flt receptors Flt1(1-3)-Fc (A40), Flt1D2.Flk1D3.FcΔC1(a) and Flt1D2.VEGFR3D3.FcΔC1(a). In this in vivo model, the normal weight of the rat uterus is about 50 mg and this can be induced to 300-350 mg by PMSG. Desiccation of the tissue reveals that this is all water weight. Subcutaneous injection of Flt1(1-3)-Fc (A40), Flt1D2.Flk1D3.FcΔC1(a) and Flt1D2.VEGFR3D3.FcΔC1(a) at 25 mg/kg at 1 hr after PMSG injection results in about a 50% inhibition of the increase in uterine wet weight. Increasing the dose of modified Flt receptor does not further reduce the increase in wet weight suggesting that there is a VEGF-independent component to this model. The results of this experiment are shown in FIG. 41.

Figure 42A:
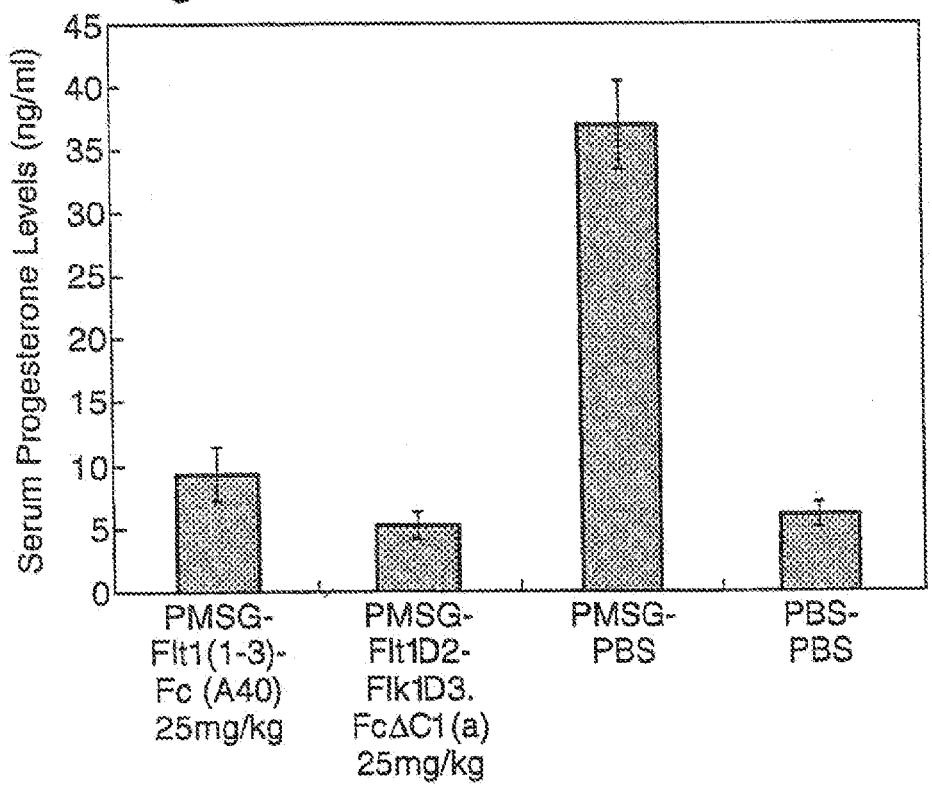
FIGS. 42A-42B. Assessment of Corpus Luteum Angiogenesis Using Progesterone as a Readout. PMSG was injected subcutaneously (5 IU) to induce ovulation in prepubertal female rats, resulting in a fully functioning corpus luteum containing a dense network of blood vessels that secretes progesterone into the blood stream to prepare the uterus for implantation. The induction of angiogenesis in the corpus luteum requires VEGF. Resting levels of progesterone are about 5 ng/ml and can be induced to 25-40 ng/ml after PMSG. Subcutaneous injection of Flt1(1-3)-Fc (A40) or Flt1D2.Flk1D3.FcΔC1(a) at 25 mg/kg or 5 mg/kg at 1 hr after PMSG injection resulted in a complete inhibition of the progesterone induction on day 4.
Figure 42B:
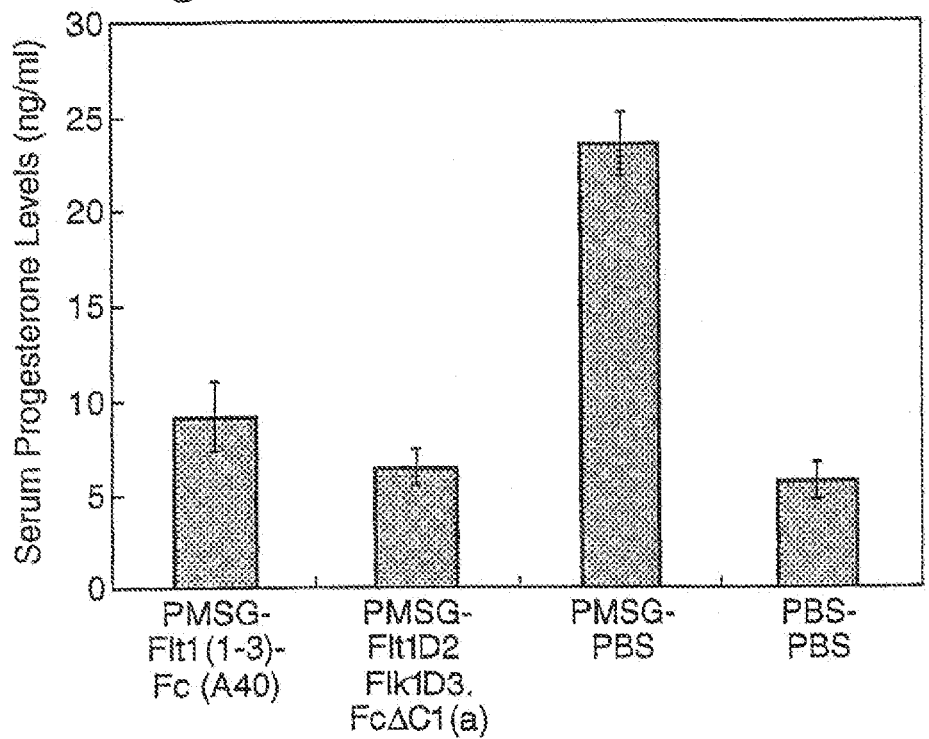

Assessment of corpus luteum angiogenesis using progesterone as a readout. Pregnant mare's serum gonadotrophin (PMSG) is injected subcutaneously (5 IU) to induce ovulation in prepubertal females rats. This results in a fully functioning corpus luteum containing a dense, network of blood vessels after 4 days that allows for the secretion of progesterone into the blood stream in order to prepare the uterus for implantation. The induction of angiogenesis in the corpus luteum requires VEGF; therefore, blocking VEGF would result in a lack of new blood vessels and thus a lack of progesterone secreted into the blood stream. In this in vivo model, resting levels of progesterone are about 5 ng/ml and this can be induced to a level of 25-40 ng/ml after PMSG. Subcutaneous injection of Flt1(1-3)-Fc (A40) or Flt1D2.Flk1D3.FcΔC1(a) at 25 mg/kg or 5 mg/kg at 1 hr after PMSG injection results in a complete inhibition of the progesterone induction on day 4. The results of this experiment are shown in FIG. 42A-42B.

Example 33

Pharmacokinetic Analysis of Flt1(1-3)-Fc (A40) and Pegylated Flt1(1-3)-Fc

Flt1(1-3)-Fc was PEGylated with either 10 kD PEG or 20 kD PEG and tested in balb/c mice for their pharmacokinetic profile. Both PEGylated forms of Flt1(1-3)-FC were found to have much better PK profiles than Flt1(1-3)-Fc (A40), with the $T_m$ occurring at 24 hrs for the PEGylated molecules as opposed to 6 hrs for Flt1(1-3)-Fc (A40).

Example 34

VEGF165 ELISA to Test Affinity of Modified Flt1 Receptor Variants

Ten pM of VEGF165 was incubated overnight at room temperature with modified. Flt1 receptor variants ranging from 160 pM to 0.1 pM. The modified Flt1 receptor variants used in this experiment were Flt1(1-3)-Fc, Flt1(1-3)-Fc (A40), transiently expressed Flt1D2Flk1D3.FcΔC1(a), transiently expressed Flt1D2VEFGFR3D3-FcΔC1(a), Flt1-(1-3$_{NAS}$)-Fc, Flt1(1-3$_{R \to C}$)-Fc and Tie2-Fc. Flt1(1-3$_{NAS}$)-Fc is a modified version of Flt1(1-3)-Fc in which the highly basic amino acid sequence KNKRASVRRR (SEQ ID NO:32) is replaced by NASVNGSR (SEQ ID NO:33), resulting in the incorporation of two new glycosylation sites and a net reduction of five positive charges, both with the purpose of reducing the unfavorable effects of this sequence on PK. Flt1(1-3$_{R \to C}$)-Fc is a modification in which a single arginine (R) residue within the same basic amino acid sequence is changed to a cysteine (C) (KNKRASVRRR (SEQ D NO:36)→KNK-CASVRRR (SEQ ID NO:34)) to allow for pegylation at that residue, which could then shield the basic region from exerting its unfavorable effects on PK. After incubation the solution was transferred to a plate containing a capture antibody for VEGF165 (R&D). The amount of free VEGF165 was then determined using an antibody to report free VEGF165. This showed that the modified Flt1 receptor variant with the highest affinity for VEGF165 (determined as the lowest amount of free VEGF165) was Flt1D2Flk1D3.FcΔC1(a), followed by Flt1(1-3)-Fc and Flt1(1-3)-Fc (A40) and then by Flt1(1-3$_{R \to C}$)-Fc, Flt1(1-3$_{NAS}$)-Fc and Flt1D2VEFGFR3D3-FcΔC1(a). Tie2Fc has no affinity for VEGF165.

What is claimed is:

1. A cell culture composition comprising cells suspended in culture medium, wherein the cells contain an expression vector comprising a nucleic acid molecule that encodes the amino acid sequence of Flt1D2.Flk1D3.FcΔC1(a) (SEQ ID NO:12) or VEGFR1R2-FcΔC1(a) (SEQ ID NO:16).

2. The cell culture composition of claim 1, wherein the cells are selected from the group consisting of bacterial cells, yeast cells, insect cells and mammalian cells.

3. The cell culture composition of claim 2, wherein the cells are *E. coli* cells, COS cells or CHO cells.

4. The cell culture composition of claim 3, wherein the cells are CHO cells.

5. The cell culture composition of claim 1, wherein the culture medium is a glutamine-free medium.

6. The cell culture composition of claim 1, wherein the culture medium contains 5% fetal bovine serum.

7. The cell culture composition of claim 1, wherein the culture medium has a pH of 7.2.

8. The cell culture composition of claim 1 contained within a roller bottle.

9. The cell culture composition of claim 1 contained within a bioreactor.

10. The cell culture composition of claim 9, wherein the bioreactor is a 5 L bioreactor.

11. The cell culture composition of claim 9, wherein the bioreactor is a 40 L bioreactor.

12. The cell culture composition of claim 1, wherein the density of the cells in the culture medium is $4 \times 10^6$ cells/mL.

* * * * *